United States Patent
Bourne et al.

(10) Patent No.: US 12,234,300 B2
(45) Date of Patent: Feb. 25, 2025

(54) CONJUGATED HEPCIDIN MIMETICS

(71) Applicant: Protagonist Therapeutics, Inc., Newark, CA (US)

(72) Inventors: Gregory Thomas Bourne, Brisbane (AU); Ashok Bhandari, Pleasanton, CA (US); Brian Troy Frederick, Ben Lomand, CA (US); Jie Zhang, Salisbury (AU); Adam Stephenson, Chapel Hill (AU); Mark Leslie Smythe, Bardon (AU); Roopa Taranath, Cupertino, CA (US); David Y. Liu, Newark, CA (US)

(73) Assignee: Protagonist Therapeutics, Inc., Newark, CA (US)

( * ) Notice: Subject to any disclaimer, the term of this patent is extended or adjusted under 35 U.S.C. 154(b) by 0 days.

(21) Appl. No.: 18/366,558

(22) Filed: Aug. 7, 2023

(65) Prior Publication Data
US 2024/0209024 A1  Jun. 27, 2024

Related U.S. Application Data

(63) Continuation of application No. 16/964,708, filed as application No. PCT/US2019/017192 on Feb. 8, 2019, now Pat. No. 11,753,443.

(60) Provisional application No. 62/749,450, filed on Oct. 23, 2018, provisional application No. 62/717,390, filed on Aug. 10, 2018, provisional application No. 62/627,948, filed on Feb. 8, 2018, provisional application No. 62/627,952, filed on Feb. 8, 2018.

(51) Int. Cl.
*C07K 7/08* (2006.01)
*A61K 9/00* (2006.01)
*A61K 38/00* (2006.01)

(52) U.S. Cl.
CPC .............. *C07K 7/08* (2013.01); *A61K 9/0053* (2013.01); *A61K 38/00* (2013.01)

(58) Field of Classification Search
CPC ......... C07K 7/08; A61K 9/0053; A61K 38/00
See application file for complete search history.

(56) References Cited

U.S. PATENT DOCUMENTS

| | | | |
|---|---|---|---|
| 4,684,620 A | 8/1987 | Hruby et al. | |
| 4,724,229 A | 2/1988 | Ali | |
| 5,192,746 A | 3/1993 | Lobl et al. | |
| 5,494,897 A | 2/1996 | Ishikawa et al. | |
| 5,569,741 A | 10/1996 | Coy et al. | |
| 5,990,084 A | 11/1999 | Richter et al. | |
| 6,087,334 A | 7/2000 | Beeley et al. | |
| 6,235,711 B1 | 5/2001 | Dutta | |
| 7,534,764 B2 | 5/2009 | Ganz et al. | |
| 7,589,170 B1 | 9/2009 | Smythe et al. | |
| 7,718,598 B1 | 5/2010 | Smythe et al. | |
| 7,745,391 B2 | 6/2010 | Mintz et al. | |
| 8,313,950 B2 | 11/2012 | Rovin et al. | |
| 8,435,941 B2 | 5/2013 | Ganz et al. | |
| 8,536,140 B2 | 9/2013 | Clandinin et al. | |
| 8,568,706 B2 | 10/2013 | Grabstein et al. | |
| 8,796,418 B2 | 8/2014 | Walensky et al. | |
| 8,946,150 B2 | 2/2015 | Gallagher et al. | |
| 8,999,935 B2 | 4/2015 | Huang | |
| 9,169,292 B2 | 10/2015 | Gallagher et al. | |
| 9,315,545 B2 | 4/2016 | Merutka | |
| 9,822,157 B2 | 11/2017 | Smythe et al. | |
| 10,030,061 B2 * | 7/2018 | Smythe | A61P 3/00 |
| 10,442,846 B2 * | 10/2019 | Smythe | A61P 3/12 |
| 10,501,515 B2 * | 12/2019 | Smythe | A61P 3/12 |
| 11,472,842 B2 | 10/2022 | Bourne et al. | |
| 11,753,443 B2 * | 9/2023 | Bourne | A61K 38/22 |
| | | | 514/5.4 |
| 11,807,674 B2 * | 11/2023 | Smythe | A61P 3/00 |
| 2003/0166138 A1 | 9/2003 | Kinsella et al. | |
| 2003/0166514 A1 | 9/2003 | Jones et al. | |
| 2004/0052785 A1 | 3/2004 | Goodman et al. | |
| 2004/0123343 A1 | 6/2004 | La Rosa et al. | |
| 2004/0152868 A1 | 8/2004 | Larsen et al. | |
| 2006/0166881 A1 | 7/2006 | Hotchkiss et al. | |
| 2006/0183884 A1 | 8/2006 | Blaschuk et al. | |
| 2007/0032417 A1 | 2/2007 | Baell | |
| 2007/0191272 A1 | 8/2007 | Stemmer et al. | |
| 2007/0197430 A1 | 8/2007 | Baell et al. | |
| 2008/0019913 A1 | 1/2008 | Polt et al. | |
| 2008/0213277 A1 | 9/2008 | Sasu et al. | |
| 2008/0260820 A1 | 10/2008 | Borrelly et al. | |
| 2008/0300180 A1 | 12/2008 | Schambye et al. | |
| 2009/0053819 A1 | 2/2009 | Seymour et al. | |
| 2009/0257952 A1 | 10/2009 | Cochran et al. | |

(Continued)

FOREIGN PATENT DOCUMENTS

| | | |
|---|---|---|
| CA | 2015761 A1 | 11/1990 |
| CN | 101307085 A | 11/2008 |

(Continued)

OTHER PUBLICATIONS

Adams and MacMillan, "Investigation of peptide thioester formation via N→Se acyl transfer." Journal of Peptide Science (2013); 19 (2): 65-73.
Andreu, et al., "Formation of Disulfide Bonds in Synthetic Peptides and Proteins" Ch. 7 in Synthetic Peptides and Proteins. In: Pennington M.W., Dunn B.M. (eds) Peptide Synthesis Protocols. Methods in Molecular Biology (1994); 35: 91-169.
Angelucci, et al., "Myelodysplastic Syndromes and Iron Chelation Therapy". Mediterr J Hematol Infect Dis. (Mar. 1, 2017); 9(1): e2017021, 10 pages. eCollection 2017.

(Continued)

*Primary Examiner* — Amber D Steele
(74) *Attorney, Agent, or Firm* — Cooley LLP

(57) ABSTRACT

The present invention provides hepcidin analogues with improved in vivo half lives, and related pharmaceutical compositions and methods of use thereof.

18 Claims, 5 Drawing Sheets
Specification includes a Sequence Listing.

(56) References Cited

U.S. PATENT DOCUMENTS

| | | |
|---|---|---|
| 2010/0151487 A1 | 6/2010 | Rovin et al. |
| 2010/0190710 A1 | 7/2010 | Chemtob et al. |
| 2010/0196441 A1 | 8/2010 | Sondermeijer et al. |
| 2011/0118186 A1 | 5/2011 | Schteingart et al. |
| 2011/0142889 A1 | 6/2011 | Lee et al. |
| 2011/0282029 A1 | 11/2011 | Holmes et al. |
| 2012/0021975 A1 | 1/2012 | Hoffmann et al. |
| 2012/0040894 A1 | 2/2012 | Ganz et al. |
| 2012/0071422 A1 | 3/2012 | Gallagher et al. |
| 2012/0115930 A1 | 5/2012 | Monia et al. |
| 2013/0029907 A1 | 1/2013 | Gallagher et al. |
| 2013/0172272 A1 | 7/2013 | Gallagher et al. |
| 2013/0183755 A1 | 7/2013 | Gallagher et al. |
| 2013/0310303 A1 | 11/2013 | Eldar-Finkelman et al. |
| 2013/0338132 A1 | 12/2013 | Koshiba et al. |
| 2014/0286953 A1 | 9/2014 | Sasu et al. |
| 2014/0336110 A1 | 11/2014 | Ganz et al. |
| 2015/0056301 A1 | 2/2015 | Kawabe et al. |
| 2015/0118315 A1 | 4/2015 | Wilson |
| 2015/0203555 A1 | 7/2015 | Gellman et al. |
| 2015/0284429 A1 | 10/2015 | Merutka |
| 2016/0039878 A1 | 2/2016 | Gallagher et al. |
| 2016/0199437 A1 | 7/2016 | Wilson |
| 2016/0222076 A1 | 8/2016 | Smythe et al. |
| 2016/0228491 A1 | 8/2016 | Wilson |
| 2017/0051013 A1 | 2/2017 | Merutka |
| 2017/0313754 A1 | 11/2017 | Bourne et al. |
| 2017/0327541 A1 | 11/2017 | Bhandari et al. |
| 2017/0362292 A1 | 12/2017 | Ruchala et al. |
| 2018/0086811 A1 | 3/2018 | Smythe et al. |
| 2018/0100004 A1 | 4/2018 | Smythe et al. |
| 2019/0002503 A1 | 1/2019 | Bourne et al. |
| 2019/0185535 A1 | 6/2019 | Smythe et al. |
| 2019/0185536 A1 | 6/2019 | Smythe et al. |
| 2019/0264197 A1 | 8/2019 | Barkan et al. |
| 2020/0017566 A1 | 1/2020 | Bourne et al. |
| 2020/0239516 A1 | 7/2020 | Richelle et al. |
| 2020/0361992 A1 | 11/2020 | Bourne et al. |
| 2021/0061872 A1 | 3/2021 | Liu et al. |
| 2021/0147483 A1 | 5/2021 | Bourne et al. |
| 2022/0348626 A1 | 11/2022 | Smythe et al. |
| 2022/0372099 A1 | 11/2022 | Liu et al. |
| 2024/0016895 A1 | 1/2024 | Liu et al. |
| 2024/0018189 A1 | 1/2024 | Bourne et al. |
| 2024/0066131 A1 | 2/2024 | Bourne et al. |
| 2024/0174726 A1 | 5/2024 | Smythe et al. |
| 2024/0209053 A1 | 6/2024 | Bourne et al. |
| 2024/0226225 A1 | 7/2024 | Bourne et al. |

FOREIGN PATENT DOCUMENTS

| | | |
|---|---|---|
| CN | 101358201 A | 2/2009 |
| JP | 2010517529 A | 5/2010 |
| JP | 2010536364 A | 12/2010 |
| JP | 2012525124 A | 10/2012 |
| JP | 2016521257 A | 7/2016 |
| JP | 2017530090 A | 10/2017 |
| WO | WO-9217492 A1 | 10/1992 |
| WO | WO-9411018 A1 | 5/1994 |
| WO | WO-9617617 A1 | 6/1996 |
| WO | WO-9725351 A2 | 7/1997 |
| WO | WO-9808871 A1 | 3/1998 |
| WO | WO-9833524 A1 | 8/1998 |
| WO | WO-9926615 A1 | 6/1999 |
| WO | WO-0009560 A2 | 2/2000 |
| WO | WO-0018789 A1 | 4/2000 |
| WO | WO-0018790 A1 | 4/2000 |
| WO | WO-0023474 A1 | 4/2000 |
| WO | WO-0055119 A1 | 9/2000 |
| WO | WO-0055184 A1 | 9/2000 |
| WO | WO-0061580 A1 | 10/2000 |
| WO | WO-0168586 A2 | 9/2001 |
| WO | WO-03066678 A1 | 8/2003 |
| WO | WO-2004011650 A2 | 2/2004 |
| WO | WO-2004092405 A2 | 10/2004 |
| WO | WO-2006032104 A1 | 3/2006 |
| WO | WO-2007138291 A2 | 12/2007 |
| WO | WO-2008097461 A2 | 8/2008 |
| WO | WO-2008101017 A2 | 8/2008 |
| WO | WO-2008134659 A2 | 11/2008 |
| WO | WO-2008140602 A2 | 11/2008 |
| WO | WO-2009002947 A2 | 12/2008 |
| WO | WO-2009027752 A2 | 3/2009 |
| WO | WO-2010065815 A2 | 6/2010 |
| WO | WO-2010116752 A1 | 10/2010 |
| WO | WO-2010124874 A1 | 11/2010 |
| WO | WO-2011091357 A1 | 7/2011 |
| WO | WO-2011149942 A2 | 12/2011 |
| WO | WO-2012052205 A1 | 4/2012 |
| WO | WO-2013086143 A1 | 6/2013 |
| WO | WO-2013172954 A1 | 11/2013 |
| WO | WO-2014059213 A1 | 4/2014 |
| WO | WO-2014127316 A2 | 8/2014 |
| WO | WO-2014145561 A2 | 9/2014 |
| WO | WO-2014165448 A1 | 10/2014 |
| WO | WO-2014165449 A1 | 10/2014 |
| WO | WO-2014210056 A1 | 12/2014 |
| WO | WO-2015054500 A2 | 4/2015 |
| WO | WO-2015157283 A1 | 10/2015 |
| WO | WO-2015176035 A1 | 11/2015 |
| WO | WO-2015183963 A2 | 12/2015 |
| WO | WO-2015200916 A2 | 12/2015 |
| WO | WO-2016004093 A2 | 1/2016 |
| WO | WO-2016011208 A1 | 1/2016 |
| WO | WO-2016054411 A1 | 4/2016 |
| WO | WO-2016054445 A1 | 4/2016 |
| WO | WO-2016109363 A1 | 7/2016 |
| WO | WO-2016115168 A1 | 7/2016 |
| WO | WO-2016195663 A1 | 12/2016 |
| WO | WO-2016200364 A1 | 12/2016 |
| WO | WO-2017011820 A2 | 1/2017 |
| WO | WO-2017068089 A2 | 4/2017 |
| WO | WO-2017117411 A1 | 7/2017 |
| WO | WO-2017165676 A1 | 9/2017 |
| WO | WO-2018022917 A1 | 2/2018 |
| WO | WO-2018022937 A1 | 2/2018 |
| WO | WO-2018048944 A1 | 3/2018 |
| WO | WO-2018089693 A2 | 5/2018 |
| WO | WO-2018128828 A1 | 7/2018 |
| WO | WO-2018136646 A1 | 7/2018 |
| WO | WO-2019051494 A1 | 3/2019 |
| WO | WO-2019157268 A1 | 8/2019 |
| WO | WO-2019246273 A1 | 12/2019 |
| WO | WO-2019246349 A1 | 12/2019 |
| WO | WO-2020014646 A1 | 1/2020 |
| WO | WO-2020198682 A1 | 10/2020 |
| WO | WO-2021007433 A1 | 1/2021 |
| WO | WO-2021046246 A1 | 3/2021 |
| WO | WO-2021142373 A1 | 7/2021 |
| WO | WO-2021146441 A1 | 7/2021 |
| WO | WO-2021146454 A1 | 7/2021 |
| WO | WO-2021146458 A1 | 7/2021 |
| WO | WO-2022026629 A1 | 2/2022 |
| WO | WO-2022026631 A1 | 2/2022 |
| WO | WO-2022026633 A1 | 2/2022 |
| WO | WO-2022109328 A1 | 5/2022 |
| WO | WO-2022212696 A1 | 10/2022 |
| WO | WO-2022212698 A1 | 10/2022 |
| WO | WO-2022212700 A2 | 10/2022 |
| WO | WO-2022266060 A1 | 12/2022 |
| WO | WO-2023288017 A2 | 1/2023 |
| WO | WO-2023288019 A2 | 1/2023 |
| WO | WO-2023288028 A2 | 1/2023 |
| WO | WO-2023009891 A2 | 2/2023 |
| WO | WO-2023150618 A2 | 8/2023 |
| WO | WO-2023150630 A2 | 8/2023 |
| WO | WO-2023240077 A1 | 12/2023 |
| WO | WO-2024011188 A1 | 1/2024 |

OTHER PUBLICATIONS

Annis, et al., "[10] Disulfide bond formation in peptides". Methods Enzymol. (1997); 289: 198-221.

(56) References Cited

OTHER PUBLICATIONS

Arber, Daniel A., et al., "The 2016 revision to the World Health Organization classification of myeloid neoplasms and acute leukemia", Blood, The Journal of the American Society of Hematology (May 19, 2016); 127(20): 2391-2405.

Ashby, et al., "Plasma hepcidin levels are elevated but responsive to erythropoietin therapy in renal disease." Kidney International (2009); 75 (9): 976-981.

[Author Unknown] "FDA Grants Orphan Drug Designation For Protagonist Therapeutics' PTG-300 For The Treatment Of Beta-Thalassemia", Protagonist Therapeutics, Cision PR Newswire (Mar. 6, 2018); [Press release] http://www.prnewswire.com/news-releases/fda-grants-orphan-drug-designation-for-protagonist-therapeuticsptg-300-for-the-treatment-of-beta-thalassemia-300609386.html, 2 pages.

[Author Unknown] "Protagonist Announces Phase 1 and Preclinical Data on Hepcidin Mimetic PTG-300 Presented at European Hematology Association Annual Meeting", Protagonist Therapeutics, Cision PR Newswire (Jun. 18, 2018); [Press release] https://www.prnewswire.com/news-releases/protagonist-announces-phase-1-and-pre-clinical-data-on-hepcidin-mimetic-ptg-300-presented-at-european-hematology-association-annual-meeting-300667520.html, 2 pages.

[Author Unknown] "Protagonist Therapeutics Announces Fast Track Designation Granted by U.S. FDA to Hepcidin Mimetic PTG-300", Protagonist Therapeutics, Cision PR Newswire (Sep. 27, 2018); [Press release] https://www.prnewswire.com/news-releases/protagonist-therapeutics-announces-fast-track-designation-granted-by-us-fda-to-hepcidin-mimetic-ptg-300-300720035.html, 2 pages.

[Author Unknown] "Protagonist Therapeutics Expands Intellectual Property Portfolio", Protagonist Therapeutics, Cision PR Newswire (Sep. 6, 2018); [Press release] https://www.prnewswire.com/news-releases/protagonist-therapeutics-expands-intellectual-property-portfolio-300707765.html, 1 page.

[Author Unknown] "Protagonist Therapeutics Initiates Phase 2 Study of Novel Hepcidin Mimetic PTG-300 in the Treatment of Patients with Polycythemia Vera", Protagonist Therapeutics, Cision PR Newswire (Oct. 30, 2019); [Press release] https://www.prnewswire.com/news-releases/protagonist-therapeutics-initiates-phase-2-study-of-novel-hepcidin-mimetic-ptg-300-in-the-treatment-of-patients-with-polycythemia-vera-300948611.html, 2 pages.

[Author Unknown] "Protagonist Therapeutics Initiates Phase 2 Trial of Novel Hepcidin Mimetic PTG-300 for the Treatment of Patients with Beta Thalassemia", Protagonist Therapeutics, Cision PR Newswire (Jan. 9, 2019); [Press release] https://www.prnewswire.com/news-releases/protagonist-therapeutics-initiates-phase-2-trial-of-novel-hepcidin-mimetic-ptg-300-for-the-treatment-of-patients-with-beta-thalassemia-300775348.html, 2 pages.

[Author Unknown] "Protagonist Therapeutics Reports Second Quarter 2019 Financial Results", Protagonist Therapeutics, Cision PR Newswire (Aug. 7, 2019); [Press release] https://www.prnewswire.com/news-releases/protagonist-therapeutics-reports-second-quarter-2019-financial-results-300897892.html, 3 pages.

Balwani, Manisha, "Erythropoietic Protoporphyria and X-Linked Protoporphyria: pathophysiology, genetics, clinical manifestations, and management". Mol Genet Metab (Nov. 2019); 128(3): 298-303. Epub Jan. 24, 2019.

Barman-Aksözen, et al., "Delta-aminolevulinic acid synthase 2 expression in combination with iron as modifiers of disease severity in erythropoietic protoporphyria". Molecular Genetics and Metabolism (Nov. 2019); 128(3): 304-308.

Boccia, Ralph V., et al., "Examining the frequency of phlebotomy in patients with polycythemia vera (PV) in the United States: an analysis of data from the REVEAL study", Blood (Dec. 8, 2017); 130(1): 5271, 3 pages.

Boer, J., et al., "Design and Synthesis of Potent and Selective 47 Integrin Antagonists." J. Med. Chem. (2001); 44 (16): 2586-2592.

Bowie, J. U. et al., "Deciphering the message in protein sequences: Tolerance to amino acid substitutions," Science, (Mar. 16, 1990), 247(4948):1306-1310.

Brayden, D.J., and Mrsny, R.J., "Oral peptide delivery: prioritizing the leading technologies". Therapeutic Delivery (2011); 2(12): 1567-1573.

Burton, et al., "Systemic administration of a pharmacologic iron chelator reduces cartilage lesion development in the Dunkin-Hartley model of primary osteoarthritis". Free Radical Biology and Medicine (Feb. 1, 2022); 179: 47-58.

Carroll, et al., "Hereditary hemochromatosis is characterized by a clinically definable arthropathy that correlates with iron load". Arthritis & Rheumatism (Jan. 2011); 63(1): 286-294.

Casu, Carla, et al., "Minihepcidin peptides as disease modifiers in mice affected by β-thalassemia and polycythemia vera", Blood, The Journal of the American Society of Hematology (2016); 128(2): 265-276.

Casu, et al., "Hepcidin agonists as therapeutic tools". Blood, The Journal of the American Society of Hematology (Apr. 19, 2018); 131(16): 1790-1794.

Chang, et al., Role of disulfide bonds in the structure and activity of human insulin. Mol Cells (Dec. 2003); 16(3): 323-330.

Chatterjee, Jayanta, et al., "N-Methylation of Peptides: A New Perspective in Medicinal Chemistry", Accounts of Chemical Research (2008); 41(10): 1331-1342.

Chermahini et al., "Cyclic peptide nanocapsule as ion carrier for halides: a theoretical survey", Structural Chemistry (Oct. 2018); 29(5): 1351-1357.

Clark, et al., "The Engineering of an Orally Active Conotoxin for the Treatment of Neuropathic Pain." Angew Chem Int Ed (Sep. 2010); 49: 6545-6548.

Clark, et al., "Understanding the Structure/Activity Relationships of the Iron Regulatory Peptide Hepcidin." Chem Biol. (Mar. 2011); 18(3): 336-343.

Clark, Richard J., et al. "Design, synthesis, and characterization of cyclic analogues of the iron regulatory peptide hormone hepcidin." Peptide Science (2013); 100.5: 519-526.

Co-pending U.S. Appl. No. 18/284,835, inventors Bhandari; Ashok et al., filed Sep. 28, 2023.

Co-pending U.S. Appl. No. 18/285,198, inventors Bourne; Gregory Thomas et al., filed Sep. 29, 2023.

Co-pending U.S. Appl. No. 18/285,203, inventors Bourne; Gregory Thomas et al., filed Sep. 29, 2023.

Co-pending U.S. Appl. No. 18/355,992, inventors Liu; David Y. et al., filed Jul. 20, 2023.

Craik, et al., "Potential therapeutic applications of the cyclotides and related cystine knot mini-proteins." Expert Opin Investig Drugs (May 2007); 16(5): 595-604.

"Crushing Guide for Oral Medication in Residential Aged Care", Waitemata District Health Board, 2011, 2 pages.

Cui, et al., "Serum iron metabolism and erythropoiesis in patients with myelodysplastic syndrome not receiving RBC transfusions". Leuk Res. (2014); 38(5): 545-550.

Database EPO Proteins [Online] Dec. 3, 2010 (Dec. 3, 2010), "Sequence from Patent WO2010124874." XP002761649, retrieved from EBI accession No. EPOP:HI656765 Database accession No. HI656765, 1 page.

Database USPTO Proteins [Online] Dec. 17, 2012 (Dec. 17, 2012), "Sequence from patent U.S. Pat. No. 8,313,950.", XP002761650, retrieved from EBI accession No. USPOP:AGA36544 Database accession No. AGA36544, 1 page.

Davies, J.S., "The Cyclization of Peptides and Depsipeptides", J Pept Sci. (Aug. 2003); 9(8): 471-501.

De Mast, et al., "Increased serum hepcidin and alterations in blood iron parameters associated with asymptomatic P. falciparum and P. vivax malaria." Haematologica (2010); 95 (7): 1068-1074.

De Vega, et al., "Modulation of Protein-Protein Interactions by Stabilizing/Mimicking Protein Secondary Structure Elements." Curr Top Med Chem (2007); 7(1): 33-62.

Definition of Isostere, Medical Definition and More from Merriam-Webster Dictionary, www.merriam-webster.com/medical/isostere accessed on Feb. 5, 2015, 3 pages.

Delgado et al., "The uses and properties of PEG-linked proteins". Critical Reviews in Therapeutic Drug Carrier Systems (Jan. 1, 1992); 9(3-4): 249-304.

(56) References Cited

OTHER PUBLICATIONS

Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing-Helices in Short Oligopeptides through Binding by an Artificial Hydrophobic Cavity." Journal of the American Chemical Society (2010); 132.16: 5564-5565.
Dutta, Anand S., "Potent Cyclic Monomeric and Dimeric Peptide Inhibitors of VLA-4 (a4b1 Integrin)-Mediated Cell Adhesion Based on the lle-Leu-Asp-Val Tetrapeptide", J. Peptide Sci. (2000); 6: 321-341.
Dutton, et al., "A New Level of Conotoxin Diversity, a Non-native Disulfide Bond Connectivity in-Conotoxin AulB Reduces Structural Definition but Increases Biological Activity." J Biol Chem (Oct. 2002); 277(50): 48849-48857.
European Application No. 19750312.1, Extended European Search Report dated Mar. 3, 2022, 11 pages.
European Application No. 19750312.1, Partial Supplementary European Search Report dated Nov. 29, 2021, 13 pages.
Fass, D., "Disulfide bonding in protein biophysics." Annu Rev Biophys (2012); 41: 63-79. Epub Dec. 20, 2011.
Fosgerau and Hoffman, "Peptide therapeutics: current status and future directions." Drug Discovery Today (2015); 20(1): 122-128.
Foster "Deuterium Isotope Effects in Studies of Drug Metabolism", Trends Pharmacol. Sci. (1984); 5(12): 524-527.
Francis, G., et al., "PEGylation of Cytokines and other Therapeutic Proteins and Peptides: the Importance of Biological Optimisation of Coupling Techniques," International Journal of Hematology, Jul. 1998, vol. 68, pp. 1-18, 19 pages.
Fruchtman, Steven M., et al., "From efficacy to safety: a Polycythemia Vera Study group report on hydroxyurea in patients with polycythemia vera", Seminars in hematology (1997); 34(1): 17-23.
Ganz and Nemeth, "Hepcidin and iron homeostasis." Biochimica et Biophysica Acta (BBA)—Molecular Cell Research (Sep. 2012); 1823 (9): 1434-1443.
Garcia, Josep et al., "D-Polyarginine Lipopeptides as Intestinal Permeation Enhancers". ChemMedChem Oct. 8, 2018; 13(19): 2045-2052. Epub Aug. 20, 2018.
Gee et al. "Cyclic Peptides as Non-carboxyl-terminal Ligands of Syntrophin PDZ Domains," The Journal of Biological Chemistry, 273(34): 21980-21987 (1998).
Gentilucci, et al., "Chemical Modifications Designed to Improve Peptide Stability: Incorporation of Non-Natural Amino Acids, Pseudo-Peptide Bonds, and Cyclization". Curr Pharm Des. (2010); 16(28): 3185-3203.
Girelli, Domenico, et al. "Hepcidin in the diagnosis of iron disorders." Blood (2016); 127.23: 2809-2813.
Gombotz and Pettit, "Biodegradable Polymers for Protein and Peptide Drug Delivery". Bioconjugate Chem. (Jul. 1, 1995); 6(4): 332-351.
Goptar, I.A., et al., "Properties of Post-Proline Cleaving Enzymes from Tenebrio Molitor," Russian Journal of Bioorganic Chemistry, 2008, vol. 34(3), pp. 280-285.
Görmer, et al., "Efficient Microwave-Assisted Synthesis of Unsymmetrical Disulfides", J. Org. Chem. (Feb. 1, 2010); 75(5): 1811-1813.
Gruschow, et al., "New pacidamycin antibiotics through precursor-directed biosynthesis". Chembiochem. Jan. 26, 2009; 10(2): 355-360.
Guerler and Knapp, "Novel protein folds and their nonsequential structural analogs." Protein Sci (Aug. 2008); 17(8): 1374-1382.
Guharoy and Chakrabarti, "Secondary structure based analysis and classification of biological interfaces: identification of binding motifs in protein-protein interactions." Bioinformatics (2007); 23(15): 1909-1918. Epub May 17, 2007.
Gupta, et al., "A classification of disulfide patterns and its relationship to protein structure and function." Protein Sci (Aug. 2004); 13(8): 2045-2058.

Hartig, et al., "Intramolecular disulphide bond arrangements in nonhomologous proteins." Protein Sci Publ Protein Soc (Feb. 2005); 14(2): 474-482.
Hawe, et al., "Forced degradation of therapeutic proteins." J Pharm Sci. (Mar. 2012); 101(3): 895-913. Epub Nov. 14, 2011.
Henikoff et al., "Amino acid substitution matrices from protein blocks," Proc. Natl. Acad. Sci. U.S.A., Nov. 1992, 89: 10915-10919.
Hruby and Bonner, "Design of Novel Synthetic Peptides Including Cyclic Conformationally and Topographically Constrained Analogs". Methods in Molecular Biology, Ch. 11, vol. 35 Peptide Synthesis Protocols, Edited by M.W Pennington and B. M. Dunn Copyright, 1994 Humana Press Inc, Totowa, NJ, pp. 201-241, 40 pages.
Hudecz, et al., "Synthesis, conformation, biodistribution and in vitro cytotoxicity of daunomycin-branched polypeptide conjugates". Bioconjugate Chem. (Jan. 1, 1992); 3(1): 49-57.
Ilyin, Gennady, et al. "Comparative analysis of mouse hepcidin 1 and 2 genes: evidence for different patterns of expression and inducibility during iron overload 1." FEBS Letters (2003); 542.1-3: 22-26.
Jagasia et al., "Peptide Cyclization and Cyclodimerization by Cu-Mediated Azide-Alkyne Cycloaddition", Journal of Organic Chemistry (Apr. 17, 2009); 74(8): 2964-2974.
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Jordan, John B., et al., "Hepcidin revisited, disulfide connectivity, dynamics, and structure", Journal of Biological Chemistry (2009); 284(36): 24155-24167.
Karim, et al., "The role of disrupted iron homeostasis in the development and progression of arthropathy". Journal of Orthopaedic Research (Jun. 2022); 40(6): 1243-1250.
Kelleman, A. et al., "Incorporation of thioether building blocks into an v3-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, p. 9, 3 pages.
Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Kowdley, et al., "An-Open Label Phase 2, Dose-Finding Study of the Safety and Efficacy of Rusfertide (PTG-300), A Hepcidin Mimetic, In Patients with Hereditary Hemochromatosis". AASLD Abstract 649, AASLD Hepatology (2021); 74, No. 1(Suppl), p. 25A-25B, 2 pages.
Kowdley, et al., "Monitoring and Management of Nash is an Unmet Need Among Hepatologists and Endocrinologists: An International Mixed-Method Study in Europe and the USA". AASLD Abstract (Poster) 649, AASLD Hepatology (2021); 74, No. 1(Suppl), pp. 394A, 1 page.
Krause, Alexander, et al. "LEAP 1, a novel highly disulfide bonded human peptide, exhibits antimicrobial activity." FEBS Letters (2000); 480.2-3: 147-150.
Kuchař, et al., "Human interleukin-23 receptor antagonists derived from an albumin-binding domain scaffold inhibit IL-23-dependent ex vivo expansion of IL-17-producing T-cells". Proteins (Jun. 2014); 82(6): 975-989. Epub Nov. 23, 2013.
Lecha, et al., "Erythropoietic protoporphyria". Orphanet Journal of Rare Diseases (2009); 4: 19, 10 pages.
Legge and Morieson, "On the prediction of partition coefficients and RF values of peptides." Aust. J. Biol. Sci. (1964); 17: 561-571.
Li and Roller, "Cyclization Strategies in Peptide Derived Drug Design." Curr. Topics Med. Chem. (2002); 2: 325-341.
List, A.F., "Iron overload in myelodysplastic syndromes: diagnosis and management". Cancer Control (Jan. 2010); 17(1_suppl):2-8, 7 pages.

(56) References Cited

OTHER PUBLICATIONS

Liu and Wang, "Endomorphins: potential roles and therapeutic indications in the development of opioid peptide analgesic drugs". Med Res Rev. (May 2012); 32(3): 536-580. Epub Feb. 1, 2011.
Liu, Shuang, "Radiolabeled Cyclic RGD Peptides as Integrin v3-Targeted Radiotracers: Maximizing Binding Affinity via Bivalency." Bioconjugate Chem. (2009); 20 (12): 2199-2213.
Liu, Shuang, "Radiolabeled Multimeric Cyclic Rgd Peptides as Integrin Alphavbeta3 Targeted Radiotracers For Tumor Imaging" School of Health Science, Purdue University, Molecular Pharmaceuticals (2006); 3(5):472-487.
Longobardo, et al., "β-Casomorphins: substitution of phenylalanine with β-homo-phenylalanine increases the μ-type opioid receptor affinity." Bioorganic & Medicinal Chemistry Letters (2000); 10(11): 1185-1188.
Longobardo, et al., "Incorporation of β-amino acids in bioactive peptides: a β-casomorphin case study." Peptides 2002, Abstract P A97, Proceedings of the European Peptide Symposium, 27th, Sorrento, Italy, Aug. 31-Sep. 6, 2002 (2002), 198-199.
Madsen, Kjeld, et al. "Structure-activity and protraction relationship of long-acting glucagon-like peptide-1 derivatives: importance of fatty acid length, polarity, and bulkiness." Journal of Medicinal Chemistry (2007); 50.24: 6126-6132.
Maeda, et al., "Conjugates of anticancer agents and polymers: advantages of macromolecular therapeutics in vivo". Bioconjugate Chem. (Sep./Oct. 1992); 3(5): 3511-362.
Maher, Sam et al., "Safety and efficacy of sodium caprate in promoting oral drug absorption: from in vitro to the clinic". Advanced Drug Delivery Reviews Dec. 17, 2009; 61 (15): 1427-1449. Epub Oct. 1, 2009.
Maher, Sam et al., "Application of Permeation Enhancers in Oral Delivery of Macromolecules: An Update". Pharmaceutics Jan. 19, 2019; 11 (1): 41,23 pages.
Martinez, et al., "Hepatic damage and oxidative stress induced by griseofulvin in mice". Cellular and Molecular Biology (Jul. 1, 2009); 55(2): 127-139.
Muheem, Abdul et al., "A review on the strategies for oral delivery of proteins and peptides and their clinical perspectives". Saudi Pharmaceutical Journal Jul. 2016; 24(4):413-428. Epub Jun. 16, 2014.
Muñoz, Manuel, et al. "Disorders of iron metabolism. Part II: iron deficiency and iron overload." Journal of Clinical Pathology (2011); 64.4: 287-296.
Nemeth, Elizabeta, et al., "The N-terminus of hepcidin is essential for its interaction with ferroportin: structure-function study", Blood (2006); 107(1): 328-333.
Nguyen, et al., "Bone and joint complications in patients with hereditary hemochromatosis: a cross-sectional study of 93 patients". Therapeutic Advances in Musculoskeletal Disease (Jul. 2020); 12: 1759720X20939405, 14 pages. eCollection 2020.
Park, C.H., et al., "Hepcidin, a urinary antimicrobial peptide synthesized in the liver." J Biol Chem. (2001); 276(11): 7806-7810. Epub Dec. 11, 2000.
Parrow, et al., "Prospects for a hepcidin mimic to treat-thalassemia and hemochromatosis." Expert Review of Hematology (2011); 4 (3): 233-235.
Paterson, I.C., et al., "Partial Characterization of Specific Inducers of a Cuticle-Degrading Protease from the Insect Pathogenic Fungus Metarhizium Anisopliae," Microbiology, 1994, vol. 140(11), pp. 3153-3159.
Pattarawarapan, "Selective Formation of Homo-and Heterobivalent Peptidomimetics." J. Med. Chem. (Aug. 2003); 46 (17): 3565-3567.
PCT/US2019/017192, International Preliminary Report on Patentability, dated Aug. 11, 2020, 7 pages.
PCT/US2019/017192, International Search Report and Written Opinion, mailed Jun. 11, 2019, 11 pages.
PCT/US2019/017192, Invitation to Pay Additional Fees, mailed Apr. 16, 2019, 2 pages.

Pearson, T. C. and Wetherley-Mein, G., "Vascular occlusive episodes and venous haematocrit in primary proliferative polycythaemia", The Lancet (Dec. 9, 1978); 312(8102): 1219-1222.
Pelton, J.T. et al., "Somatostatin Analogs with Affinity for Opiate Receptors in Rat Brain Binding Assay", Peptides, 6(Suppl 1): 159-163 (1985).
Pettit, L.D., et al., "Influence of the Proline Residue on the Co-Ordination of Cu(II) to Peptides Containing-Pro-and-Pro-Pro-Subunits," Polyhedron, 1987, vol. 6(1), pp. 45-52.
Preza, Gloria C., et al., "Minihepcidins are rationally designed small peptides that mimic hepcidin activity in mice and may be useful for the treatment of iron overload", The Journal of Clinical Investigation (2011); 121(12): 4880-4888.
Quiniou, et al., "Specific targeting of the IL-23 receptor, using a novel small peptide noncompetitive antagonist, decreases the inflammatory response". Am J Physiol Regul Integr Comp Physiol. (Nov. 15, 2014); 307(10): R1216-R1230. Epub Aug. 20, 2014.
Ramos, E., et al., "Minihepcidins prevent iron overload in a hepcidin-deficient mouse model of severe hemochromatosis." Blood (Nov. 2012); 120(18): 3829-3836. Epub Sep. 18, 2012.
Rampal, Raajit, et al., "Integrated genomic analysis illustrates the central role of JAK-STAT pathway activation in myeloproliferative neoplasm pathogenesis", e-Blood (May 29, 2014); 123(22): e123-33.
Rector Jr., William G., et al., "Non-hematologic effects of chronic iron deficiency: a study of patients with polycythemia vera treated solely with venesections", Medicine (Nov. 1982); 61(6): 382-389.
Rivera, Seth, et al., "Synthetic hepcidin causes rapid dose-dependent hypoferremia and is concentrated in ferroportin-containing organs", Blood (2005); 106: 2196-2199.
Rostovtsev, et al., "A Stepwise Huisgen Cycloaddition Process: Copper(I)Catalyzed Regioselective "Ligation" of Azides and Terminal Alkynes". Angewandte Chemie Int. Ed. (Jul. 2, 2002); 41(14): 2596-2599.
Rubinstein and Niv, "Peptidic modulators of protein-protein interactions: Progress and challenges in computational design." Biopolymers (2009); 91(7): 505-513.
Sasaki, et al., "D-Arg2-dermorphin tetrapeptide analogs: a potent and long-lasting analgesic activity after subcutaneous administration." Biochem Biophys Res Commun. (1984); 120 (1): 214-218.
Schmidt, et al., "Mild iron deficiency does not ameliorate the phenotype of a murine erythropoietic protoporphyria model". American Journal of Hematology (May 2020); 95(5): 492-496.
Sekeres and Cutler, "How we treat higher-risk myelodysplastic syndromes". Blood (Feb. 6, 2014); 123(6):829-836. Epub Dec. 20, 2013.
Shenoy, et al., "Impact of iron overload and potential benefit from iron chelation in low-risk myelodysplastic syndrome". Blood (Aug. 7, 2014); 124(6): 873-881. Epub Jun. 12, 2014.
Simmerling, et al., "Hydrophobic "Collapse" in a Cyclic Hexapeptide: Computer Simulations of CHDLFC and CAAAAC in Water" Journal of American Chemical Society (1994); 116(6): 2534-2547.
Speers, et al., "Activity-Based Protein Profiling in Vivo Using a Copper(I)-Catalyzed Azide-Alkyne [3 + 2] Cycloaddition". J. Am. Chem. Soc. (Mar. 28, 2003); 125(16): 4686-4687.
Stein, Brady L., et al., "Polycythemia vera: an appraisal of the biology and management 10 years after the discovery of JAK2 V617F", Journal of Clinical Oncology (Nov. 20, 2015); 33(33): 3953-60.
Streiff, Michael B., et al., "The diagnosis and management of polycythemia vera in the era since the Polycythemia Vera Study Group: a survey of American Society of Hematology members' practice patterns", Blood, The Journal of the American Society of Hematology (Feb. 15, 2002); 99(4): 1144-1149.
Tandara, Leida, and Salamunic, Ilza . "Iron metabolism: current facts and future directions." Biochemia Medica (2012); 22.3: 311-328.
Taranath, et al., "Regulation of Iron Homeostasis By PTG-300 Improves Disease Parameters in Mouse Models for Beta-Thalassemia and Hereditary Hemochromatosis". Blood (Nov. 13, 2019); 134 (Supplement_1): 3540, 3 pages.
Tefferi and Vardiman, "Myelodysplastic syndromes". N Engl J Med. (Nov. 5, 2009); 361(19): 1872-1885.

(56) References Cited

OTHER PUBLICATIONS

Tefferi, Ayalew and Barbui, Tiziano, "Polycythemia vera and essential thrombocythemia: 2017 update on diagnosis, risk-stratification, and management", American Journal of Hematology (Jan. 1, 2017); 92(1): 94-108.

Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).

Temraz, et al., "Iron overload and chelation therapy in myelodysplastic syndromes". Crit Rev Oncol Hematol. (Jul. 2014); 91(1): 64-73. Epub Jan. 24, 2014.

Thermo Electron Corporation, Technical Information, "N-terminal and C-terminal Amidation of Peptides", 2 pages (2004).

Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).

Tornøe, et al., "Peptidotriazoles on solid phase: [1,2,3]-triazoles by regiospecific copper(i)-catalyzed 1,3-dipolar cycloadditions of terminal alkynes to azides." J Org Chem. (May 3, 2002); 67(9): 3057-3064.

Tsukada, et al., "An Anti-α-Fetoprotein Antibody-Daunorubicin Conjugate With a Novel Poly-L-glutamic Acid Derivative as Intermediate Drug Carrier ". J. Natl. Cancer Inst. (Sep. 1984); 73(3): 721-729.

Tuvia, et al., "A Novel Suspension Formulation Enhances Intestinal Absorption of Macromolecules Via Transient and Reversible Transport Mechanisms". Pharm Res. (Feb. 21, 2014); 31(8): 2010-2021.

Wang, et al., "Bioconjugation by Copper(I)-Catalyzed Azide-Alkyne [3 + 2] Cycloaddition". J Am Chem Soc. (Mar. 19, 2003); 125(11): 3192-3193.

Whalen, et al., "Association of transferrin saturation with the arthropathy of hereditary hemochromatosis". Clinical Gastroenterology and Hepatology (Oct. 1, 2017); 15(10): 1507-1508.

White and Yudin, "Contemporary strategies for peptide macrocyclization." Nat Chem (Jun. 2011); 3(7): 509-524.

Witt, Dariusz, "Recent developments in disulfide bond formation". Synthesis (2008); 16: 2491-2509.

Wulf, et al., "Inactivation of protoporphyrin IX in erythrocytes in patients with erythropoietic protoporphyria: A new treatment modality". Photodiagnosis and Photodynamic Therapy (Mar. 1, 2020); 29: 101582, 4 pages.

Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).

Yampolsky and Stoltzfus, "The Exchangeability of Amino Acids in Proteins", Genetics (Aug. 2005); 170(4): 1459-1472. Epub Jun. 8, 2005.

Yoshida, et al., "Erythropoietic protoporphyria-related hepatopathy successfully treated with phlebotomy". Internal Medicine (Sep. 1, 2018); 57(17): 2505-2509.

Zalipsky, Samuel, "Functionalized Poly(ethylene glycols) for Preparation of Biologically Relevant Conjugates". Bioconjugate Chem. (1995); 6(2): 150-165.

[Author Unknown] "Fast Track", U.S. Food and Drug Administration, Jan. 4, 2018, available online at: https://www.fda.gov/patients/fast-track-breakthrough-therapy-accelerated-approval-priority-review/fast-track. 2 pages.

[Author Unknown] "Polycythemia Vera", National Organization for Rare Disorders NORD, Nov. 16, 2023, available online at: https://rarediseases.org/rare-diseases/polycythemia-vera/. 4 printed pages.

Gerds et al., "Rusfertide for Polycythemia Vera: Similar Dosing in Patients Receiving Therapeutic Phlebotomy Alone or in Combination with Cytoreductive Treatment." Blood (2022) 140 (Supplement 1): 12241-12243. https://doi.org/10.1182/blood-2022-163847. Nov. 2022, 6 pages.

Kremyanskaya et al., "Rusfertide, a Hepcidin Mimetic, for Control of Erythrocytosis in Polycythemia Vera." N Engl J Med. Feb. 22, 2024; 390(8): 723-735. doi: 10.1056/NEJMoa2308809. 13 pages.

Mount Sinai Health System, "Novel treatment for polycythemia vera shows promise in clinical trial." News-Medical.Net, Available online at: https://www.news-medical.net/news/20240221/Novel-treatment-for-polycythemia-vera-shows-promise-in-clinical-trial.aspx. Feb. 21, 2024, 3 pages.

Protagonist Therapeutics, Inc., "Protagonist Therapeutics Receives FDA Breakthrough Therapy Designation for Rusfertide in Polycythemia Vera", PR Newswire, Jun. 3, 2021, available online at: https://www.prnewswire.com/news-releases/protagonist-therapeutics-receives-fda-breakthrough-therapy-designation-for-rusfertide-in-polycythemia-vera-301304760.html. 4 pages.

Pubchem, SID 376236348, Modify Date: Nov. 16, 2018. Retrieved from the Internet URL: https://pubchem.ncbi.nlm.nih.gov/substance/376236348. 5 pages.

Pubchem, SID 96075894, Modify Date: Jul. 6, 2010. Retrieved from the Internet URL: https://pubchem.ncbi.nlm.nih.gov/substarice/96075894. 5 pages.

Shames, Richard, et al., "Hepcidin Mimetic PTG-300 Induces Dose-Related and Sustained Reductions in Serum Iron and Transferrin Saturation in Healthy Subjects", EHA Library. Shames R. Jun. 16, 2018; 214566; S895, (Abstract). (Abstract release date: May 17, 2018). Available online at:https://library.ehaweb.org/eha/2018/stockholm/214566/richard.shames.hepcidin.mimet ic.ptg-300.induces.dose-related.and.sustained.html?f=menu=14*media=3*speaker=663819. 2 pages.

SwissProt Accession No. P81172, HEPC_Human, Dec. 15, 1998, integrated into UniProtKB/Swiss-Prot. 7 pages.

Taranath et al., "Mechanism of Systemic Iron Regulation and Hematocrit Control By Hepcidin Peptidomimetics in Pre-Clinical Models", Blood (2020) 136 (Supplement 1): 49. http://doi.org/10.1182/blood-2020-141670. 4 pages.

Triguero et al., "Low-risk polycythemia vera treated with phlebotomies: clinical characteristics, hematologic control and complications in 453 patients from the Spanish Registry of Polycythemia Vera", Ann Hematol. Oct. 2022; 101(10): 2231-2239. doi:10.1007/s00277-022-04963-z. Epub Aug. 30, 2022. 9 pages.

\* cited by examiner 3-day dosing of Compound ID#105

3-day dosing of Compound ID#105

CONJUGATED HEPCIDIN MIMETICS

CROSS REFERENCE TO RELATED APPLICATIONS

This application is a continuation of U.S. application Ser. No. 16/964,708, which is a national phase application of International PCT Application No. PCT/US2019/017192, filed Feb. 8, 2019, which claims priority to U.S. Provisional Application No. 62/749,450, filed on Oct. 23, 2018, U.S. Provisional Application No. 62/717,390, filed on Aug. 10, 2018, U.S. Provisional Application No. 62/627,948, filed on Feb. 8, 2018, and U.S. Provisional Application No. 62/627,952, filed on Feb. 8, 2018, each of which is incorporated by reference herein in its entirety.

STATEMENT REGARDING SEQUENCE LISTING

The Sequence Listing XML associated with this application is provided in XML file format and is hereby incorporated by reference into the specification. The name of the XML file containing the Sequence Listing XML is PRTH_031_04 US_ST26.xml. The XML file is 593,783 bytes, and created on Aug. 7, 2023, and is being submitted electronically via USPTO Patent Center.

FIELD OF THE INVENTION

The present invention relates, inter alia, to certain hepcidin peptide analogues, including both peptide monomers and peptide dimers, and conjugates and derivatives thereof, as well as compositions comprising the peptide analogues, and to the use of the peptide analogues in the treatment and/or prevention of a variety of diseases, conditions or disorders, including treatment and/or prevention of iron overload diseases such as hereditary hemochromatosis, iron-loading anemias, and other conditions and disorders described herein.

BACKGROUND

Hepcidin (also referred to as LEAP-1), a peptide hormone produced by the liver, is a regulator of iron homeostasis in humans and other mammals. Hepcidin acts by binding to its receptor, the iron export channel ferroportin, causing its internalization and degradation. Human hepcidin is a 25-amino acid peptide (Hep25). See Krause et al. (2000) FEBS Lett 480:147-150, and Park et al. (2001) J Biol Chem 276:7806-7810. The structure of the bioactive 25-amino acid form of hepcidin is a simple hairpin with 8 cysteines that form 4 disulfide bonds as described by Jordan et al. J Biol Chem 284:24155-67. The N terminal region is required for iron-regulatory function, and deletion of 5 N-terminal amino acid residues results in a loss of iron-regulatory function. See Nemeth et al. (2006) Blood 107:328-33.

Abnormal hepcidin activity is associated with iron overload diseases, including hereditary hemochromatosis (HH) and iron-loading anemias. Hereditary hemochromatosis is a genetic iron overload disease that is mainly caused by hepcidin deficiency or in some cases by hepcidin resistance. This allows excessive absorption of iron from the diet and development of iron overload. Clinical manifestations of HH may include liver disease (e.g., hepatic cirrhosis and hepatocellular carcinoma), diabetes, and heart failure. Currently, the only treatment for HH is regular phlebotomy, which is very burdensome for the patients. Iron-loading anemias are hereditary anemias with ineffective erythropoiesis such as β-thalassemia, which are accompanied by severe iron overload. Complications from iron overload are the main cause of morbidity and mortality for these patients. Hepcidin deficiency is the main cause of iron overload in non-transfused patients, and contributes to iron overload in transfused patients. The current treatment for iron overload in these patients is iron chelation which is very burdensome, sometimes ineffective, and accompanied by frequent side effects.

Hepcidin has a number of limitations that restrict its use as a drug, including a difficult synthesis process due in part to aggregation and precipitation of the protein during folding, which in turn leads to high cost of goods. What are needed in the art are compounds having hepcidin activity and also possessing other beneficial physical properties such as improved solubility, stability, and/or potency, so that hepcidin-like biologics might be produced affordably and used to treat hepcidin-related diseases and disorders such as, e.g., those described herein.

The present invention addresses such needs, providing novel peptide analogues, including both peptide monomer analogues and peptide dimer analogues, having hepcidin activity and also having other beneficial properties making the peptides of the present invention suitable alternatives to hepcidin.

BRIEF SUMMARY OF THE INVENTION

The present invention generally relates to peptide analogues, including both monomer and dimers, exhibiting hepcidin activity and methods of using the same.

In one aspect, the present invention includes a hepcidin analogue comprising a peptide of Formula (I):

(I)
(SEQ ID NO: 259)
$R^1$-Asp-Thr-His-B1-B2-B3-B4-Xaa1-B6-Xaa2-J-Y1-Y2-$R^2$ or a peptide dimer comprising two peptides according to Formula I, or a pharmaceutically acceptable salt, or a solvate thereof, wherein:
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
Xaa1 is B5; and
  i) B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys:
or
  ii) Xaa1 is B5(L1Z); B5 is Lys, D-Lys, Orn, homoSer, Gln, Lys(Ac), Ile, Abu, Leu, or Nleu; and Xaa2 is B7; and B7 is Glu or absent:
each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me); or
  iii) substituted Phe, substituted bhPhe, or substituted Trp, or substituted bhTrp:
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B7 is Dapa, Lys, D-Lys, homoLys, or a-Me-Lys;

L1 is absent, Dapa, D-Dapa, or isoGlu, PEG, Ahx, isoGlu-PEG, PEG-Ahx, isoGlu-Ahx, or isoGlu-PEG-Ahx; Ahx is an aminohexanoic acid moiety;

Z is a half-life extension moiety;

J is Pro, -Pro-Arg-, -Pro-Lys-, -Pro-(D)Lys-, -Pro-Arg-Ser-, -Pro-Arg-Ser-Lys- (SEQ ID NO:249), -Pro-Arg-Ser-Lys-Sar- (SEQ ID NO:250), -Pro-Arg-Ser-Lys-Gly- (SEQ ID NO:251), or absent; or J is any amino acid;

Y1 is Cys, homoCys, (D)Cys, NMeCys, aMeCys, or Pen: Y2 is an amino acid or absent;

Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homo Tryptophane, 1-Nal is 1-naphthylalanine, 2-Nal is 2-naphthylalanine, Orn is orinithine, Nleu is norleucine, Abu is 2-aminobutyric acid;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;

wherein
  i) the peptide of formula I is optionally PEGylated on one or more $R^1$, B1, B2, B3, B4, B5, B6, B7, J, Y1, Y2, or R2; and
  ii) the peptide is cyclized via a disulfide bond between B3 and Y1.

In one embodiment, the half-life extension moiety is $C_{10}$-$C_{21}$ alkanoyl.

In one embodiment, Xaa1 is B5; B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys; and L1 is attached to $N^\varepsilon$ of Lys, D-Lys, homoLys, or a-Me-Lys; or $N^\beta$ of Dapa.

In another embodiment, Xaa1 is B5(L1Z); B5 is Lys, or D-Lys; and Xaa2 is B7; and B7 is Glu or absent; and L1 is attached to $N^\varepsilon$ of Lys.

In another aspect, the present invention includes a hepcidin analogue comprising a peptide of Formula (A-I):

(A-I)
(SEQ ID NO: 260)
$R^1$-Asp-Thr-His-B1-B2-B3-B4-B5-B6-B7(L1Z)-J-Y1-Y2-$R^2$ or a peptide dimer comprising two peptides according to Formula A-I, or a pharmaceutically acceptable salt, or a solvate thereof, wherein:

$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;

$R^2$ is —$NH_2$ or —OH;

each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me);
  iii) when B6 is Phe, then B5 is other than Lys; or
  iii) substituted Phe, substituted bhPhe, substituted Trp, or substituted bhTrp:

B2 is Pro, D-Pro, bhPro, D-bhPro, NPC, or D-NPC;

B3 is Cys, homoCys, (D)Cys, a-MeCys, or Pen;

B4 is Ile, Val, Leu, or NLeu;

B5 is absent, Lys, D-Lys, Orn, homoSer, Gln, (D)Gln, Lys(Ac), Ile, Abu, Leu, Ala, D-Ala, bAla, or Nleu;

B7 is a lower or a higher homolog of Lys, a-MeLys, D-Lys, or Dapa; and wherein L1 is attached to $N^\varepsilon$ of Lys, D-Lys, homoLys, or a-Me-Lys; or $N^\beta$ of Dapa;

L1 is absent or isoGlu, PEG, Ahx, isoGlu-PEG, PEG-Ahx, isoGlu-Ahx, or isoGlu-PEG-Ahx;

Ahx is an aminohexanoic acid moiety;

Z is a half-life extension moiety;

J is Pro, -Pro-Arg-, -Pro-Lys-, -Pro-(D)Lys-, -Pro-Arg-Ser-, -Pro-Arg-Ser-Lys- (SEQ ID NO:249), -Pro-Arg-Ser-Lys-Sar- (SEQ ID NO:250), -Pro-Arg-Ser-Lys-Gly- (SEQ ID NO:251), or absent; or J is any amino acid;

Y1 is Cys, homoCys, NMeCys, aMeCys, or Pen: Y2 is an amino acid or absent;

Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homoTryptophane, 1-Nal is 1-naphthylalanine, 2-Nal is 2-naphthylalanine, Or is orinithine, Nleu is norleucine, Abu is 2-aminobutyric acid;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;

wherein
  i) the peptide of formula I is optionally PEGylated on one or more $R^1$, B1, B2, B3, B4, B5, B6, J, Y1, Y2, or R2;
  ii) the peptide is cyclized via a disulfide bond between B3 and Y1:
  iii) when the peptide is a peptide dimer, then B7(L1Z)-J-Y1-Y2 is absent;
  iv) when the peptide is a peptide dimer, the peptide dimer is dimerized
    a) via a linker moiety,
    b) via an intermolecular disulfide bond between two B3 residues, one in each monomer subunit, or
    c) via both a linker moiety and an intermolecular disulfide bond between two B3 residues; and d) the linker moiety comprises a half-life extending moiety.

In one embodiment, the half-life extension moiety is $C_{10}$-$C_{21}$ alkanoyl.

In another aspect, the present invention includes a hepcidin analogue comprising a peptide of Formula (B-I):

(B-I) (SEQ ID NO: 261)
$R^1$-Asp-Thr-His-B1-B2-B3-B4-B5(L1Z)-B6-B7-J-Y1-Y2-$R^2$ or a peptide dimer comprising two peptides according to Formula B-I, or a pharmaceutically acceptable salt, or a solvate thereof,
wherein:
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me); or
  iii) substituted Phe, substituted bhPhe, or substituted Trp, or substituted bhTrp:
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B5 is Lys, D-Lys, Orn, homoSer, Gln, Lys(Ac), Ile, Abu, Leu, or Nleu;
B7 is Glu or absent;
L1 is absent or isoGlu, PEG, Ahx, isoGlu-PEG, PEG-Ahx, isoGlu-Ahx, or isoGlu-PEG-Ahx;
Ahx is an aminohexanoic acid moiety;
Z is a half-life extension moiety;
J is Pro, Arg, Gly, -Pro-Arg-, -Pro-Arg-Ser-, -Pro-Arg-Ser-Lys- (SEQ ID NO:249), -Pro-Arg-Ser-Lys-Sar- (SEQ ID NO:250), -Pro-Arg-Ser-Lys-Gly-(SEQ ID NO:251), or absent; or J is any amino acid;
Y1 is Cys, homoCys or Pen;
Y2 is an amino acid or absent;
the half-life extension moiety is $C_{10}$-$C_{21}$ alkanoyl;
Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydroisoquinoline-3-carboxylic acid, Npc is L-nipecotic acid, bhomoTrp is L-b-homotryptophan, 1-Nal is 1-naphthylalanine, 2-Nal is 2-naphthylalanine, Or is ornithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted b-hTrp is N-methyl-L-b-homotryptophan, a-methyl-b-homotryptophan, or b-homotryptophan substituted with F, Cl, OH, or t-Bu;

wherein
  i) the peptide of formula I is optionally PEGylated on one or more $R^1$, B1, B2, B3, B4, B6, B7, J, Y1, Y2, or R2; and
  ii) the peptide is cyclized via a disulfide bond between B3 and Y1; and
  iii) when B6 is Phe, Y1 is Cys, and Y2 is Lys, then J is Pro, Arg, Gly, -Pro-Arg-, -Pro-Lys-, -Pro-(D)Lys-, -Pro-Arg-Ser-, -Pro-Arg-Ser-Lys-(SEQ ID NO:249), or absent.

In particular embodiments of hepcidin analogues disclosed herein, the half-life extending moiety is $C_{10}$-$C_{21}$ alkanoyl.

In one particular embodiment, B7 is Lys, D-Lys, homo-Lys, or a-Me-Lys.

In particular embodiments of any of the hepcidin analogues or dimers of the present invention, the linker moiety is selected from IsoGlu, Dapa, PEGn where n=1 to 25, PEG11(40 atoms), OEG, IsoGlu-Ahx, IsoGlu-OEG-OEG, IsoGlu-PEG5, IsoGlu-PEGn where n=1 to 25 βAla-PEG2, and BAla-PEG11(40 atoms). In certain embodiments, more than one linker moiety is conjugated to a peptide of the hepcidin analogue or dimer.

In another aspect, the present invention includes a hepcidin analogue comprising a peptide dimer of Formula (A-II):

A-II (SEQ ID NO: 262)

$R^1$-Asp-Thr-His-B1—B2—B3—B4—B5—B6
                                          \
                                           B8B9(L1Z)—$R^2$
                                          /
$R^1$-Asp-Thr-His-B1—B2—B3—B4—B5—B6 wherein each B8 and B9 is independently Lys, D-Lys, homoLys, or a-Me-Lys; and L1, Z, and R2 are as described for Formula (A-I); and wherein one of the B6s is attached to $N^\varepsilon$ of B8.

In one particular embodiment, B8 is Lys. In another particular embodiment, B8 is D-Lys.

In one particular embodiment, B9 is Lys.

In another aspect, the present invention includes a hepcidin analogue comprising a peptide dimer of Formula (A-III):

A-III (SEQ ID NO: 263)

$R^1$-Asp-Thr-His-B1—B2—B3—B4—B5—B6—$R^2$
                                          \
                                           IDA(B10Z)
                                          /
$R^1$-Asp-Thr-His-B1—B2—B3—B4—B5—B6—$R^2$ wherein B1, B2, B3, B4, B5, B6, $R^1$, and $R^2$ are as described for Formula (A-I); B10 is a natural or unnatural amino acid; and Z is a half-life extending moiety.

In a particular embodiment, B10 is b-Ala.

In one embodiment, B5 is Lys. In another embodiment, B7 is Lys.

In one embodiment, B5 is D-Lys. In another embodiment, B7 is D-Lys.

In certain embodiments, a hepcidin analogue comprises or consists of a peptide according to the following structure:

Formula Ia (SEQ ID NO: 330)

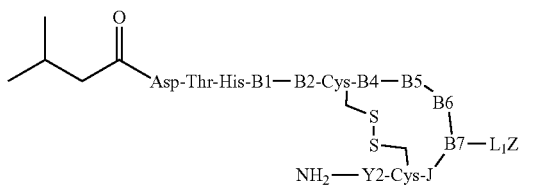

wherein L1, J, Y2, Z, and B1-B7 are as described for Formula (A-I).

In particular embodiments of any of the hepcidin analogues or dimers of the present invention, the half-life extension moiety is selected from C12 (Lauric acid), C14 (Mysteric acid), C16(Palmitic acid), C18 (Stearic acid), C20, C12 diacid, C14 diacid, C16 diacid, C18 diacid, C20 diacid, biotin, and isovaleric acid. In certain embodiments, the half-life extension moiety is attached to a linker moiety that is attached to the peptide. In certain embodiments, the half-life extension moiety increases the molecular weight of the hepcidin analogue by about 50 D to about 2 KD. In various embodiments, the half-life extension moiety increases serum half-life, enhances solubility, and/or improves bioavailability of the hepcidin analogue.

In certain embodiments, a peptide analogue or dimer of the present invention comprises an isovaleric acid moiety conjugated to an N-terminal Asp residue.

In certain embodiments, a peptide analogue of the present invention comprises an amidated C-terminal residue.

In certain embodiments, the present invention provides hepcidin analogues, including any hepcidin analogue or peptide disclosed herein or comprising or consisting of a sequence or structure disclosed herein, including but not limited to wherein the hepcidin analogue or peptide comprises a disulfide bond between two Cys residues.

In certain embodiments, a hepcidin analogue or dimer of the present invention comprises the sequence: Asp-Thr-His-Phe-Pro-Cys-Ile-Lys-Phe-Glu-Pro-Arg-Ser-Lys-Gly-Cys-Lys (SEQ ID NO:252), or comprises a sequence having at least 80%, at least 90%, or at least 94% identity to this sequence.

In certain embodiments, a hepcidin analogue or dimer of the present invention comprises the sequence: Asp-Thr-His-Phe-Pro-Cys-Ile-Lys-Phe-Lys-Pro-Arg-Ser-Lys-Gly-Cys-Lys (SEQ ID NO:1), or comprises a sequence having at least 80%, at least 90%, or at least 94% identity to this sequence.

In a related embodiment, the present invention includes a polynucleotide that encodes a peptide of a hepcidin analogue or dimer (or monomer subunit of a dimer) of the present invention.

In a further related embodiment, the present invention includes a vector comprising a polynucleotide of the invention. In particular embodiments, the vector is an expression vector comprising a promoter operably linked to the polynucleotide, e.g., in a manner that promotes expression of the polynucleotide.

In another embodiment, the present invention includes a pharmaceutical composition, comprising a hepcidin analogue, dimer, polynucleotide, or vector of the present invention, and a pharmaceutically acceptable carrier, excipient or vehicle.

In another embodiments, the present invention provides a method of binding a ferroportin or inducing ferroportin internalization and degradation, comprising contacting the ferroportin with at least one hepcidin analogue, dimer or composition of the present invention.

In a further embodiment, the present invention includes a method for treating a disease of iron metabolism in a subject in need thereof comprising providing to the subject an effective amount of a pharmaceutical composition of the present invention. In certain embodiments, the pharmaceutical composition is provided to the subject by an oral, intravenous, peritoneal, intradermal, subcutaneous, intramuscular, intrathecal, inhalation, vaporization, nebulization, sublingual, buccal, parenteral, rectal, vaginal, or topical route of administration. In certain embodiments, the pharmaceutical composition is provided to the subject by an oral or subcutaneous route of administration. In certain embodiments, the disease of iron metabolism is an iron overload disease. In certain embodiments, the pharmaceutical composition is provided to the subject at most or about twice daily, at most or about once daily, at most or about once every two days, at most or about once a week, or at most or about once a month.

In particular embodiments, the hepcidin analogue is provided to the subject at a dosage of about 1 mg to about 100 mg or about 1 mg to about 5 mg.

In another embodiment, the present invention provides a device comprising pharmaceutical composition of the present invention, for delivery of a hepcidin analogue or dimer of the invention to a subject, optionally orally or subcutaneously.

In yet another embodiment, the present invention includes a kit comprising a pharmaceutical composition of the invention, packaged with a reagent, a device, or an instructional material, or a combination thereof.

DETAILED DESCRIPTION OF THE INVENTION

Figure 1A:
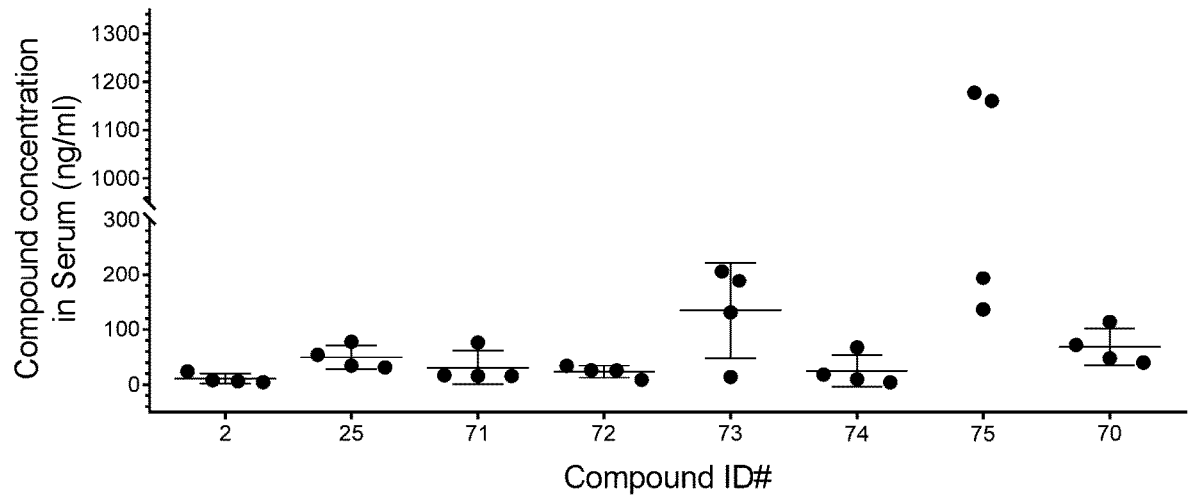
FIGS. 1A and 1B show the reduction of serum iron concentration after dosing of compounds ID 2, 25, 71, 72, 73, 74, 75, and 70 in mice.

The present invention relates generally to hepcidin analogue peptides and methods of making and using the same. In certain embodiments, the hepcidin analogues exhibit one or more hepcidin activity. In certain embodiments, the present invention relates to hepcidin peptide analogues comprising one or more peptide subunit that forms a cyclized structures through an intramolecular bond, e.g., an intramolecular disulfide bond. In particular embodiments, the cyclized structure has increased potency and selectivity as compared to non-cyclized hepcidin peptides and analogies thereof. In particular embodiments, hepcidin analogue peptides of the present invention exhibit increased half-lives, e.g., when delivered orally, as compared to hepcidin or previous hepcidin analogues.

Definitions and Nomenclature

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein, the following terms have the meanings ascribed to them unless specified otherwise.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats). The term "mammal" refers to any mammalian species such as a human, mouse, rat, dog, cat, hamster, guinea pig, rabbit, livestock, and the like.

The term "peptide," as used herein, refers broadly to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring.

The term "peptide analogue" or "hepcidin anloguuue" as used herein, refers broadly to peptide monomers and peptide dimers comprising one or more structural features and/or functional activities in common with hepcidin, or a functional region thereof. In certain embodiments, a peptide analogue includes peptides sharing substantial amino acid sequence identity with hepcidin, e.g., peptides that comprise one or more amino acid insertions, deletions, or substitutions as compared to a wild-type hepcidin, e.g., human hepcidin, amino acid sequence. In certain embodiments, a peptide analogue comprises one or more additional modification, such as, e.g., conjugation to another compound. Encompassed by the term "peptide analogue" is any peptide monomer or peptide dimer of the present invention. In certain instances, a "peptide analog" may also or alternatively be referred to herein as a "hepcidin analogue," "hepcidin peptide analogue," or a "hepcidin analogue peptide."

The recitations "sequence identity", "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250) matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997).

When utilizing BLAST and Gapped BLAST programs, the default parameters of the respective programs (e.g., XBLAST and NBLAST) can be used.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. In some embodiments of the invention, one or more Met residues are substituted with norleucine (Nle) which is a bioisostere for Met, but which, as opposed to Met, is not readily oxidized. In some embodiments, one or more Trp residues are substituted with Phe, or one or more Phe residues are substituted with Trp, while in some embodiments, one or more Pro residues are substituted with Npc, or one or more Npc residues are substituted with Pro. Another example of a conservative substitution with a residue normally not found in endogenous, mammalian peptides and proteins is the conservative substitution of Arg or Lys with, for example, ornithine, canavanine, aminoethylcysteine or another basic amino acid. In some embodiments, another conservative substitution is the substitution of one or more Pro residues with bhPro or Leu or D-Npc (isonipecotic acid). For further information concerning phenotypically silent substitutions in peptides and proteins, see, for example, Bowie et. al. Science 247, 1306-1310, 1990. In the scheme below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|----|-----|----|---|
| A | N | H | M | F |
| S | D | R | L | Y |
| T | E | K | I | W |
| P | Q |   | V |   |
| G |   |   | C |   |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|----|-----|------|----|---|
| A | E | H | M | F |
| L | D | R | S | Y |
| I |   | K | T | W |
| P |   |   | C |   |
| G |   |   | N |   |
| V |   |   | Q |   |

The term "amino acid" or "any amino acid" as used here refers to any and all amino acids, including naturally occurring amino acids (e.g., a-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid.

As is clear to the skilled artisan, the peptide sequences disclosed herein are shown proceeding from left to right, with the left end of the sequence being the N-terminus of the peptide and the right end of the sequence being the C-terminus of the peptide. Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom, corresponding to the presence of a free primary or secondary amino group at the N-terminus, while an "—OH" or an "—NH$_2$" moiety at the C-terminus of the sequence indicates a hydroxy group or an amino group, corresponding to the presence of an amido (CONH$_2$) group at the C-terminus, respectively. In each sequence of the invention, a C-terminal "—OH" moiety may be substituted for a C-terminal "—NH$_2$" moiety, and vice-versa. It is further understood that the moiety at the amino terminus or carboxy terminus may be a bond, e.g., a covalent bond, particularly in situations where the amino terminus or carboxy terminus is bound to a linker or to another chemical moiety, e.g., a PEG moiety.

The term "NH$_2$," as used herein, refers to the free amino group present at the amino terminus of a polypeptide. The term "OH," as used herein, refers to the free carboxy group present at the carboxy terminus of a peptide. Further, the term "Ac," as used herein, refers to Acetyl protection through acylation of the C- or N-terminus of a polypeptide.

The term "carboxy," as used herein, refers to —CO$_2$H.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Abbreviations of Non-Natural Amino Acids and Chemical Moieties

| Abbreviation | Definition |
|---|---|
| bh, b-h, bhomo, or b-homo | β-homo |
| DIG | Diglycolic acid |
| Dapa or Dap | Diaminopropionic acid |
| Daba or Dab | Diaminobutyric acid |
| Pen | Penicillamine |
| Sarc or Sar | Sarcosine |
| Cit | Citroline |
| Cav | Cavanine |
| NMe-Arg | N-Methyl-Arginine |
| NMe-Trp | N-Methyl-Tryptophan |
| NMe-Phe | N-Methyl-Phenylalanine |
| Ac- | Acetyl |
| 2-Nal | 2-Napthylalanine |
| 1-Nal | 1-Napthylalanine |
| Bip | Biphenylalanine |
| βAla or bAla | beta-Alanine |
| Aib | 2-aminoisobutyric acid |
| Azt | azetidine-2-carboxylic acid |
| Tic | L-1,2,3,4-Tetrahydroisoquinoline-3-carboxylic acid |
| Phe(OMe) or Tyr(Me) | Tyrosine (4-Methyl) |
| N-MeLys | N-Methyl-Lysine |
| Dpa or DIP | β,β-diphenylalanine |
| $NH_2$ | Free Amine |
| $CONH_2$ | Amide |
| COOH | Acid |
| Phe(4-F) | 4-Fluoro-Phenylalanine |
| PEG3 | $NH_2CH_2CH_2(OCH_2CH_2)_3CH_2CH_2CO_2H$ |
| m-PEG3 | $CH_3OCH_2CH_2(OCH_2CH_2)_2CH_2CH_2CO_2H$ |
| m-PEG4 | $CH_3OCH_2CH_2(OCH_2CH_2)_3CH_2CH_2CO_2H$ |
| m-PEG8 | $CH_3OCH_2CH_2(OCH_2CH_2)_7CH_2CH_2CO_2H$ |
| PEG11 | O-(2-aminoethyl)-O'-(2-carboxyethyl)-undecaethyleneglycol $NH_2CH_2CH_2(OCH_2CH_2)_{11}CH_2CH_2CO_2H$ |
| PEG13 | Bifunctional PEG linker with 13 PolyEthylene Glycol units |
| PEG25 | Bifunctional PEG linker with 25 PolyEthylene Glycol units |
| PEG1K | Bifunctional PEG linker with PolyEthylene Glycol Mol wt of 1000Da |
| PEG2K | Bifunctional PEG linker with PolyEthylene Glycol Mol wt of 2000Da |
| PEG3.4K | Bifunctional PEG linker with PolyEthylene Glycol Mol wt of 3400Da |
| PEG5K | Bifunctional PEG linker with PolyEthylene Glycol Mol wt of 5000Da |
| IDA or Ida | Iminodiacetic acid |
| IDA-Palm | (Palmityl)-Iminodiacetic acid |
| hPhe | homoPhenylalanine |
| Ahx | Aminohexanoic acid |
| DIG-OH | Glycolic monoacid |
| Triazine | Amino propyl Triazine di-acid |
| Boc-Triazine | Boc-Triazine di-acid |
| Trifluorobutyric acid | 4,4,4-Trifluorobutyric acid |
| 2-Methyltrifluorobutyric acid | 2-methyl-4,4,4-Butyric acid |
| Trifluorpentanoic acid | 5,5,5-Trifluoropentanoic acid |
| 1,4-Phenylenediacetic acid | para-Phenylenediacetic acid |
| 1,3-Phenylenediacetic acid | meta-Phenylenediacetic acid |
| DTT | Dithiothreotol |
| Nle | Norleucine |
| βhTrp or bhTrp | β-homoTryptophane |
| βhPhe or bhPhe | β-homophenylalanine |
| Phe(4-$CF_3$) | 4-TrifluoromethylPhenylalanine |
| βGlu or bGlu | β-Glutamic acid |
| βhGlu or bhGlu | β-homoglutamic acid |
| 2-2-Indane | 2-Aminoindane-2-carboxylic acid |
| 1-1-Indane | 1-Aminoindane-1-carboxylic acid |
| hCha | homocyclohexylalanine |
| Cyclobutyl | Cyclobutylalanine |
| hLeu | Homoleucine |
| Gla | γ-Carboxy-glutamic acid |
| Aep | 3-(2-aminoethoxy)propanoic acid |
| Aea | (2-aminoethoxy)acetic acid |
| IsoGlu-octanoic acid | octanoyl-γ-Glu |
| K-octanoic acid | octanoyl-ε-Lys |
| Dapa(Palm) | Hexadecanoyl-β-Diaminopropionic acid |
| IsoGlu-Palm | hexadecanoyl-γ-Glu |
| C-StBu | S-tert-butylthio-cysteine |
| C-tBu | S-tert-butyl-cysteine |
| N-MeCys or NMeCys | N-methyl-cysteine |
| a-MeCys, aMeCys, or α-MeCys | α-methyl-cysteine |
| hCys | homo-cysteine |
| Dapa(AcBr) | NY-(bromoacetyl)-2,3-diaminopropionic acid |
| Tle | tert-Leucine |
| Phg | phenylglycine |
| Oic | octahydroindole-2-carboxylic acid |
| Chg | α-cyclohexylglycine |
| GP-(Hyp) | Gly-Pro-HydroxyPro |
| Inp | isonipecotic acid |
| Amc | 4-(aminomethyl)cyclohexane carboxylic acid |
| Betaine | $(CH_3)_3NCH_2CH_2CO_2H$ |
| D-Npc or D-NPC | Isonipecotic acid |
| Npc or NPC | Nipecotic acid |
| (D)Lys, D-Lys, k, or dK | D-Lysine |
| Orn | Orinithine |
| Homoserine | homoserine |
| Nleu or Nle | Norleucine |
| bhPro | b-homoproline |

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). In the case of less common or non-naturally occurring amino acids, unless they are referred to by their full name (e.g., sarcosine, ornithine, etc.), frequently employed three- or four-character codes are employed for residues thereof, including, Sar or Sarc (sarcosine, i.e. N-methylglycine), Aib (α-aminoisobutyric acid), Daba (2,4-diaminobutanoic acid), Dapa (2,3-diaminopropanoic acid), γ-Glu (γ-glutamic acid), pGlu (pyroglutamic acid), Gaba (γ-aminobutanoic acid), β-Pro (pyrrolidine-3-carboxylic acid), 8Ado (8-amino-3,6-dioxaoctanoic acid), Abu (4-aminobutyric acid), bhPro (β-homo-proline), bhPhe (β-homo-L-phenylalanine), bhAsp (β-homo-aspartic acid]), Dpa (β;β diphenylalanine), Ida (Iminodiacetic acid), hCys (homocysteine), bhDpa (β-homo-β,β-diphenylalanine).

Furthermore, $R^1$ can in all sequences be substituted with isovaleric acid or equivalent. In some embodiments, wherein a peptide of the present invention is conjugated to an acidic compound such as, e.g., isovaleric acid, isobutyric acid, valeric acid, and the like, the presence of such a conjugation is referenced in the acid form. So, for example, but not to be limited in any way, instead of indicating a conjugation of isovaleric acid to a peptide by referencing isovaleroyl, in some embodiments, the present application may reference such a conjugation as isovaleric acid.

The term "L-amino acid," as used herein, refers to the "L" isomeric form of a peptide, and conversely the term "D-amino acid" refers to the "D" isomeric form of a peptide. In certain embodiments, the amino acid residues described herein are in the "L" isomeric form, however, residues in the "D" isomeric form can be substituted for any L-amino acid residue, as long as the desired functional is retained by the peptide.

Unless otherwise indicated, reference is made to the L-isomeric forms of the natural and unnatural amino acids in question possessing a chiral center. Where appropriate, the D-isomeric form of an amino acid is indicated in the conventional manner by the prefix "D" before the conventional three-letter code (e.g. Dasp, (D)Asp or D-Asp: Dphe, (D)Phe or D-Phe).

As used herein, a "lower homolog of Lys" refers to an amino acid having the structure of Lysine but with one or more fewer carbons in its side chain as compared to Lysine.

As used herein, a "higher homolog of Lys" refers to an amino acid having the structure of Lysine but with one or more additional carbon atoms in its side chain as compared to Lysine.

The term "DRP," as used herein, refers to disulfide rich peptides.

The term "dimer," as used herein, refers broadly to a peptide comprising two or more monomer subunits. Certain dimers comprise two DRPs. Dimers of the present invention include homodimers and heterodimers. A monomer subunit of a dimer may be linked at its C- or N-terminus, or it may be linked via internal amino acid residues. Each monomer subunit of a dimer may be linked through the same site, or each may be linked through a different site (e.g., C-terminus, N-terminus, or internal site).

The term "isostere replacement" or "isostere substitution" are used interchangeably herein to refer to any amino acid or other analog moiety having chemical and/or structural properties similar to a specified amino acid. In certain embodiments, an isostere replacement is a conservative substitution with a natural or unnatural amino acid.

The term "cyclized," as used herein, refers to a reaction in which one part of a polypeptide molecule becomes linked to another part of the polypeptide molecule to form a closed ring, such as by forming a disulfide bridge or other similar bond.

The term "subunit," as used herein, refers to one of a pair of polypeptide monomers that are joined to form a dimer peptide composition.

The term "linker moiety," as used herein, refers broadly to a chemical structure that is capable of linking or joining together two peptide monomer subunits to form a dimer.

The term "solvate" in the context of the present invention refers to a complex of defined stoichiometry formed between a solute (e.g., a hepcidin analogue or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

As used herein, a "disease of iron metabolism" includes diseases where aberrant iron metabolism directly causes the disease, or where iron blood levels are dysregulated causing disease, or where iron dysregulation is a consequence of another disease, or where diseases can be treated by modulating iron levels, and the like. More specifically, a disease of iron metabolism according to this disclosure includes iron overload diseases, iron deficiency disorders, disorders of iron biodistribution, other disorders of iron metabolism and other disorders potentially related to iron metabolism, etc. Diseases of iron metabolism include hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, sickle cell disease, polycythemia vera (primary and secondary), myelodysplasia, pyruvate kinase deficiency, iron-deficiency anemia, iron-refractory iron deficiency anemia, anemia of chronic kidney disease, erythropoietin resistance, iron deficiency of obesity, other anemias, benign or malignant tumors that overproduce hepcidin or induce its overproduction, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease.

In some embodiments, the disease and disorders are related to iron overload diseases such as iron hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia, sickle cell disease, polycythemia vera (primary and secondary), mylodysplasia, and pyruvate kinase deficiency.

In some embodiments, the hepcidin analogues of the invention are used to treat diseases and disorders that are not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, peptides of the invention may be used to treat these diseases and conditions. Those skilled in the art are readily able to determine whether a given disease can be treated with a peptide according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In certain embodiments of the present invention, the diseases of iron metabolism are iron overload diseases, which include hereditary hemochromatosis, iron-loading anemias, alcoholic liver diseases and chronic hepatitis C.

The term "pharmaceutically acceptable salt." as used herein, represents salts or zwitterionic forms of the peptides or compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see *Handbook of Pharmaceutical Salts: Properties. Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts.

The term "N(alpha)Methylation", as used herein, describes the methylation of the alpha amine of an amino acid, also generally termed as an N-methylation.

The term "sym methylation" or "Arg-Me-sym", as used herein, describes the symmetrical methylation of the two nitrogens of the guanidine group of arginine. Further, the term "asym methylation" or "Arg-Me-asym" describes the methylation of a single nitrogen of the guanidine group of arginine.

The term "acylating organic compounds", as used herein refers to various compounds with carboxylic acid functionality that are used to acylate the N-terminus of an amino acid subunit prior to forming a C-terminal dimer. Non-limiting examples of acylating organic compounds include cyclopropylacetic acid, 4-Fluorobenzoic acid, 4-fluorophenylacetic acid, 3-Phenylpropionic acid, Succinic acid, Glutaric acid, Cyclopentane carboxylic acid, 3,3,3-trifluoropropeonic acid, 3-Fluoromethylbutyric acid, Tetrahedro-2H-Pyran-4-carboxylic acid.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

As used herein, a "therapeutically effective amount" of the peptide agonists of the invention is meant to describe a sufficient amount of the peptide agonist to treat an hepcidin-related disease, including but not limited to any of the diseases and disorders described herein (for example, a disease of iron metabolism). In particular embodiments, the therapeutically effective amount will achieve a desired benefit/risk ratio applicable to any medical treatment.

Peptide Analogues of Hepcidin

The present invention provides peptide analogues of hepcidin, which may be monomers or dimers (collectively "hepcidin analogues").

In some embodiments, a hepcidin analogue of the present invention binds ferroportin, e.g., human ferroportin. In certain embodiments, hepcidin analogues of the present invention specifically bind human ferroportin. As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art. In some embodiments, a hepcidin analogue of the present invention binds ferroportin with greater specificity than a hepcidin reference compound (e.g., any one of the hepcidin reference compounds provided herein). In some embodiments, a hepcidin analogue of the present invention exhibits ferroportin specificity that is at least about 10%, 20%, 30%, 40%, 50%, 60%, 70%, 80%, 90%, 100%, 200%, 300%, 400%, 500%, 700%, 1000%, or 10,000% higher than a hepcidin reference compound (e.g., any one of the hepcidin reference compounds provided herein. In some embodiments, a hepcidin analogue of the present invention exhibits ferroportin specificity that is at least about 5 fold, or at least about 10, 20, 50, or 100 fold higher than a hepcidin reference compound (e.g., any one of the hepcidin reference compounds provided herein.

In certain embodiments, a hepcidin analogue of the present invention exhibits a hepcidin activity. In some embodiments, the activity is an in vitro or an in vivo activity, e.g., an in vivo or an in vitro activity described herein. In some embodiments, a hepcidin analogue of the present invention exhibits at least about 50%, 60%, 70%, 80%, 90%, 95%, 97%, 98%, 99%, or greater than 99% of the activity exhibited by a hepcidin reference compound (e.g., any one of the hepcidin reference compounds provided herein.

In some embodiments, a hepcidin analogue of the present invention exhibits at least about 50%, 60%, 70%, 80%, 90%, 95%, 97%, 98%, 99%, or greater than 99% of the ferroportin binding ability that is exhibited by a hepcidin reference compound. In some embodiments, a hepcidin analogue of the present invention has a lower $IC_{50}$ (i.e., higher binding affinity) for binding to ferroportin, (e.g., human ferroportin) compared to a hepcidin reference compound. In some embodiments, a hepcidin analogue the present invention has an $IC_{50}$ in a ferroportin competitive binding assay which is at least about 10%, 20%, 30%, 40%, 50%, 60%, 70%, 80%, 90%, 100%, 200%, 300%, 400%, 500%, 700%, or 1000% lower than a hepcidin reference compound.

In certain embodiments, a hepcidin analogue of the present invention exhibits increased hepcidin activity as compared to a hepcidin reference compound. In some embodiments, the activity is an in vitro or an in vivo activity, e.g., an in vivo or an in vitro activity described herein. In certain embodiments, the hepcidin analogue of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater hepcidin activity than a hepcidin reference compound. In certain embodiments, the hepcidin analogue of the present invention exhibits at least about 10%, 20%, 30%, 40%, 50%, 60%, 70%, 80%, 90%, 95%, 97%, 98%, 99% or greater than 99%, 100%, 200% 300%, 400%, 500%, 700%, or 1000% greater activity than a hepcidin reference compound.

In some embodiments, a peptide analogue of the present invention exhibits at least about 50%, 60%, 70%, 80%, 90%, 95%, 97%, 98%, 99%, or greater than 99%, 100%, 200% 300%, 400%, 500%, 700%, or 1000% greater in vitro activity for inducing the degradation of human ferroportin protein as that of a hepcidin reference compound, wherein the activity is measured according to a method described herein.

In some embodiments, a peptide or a peptide dimer of the present invention exhibits at least about 50%, 60%, 70%, 80%, 90%, 95%, 97%, 98%, 99%, or greater than 99%, 100%, 200% 300%, 400%, 500%, 700%, or 1000% greater in vivo activity for inducing the reduction of free plasma iron in an individual as does a hepcidin reference compound, wherein the activity is measured according to a method described herein.

In some embodiments, the activity is an in vitro or an in vivo activity, e.g., an in vivo or an in vitro activity described herein. In certain embodiments, a hepcidin analogue of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, 500%, 700%, or 1000% greater activity than a hepcidin reference compound, wherein the activity is an in vitro activity for inducing the degradation of ferroportin, e.g., as measured according to the Examples herein; or wherein the activity is an in vivo activity for reducing free plasma iron, e.g., as measured according to the Examples herein.

In some embodiments, the hepcidin analogues of the present invention mimic the hepcidin activity of Hep25, the bioactive human 25-amino acid form, are herein referred to as "mini-hepcidins". As used herein, in certain embodiments, a compound (e.g., a hepcidin analogue) having a "hepcidin activity" means that the compound has the ability to lower plasma iron concentrations in subjects (e.g. mice or humans), when administered thereto (e.g. parenterally injected or orally administered), in a dose-dependent and time-dependent manner. See e.g. as demonstrated in Rivera et al. (2005), Blood 106:2196-9. In some embodiments, the peptides of the present invention lower the plasma iron concentration in a subject by at least about 1.2, 1.5, 2, 3, 4, 5, 6, 7, 8, 9, or 10-fold, or at least about 5%, 10%, 20%, 25%, 30%, 40%, 50%, 60%, 70%, 80%, 90%, or about 99%.

In some embodiments, the hepcidin analogues of the present invention have in vitro activity as assayed by the ability to cause the internalization and degradation of ferroportin in a ferroportin-expressing cell line as taught in Nemeth et al. (2006) Blood 107:328-33. In some embodiments, in vitro activity is measured by the dose-dependent loss of fluorescence of cells engineered to display ferroportin fused to green fluorescent protein as in Nemeth et al. (2006) Blood 107:328-33. Aliquots of cells are incubated for 24 hours with graded concentrations of a reference preparation of Hep25 or a mini-hepcidin. As provided herein, the $EC_{50}$ values are provided as the concentration of a given compound (e.g. a hepcidin analogue peptide or peptide dimer of the present invention) that elicits 50% of the maximal loss of fluorescence generated by a reference compound. The $EC_{50}$ of the Hep25 preparations in this assay range from 5 to 15 nM and in certain embodiments, preferred hepcidin analogues of the present invention have $EC_{50}$ values in in vitro activity assays of about 1,000 nM or less. In certain embodiments, a hepcidin analogue of the present invention has an $EC_{50}$ in an in vitro activity assay (e.g., as described in Nemeth et al. (2006) Blood 107:328-33 or the Example herein) of less than about any one of 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, a hepcidin analogue or biotherapeutic composition (e.g., any one of the pharmaceutical compositions described herein) has an $EC_{50}$ value of about 1 nM or less.

Other methods known in the art for calculating the hepcidin activity and in vitro activity of the hepcidin analogues according to the present invention may be used. For example, in certain embodiments, the in vitro activity of the hepcidin analogues or the reference peptides is measured by their ability to internalize cellular ferroportin, which is determined by immunohistochemistry or flow cytometry using antibodies which recognizes extracellular epitopes of ferroportin. Alternatively, in certain embodiments, the in vitro activity of the hepcidin analogues or the reference peptides is measured by their dose-dependent ability to inhibit the efflux of iron from ferroportin-expressing cells that are preloaded with radioisotopes or stable isotopes of iron, as in Nemeth et al. (2006) Blood 107:328-33.

In some embodiments, the hepcidin analogues of the present invention exhibit increased stability (e.g., as measured by half-life, rate of protein degradation) as compared to a hepcidin reference compound. In certain embodiments, the stability of a hepcidin analogue of the present invention is increased at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a hepcidin reference compound. In some embodiments, the stability is a stability that is described herein. In some embodiments, the stability is a plasma stability, e.g., as optionally measured according to the method described herein. In some embodiments, the stability is stability when delivered orally.

In particular embodiments, a hepcidin analogue of the present invention exhibits a longer half-life than a hepcidin reference compound. In particular embodiments, a hepcidin analogue of the present invention has a half-life under a given set of conditions (e.g., temperature, pH) of at least about 5 minutes, at least about 10 minutes, at least about 20 minutes, at least about 30 minutes, at least about 45 minutes, at least about 1 hour, at least about 2 hour, at least about 3 hours, at least about 4 hours, at least about 5 hours, at least about 6 hours, at least about 12 hours, at least about 18 hours, at least about 1 day, at least about 2 days, at least about 4 days, at least about 7 days, at least about 10 days, at least about two weeks, at least about three weeks, at least about 1 month, at least about 2 months, at least about 3 months, or more, or any intervening half-life or range in between, about 5 minutes, about 10 minutes, about 20 minutes, about 30 minutes, about 45 minutes, about 1 hour, about 2 hour, about 3 hours, about 4 hours, about 5 hours, about 6 hours, about 12 hours, about 18 hours, about 1 day, about 2 days, about 4 days, about 7 days, about 10 days, about two weeks, about three weeks, about 1 month, about 2 months, about 3 months, or more, or any intervening half-life or range in between. In some embodiments, the half-life of a hepcidin analogue of the present invention is extended due to its conjugation to one or more lipophilic substituent or half-life extension moiety, e.g., any of the lipophilic substituents or half-life extension moieties disclosed herein. In some embodiments, the half-life of a hepcidin analogue of the present invention is extended due to its conjugation to one or more polymeric moieties, e.g., any of the polymeric moieties or half-life extension moieties disclosed herein. In certain embodiments, a hepcidin analogue of the present invention has a half-life as described above under the given set of conditions wherein the temperature is about 25° C., about 4° C., or about 37° ° C., and the pH is a physiological pH, or a pH about 7.4.

In certain embodiments, a hepcidin analogue of the present invention, comprising a conjugated half-life extension moiety, has an increased serum half-life following oral, intravenous or subcutaneous administration as compared to the same analogue but lacking the conjugated half-life extension moiety. In particular embodiments, the serum half-life of a hepcidin analogue of the present invention following any of oral, intravenous or subcutaneous administration is at least 12 hours, at least 24 hours, at least 30 hours, at least 36 hours, at least 48 hours, at least 72 hours or at least 168 h. In particular embodiments, it is between 12 and 168 hours, between 24 and 168 hours, between 36 and 168 hours, or between 48 and 168 hours.

In certain embodiments, a hepcidin analogue of the present invention, e.g., a hepcidin analogue comprising a conjugated half-life extension moiety, results in decreased concentration of serum iron following oral, intravenous or subcutaneous administration to a subject. In particular embodiments, the subject's serum iron concentration is decreased to less than 10%, less than 20%, less than 25%, less than 30%, less than 40%, less than 50%, less than 60%, less than 70%, less than 80%, or less than 90% of the serum iron concentration in the absence of administration of the hepcidin analogue to the subject. In particular embodiments, the decreased serum iron concentration remains for a least 1 hour, at least 4 hours, at least 10 hours, at least 12 hours, at least 24 hours, at least 36 hours, at least 48 hours, or at least 72 hours following administration to the subject. In particular embodiments, it remains for between 12 and 168 hours, between 24 and 168 hours, between 36 and 168 hours, or between 48 and 168 hours. In one embodiment, the serum iron concentration of the subject is reduced to less than 20% at about 4 hours or about 10 hours following administration to the subject, e.g., intravenously, orally, or subcutaneously.

In one embodiment, the serum iron concentration of the subject is reduced to less than 50% or less than 60% for about 24 to about 30 hours following administration, e.g., intravenously, orally, or subcutaneously.

In some embodiments, the half-life is measured in vitro using any suitable method known in the art, e.g., in some embodiments, the stability of a hepcidin analogue of the present invention is determined by incubating the hepcidin analogue with pre-warmed human serum (Sigma) at 37° C. Samples are taken at various time points, typically up to 24 hours, and the stability of the sample is analyzed by separating the hepcidin analogue from the serum proteins and then analyzing for the presence of the hepcidin analogue of interest using LC-MS.

In some embodiments, the stability of the hepcidin analogue is measured in vivo using any suitable method known in the art, e.g., in some embodiments, the stability of a hepcidin analogue is determined in vivo by administering the peptide or peptide dimer to a subject such as a human or any mammal (e.g., mouse) and then samples are taken from the subject via blood draw at various time points, typically up to 24 hours. Samples are then analyzed as described above in regard to the in vitro method of measuring half-life. In some embodiments, in vivo stability of a hepcidin analogue of the present invention is determined via the method disclosed in the Examples herein.

In some embodiments, the present invention provides a hepcidin analogue as described herein, wherein the hepcidin analogue exhibits improved solubility or improved aggregation characteristics as compared to a hepcidin reference compound. Solubility may be determined via any suitable method known in the art. In some embodiments, suitable methods known in the art for determining solubility include incubating peptides (e.g., a hepcidin analogue of the present invention) in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide (e.g., the hepcidin analogue of the present invention) is more soluble in a given liquid than is a hepcidin reference compound.

In certain embodiments, the present invention provides a hepcidin analogue as described herein, wherein the hepcidin analogue exhibits a solubility that is increased at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a hepcidin reference compound in a particular solution or buffer, e.g., in water or in a buffer known in the art or disclosed herein.

In certain embodiments, the present invention provides a hepcidin analogue as described herein, wherein the hepcidin analogue exhibits decreased aggregation, wherein the aggregation of the peptide in a solution is at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold less or at least about 10%, 20%, 30%, 40%, 50%, 60%, 70%, 80%, 90%, 100%, 200%, 300%, 400%, or 500% less than a hepcidin reference compound in a particular solution or buffer, e.g., in water or in a buffer known in the art or disclosed herein.

In some embodiments, the present invention provides a hepcidin analogue, as described herein, wherein the hepcidin analogue exhibits less degradation (i.e., more degradation stability), e.g., greater than or about 10% less, greater than or about 20% less, greater than or about 30% less, greater than or about 40 less, or greater than or about 50% less than a hepcidin reference compound. In some embodiments, degradation stability is determined via any suitable method known in the art. In some embodiments, suitable methods known in the art for determining degradation stability include the method described in Hawe et al J Pharm Sci, VOL. 101, NO. 3, 2012, p 895-913, incorporated herein in its entirety. Such methods are in some embodiments used to select potent sequences with enhanced shelf lives.

In some embodiments, the hepcidin analogue of the present invention is synthetically manufactured. In other embodiments, the hepcidin analogue of the present invention is recombinantly manufactured.

The various hepcidin analogue monomer and dimer peptides of the invention may be constructed solely of natural amino acids. Alternatively, these hepcidin analogues may include unnatural or non-natural amino acids including, but not limited to, modified amino acids. In certain embodiments, modified amino acids include natural amino acids that have been chemically modified to include a group, groups, or chemical moiety not naturally present on the amino acid. The hepcidin analogues of the invention may additionally include D-amino acids. Still further, the hepcidin analogue peptide monomers and dimers of the invention may include amino acid analogs. In particular embodiments, a peptide analogue of the present invention comprises any of those described herein, wherein one or more natural amino acid residues of the peptide analogue is substituted with an unnatural or non-natural amino acid, or a D-amino acid.

In certain embodiments, the hepcidin analogues of the present invention include one or more modified or unnatural amino acids. For example, in certain embodiments, a hepcidin analogue includes one or more of Daba, Dapa, Pen, Sar, Cit, Cav, HLeu, 2-Nal, 1-Nal, d-1-Nal, d-2-Nal, Bip, Phe(4-OMe), Tyr(4-OMe), BhTrp, BhPhe, Phe(4-CF$_3$), 2-2-Indane, 1-1-Indane, Cyclobutyl, BhPhe, hLeu, Gla, Phe(4-NH$_2$), hPhe, 1-Nal, Nle, 3-3-diPhe, cyclobutyl-Ala, Cha, Bip, β-Glu, Phe(4-Guan), homo amino acids, D-amino acids, and various N-methylated amino acids. One having skill in the art will appreciate that other modified or unnatural amino acids, and various other substitutions of natural amino acids with modified or unnatural amino acids, may be made to achieve similar desired results, and that such substitutions are within the teaching and spirit of the present invention.

The present invention includes any of the hepcidin analogues described herein, e.g., in a free or a salt form.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements. In particular embodiments, the compounds are isotopically substituted with deuterium. In more particular embodiments, the most labile hydrogens are substituted with deuterium.

The hepcidin analogues of the present invention include any of the peptide monomers or dimers described herein linked to a linker moiety, including any of the specific linker moieties described herein.

The hepcidin analogues of the present invention include peptides, e.g., monomers or dimers, comprising a peptide monomer subunit having at least 85%, at least 90%, at least 92%, at least 94%, at least 95%, at least 98%, or at least 99% amino acid sequence identity to a hepcidin analogue peptide sequence described herein (e.g., any one of the peptides disclosed herein), including but not limited to any of the amino acid sequences shown in Tables 2A, 2B, 3A, 3B, and 4.

In certain embodiments, a peptide analogue of the present invention, or a monomer subunit of a dimer peptide analogue of the present invention, comprises or consists of 7 to 35 amino acid residues, 8 to 35 amino acid residues, 9 to 35 amino acid residues, 10 to 35 amino acid residues, 7 to 25 amino acid residues, 8 to 25 amino acid residues, 9 to 25 amino acid residues, 10 to 25 amino acid residues, 7 to 18 amino acid residues, 8 to 18 amino acid residues, 9 to 18 amino acid residues, or 10 to 18 amino acid residues, and, optionally, one or more additional non-amino acid moieties, such as a conjugated chemical moiety, e.g., a half-life extension moiety, a PEG or linker moiety. In particular embodiments, a monomer subunit of a hepcidin analogue comprises or consists of 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues. In particular embodiments, a monomer subunit of a hepcidin analogue of the present invention comprises or consists of 10 to 18 amino acid residues and, optionally, one or more additional non-amino acid moieties, such as a conjugated chemical moiety, e.g., a PEG or linker moiety. In various embodiments, the monomer subunit comprises or consists of 7 to 35 amino acid residues, 9 to 18 amino acid residues, or 10 to 18 amino acid residues. In particular embodiments of any of the various Formulas described herein, X comprises or consists of 7 to 35 amino acid residues, 8 to 35 amino acid residues, 9 to 35 amino acid residues, 10 to 35 amino acid residues, 7 to 25 amino acid residues, 8 to 25 amino acid residues, 9 to 25 amino acid residues, 10 to 25 amino acid residues, 7 to 18 amino acid residues, 8 to 18 amino acid residues, 9 to 18 amino acid residues, or 10 to 18 amino acid residues.

In particular embodiments, a hepcidin analogue or dimer of the present invention does not include any of the compounds described in PCT/US2014/030352 or PCT/US2015/038370.

Peptide Hepcidin Analogues

In certain embodiments, hepcidin analogues of the present invention comprise a single peptide subunit, optionally conjugated to a half-life extension moiety. In certain embodiments, these hepcidin analogues form cyclized structures through intramolecular disulfide or other bonds.

In one aspect, the present invention includes a hepcidin analogue comprising a peptide of Formula (I):

(I)

(SEQ ID NO: 259)
R$^1$-Asp-Thr-His-B1-B2-B3-B4-Xaa1-B6-Xaa2-J-Y1-Y2-R$^2$ or a peptide dimer comprising two peptides according to Formula I, or a pharmaceutically acceptable salt, or a solvate thereof,
wherein:
R$^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
R$^2$ is —NH$_2$ or —OH;
Xaa1 is B5; and
  i) B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys;
or
  ii) Xaa1 is B5(L1Z); B5 is Lys, D-Lys, Orn, homoSer, Gln, Lys(Ac), Ile, Abu, Leu, or Nleu; and Xaa2 is B7; and B7 is Glu or absent;
each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me); or
  iii) substituted Phe, substituted bhPhe, or substituted Trp, or substituted bhTrp;
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B7 is Dapa, Lys, D-Lys, homoLys, or a-Me-Lys;
L1 is absent, Dapa, D-Dapa, or isoGlu, PEG, Ahx, isoGlu-PEG, PEG-Ahx, isoGlu-Ahx, or isoGlu-PEG-Ahx;
Ahx is an aminohexanoic acid moiety;
Z is a half-life extension moiety;
J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys, (D)Cys, NMeCys, aMeCys, or Pen;
Y2 is an amino acid or absent; Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homo Tryptophane, 1-Nal is 1-naphthylalanine, 2-Nal is 2-naphthylalanine, Orn is orinithine,
Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted bhTrp is N-methyl-L-b-homotryptophan, a-methyl-b-homotryptophan, or b-homotryptophan substituted with F, Cl, OH, or t-Bu;

wherein
  i) the peptide of formula I is optionally PEGylated on one or more R$^1$, B1, B2, B3, B4, B5, B6, B7, J, Y1, Y2, or R2; and
  ii) the peptide is cyclized via a disulfide bond between B3 and Y1.

In one embodiment, the half-life extension moiety is $C_{10}$-$C_{21}$ alkanoyl.

In one embodiment, Xaa1 is B5; B5 is absent, Lys, D-Lys, Orn, homoSer, Gln, (D)Gln, Lys(Ac), Ile, Abu, Leu, Ala, D-Ala, bAla, or Nleu; and Xaa2 is B7(L1Z); and B7 is Dapa, Lys, D-Lys, homoLys, or a-Me-Lys; and L1 is attached to N$^\epsilon$ of Lys, D-Lys, homoLys, or a-Me-Lys; or N$^\beta$ of Dapa.

In another embodiment, Xaa1 is B5(L1Z); B5 is Lys, or D-Lys; and Xaa2 is B7; and B7 is Glu or absent; and L1 is attached to N$^\epsilon$ of Lys.

In one embodiment, the present invention includes a hepcidin analogue comprising a peptide of Formula (A-I):

(A-I)

(SEQ ID NO: 260)
R$^1$-Asp-Thr-His-B1-B2-B3-B4-B5-B6-B7(L1Z)-J-Y1-Y2-R$^2$ or a peptide dimer comprising two peptides according to Formula A-I, or a pharmaceutically acceptable salt, or a solvate thereof,
wherein:
R$^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
R$^2$ is —NH$_2$ or —OH;
each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me); or
  iii) substituted Phe, substituted bhPhe, or substituted Trp, or substituted bhTrp:
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B5 is absent, Lys, D-Lys, Om, homoSer, Gln, (D)Gln, Lys(Ac), Ile, Abu, Leu, Ala, D-Ala, bAla, or Nleu;
B7 is a lower or a higher homolog of Lys, a-MeLys, D-Lys, or Dapa; and wherein L1 is attached to N$^\epsilon$ of Lys, D-Lys, homoLys, or a-Me-Lys; or N$^\beta$ of Dapa;
L1 is absent or isoGlu, PEG, Ahx, isoGlu-PEG, PEG-Ahx, isoGlu-Ahx, or isoGlu-PEG-Ahx;
Ahx is an aminohexanoic acid moiety;
Z is a half-life extension moiety;
J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys, (D)Cys, NMeCys, aMeCys, or Pen;
Y2 is an amino acid or absent;
Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4, -tetrahydro-isoquinoline-3-carboxylic acid, NPC is L-nipecotic acid, bhTrp is b-homo Tryptophane, 1-Nal is 1-naphthylalanine, 2-Nal is 2-naphthylalanine, Orn is orinithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;

and wherein
  i) the peptide of formula I is optionally PEGylated on one or more $R^1$, B1, B2, B3, B4, B5, B6, J, Y1, Y2, or R2;
  ii) the peptide is cyclized via a disulfide bond between B3 and Y1;
  iii) when B6 is Phe, then B5 is other than Lys:
  iv) when the peptide is a peptide dimer, then B7(L1Z)-J-Y1-Y2 is absent;
  v) when the peptide is a peptide dimer, the peptide dimer is dimerized
    a) via a linker moiety,
    b) via an intermolecular disulfide bond between two B3 residues, one in each monomer subunit, or
    c) via both a linker moiety and an intermolecular disulfide bond between two B3 residues; and
    d) the linker moiety comprises a half-life extending moiety.

In one embodiment, with respect to peptides of Formula (A-I), $R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl; $R^2$ is —$NH_2$ or —OH;

each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me); or
  iii) substituted Phe, substituted bhPhe, or substituted Trp, or substituted bhTrp:

B2 is Pro, D-Pro, bhPro, D-bhPro, NPC, or D-NPC; B3 is Cys, homoCys, or Pen; B4 is Ile, Val, Leu, or NLeu; B5 is Lys, D-Lys, Orn, homoSer, Gln, Lys(Ac), Ile, Abu, Leu, or Nleu; B7 is a lower or a higher homolog of Lys;

$L_1$ is absent or isoGlu, PEG, Ahx, isoGlu-PEG, PEG-Ahx, isoGlu-Ahx, or isoGlu-PEG-Ahx;

Ahx is aminohexanoic acid moiety; and wherein $L_1$ is attached to $N^\epsilon$ of B7; Z is a half-life extension moiety;

J is Pro, -Pro-Arg-, -Pro-Arg-Ser-, -Pro-Arg-Ser-Lys- (SEQ ID NO:249), -Pro-Arg-Ser-Lys-Sar-(SEQ ID NO:250), -Pro-Arg-Ser-Lys-Gly-(SEQ ID NO:251), or absent: Y1 is Cys, homoCys or Pen; and Y2 is an amino acid or absent.

In one embodiment, with respect to peptides of Formula (A-I), $R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl; $R^2$ is —$NH_2$ or —OH;

each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me); or
  iii) substituted Phe, substituted bhPhe, substituted Trp, or substituted bhTrp:

B2 is Pro, D-Pro, bhPro, D-bhPro, NPC, or D-NPC; B3 is Cys, homoCys, or Pen; B4 is Ile, Val, Leu, or NLeu; B5 is absent, Lys, D-Lys, Orn, homoSer, Gln, Lys(Ac), Ile, Abu, Leu, Ala, D-Ala, bAla, or Nleu; B7 is a lower or a higher homolog of Lys, a-MeLys, D-Lys, or Dapa;

L1 is absent or isoGlu, PEG, Ahx, isoGlu-PEG, PEG-Ahx, isoGlu-Ahx, or isoGlu-PEG-Ahx;

Ahx is aminohexanoic acid moiety; and wherein L1 is attached to $N^\epsilon$ of B7; Z is a half-life extension moiety; J is Pro, -Pro-Arg-, -Pro-Arg-Ser-, -Pro-Arg-Ser-Lys- (SEQ ID NO:249), -Pro-Arg-Ser-Lys-Sar-(SEQ ID NO:250), -Pro-Arg-Ser-Lys-Gly-(SEQ ID NO:251), or absent; or J is any amino acid: Y1 is Cys, homoCys, NMeCys, aMeCys, or Pen; and Y2 is an amino acid or absent.

In a particular embodiment, B5 is D-Lys.

In another embodiment, hepcidin analogue is a peptide dimer according to Formula A-II:

A-II (SEQ ID NO: 262)

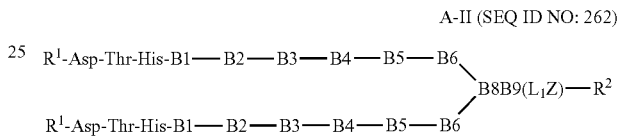

wherein L1, Z, B1-B6, $R^1$, and $R^2$ are as described for Formula (A-I); each B8 and B9 is independently Lys, D-Lys, homoLys, or a-Me-Lys; and wherein one of the B6s is attached to $N^\epsilon$ of B8.

In a particular embodiment, each B8 and B9 is independently Lys, D-Lys, homoLys, or a-Me-Lys. In a more particular embodiment, B9 is Lys. In a particular embodiment, B8 is Lys or D-Lys.

In another embodiment, the hepcidin analogue is a peptide dimer is according to Formula A-III:

A-III (SEQ ID NO: 263)

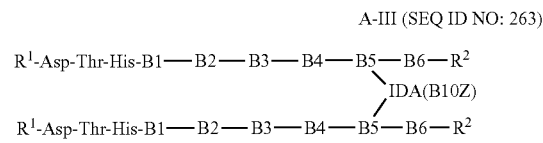

wherein B1-B6, $R^1$, and $R^2$ are as described for Formula (A-I); B10 is a natural or unnatural amino acid; and Z is a half-life extending moiety.

In one embodiment, the present invention includes a hepcidin analogue comprising a peptide of Formula (B-I):

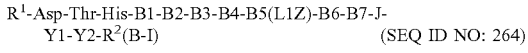

or a peptide dimer comprising two peptides according to Formula B-I, or a pharmaceutically acceptable salt, or a solvate thereof, wherein:

$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;

$R^2$ is —$NH_2$ or —OH;

each of B1 and B6 is independently
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me); or iii) substituted Phe, substituted bhPhe, or substituted Trp, or substituted bhTrp;
B2 is Pro, D-Pro, bhPro, D-bhPro, NPC, or D-NPC;
B3 is Cys, homoCys, (D)Cys, a-MeCys, or Pen;
B4 is Ile, Val, Leu, or NLeu;
B5 is Lys, D-Lys, Orn, homoSer, Gln, Lys(Ac), Ile, Abu, Leu, or Nleu;
B7 is Glu or absent;
$L_1$ is absent or isoGlu, PEG, Ahx, isoGlu-PEG, PEG-Ahx, isoGlu-Ahx, or isoGlu-PEG-Ahx;
Ahx is an aminohexanoic acid moiety;
Z is a half-life extension moiety;
J is Pro, Arg, Gly, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys or Pen;
Y2 is an amino acid or absent;
the half-life extension moiety is $C_{10}$-$C_{21}$ alkanoyl;
Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, Npc is L-nipecotic acid, bhomoTrp is L-b-homotryptophan, 1-Nal is 1-naphthylalanine, 2-Nal is 2-naphthylalanine, Orn is ornithine, Nleu is norleucine, Abu is 2-aminobutyric acid;
substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted b-hTrp is N-methyl-L-b-homotryptophan, a-methyl-b-homotryptophan, or b-homotryptophan substituted with F, Cl, OH, or t-Bu;
wherein
i) the peptide of formula I is optionally PEGylated on one or more $R^1$, B1, B2, B3, B4, B6, B7, J, Y1, Y2, or R2; and
ii) the peptide is cyclized via a disulfide bond between B3 and Y1; and
iii) when B6 is Phe, Y1 is Cys, and Y2 is Lys, then J is Pro, Arg, Gly, -Pro-Arg-, -Pro-Arg-Ser-, -Pro-Arg-Ser-Lys-(SEQ ID NO:249), or absent.

In one embodiment, with respect to peptides of Formula (B-I),
$R^1$ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
$R^2$ is —$NH_2$ or —OH;
each of B1 and B6 is independently
i) Phe, Dpa, bhPhe, a-MePhe, NMe-Phe, or D-Phe;
ii) 2-Nal, 1-Nal, D-1-Nal, D-2-Nal, 3,3-diPhenylGly, Tic, Bip, Trp, bhTrp, hPhe, or Tyr(Me); or
iii) substituted Phe, substituted bhPhe, or substituted Trp, or substituted bhTrp;
B2 is Pro, D-Pro, bhPro, D-bhPro, NPC, or D-NPC;
B3 is Cys, homoCys, or Pen;
B4 is Ile, Val, Leu, or NLeu;
B5 is Lys, D-Lys, Orn, homoSer, Gln, Lys(Ac), Ile, Abu, Leu, or Nleu;
B7 is Glu or absent;
$L_1$ is absent or isoGlu, PEG, Ahx, isoGlu-PEG, PEG-Ahx, isoGlu-Ahx, or isoGlu-PEG-Ahx;
Ahx is aminohexanoic acid moiety; and wherein $L_1$ is attached to $N^\varepsilon$ of B7;
Z is a half-life extension moiety;
J is Pro, Arg, Gly, -Pro-Arg-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent;
Y1 is Cys, homoCys or Pen;
Y2 is an amino acid or absent;
the half-life extension moiety is $C_{10}$-$C_{21}$ alkanoyl;
Dpa is 3,3-diphenylalanine or b,b-diphenylalanine, bhPhe is b-homophenylalanine, Bip is Biphenylalanine, BhPro is β-homoproline, Tic is L-1,2,3,4,-Tetrahydro-isoquinoline-3-carboxylic acid, Npc is Nipecotic acid, bhTrp is L-β-homo Tryptophan, Nal is Naphthylalanine, Orn is ornithine, Nleu is norLeucine, Abu is 2-Aminobutyric acid;
substituted Phe is Phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted β-hPhe is β-homoPhenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;
substituted Trp is N-methyl-L-tryptophan, a-methyltryptophan, or tryptophan substituted with F, Cl, OH, or t-Bu;
substituted β-hTrp is N-methyl-L-b-homoTyptophan, a-methyl-b-homotryptophan, or b-homotryptophan substituted with F, Cl, OH, or t-Bu;
wherein
i) the peptide of formula I is optionally PEGylated on $R^1$, B1, B2, B3, B4, B6, B7, J, Y1, Y2, and R2;
ii) the peptide is cyclized via a disulfide bond between B3 and Y1.

In one particular embodiment, B10 is β-Ala.
In one embodiment, $R^1$ is hydrogen, or $C_1$-$C_{20}$ alkanoyl.
In another embodiment, $R^1$ is hydrogen, isovaleric acid, isobutyric acid or
acetyl. In a particular embodiment, $R^1$ is isovaleric acid.
In one embodiment, B2 is Pro, D-Pro, bhPro, D-bhPro, NPC, or D-NPC.
In one embodiment, B3 is Cys. In another embodiment, B3 is homoCys.
In one embodiment, B4 is Ile.
In one embodiment, B5 is absent. In another embodiment, B5 is Ala, D-Ala, or bAla.
In another embodiment, B5 is Lys, D-Lys, Orn, homoSer, Gln, Lys(Ac), Ile, or Nleu.
In another embodiment, the peptide is cyclized via a disulfide bond between B3 and Y1.
In one embodiment, Y1 is Cys or homoCys.
In one embodiment, the half-life extension moiety is $C_{14}$-$C_{20}$ alkanoyl.

In one embodiment, B7 is a lower homolog of Lys. In another embodiment, B7 is a higher homolog of Lys. In a further embodiment, B7 is homoLys, a-MeLys, or abu. In a particular embodiment, B7 is Lys or D-Lys.

In another embodiment, B7 is Dapa.

In one embodiment, the lower homolog of Lys is 2,3-diaminopropanoic acid or 2,4-diaminobutyric acid. In one embodiment, the lower homolog of Lys is L-2,3-diaminopropanoic acid. In another embodiment, the lower homolog of Lys is D-2,3-diaminopropanoic acid. In another embodiment, the lower homolog of Lys is L-2,4-diaminobutyric acid. In another embodiment, the lower homolog of Lys is D-2,4-diaminobutyric acid.

In one embodiment, the higher homolog of Lys is homoLys or L-2,6-diaminohexanoic acid. In another embodiment, the higher homolog of Lys is D-homoLys or D-2,6-diaminohexanoic acid.

In another embodiment, the peptide is according to formula A-IV or B-IV:

(A-IV)
(SEQ ID NO: 265)
R$^1$-Asp-Thr-His-B1-B2-B3-Ile-B5-B6-

N(H)C[CH$_2$CH$_2$CH$_2$CH$_2$N(H)L1Z](H)-C(O)-J-Y1-

Y2-R$^2$ (B-IV)
R$^1$-Asp-Thr-His-B1-B2-B3-Ile-

N(H)C[CH$_2$CH$_2$CH$_2$CH$_2$N(H)L1Z](H)-C(O)-B6-

B7-J-Y1-Y2-R$^2$ or a peptide dimer comprising two peptides according to Formula (A-IV), or (B-IV), or a pharmaceutically acceptable salt thereof.

In one embodiment, B2 is Pro, D-Pro, or bhPro. In a particular embodiment, B2 is Pro.

In one embodiment, B3 is Cys. In another embodiment, B3 is Pen. In another embodiment, B3 is homoCys.

In another embodiment, the peptide is according to formula A-V or B-V:

(A-V)
(SEQ ID NO: 266)
R$^1$-Asp-Thr-His-B1-Pro-Cys-Ile-B5-B6-

N(H)C[CH$_2$CH$_2$CH$_2$CH$_2$N(H)L1Z](H)-C(O)-J-Y1-

Y2-R$^2$ (B-V)
(SEQ ID NO: 267)
R$^1$-Asp-Thr-His-B1-Pro-Cys-Ile-

N(H)C[CH$_2$CH$_2$CH$_2$CH$_2$N(H)L1Z](H)-C(O)-B6-

B7-J-Y1-Y2-R$^2$ or a peptide dimer comprising two peptides according to Formula (A-V), or (B-V), or a pharmaceutically acceptable salt thereof;

R$^1$ is hydrogen, C$_1$-C$_6$ alkyl, C$_6$-C$_{12}$ aryl, C$_6$-C$_{12}$ aryl-C$_1$-C$_6$ alkyl, C$_1$-C$_{20}$ alkanoyl, or C$_1$-C$_{20}$ cycloalkanoyl;

R$^2$ is —NH$_2$ or —OH;

B6 is
  i) Phe, Dpa, bhPhe, a-MePhe, NMe-Phe, or D-Phe;
  ii) 2-Nal, 1-Nal, D-1-Nal, D-2-Nal, 3,3-diPhenylGly, Tic, Bip, Trp, bhTrp, hPhe, or Tyr(Me);

iii) when B6 is Phe, then B5 is other than Lys; or
  iv) substituted Phe, substituted bhPhe, substituted Trp, or substituted bhTrp:

B5 is absent, Lys, D-Lys, Orn, homoSer, Gln, (D)Gln, Lys(Ac), Ile, Abu, Leu, Ala, D-Ala, bAla, or Nleu;

L1 is absent or isoGlu, PEG, Ahx, isoGlu-PEG, PEG-Ahx, isoGlu-Ahx, or isoGlu-PEG-Ahx;

Ahx is an aminohexanoic acid moiety; and wherein L1 is attached to N$^ε$ of B7;

Z is a half-life extension moiety;

J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;

Y1 is Cys, homoCys, NMeCys, aMeCys, or Pen;

Y2 is an amino acid or absent;

Dapa is diaminopropanoic acid, Dpa or DIP is 3,3-diphenylalanine or b,b-diphenylalanine, bhPhe is b-homophenylalanine, Bip is biphenylalanine, bhPro is b-homoproline, Tic is L-1,2,3,4,-tetrahydro-isoquinoline-3-carboxylic acid, NPC is L-nipecotic acid, bhTrp is b-homo Tryptophane, 1-Nal is 1-naphthylalanine, 2-Nal is 2-naphthylalanine, Orn is orinithine, Nleu is norleucine, Abu is 2-aminobutyric acid;

substituted Phe is phenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted bhPhe is b-homophenylalanine wherein phenyl is substituted with F, Cl, Br, I, OH, methoxy, dimethoxy, dichloro, dimethyl, difluoro, pentafluoro, allyloxy, azido, nitro, 4-carbamoyl-2,6-dimethyl, trifluoromethoxy, trifluoromethyl, phenoxy, benzyloxy, carbamoyl, t-Bu, carboxyl, CN, or guanidine;

substituted Trp is N-methyl-L-tryptophan, a-methyltryptophan, or tryptophan substituted with F, Cl, OH, or t-Bu;

substituted bhTrp is N-methyl-L-b-homotryptophan, a-methyl-b-homotryptophan, or b-homotryptophan substituted with F, Cl, OH, or t-Bu;

and B1 is
  i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
  ii) Phe(4-F), Phe(4-CF$_3$), Phe(4-CH$_3$), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
  iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In another embodiment, the peptide is according to formula A-VI or B-VI:

(A-VI)
(SEQ ID NO: 268)
R$^1$-Asp-Thr-His-B1-Pro-Cys-Ile-B5-B6-

N(H)C[CH$_2$CH$_2$CH$_2$CH$_2$N(H)L1Z](H)-C(O)-J-Y1-

Y2-R$^2$

-continued (B-VI)
(SEQ ID NO: 269)
R¹-Asp-Thr-His-B1-Pro-Cys-Ile-

N(H)C[CH₂CH₂CH₂CH₂N(H)L1Z](H)-C(O)-B6-

B7-J-Y1-Y2-R² or a peptide dimer comprising two peptides according to Formula Formula (A-VI), or (B-VI),
or a pharmaceutically acceptable salt thereof;
wherein
R¹ is hydrogen, $C_1$-$C_6$ alkyl, $C_6$-$C_{12}$ aryl, $C_6$-$C_{12}$ aryl-$C_1$-$C_6$ alkyl, $C_1$-$C_{20}$ alkanoyl, or $C_1$-$C_{20}$ cycloalkanoyl;
R² is —NH₂ or —OH;
B5 is absent, Lys, D-Lys, Orn, homoSer, Gln, (D)Gln, Lys(Ac), Ile, Abu, Leu, Ala, D-Ala, bAla, or Nleu;
L1 is absent or isoGlu, PEG, Ahx, isoGlu-PEG, PEG-Ahx, isoGlu-Ahx, or isoGlu-PEG-Ahx;
Ahx is an aminohexanoic acid moiety; and wherein L1 is attached to $N^\varepsilon$ of B7;
Z is a half-life extension moiety;
J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), -Pro-Arg-Ser-Lys-Gly-(SEQ ID NO:251), or absent; or J is any amino acid;
Y1 is Cys, homoCys, NMeCys, aMeCys, or Pen;
Y2 is an amino acid or absent;
and one of B1 and B6 is
  i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
  ii) Phe(4-F), Phe(4-CF₃), Phe(4-CH₃), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
  iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2);
  and the other is as described for Formula (A-I).
In one embodiment, B1 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe(4-F), Phe(4-CF₃), Phe(4-CH₃), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2);
and B6 is as described for Formula (A-I).
In another embodiment, B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe(4-F), Phe(4-CF₃), Phe(4-CH₃), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2);
and B1 is as described herein.
In a particular embodiment, B6 is Phe.
In a particular embodiment, B1 is Phe.
In another embodiment, the peptide is according to formula A-VII or B-VII:

(A-VII)
(SEQ ID NO: 270)
R¹-Asp-Thr-His-B1-Pro-Cys-Ile-B5-Phe-

N(H)C[CH₂CH₂CH₂CH₂N(H)L1Z](H)-C(O)-J-Y1-

Y2-R²

(B-VII)
(SEQ ID NO: 271)
R¹-Asp-Thr-His-B1-Pro-Cys-Ile-

N(H)C[CH₂CH₂CH₂CH₂N(H)L1Z](H)-C(O)-Phe-

B7-J-Y1-Y2-R² or a peptide dimer comprising two peptides according to Formula A-VII or B-VII, or a pharmaceutically acceptable salt thereof;
wherein R¹, R², B5, B7, L1, Z, J, Y1, and Y2 are as described for Formula (A-I); B7 is as described for Formula (B-I); and B1 is
  i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
  ii) Phe(4-F), Phe(4-CF₃), Phe(4-CH₃), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
  iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).
In another embodiment, the peptide is according to formula A-VIII or B-VIII:

(A-VIII)
(SEQ ID NO: 272)
R¹-Asp-Thr-His-Phe-Pro-Cys-Ile-B5-B6-

N(H)C[CH₂CH₂CH₂CH₂N(H)L1Z](H)-C(O)-J-Y1-

Y2-R²

(B-VIII)
(SEQ ID NO: 273)
R¹-Asp-Thr-His-Phe-Pro-Cys-Ile-

N(H)C[CH₂CH₂CH₂CH₂N(H)L1Z](H)-C(O)-B6-

B7-J-Y1-Y2-R² or a peptide dimer comprising two peptides according to Formula A-VIII or B-VIII, or a pharmaceutically acceptable salt thereof;
wherein wherein R¹, R², B5, B7, L1, Z, J, Y1, and Y2 are as described for Formula (A-I); B7 is as described for Formula (B-I);

and B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe(4-F), Phe(4-CF$_3$), Phe(4-CH$_3$), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In one embodiment, Y1 is Cys. In another embodiment, Y1 is homoCys. In another embodiment, Y1 is NMeCys. In another embodiment, Y1 is aMeCys.

In another embodiment, the peptide is according to formula A-IXa, A-IXb, B-IXa, or B-IXb:

```
(A-IXa)
                                    (SEQ ID NO: 274)
R¹-Asp-Thr-His-Phe-Pro-Cys-Ile-B5-B6-

N(H)C[CH₂CH₂CH₂CH₂N(H)L1Z](H)-C(O)-J-

Cys-Y2-R², (A-IXb)
                                    (SEQ ID NO: 275)
R¹-Asp-Thr-His-B1-Pro-Cys-Ile-B5-Phe-

N(H)C[CH₂CH₂CH₂CH₂N(H)L1Z](H)-C(O)-J-

Cys-Y2-R², (B-IXa)
                                    (SEQ ID NO: 276)
R¹-Asp-Thr-His-Phe-Pro-Cys-Ile-

N(H)C[CH₂CH₂CH₂CH₂N(H)L1Z](H)-C(O)-

B6-B7-J-Cys-Y2-R²,
or (B-IXb)
                                    (SEQ ID NO: 277)
R¹-Asp-Thr-His-B1-Pro-Cys-Ile-

N(H)C[CH₂CH₂CH₂CH₂N(H)L1Z](H)-C(O)-

Phe-B7-J-Cys-Y2-R²
``` or a peptide dimer comprising two peptides according to Formula A-IXa, A-IXb, B-IXa, or B-IXb, or a pharmaceutically acceptable salt thereof;
wherein wherein R$^1$, R$^2$, B5, B7, L1, Z, J, and Y2 are as described for Formula (A-I); B7 is as described for Formula (B-I);
and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe(4-F), Phe(4-CF$_3$), Phe(4-CH$_3$), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In one embodiment, Y2 is Lys.
In a particular embodiment, Y2 is absent.
In another embodiment, the peptide is according to formula A-Xa or A-Xb, B-Xa, or B-Xb:

```
(A-Xa)
                                    (SEQ ID NO: 278)
R¹-Asp-Thr-His-Phe-Pro-Cys-Ile-B5-B6-

N(H)C[CH₂CH₂CH₂CH₂N(H)L1Z](H)-C(O)-J-

Cys-R², (A-Xb)
                                    (SEQ ID NO: 279)
R¹-Asp-Thr-His-B1-Pro-Cys-Ile-B5-Phe-

N(H)C[CH₂CH₂CH₂CH₂N(H)L1Z](H)-C(O)-J-

Cys-R², (B-Xa)
                                    (SEQ ID NO: 280)
R¹-Asp-Thr-His-Phe-Pro-Cys-Ile-

N(H)C[CH₂CH₂CH₂CH₂N(H)L1Z](H)-C(O)-B6-

B7-J-Cys-R²

(B-Xb)
                                    (SEQ ID NO: 281)
R₁-Asp-Thr-His-B1-Pro-Cys-Ile-

N(H)C[CH₂CH₂CH₂CH₂N(H)L1Z](H)-C(O)-

Phe-B7-J-Cys-R₂
``` or a peptide dimer comprising two peptides according to Formula A-Xa or A-Xb, B-Xa. or B-Xb, or a pharmaceutically acceptable salt thereof;
wherein wherein R$^1$, R$^2$, B5, B7, L1, Z, and J are as described for Formula (A-I); B7 is as described for Formula (B-I);
and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe(4-F), Phe(4-CF$_3$), Phe(4-CH$_3$), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In one embodiment, J is Pro, -Pro-Arg-, -Pro-Lys-, -Pro-(D)Lys-, -Pro-Arg-Ser-, -Pro-Arg-Ser-Lys-(SEQ ID NO:249), -Pro-Arg-Ser-Lys-Sar-(SEQ ID NO:250), or -Pro-Arg-Ser-Lys-Gly-(SEQ ID NO:251).

In another embodiment, J is Pro. In another embodiment, J is -Pro-Arg-. In another embodiment, J is -Pro-Arg-Ser -. In another embodiment, J is -Pro-Arg-Ser-Lys-(SEQ ID NO:249). In another embodiment, J is -Pro-Arg-Ser-Lys-Sar-(SEQ ID NO:250). In another embodiment, J is -Pro-Arg-Ser-Lys-Gly-(SEQ ID NO:251). In a particular embodiment, J is absent.

In another embodiment, J is any amino acid. In a particular embodiment, J is Lys, a lower or higher homolog of Lys, D-Lys, or substituted or unsubstituted Lys.

In another embodiment, the peptide is according to formula A-XIa, A-XIb, B-XIa or B-XIb:

(A-XIa)
(SEQ ID NO: 282)
R¹-Asp-Thr-His-Phe-Pro-Cys-Ile-B5-B6-

N(H)C[CH₂CH₂CH₂CH₂N(H)L1Z)](H)-C(O)-Cys-

R², (A-XIb)
(SEQ ID NO: 283)
R¹-Asp-Thr-His-B1-Pro-Cys-Ile-B5-Phe-

N(H)C[CH₂CH₂CH₂CH₂N(H)L1Z)](H)-C(O)-Cys-

R², (B-XIa)
(SEQ ID NO: 284)
R¹-Asp-Thr-His-Phe-Pro-Cys-Ile-

N(H)C[CH₂CH₂CH₂CH₂N(H)L1Z)](H)-C(O)-B6-B7-Cys-

R²,
or (B-XIb)
(SEQ ID NO: 285)
R¹-Asp-Thr-His-B1-Pro-Cys-Ile-

N(H)C[CH₂CH₂CH₂CH₂N(H)L1Z)](H)-C(O)-Phe-B7-Cys-

R² or a peptide dimer comprising two peptides according to Formula A-XIa, A-XIb, B-XIa or B-XIb, or a pharmaceutically acceptable salt thereof;
wherein wherein R¹, R², B5, B7, L1, and Z are as described for Formula (A-I); B7 is as described for Formula (B-I);
and B1 or B6 is
  i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
  ii) Phe(4-F), Phe(4-CF₃), Phe(4-CH₃), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
  iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In another embodiment, B5 is Lys, D-Lys, Orn, homoSer, Gln, Lys(Ac), Ile, or Nleu.

In a particular embodiment, B5 is Lys, or D-Lys.

In one embodiment, B7 is Glu or absent. In another embodiment, B7 is Glu.

In another embodiment, the peptide is according to formula A-XIIa, A-XIIb, A-XIIc, A-XIId, B-XIIa, B-XIIb, B-XIIc, or B-XIId:

(A-XIIa)
(SEQ ID NO: 286)
R¹-Asp-Thr-His-Phe-Pro-Cys-Ile-Lys-B6-

N(H)C[CH₂CH₂CH₂CH₂N(H)L1Z)](H)-C(O)-Cys-

R², (A-XIIb)
(SEQ ID NO: 287)
R¹-Asp-Thr-His-B1-Pro-Cys-Ile-Lys-Phe-

N(H)C[CH₂CH₂CH₂CH₂N(H)L1Z)](H)-C(O)-Cys-

R², (A-XIIc)
(SEQ ID NO: 288)
R¹-Asp-Thr-His-Phe-Pro-Cys-Ile-(D)Lys-B6-

N(H)C[CH₂CH₂CH₂CH₂N(H)L1Z)](H)-C(O)-

Cys-R², (A-XIId)
(SEQ ID NO: 289)
R¹-Asp-Thr-His-B1-Pro-Cys-Ile-(D)Lys-Phe-

N(H)C[CH₂CH₂CH₂CH₂N(H)L1Z)](H)-C(O)-

Cys-R², (B-XIIa)
(SEQ ID NO: 290)
R¹-Asp-Thr-His-Phe-Pro-Cys-Ile-

N(H)C[CH₂CH₂CH₂CH₂N(H)L1Z)](H)-C(O)-B6-

Glu-Cys-R², (B-XIIb)
(SEQ ID NO: 291)
R¹-Asp-Thr-His-B1-Pro-Cys-Ile-Lys-Phe-

N(H)C[CH₂CH₂CH₂CH₂N(H)L1Z)](H)-C(O)-Phe-

Glu-Cys-R², (B-XIIc)
(SEQ ID NO: 292)
R¹-Asp-Thr-His-Phe-Pro-Cys-Ile-

N(H)C[CH₂CH₂CH₂CH₂N(H)L1Z)](H)-C(O)-B6-

Cys-R²,
or (B-XIId)
(SEQ ID NO: 293)
R¹-Asp-Thr-His-B1-Pro-Cys-Ile-

N(H)C[CH₂CH₂CH₂CH₂N(H)L1Z)](H)-C(O)-Phe-

Cys-R² or a peptide dimer thereof, or a pharmaceutically acceptable salt thereof;
wherein wherein R¹, R², L1, and Z are as described for Formula (A-I); and B1 or B6 is
  i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
  ii) Phe(4-F), Phe(4-CF₃), Phe(4-CH₃), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
  iii) -homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In another embodiment, R1 is isovaleric acid or IVA.

In another embodiment, the peptide is according to formula A-XIIIa, A-XIIIb, A-XIIIc, A-XIIId, B-XIIIa, B-XIIIb, B-XIIIc, or B-XIIId:

(A-XIIIa)
(SEQ ID NO: 294)
IVA-Asp-Thr-His-Phe-Pro-Cys-Ile-Lys-B6-

N(H)C[CH₂CH₂CH₂CH₂N(H)L1Z](H)-C(O)-

Cys-R², (A-XIIIb)
(SEQ ID NO: 295)
IVA-Asp-Thr-His-B1-Pro-Cys-Ile-Lys-Phe-

N(H)C[CH₂CH₂CH₂CH₂N(H)L1Z](H)-C(O)-

Cys-R², (A-XIIIc)
(SEQ ID NO: 296)
IVA-Asp-Thr-His-Phe-Pro-Cys-Ile-(D)Lys-B6-

N(H)C[CH₂CH₂CH₂CH₂N(H)L1Z](H)-C(O)-

Cys-R², (A-XIIId)
(SEQ ID NO: 297)
IVA-Asp-Thr-His-B1-Pro-Cys-Ile-(D)Lys-Phe-

N(H)C[CH₂CH₂CH₂CH₂N(H)L1Z](H)-C(O)-

Cys-R², (B-XIIIa)
(SEQ ID NO: 298)
IVA-Asp-Thr-His-Phe-Pro-Cys-Ile-

N(H)C[CH₂CH₂CH₂CH₂N(H)L1Z)](H)-C(O)-B6-Glu-

Cys-R², (B-XIIIb)
(SEQ ID NO: 299)
IVA-Asp-Thr-His-B1-Pro-Cys-Ile-Lys-Phe-

N(H)C[CH₂CH₂CH₂CH₂N(H)L1Z)](H)-C(O)-

Phe-Glu-Cys-R², (B-XIIIc)
(SEQ ID NO: 300)
IVA-Asp-Thr-His-Phe-Pro-Cys-Ile-

N(H)C[CH₂CH₂CH₂CH₂N(H)L1Z)](H)-C(O)-B6-Cys-

R²,
or (B-XIIId)
(SEQ ID NO: 301)
IVA-Asp-Thr-His-B1-Pro-Cys-Ile-

N(H)C[CH₂CH₂CH₂CH₂N(H)L1Z)](H)-C(O)-Phe-Cys-

R² or a peptide dimer thereof, or a pharmaceutically acceptable salt thereof;
wherein R², L1, and Z; are as described for Formula (A-I); IVA is isovaleric acid; and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe(4-F), Phe(4-CF₃), Phe(4-CH₃), Phe(4-tBu), Bip, Phe(4-COOH), Phe(2,4-diCl), Phe(3,4-diCl), Phe(4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In one embodiment, L1 is a single bond or is absent. In another embodiment, L1 is iso-Glu. In another embodiment, L1 is Ahx. In another embodiment, L1 is iso-Glu-Ahx. In another embodiment, L1 is PEG. In another embodiment, L1 is iso-Glu-PEG. In another embodiment, L1 is PEG-Ahx. In another embodiment, L1 is iso-Glu-PEG-Ahx. In another embodiment, L1 is Dapa or D-Dapa.

In another embodiment, PEG is PEG1, PEG2, PEG3, PEG4, PEG53, or PEG11.

In one embodiment, Z is Palm. In another embodiment, B1 is Phe. In another embodiment, B6 is Phe. In another embodiment, the peptide is according to formula A-XIVa, A-XIVb, B-XIVa, or B-XIVb:

(A-XIVa)
(SEQ ID NO: 302)
IVA-Asp-Thr-His-Phe-Pro-Cys-Ile-Lys-Phe-

N(H)C[CH₂CH₂CH₂CH₂N(H)L1Z](H)-C(O)-

Cys-R², (A-XIVb)
(SEQ ID NO: 303)
IVA-Asp-Thr-His-Phe-Pro-Cys-Ile-(D)Lys-

Phe-N(H)C[CH₂CH₂CH₂CH₂N(H)L1Z](H)-

C(O)-Cys-R², (B-XIVa)
(SEQ ID NO: 304)
IVA-Asp-Thr-His-Phe-Pro-Cys-Ile-

N(H)C[CH₂CH₂CH₂CH₂N(H)L1Z](H)-C(O)-Phe-Glu-

Cys-R²,
or (B-XIVb)
(SEQ ID NO: 305)
IVA-Asp-Thr-His-Phe-Pro-Cys-Ile-

N(H)C[CH₂CH₂CH₂CH₂N(H)L1Z](H)-C(O)-Phe-Cys-

R² or a peptide dimer thereof, or a pharmaceutically acceptable salt thereof;
wherein R², L1, and Z, are as described for Formula (A-I); and IVA is isovaleric acid.

In one embodiment, J is X and X is an amino acid selected from Lys, D-Lys, Arg, D-Arg, Pro, His, Orn, Daba, Dapa, or homoLys.

In one embodiment, the peptide is according to formula A-XXIa or A-XXIb:

(A-XXIa)
(SEQ ID NO: 306)
R¹-Asp-Thr-His-Phe-Pro-Cys-Ile-B5-B6-

N(H)C[CH₂CH₂CH₂CH₂N(H)L1Z](H)-C(O)-X-

Cys-Y2-R²

-continued (A-XXIb)
(SEQ ID NO: 307)
R¹-Asp-Thr-His-B1-Pro-Cys-Ile-B5-Phe-

N(H)C[CH₂CH₂CH₂CH₂N(H)L1Z]](H)-C(O)-X-

Cys-Y2-R² or a peptide dimer thereof, or a pharmaceutically acceptable salt thereof;
wherein $R^1$, $R^2$, B5, L1, Y2, and Z, are as described for Formula (A-I); and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe, Phe(4-F), Phe(4-CF₃), Phe(4-CH₃), Phe(4-tBu), Bip, Phe(4-COOH), Phe(2,4-diCl), Phe(3,4-diCl), Phe (4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe (4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In one embodiment, B5 is Lys, D-Lys, Orn, homoSer, Gln, Lys(Ac), Ile, or Nleu. In another embodiment, B5 is Lys, or D-Lys. In another embodiment, B5 is bAla, or D-Ala. In anther embodiment, B5 is Ile. In anther embodiment, B5 is absent.

In another embodiment, the peptide is according to formula A-XXIIa, A-XXIIb, A-XXIIc, or A-XXIId:

(A-XXIIa)
(SEQ ID NO: 308)
R¹-Asp-Thr-His-Phe-Pro-Cys-Ile-Lys-B6-

N(H)C[CH₂CH₂CH₂CH₂N(H)L1Z]](H)-C(O)-X-

Cys-Y2-R²

(A-XXIIb)
(SEQ ID NO: 309)
R¹-Asp-Thr-His-B1-Pro-Cys-Ile-Lys-Phe-

N(H)C[CH₂CH₂CH₂CH₂N(H)L1Z]](H)-C(O)-X-

Cys-Y2-R²

(A-XXIIc)
(SEQ ID NO: 310)
R¹-Asp-Thr-His-Phe-Pro-Cys-Ile-(D)Lys-

B6-N(H)C[CH₂CH₂CH₂CH₂N(H)L1Z]](H)-C(O)-

X-Cys-Y2-R²

(A-XXIId)
(SEQ ID NO: 311)
R¹-Asp-Thr-His-B1-Pro-Cys-Ile-(D)Lys-

Phe-N(H)C[CH₂CH₂CH₂CH₂N(H)L1Z]](H)-

C(O)-X-Cys-Y2-R² or a peptide dimer thereof, or a pharmaceutically acceptable salt thereof;
wherein $R^1$, $R^2$, L1, Y2, and Z, are as described for Formula (A-I); and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe, Phe(4-F), Phe(4-CF₃), Phe(4-CH₃), Phe(4-tBu), Bip, Phe(4-COOH), Phe(2,4-diCl), Phe(3,4-diCl), Phe (4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe (4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In a particular embodiment, R1 is isovaleric acid or IVA.

In one embodiment, the peptide is according to formula A-XXIIIa, A-XXIIIb, A-XXIIIc, or A-XXIIId:

(A-XXIIIa)
(SEQ ID NO: 312)
IVA-Asp-Thr-His-Phe-Pro-Cys-Ile-Lys-B6-

N(H)C[CH₂CH₂CH₂CH₂N(H)L1Z]](H)-C(O)-X-

Cys-Y2-R²

(A-XXIIIb)
(SEQ ID NO: 313)
IVA-Asp-Thr-His-B1-Pro-Cys-Ile-Lys-Phe-

N(H)C[CH₂CH₂CH₂CH₂N(H)L1Z]](H)-C(O)-X-

Cys-Y2-R2

(A-XXIIIc)
(SEQ ID NO: 314)
IVA-Asp-Thr-His-Phe-Pro-Cys-Ile-(D)Lys-

B6-N(H)C[CH₂CH₂CH₂CH₂N(H)L1Z]](H)-C(O)-

X-Cys-Y2-R²

(A-XXIIId)
(SEQ ID NO: 315)
IVA-Asp-Thr-His-B1-Pro-Cys-Ile-(D)Lys-

Phe-N(H)C[CH₂CH₂CH₂CH₂N(H)L1Z]](H)-C(O)-

X-Cys-Y2-R² or a peptide dimer thereof, or a pharmaceutically acceptable salt thereof;
wherein $R^2$, L1, Y2, and Z, are as described for Formula (A-I); IVA is isovaleric acid; and B1 or B6 is
i) 2-Nal, 1-Nal, D-1-Nal, D-2-Nal, 3,3-DiPhenylGly, Tic, Trp, bhTrp, HomoPhe, N-Me-Phe, (D)N-Me-Phe, or Tyr(Me);
ii) Phe, Phe(4-F), Phe(4-CF₃), Phe(4-CH₃), Phe(4-tBu), Bip, Phe(4-COOH), Phe(2,4-diCl), Phe(3,4-diCl), Phe (4-carbomyl), Phe(3-carbomyl), Phe(3,4-dimethoxy), Phe(4-CN), β-homoPhe, a substituted β-homoPhe; or
iii) β-homoPhe(2-Me), β-homoPhe(3-Me), β-homoPhe (4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), or β-homoPhe(4-NO2).

In one embodiment, B1 is Phe. In another embodiment, B6 is Phe.

In one embodiment, B1 is Phe; and B6 is Phe, Dpa, bhPhe, Nap, or hPhe. In another embodiment, B1 is Dpa; and B6 is Phe, Dpa, bhPhe, Nap, or hPhe.

In another embodiment, B6 is Dpa, bhPhe, hPhe, or Nal. In anther embodiment, B6 is Dpa. In another embodiment, B6 is bhPhe. In another embodiment, B6 is hPhe or homoPhe.

In one embodiment, the peptide is according to formula A-XXIVa, or A-XXIVb:

```
                                    (SEQ ID NO: 316)
IVA-Asp-Thr-His-Phe-Pro-Cys-Ile-Lys-Phe-N(H)C

[CH₂CH₂CH₂CH₂N(H)LIZ](H)—C(O)—X-Cys-Y2-R²  (A-XXIVa)

(SEQ ID NO: 317)
IVA-Asp-Thr-His-Phe-Pro-Cys-Ile-(D)Lys-Phe-N(H)C

[CH₂CH₂CH₂CH₂N(H)LIZ](H)—C(O)—X-Cys-Y2-R²(A-XXIVb)
``` or a peptide dimer thereof, or a pharmaceutically acceptable salt thereof;
wherein R², L1, Y2, and Z, are as described for Formula (A-I); and IVA is isovaleric acid.

In one embodiment, Y2 is absent, Lys, (D)Lys, His, (D)His, Arg, or (D)Arg. In another embodiment, Y2 is Lys, (D)Lys, His, (D)His, Arg, or (D)Arg.

In a particular embodiment, Y2 is absent.

In one embodiment, the peptide is according to formula A-XXVa, or A-XXVb:

```
                                    (SEQ ID NO: 318)
IVA-Asp-Thr-His-Phe-Pro-Cys-Ile-Lys-Phe-N(H)C

[CH₂CH₂CH₂CH₂N(H)LIZ](H)—C(O)—X-Cys-R²  (A-XXVa)

(SEQ ID NO: 319)
IVA-Asp-Thr-His-Phe-Pro-Cys-Ile-(D)Lys-Phe-N(H)C

[CH₂CH₂CH₂CH₂N(H)LIZ](H)—C(O)—X-Cys-R²  (A-XXVb)
``` or a peptide dimer thereof, or a pharmaceutically acceptable salt thereof;
wherein R², L1, and Z, are as described for Formula (A-I); and IVA is isovaleric acid.

In one embodiment, X is His, Pro, Lys, D-Lys, Arg, or D-Arg. In another embodiment, X is Lys, or D-Lys. In another embodiment, X is Lys. In another embodiment, X is D-Lys. In another embodiment, X is Pro. In another embodiment, X is His. In another embodiment, X is Dapa. In another embodiment, X is Orn. In another embodiment, X is Daba. In another embodiment, X is homoLys.

In a particular embodiment, with respect to the peptide according to formula A-I, B1 is F, Dpa, BIP, or bhPhe; B2 is Pro, NCP, (D)Pro, or (D)NCP; B3 is Cys, a-MeCys, or homoCys; B4 is Ile; B5 is D)Lys, bAla, (D)Gln, (D)Ala, Orn, or Ile; B6 is Phe, substituted Phe, or bhPhe; and B7 is Lys, (D)Lys, or Dap.

In a more particular embodiment, with respect to the peptide according to formula A-I, B2 is Pro, B3 is Cys, B4 is Ile, and B6 is Phe or bhPhe.

In a more particular embodiment, with respect to the peptide according to formula A-I, B7(L1Z) is —N(H)C[CH₂(CH₂CH₂CH₂)ₘN(H)L1Z](H)—C(O)—; and wherein m is 0 or 1.

In one embodiment, with respect to the peptide according to formula A-I, B7(L1Z) is —N(H)C[CH₂N(H)L1Z](H)—C(O)—.

In a most particular embodiment, with respect to the peptide according to formula A-I, B7(L1Z) is —N(H)C[CH₂CH₂CH₂CH₂N(H)L1Z](H)—C(O)—.

In a particular aspect, the present invention provides hepcidin analogue comprising a peptide according to formula C-Ia or C-Ib:

```
                                          (SEQ ID NO: 320)
R¹-Asp-Thr-His-B1-Pro-Cys-Ile-B5-B6-N(H)C[CH₂N(H)

LIZ](H)-C(O)-J-Y1-Y2-R²  (C-Ia),
or
                                          (SEQ ID NO: 321)
R¹-Asp-Thr-His-B1-Pro-Cys-Ile-B5-B6-N(H)C

[CH₂CH₂CH₂CH₂N(H)LIZ](H)-C(O)-J-Y1-Y2-R² (C-Ib)
``` or a peptide dimer thereof, or a pharmaceutically acceptable salt thereof;
wherein R¹, R², L1, Z, J, Y1, and Y2 are as described for for Formula (A-I); and
B1 is F, b-hPhe, or Dpa; B5 is (D)Lys, bAla, (D)Gln, (D)Ala, or Ile; and B6 is Phe, Phe(4-t-Bu), or bhPhe.

In one embodiment, B5 is (D)Lys. In another embodiment, B5 is bAla. In another embodiment, B5 is (D)Ala. In another embodiment, B5 is (D)Gln. In another embodiment, B5 is Ile.

In a more particular embodiment B5 is (D)Lys.

In one embodiment, the peptide is according to formula C-IIa or C-IIb:

```
                                          (SEQ ID NO: 322)
R¹-Asp-Thr-His-B1-Pro-Cys-Ile-(D)Lys-B6-N(H)C

[CH₂N(H)LIZ](H)-C(O)-J-Y1-Y2-R² (C-IIa),
or
                                          (SEQ ID NO: 323)
R¹-Asp-Thr-His-B1-Pro-Cys-Ile-(D)Lys-B6-N(H)C

[CH₂CH₂CH₂CH₂N(H)LIZ](H)-C(O)-J-Y1-Y2-R² (C-IIb),
``` or a peptide dimer thereof, or a pharmaceutically acceptable salt thereof;
wherein R¹, R², L1, Z, J, Y1, and Y2 are as described for for Formula (A-I); and
B1 is F, b-hPhe, or Dpa; and B6 is Phe, Phe(4-t-Bu), or bhPhe.

In a more particular embodiment B1 is F. In another embodiment, B1 is Dpa. In another embodiment, B1 is b-hPhe.

In one embodiment, the peptide is according to formula C-IIIa or C-IIIb:

```
                                          (SEQ ID NO: 324)
R¹-Asp-Thr-His-F-Pro-Cys-Ile-(D)Lys-B6-N(H)C

[CH₂CH₂CH₂CH₂N(H)LIZ](H)-C(O)-J-Y1-Y2-R² (C-IIIa),
or
                                          (SEQ ID NO: 325)
R¹-Asp-Thr-His-Dpa-Pro-Cys-Ile-(D)Lys-B6-N(H)C

[CH₂CH₂CH₂CH₂N(H)LIZ](H)-C(O)-J-Y1-Y2-R² (C-IIIb),
``` or a peptide dimer thereof, or a pharmaceutically acceptable salt thereof;
wherein R¹, R², L1, Z, J, Y1, and Y2 are as described for Formula (A-I); and B6 is Phe Phe(4-t-Bu), or bhPhe.

In a more particular embodiment B6 is Phe. In another embodiment, B6 is bhPhe. In another embodiment, B6 is Phe(4-t-Bu).

In one embodiment, the peptide is according to formula C-IVa, C-IVb, C-IVc, or C-IVd:

```
                                          (SEQ ID NO: 326)
R¹-Asp-Thr-His-F-Pro-Cys-Ile-(D)Lys-Phe-N(H)C
```

-continued

[CH₂CH₂CH₂CH₂N(H)L1Z](H)-C(O)-J-Y1-Y2-R² (C-IVa), (SEQ ID NO: 327)
R¹-Asp-Thr-His-Dpa-Pro-Cys-Ile-(D)Lys-Phe-N(H)C

[CH₂CH₂CH₂CH₂N(H)L1Z](H)-C(O)-J-Y1-Y2-R² (C-IVb), (SEQ ID NO: 328)
R¹-Asp-Thr-His-F-Pro-Cys-Ile-(D)Lys-bhPhe-N(H)C

[CH₂CH₂CH₂CH₂N(H)L1Z](H)-C(O)-J-Y1-Y2-R² (C-IVc), (SEQ ID NO: 329)
R¹-Asp-Thr-His-Dpa-Pro-Cys-Ile-(D)Lys-bhPhe-N(H)C

[CH₂CH₂CH₂CH₂N(H)L1Z](H)-C(O)-J-Y1-Y2-R² (C-IVd), or a peptide dimer thereof, or a pharmaceutically acceptable salt thereof;
wherein R¹, R², L1, Z, J, Y1, and Y2 are as described for Formula (A-I).

In one embodiment, with respective to the peptide of invention, Asp of -Asp-Thr-His-B1- is replaced with dAsp.

In one embodiment, with respective to the peptide of invention, Pro of -Asp-Thr-His-B1-Pro-Cys-Ile-B5-B6- is replaced with dPro, or Npc.

In a particular embodiment, with respective to the peptide of invention, the peptide is cyclized via a disulfide bond between two Cys.

In one embodiment, with respective to the peptide of invention, —N(H)C[CH₂N(H)L1Z](H)—C(O)— is an L-amino acid. In another embodiment, with respective to the peptide of invention, —N(H)C[CH₂N(H)L1Z](H)—C(O)— is an D-amino acid.

In one embodiment, with respective to the peptide of invention, —N(H)C[CH₂CH₂CH₂CH₂N(H)L1Z](H)—C(O)— is an L-amino acid. In another embodiment, with respective to the peptide of invention, —N(H)C[CH₂CH₂CH₂CH₂N(H)L1Z](H)—C(O)— is an D-amino acid.

In one embodiment, -J-Y1-Y2- is -Cys-, -Pro-Cys-, -Lys-Cys-, -(D)Lys-Cys-, -Dap-Cys-, -Cys-(D)Lys-, -Dap-hCys-, -Pro-Arg-Cys-, -Pro-Arg-Ser-Cys-(SEQ ID NO:253), -Pro-Arg-Ser-Lys-Cys-(SEQ ID NO:254), or -Pro-Arg-Ser-Lys-Sar-Cys-(SEQ ID NO:255).

In one embodiment, -J-Y1-Y2- is -Cys-, -Pro-Cys-, -Lys-Cys-, -(D)Lys-Cys-, -Dap-Cys-, -Cys-(D)Lys-, -Dap-hCys-, -Pro-Arg-Cys-, -Pro-Arg-Ser-Cys-(SEQ ID NO:253), or -Pro-Arg-Ser-Lys-Cys-(SEQ ID NO:254).

In one embodiment, -J-Y1-Y2- is -Cys-, -Pro-Cys-, -Pro-Lys-Cys-, -Pro-(D)Lys-Cys-, -Lys-Cys-, -(D)Lys-Cys-, -Dap-Cys-, -Cys-(D)Lys-, -Dap-hCys-, -Pro-Arg-Cys-, or -Pro-Arg-Ser-Cys-(SEQ ID NO:253).

In another embodiment, -J-Y1-Y2- is -(D)Lys-Cys- or -Lys-Cys-.

In another embodiment, -J-Y1-Y2- is -Cys-(D)Lys-.

In another embodiment, -J-Y1-Y2- is -Pro-Arg-Ser-Lys-Cys-(SEQ ID NO:254).

In another embodiment, -J-Y1-Y2- is -Pro-Arg-Ser-Lys-Cys-Lys-(SEQ ID NO:255).

In another embodiment, -J-Y1-Y2- is -Pro-Cys -.

In another embodiment, -J-Y1-Y2- is -Cys -.

In another embodiment, -J-Y1-Y2- is -(D)Lys-Pen -.

In one embodiment, R² is NH₂. In another embodiment, R² is OH.

In one embodiment, L1 is a single bond. In another embodiment, L1 is iso-Glu. In another embodiment, L1 is Ahx. In another embodiment, L1 is iso-Glu-Ahx. In another embodiment, PEG. In another embodiment, L1 is iso-Glu-PEG. In another embodiment, L1 is PEG-Ahx. In another embodiment, L1 is iso-Glu-PEG-Ahx. In another embodiment, PEG is PEG1, PEG2, PEG3, PEG4, PEG53, or PEG11. In another embodiment, Z is Palm.

In another embodiment, L1 is Ahx; and Z is Palm.
In another embodiment, L1 is PEG11; and Z is Palm.
In another embodiment, L1 is Dap; and Z is Palm.
In another embodiment, L1 is dDap; and Z is Palm.

In a particular embodiment, the peptide is according to formula (A-I):

R¹-Asp-Thr-His-B1-B2-B3-B4-B5-B6-B7(L1Z)-J-Y1-Y2-R² (A-I)

wherein the peptide comprises any of the combinations of B1, B2, B3, B4, B5, B6, B7(L1Z), J, Y1 and Y2 set forth in a row of Table 2A, wherein R¹ is IVA, R² is NH₂, and "abs" indicates "absent". The accompanying sequence identifiers represent the amino acid sequence of peptides according to formula (A-I) having the amino acids indicated for each row Table 2A and indicating the indicated conjugated half-life extension moiety when present.

TABLE 2A

| SEQ ID NO. | B1 | B2 | B3 | B4 | B5 | B6 | B7(L1Z) | J | Y1 | Y2 |
|---|---|---|---|---|---|---|---|---|---|---|
| 3 | F | P | C | I | K | F | K(PEG11-Palm) | PRSKG | C | abs |
| 4 | F | P | C | I | K | F | K(PEG11-Palm) | PRSK | C | abs |
| 5 | F | P | C | I | K | F | K(PEG11-Palm) | PRS | C | abs |
| 6 | F | P | C | I | K | F | K(PEG11-Palm) | PR | C | abs |
| 7 | F | P | C | I | K | F | K(PEG11-Palm) | P | C | abs |
| 8 | F | P | C | I | K | F | K(PEG11-Palm) | abs | C | abs |
| 9 | F | P | C | I | K | F | K(PEG11-Palm) | P | C | K |
| 8 | F | P | C | I | K | F | K(PEG11-Palm) | abs | C | abs |
| 10 | F | P | C | I | (D)Lys | F | K(PEG11-Palm) | abs | C | abs |
| 11 | F | P | C | I | Orn | F | K(PEG11-Palm) | abs | C | abs |
| 12 | F | P | C | I | hSer | F | K(PEG11-Palm) | abs | C | abs |
| 13 | F | P | C | I | Q | F | K(PEG11-Palm) | abs | C | abs |
| 14 | F | P | C | I | K(Ac) | F | K(PEG11-Palm) | abs | C | abs |
| 15 | F | P | C | I | Nleu | F | K(PEG11-Palm) | abs | C | abs |
| 16 | F | P | C | I | I | F | K(PEG11-Palm) | abs | C | abs |
| 17 | F | P | C | I | K | NMePhe | K(PEG11-Palm) | abs | C | abs |
| 18 | F | P | C | I | K | aMePhe | K(PEG11-Palm) | abs | C | abs |
| 19 | F | P | C | I | K | bhPhe | K(PEG11-Palm) | abs | C | abs |
| 20 | F | P | C | I | K | W | K(PEG11-Palm) | abs | C | abs |

TABLE 2A-continued

| SEQ ID NO. | B1 | B2 | B3 | B4 | B5 | B6 | B7(L1Z) | J | Y1 | Y2 |
|---|---|---|---|---|---|---|---|---|---|---|
| 21 | F | P | C | I | (D)Lys | F | K(Peg8-Palm) | abs | C | abs |
| 22 | F | P | C | I | (D)Lys | F | K(PEG4-Palm) | abs | C | abs |
| 23 | F | P | C | I | (D)Lys | F | K(PEG2-Palm) | abs | C | abs |
| 24 | F | P | C | I | (D)Lys | F | K(PEG1-Palm) | abs | C | abs |
| 25 | F | P | C | I | (D)Lys | F | K(Ahx-Palm) | abs | C | abs |
| 26 | F | P | C | I | (D)Lys | F | K(PEG2-IsoGlu-Palm) | abs | C | abs |
| 27 | F | P | C | I | (D)Lys | F | K(IsoGlu-Palm) | abs | C | abs |
| 28 | F | P | C | I | (D)Lys | F | K(IsoGlu-Peg2-Palm) | abs | C | abs |
| 29 | F | P | C | I | (D)Lys | F | K(Peg2-Ahx-Palm) | abs | C | abs |
| 30 | F | P | C | I | (D)Lys | F | K(Palm) | abs | C | abs |
| 33 | F | NPC | C | I | (D)Lys | F | K(PEG11-Palm) | abs | C | abs |
| 34 | F | (D)NPC | C | I | (D)Lys | F | K(PEG11-Palm) | abs | C | abs |
| 35 | F | (D)Pro | C | I | (D)Lys | F | K(PEG11-Palm) | abs | C | abs |
| 36 | F | (D)bhPro | C | I | (D)Lys | F | K(PEG11-Palm) | abs | C | abs |
| 37 | F | bhPro | C | I | (D)Lys | F | K(PEG11-Palm) | abs | C | abs |
| 10 | F | P | C | I | (D)Lys | F | K(PEG11-Palm) | abs | C | abs |
| 38 | BIP | P | C | I | (D)Lys | F | K(PEG11-Palm) | abs | C | abs |
| 135 | Dpa | P | C | I | (D)Lys | F | K(PEG11-Palm) | abs | C | abs |
| 135 | Dpa | P | C | I | (D)Lys | F | K(PEG11-Palm) | abs | C | abs |
| 67 | F | P | C(SH) | I | K | F | K(PEG11-Palm) | P | C(SH) | abs |
| 68 | F | P | C(SH) | I | K | F | K(PEG11-Palm) |  | C(SH) | abs |
| 69 | F | P | C(SH) | I | K | F | K(PEG11-Palm) |  | C(SH) | abs |
| 70 | F | P | C | I | (D)Lys | F | K(PEG11-Palm) | P | C | abs |
| 71 | F | P | C | I | (D)Lys | F | K(PEG11-Palm) | PR | C | abs |
| 72 | F | P | C | I | (D)Lys | F | K(PEG11-Palm) | PRS | C | abs |
| 73 | F | P | C | I | (D)Lys | F | K(PEG11-Palm) | PRSK | C | abs |
| 74 | F | P | C | I | (D)Lys | F | K(PEG11-Palm) | PRSKSar | C | abs |
| 75 | F | P | C | I | (D)Lys | F | K(PEG11-Palm) | PRSK | C | K |
| 76 | F | P | C | I | (D)Lys | F | K(PEG11-Palm) | PRS | C | K |
| 77 | F | P | C | I | (D)Lys | F | K(PEG11-Palm) | PR | C | K |
| 78 | F | P | C | I | (D)Lys | F | K(PEG11-Palm) |  | C | K |
| 79 | F | P | C | I | (D)Lys | F | K(PEG11-Palm) | R | C | abs |
| 80 | F | P | C | I | (D)Lys | F | K(PEG11-Palm) | K | C | abs |
| 81 | F | P | C | I | (D)Lys | F | K(PEG11-Palm) | r | C | abs |
| 82 | F | P | C | I | (D)Lys | F | K(PEG11-Palm) | (D)Lys | C | abs |
| 83 | F | P | C | I | (D)Lys | F | K(PEG11-Palm) | K | C | (D)Lys |
| 84 | F | P | C | I | (D)Lys | F | K(PEG11-Palm) | H | C | h |
| 85 | F | P | C | I | (D)Lys | F | K(PEG11-Palm) | R | C | r |
| 86 | F | P | C | I | (D)Lys | F | K(Ahx-Palm) | K | C | abs |
| 87 | F | P | C | I | (D)Lys | F | K(PEG2-Palm) | K | C | abs |
| 88 | F | P | C | I | (D)Lys | F | K(PEG2-PEG2-Palm) | K | C | abs |
| 89 | F | P | C | I | (D)Lys | F | K(PEG2-PEG2-C18 acid) | K | C | abs |
| 90 | F | P | C | I | (D)Lys | F | K(PEG2-PEG2-Ahx-Palm) | K | C | abs |
| 91 | F | P | C | I | (D)Lys | F | K(PEG4-Palm) | K | C | abs |
| 92 | F | P | C | I | (D)Lys | F | K(PEG4-Ahx-Palm) | K | C | abs |
| 93 | F | P | C | I | (D)Lys | F | K(PEG4-PEG4-Palm) | K | C | abs |
| 94 | F | P | C | I | (D)Lys | F | K(PEG4-isoGlu-Palm) | K | C | abs |
| 95 | F | P | C | I | (D)Lys | F | K(PEG8-Palm) | K | C | abs |
| 96 | F | P | C | I | (D)Lys | F | K(Behenic acid) | K | C | abs |
| 97 | F | P | C | I | (D)Lys | F | K(PEG11-Palm) | K | c | abs |
| 98 | F | P | C | I | (D)Lys | F | K(PEG11-Palm) | K | Pen | abs |
| 99 | F | P | C | I | (D)Lys | F | K(PEG11-Palm) | Dap | C | abs |
| 100 | F | P | C | I | (D)Lys | Dpa | K(PEG11-Palm) | K | C | abs |
| 101 | F | P | C | I | (D)Lys | bhPhe | K(PEG11-Palm) | K | C | abs |
| 102 | F | P | C | I | (D)Lys | 2-Nal | K(PEG11-Palm) | K | C | abs |
| 103 | F | P | C | I | (D)Lys | bhPhe | K(PEG11-Palm) | K | C | abs |
| 104 | Dpa | P | C | I | (D)Lys | F | K(PEG11-Palm) | K | C | abs |
| 105 | Dpa | P | C | I | (D)Lys | bhPhe | K(PEG11-Palm) | (D)Lys | C | abs |
| 99 | F | P | C | I | (D)Lys | F | K(PEG11-Palm) | Dap | C | abs |
| 107 | F | P | C | I | (D)Lys | F | k(PEG11-Palm) | (D)Lys | C | abs |
| 110 | Dpa | Npc | C | I | (D)Lys | Phe(4-tBu) | K(PEG11-Palm) | K | C | abs |
| 111 | Dpa | Npc | C | I | (D)Lys | Phe(4-(2-aminoethoxy)) | K(PEG11-Palm) | K | C | abs |
| 112 | Dpa | Npc | C | I | (D)Lys | 2-Nal | K(PEG11-Palm) | K | C | abs |
| 113 | Dpa | Npc | C | I | (D)Lys | Phe(4-COOH) | K(PEG11-Palm) | K | C | abs |
| 114 | F | P | C | I | (D)Lys | F | K(PEG11-Palm) | K | (a-Me)C | abs |
| 115 | F | P | (a-Me)C | I | (D)Lys | F | K(PEG11-Palm) | K | (a-Me)C | abs |
| 116 | F | P | (a-Me)C | I | (D)Lys | F | K(PEG11-Palm) | K | C | abs |

TABLE 2A-continued

| SEQ ID NO. | B1 | B2 | B3 | B4 | B5 | B6 | B7(L1Z) | J | Y1 | Y2 |
|---|---|---|---|---|---|---|---|---|---|---|
| 117 | Dpa | Npc | C | I | (D)Lys | F | K(PEG11-Palm) | (D)Lys | C | abs |
| 118 | F | Npc | C | I | (D)Lys | F | K(PEG11-Palm) | (D)Lys | C | abs |
| 119 | Dpa | bhPhe | C | I | (D)Lys | F | K(PEG11-Palm) | (D)Lys | C | abs |
| 120 | Phe(4-COOH) | P | C | I | (D)Lys | F | K(PEG11-Palm) | (D)Lys | C | abs |
| 121 | bhPhe | P | C | I | (D)Lys | F | K(PEG11-Palm) | (D)Lys | C | abs |
| 122 | Dpa | P | C | I | (D)Lys | bhPhe | K(PEG11-Palm) | (D)Lys | C | abs |
| 125 | Dpa | Npc | C | I | (D)Lys | (a-MePhe) | K(PEG11-Palm) | K | C | abs |
| 126 | Dpa | Npc | C | I | (D)Lys | Phe(4-CN) | K(PEG11-Palm) | K | C | abs |
| 127 | Dpa | Npc | C | I | (D)Lys | Phe(3,4-diF) | K(PEG11-Palm) | K | C | abs |
| 128 | (a-MePhe) | P | C | I | (D)Lys | F | K(PEG11-Palm) | (D)Lys | C | abs |
| 129 | Phe(4-(2-aminoethoxy)) | P | C | I | (D)Lys | F | K(PEG11-Palm) | (D)Lys | C | abs |
| 130 | Dpa | P | C | I | (D)Lys | F | K(PEG11-Palm) | (D)Lys | C | abs |
| 131 | Dpa | P | C | I | (D)Lys | Dpa | K(PEG11-Palm) | (D)Lys | C | abs |
| 132 | Dpa | P | C | I | (D)Lys | F | K(PEG11-Palm) | (D)Lys | Pen | abs |
| 133 | Dpa | P | C | I | (D)Lys | F | K(Peg11-Palm) | K | N-Me-Cys | abs |
| 134 | Dpa | P | C | I | (D)Lys | F | K(Peg11-Palm) | (D)Lys | N-Me-Cys | abs |
| 135 | Dpa | P | C | I | (D)Lys | F | K(Peg11-Palm) | C | | abs |
| 136 | Dpa | P | C | I | (D)Lys | F | K(Peg11-Palm) | Orn | C | abs |
| 137 | Dpa | P | C | I | (D)Lys | F | K(Peg11-Palm) | Dab | C | abs |
| 138 | Dpa | P | C | I | (D)Lys | F | K(Peg11-Palm) | b-hLys | C | abs |
| 139 | Dpa | P | C | I | (D)Lys | F | K(Peg11-Palm) | (D)Lys | C | abs |
| 140 | Dpa | P | C | I | (D)Lys | F | K(Peg11-Palm) | Dap | Pen | abs |
| 141 | Dpa | P | hCys | I | (D)Lys | F | K(Peg11-Palm) | Dap | C | abs |
| 142 | Dpa | P | hCys | I | (D)Lys | F | K(Peg11-Palm) | Dap | hCys | abs |
| 143 | Dpa | P | C | I | (D)Lys | F | K(Peg11-Palm) | Dap | hCys | abs |
| 144 | F | P | C | I | (D)Lys | F | K(Peg11-Palm) | | C | K |
| 145 | Dpa | P | C | I | bAla | bhPhe | K(Peg11-Palm) | (D)Lys | C | abs |
| 146 | Dpa | P | C | I | (D)Ala | bhPhe | K(Peg11-Palm) | (D)Lys | C | abs |
| 147 | Dpa | P | C | I | I | bhPhe | K(Peg11-Palm) | (D)Lys | C | abs |
| 148 | Dpa | P | C | I | abs | bhPhe | K(Peg11-Palm) | (D)Lys | C | abs |
| 149 | Dpa | Npc | C | I | (D)Lys | Phe(4-tBu) | K(Peg11-Palm) | (D)Lys | C | abs |
| 150 | Dpa | Npc | C | I | (D)Lys | Phe(4-tBu) | K(Peg11-Palm) | abs | C | (D)Lys |
| 182 | Dpa | Npc | C | I | (D)Lys | Phe(4-tBu) | (D)Lys | abs | C | Lys(Peg11-Palm) |
| 151 | Dpa | P | C | I | (D)Lys | bhPhe | K(Ahx-Palm) | Dap | N-Me-Cys | abs |
| 152 | Dpa | P | C | I | (D)Lys | bhPhe | K(Ac) | (D)Lys | C | abs |
| 153 | Dpa | P | C | I | (D)Lys-Peg11* | bhPhe | K(Peg11-Palm) | (D)Lys-Peg11* | C | abs |
| 154 | Dpa | P | C | I | (D)Lys | bhPhe | K(Peg11) | (D)Lys | C | abs |
| 155 | Dpa | P | C | I | (D)Lys | bhPhe | K(Peg11-Octane) | (D)Lys | C | abs |
| 156 | Dpa | P | C | I | (D)Lys | bhPhe | K(Peg11-Lauryl) | (D)Lys | C | abs |
| 157 | Dpa | P | C | I | (D)Lys | bhPhe | K(Peg11*) | (D)Lys | C | abs |
| 158 | Dpa | P | C | I | (D)Lys | bhPhe | K(IsoGlu-Palm) | (D)Lys | C | abs |
| 159 | Dpa | P | C | I | (D)Lys-Ac | bhPhe | K(Peg11-Palm) | (D)Lys-Ac | C | abs |
| 160 | Dpa | P | C | I | (D)Lys | bhPhe | K(Dap-Palm) | abs | C | abs |
| 161 | Dpa | P | C | I | (D)Lys | bhPhe | K(dDap-Palm) | abs | C | abs |
| 162 | Dpa | P | C | I | (D)Lys | bhPhe | Dap(Dap-Palm) | abs | C | abs |
| 163 | Dpa | P | C | I | (D)Lys | bhPhe | Dap(dDap-Palm) | abs | C | abs |
| 164 | Dpa | P | C | I | (D)Lys | bhPhe | Dap(dDap-Palm) | abs | C | abs |
| 165 | Dpa | P | C | I | (D)Lys | bhPhe | K(Ahx-Palm) | (D)Lys | C | abs |
| 166 | Dpa | P | C | I | (D)Lys-Peg11* | bhPhe | K(Ahx-Palm) | (D)Lys-Peg11* | C | abs |
| 167 | Dpa | (D)Pro | C | I | (D)Lys | F | K(Peg11-Palm) | (D)Lys | C | abs |
| 168 | bhPhe | (D)Pro | C | I | (D)Lys | F | K(Peg11-Palm) | (D)Lys | C | abs |
| 169 | Dpa** | P | C | I | (D)Lys | bhPhe | K(Peg11-Palm) | (D)Lys | C | abs |
| 170 | Dpa | P | C | I | (D)Lys | bhPhe | K(Peg11-Palm) | abs | C | (D)Lys |
| 171 | bhPhe | P | C | I | (D)Lys | F | K(Peg11-Palm) | abs | C | (D)Lys |
| 172 | bhPhe | Npc | C | I | (D)Lys | F | K(Peg11-Palm) | abs | C | (D)Lys |
| 173 | Dpa | Npc | C | I | (D)Lys | bhPhe | K(Peg11-Palm) | abs | C | (D)Lys |
| 174 | Dpa | P | C | I | dQ | bhPhe | K(Peg11-Palm) | (D)Lys | C | abs |
| 175 | Dpa | P | C | I | (D)Lys | bhPhe | K(Peg11-Palm) | (D)Lys_Ac | C | abs |
| 176 | bhPhe | dP | C | I | (D)Lys | bhPhe | K(Peg11-Palm) | abs | C | (D)Lys |

*PEG11-OMe,
**Asp of "R¹-Asp-Thr-His- . . ." is D-aspartic acid instead of L-. or a peptide dimer thereof; and wherein the peptide is cyclized via a disulfide bond between B3 and Y1.

In a particular embodiment, the peptide is according to formula (B-I):

(SEQ ID NO: 329)
R¹-Asp-Thr-His-B1-B2-B3-B4-B5(L1Z)-B6-B7-J-
Y1-Y2-R² (B-I)

the peptide comprises any of the combinations of B1, B2, B3, B4, B5, B6, B7(L1Z), J, Y1 and Y2 set forth in a row of Table 2B, wherein R¹ is IVA, R² is NH₂, and "abs" indicates "absent."

TABLE 2B

| SEQ ID NO | B1 | B2 | B3 | B4 | B5(L1Z) | B6 | B7 | J | Y1 | Y2 |
|---|---|---|---|---|---|---|---|---|---|---|
| 201 | F | P | C | I | K(isoGlu-Palm) | F | E | PRSKG | C | abs |
| 202 | F | P | C | I | K(isoGlu-Palm) | F | E | PRSK | C | abs |
| 203 | F | P | C | I | K(isoGlu-Palm) | F | E | PRS | C | abs |
| 204 | F | P | C | I | K(isoGlu-Palm) | F | E | PR | C | abs |
| 205 | F | P | C | I | K(isoGlu-Palm) | F | E | P | C | abs |
| 206 | F | P | C | I | K(isoGlu-Palm) | F | E | abs | C | abs |
| 207 | F | P | C | I | K(isoGlu-Palm) | F | abs | abs | C | abs |
| 183 | F | P | C | I | K(isoGlu-Palm) | F | E | PK | C | abs |
| 184 | F | P | C | I | K(isoGlu-Palm) | F | E | (D)Lys | C | abs |
| 210 | F | P | C | I | K(isoGlu-Palm) | F | abs | abs | C | K |
| 211 | F | P | C | I | K(isoGlu-Palm) | F | abs | R | C | K |
| 212 | F | P | C | I | dk[isoGlu-Palm] | NMePhe | abs | G | C | abs |
| 185 | F | P | C | I | dk[isoGlu-Palm] | F | abs | G | C | abs |
| 214 | F | P | C | I | K(isoGlu-Palm) | bhPhe | abs | abs | C | abs |
| 215 | F | P | C | I | K(isoGlu-Palm) | aMePhe | abs | abs | C | abs |
| 216 | DPA | P | C | I | K(isoGlu-Palm) | aMePhe | abs | abs | C | abs |
| 217 | aMePhe | P | C | I | K(isoGlu-Palm) | aMePhe | abs | abs | C | abs |
| 218 | NMePhe | P | C | I | K(isoGlu-Palm) | aMePhe | abs | abs | C | abs |
| 219 | bhPhe | P | C | I | K(isoGlu-Palm) | aMePhe | abs | abs | C | abs |
| 220 | W | P | C | I | K(isoGlu-Palm) | aMePhe | abs | abs | C | abs |
| 221 | F | Npc | C | I | K(isoGlu-Palm) | aMePhe | abs | abs | C | abs |
| 222 | F | P | C | I | K(Peg11-Palm) | F | abs | abs | C | abs |
| 223 | F | P | C | I | K(isoGlu-Palm) | F | abs | abs | C | abs |
| 224 | F | P | C | I | (D)Lys(Peg11-Palm) | F | abs | K | C | abs |
| 225 | F | P | C | I | (D)Lys (Peg11-Palm) | F | abs | (D)Lys | C | abs |
| 226 | F | P | C | I | (D)Lys (Peg11-Palm) | F | (D)Arg | abs | C | Lys |
| 227 | F | P | C | I | K(isoGlu-Palm) | F | abs | K | C | abs |
| 228 | Dpa | P | C | I | K(Peg11-Palm) | bhPhe | abs | (D)Lys | C | abs |
| 229 | Dpa | P | C | I | Lys(Ahx-Palm) | bhPhe | abs | abs | C | abs |
| 230 | Dpa | P | C | I | Lys(Ahx-Palm) | bhPhe | abs | (D)Lys | C | abs | or a dimer thereof; and wherein the peptide is cyclized via a disulfide bond between B3 and Y1.

Particular embodiments of hepcidin analogues comprises a peptide according to the following illustrative structure:

Formula Ia (SEQ ID NO: 330)

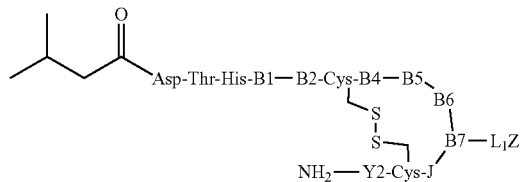

In certain embodiments of any of the peptide analogues having any of the various Formulae set forth herein, R¹ is selected from methyl, acetyl, formyl, benzoyl, trifluoroacetyl, isovaleryl, isobutyryl, octanyl, and conjugated amides of lauric acid, hexadecanoic acid, and γ-Glu-hexadecanoic acid.

In certain embodiments, the linker between the peptide and the half-life extension moiety is PEG11, Ahx, or any of the others described herein.

In certain embodiments, the half-life extension moiety is Palm.

In certain embodiment, the present invention includes a polypeptide comprising an amino acid sequence set forth in any of Tables 2A, 2B, 3A, 3B, and 4 (with or without the indicated linker moieties and half-life extension moieties), or having any amino acid sequence with at least 85%, at least 90%, at least 92%, at least 94%, or at least 95% identity to any of these amino acid sequences.

In certain embodiment, the present invention provides a cyclized form of any one of the hepcidin analogues disclosed herein or listed in any of Tables 2A, 2B, 3A, 3B, and 4, comprising a disulfide bond between the two Cys and/or Pen residues. The conjugated half-life extension moiety and the amino acid residue to which it is conjugated are indicated by parentheses and brackets, respectively. Compound ID numbers are indicated by "Compd ID," and reference compounds are indicated by "Ref. Compd."

TABLE 3A

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| Ref. Compd 1 | 1 | Isovaleric acid-DTHFPCIKF-Lys[PEG11-Palm]-PRSKGCK-NH$_2$ | 30 | <15 (1%) | <15 (6%) |
| Ref. Compd. 2 | 2 | Isovaleric acid-DTHFPCIKF-Lys[PEG11-Palm]-PRSK-[SAR]-CK-NH$_2$ | 13 | <15 (1%) | 26 |
| 3 | 3 | Isovaleric acid-DTHFPCIKF-Lys[PEG11-Palm]-PRSKGC-NH$_2$ | 16 | <15 (2%) | <15 (1%) |
| 4 | 4 | Isovaleric acid-DTHFPCIKF-Lys[PEG11-Palm]-PRSKC-NH$_2$ | 32 | <15 (5%) | <15 (10%) |
| 5 | 5 | Isovaleric acid-DTHFPCIKF-Lys[PEG11-Palm]-PRSC-NH$_2$ | 30 | <15 (3%) | <15 (11%) |
| 6 | 6 | Isovaleric acid-DTHFPCIKF-Lys[PEG11-Palm]-PRC-NH$_2$ | 17 | 21 | <15 (10%) |
| 7 | 7 | Isovaleric acid-DTHFPCIKF-Lys[PEG11-Palm]-PC-NH$_2$ | 10 | 29 | 22 |
| 8 | 8 | Isovaleric acid-DTHFPCIKF-Lys[PEG11-Palm]-C-NH$_2$ | 6 | >180 (75%) | 23 |
| 9 | 9 | Isovaleric acid-DTHFPCIKF-Lys[PEG11-Palm]-PCK-NH$_2$ | 15 | <15 min (2%) | 37 |
| 10 | 10 | Isovaleric acid-DTHFPCI-[(D)Lys]-[Phe]-Lys[PEG11-Palm]C-NH$_2$ | 5-60 | >1440 (88%) | <15 (3%) |
| 11 | 11 | Isovaleric acid-DTHFPCI-[Orn]-[Phe]-Lys[PEG11-Palm]-C-NH$_2$ | 4 | 174 | <15 (8%) |
| 12 | 12 | Isovaleric acid-DTHFPCI-[hSer]-[Phe]-Lys[PEG11-Palm]-C-NH$_2$ | 2 | 405 | <15 (10%) |
| 13 | 13 | Isovaleric acid-DTHFPCIQ-[Phe]-Lys[PEG11-Palm]-C-NH$_2$ | 4 | 251 | <15 (7%) |
| 14 | 14 | Isovaleric acid-DTHFPCI-[Lys(Ac)]-[Phe]-Lys[PEG11-Palm]-C-NH$_2$ | 3 | 200 | <15 (7%) |
| 15 | 15 | Isovaleric acid-DTHFPCI-[nLeu]-[Phe]-Lys[PEG11-Palm]-C-NH$_2$ | 2 | 455 | <15 (20%) |
| 16 | 16 | Isovaleric acid-DTHFPCIIF-Lys[PEG11-Palm]-C-NH$_2$ | N.D. | 641 | <15 (41%) |
| 17 | 17 | Isovaleric acid-DTHFPCIK-[NMe-Phe]-Lys[PEG11-Palm]-C-NH$_2$ | N.D. | — | — |
| 18 | 18 | Isovaleric acid-DTHFPCIK-[α-MePhe]-Lys[PEG11-Palm]-C-NH$_2$ | N.D. | — | — |
| 19 | 19 | Isovaleric acid-DTHFPCIK-[β-homoPhe]-Lys[PEG11-Palm]-C-NH$_2$ | N.D. | — | — |
| 20 | 20 | Isovaleric acid-DTHFPCIKW-Lys[PEG11-Palm]-C-NH$_2$ | 4 | — | — |
| 21 | 21 | Isovaleric acid-DTHFPCI-[(D)Lys]-[Phe]-Lys[PEG8-Palm]-C-NH$_2$ | 30 | — | — |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 22 | 22 | Isovaleric acid-DTHFPCI-[(D)Lys]-[Phe]-Lys[PEG4-Palm]-C-NH$_2$ | 17 | — | — |
| 23 | 23 | Isovaleric acid-DTHFPCI-[(D)Lys]-[Phe]-Lys[PEG2-Palm]-C-NH$_2$ | 40 | — | — |
| 24 | 24 | Isovaleric acid-DTHFPCI-[(D)Lys]-[Phe]-Lys[PEG1-Palm]-C-NH$_2$ | 17 | — | — |
| 25 | 25 | Isovaleric acid-DTHFPCI-[(D)Lys]-[Phe]-Lys[Ahx-Palm]-C-NH$_2$ | 11 | — | — |
| 26 | 26 | Isovaleric acid-DTHFPCI-[(D)Lys]-[Phe]-Lys[PEG2-isoGlu-Palm]-C-NH$_2$ | 13 | — | — |
| 27 | 27 | Isovaleric acid-DTHFPCI-[(D)Lys]-[Phe]-Lys[isoGlu-Palm]-C-NH$_2$ | 35 | — | — |
| 28 | 28 | Isovaleric acid-DTHFPCI-[(D)Lys]-[Phe]-Lys[isoGlu-PEG2-Palm]-C-NH$_2$ | 23 | — | — |
| 29 | 29 | Isovaleric acid-DTHFPCI-[(D)Lys]-[Phe]-Lys[PEG2-Ahx-Palm]-C-NH$_2$ | 30 | — | — |
| 30 | 30 | Isovaleric acid-DTHFPCI-[(D)Lys]-[Phe]-Lys[Palm]-C-NH$_2$ | 31 | — | — |
| 31 | 31 | Isovaleric acid-DTHFPCIKF-Lys[PEG11-Palm]-PRSK-[SAR]-[Pen]-K-NH$_2$ | — | — | — |
| 32 | 32 | Isovaleric acid-DTHFPCI-[(D)Lys]-F-Lys[PEG11-Palm]-[Pen]-NH$_2$ | — | — | — |
| 33 | 33 | Isovaleric acid-DTHF-[NPC]-CI-[(D)Lys]-F-Lys[PEG11-Palm]-C-NH$_2$ | — | — | — |
| 34 | 34 | Isovaleric acid-DTHF-[(D)NPC]-CI-[(D)Lys]-F-Lys[PEG11-Palm]-C-NH$_2$ | — | — | — |
| 35 | 35 | Isovaleric acid-DTHF-[(D)Pro]-CI-[(D)Lys]-F-Lys[PEG11-Palm]-C-NH$_2$ | — | — | — |
| 36 | 36 | Isovaleric acid-DTHF-[(D)bhPro]-CI-[(D)Lys]-F-Lys[PEG11-Palm]-C--NH$_2$ | — | — | — |
| 37 | 37 | Isovaleric acid-DTHF-[bhPro]-CI-[(D)Lys]-F-Lys[PEG11-Palm]-C-NH$_2$ | — | — | — |
| 38 | 38 | Isovaleric acid-DTH-[BIP]-PCI-[(D)Lys]-F-Lys[PEG11-Palm]-C-NH$_2$ | — | — | — |
| 39 | 39 | Isovaleric acid-DTH-[BIP]-[NPC]-CI-[(D)Lys]-F-Lys[PEG11-Palm]-C-NH$_2$ | — | — | — |
| 40 | 40 | Isovaleric acid-DTHF-[NPC]-CI-[(D)Lys]-F-Lys[PEG11-Palm]-C-NH$_2$ | — | — | — |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 41 | 41 | Isovaleric acid-DTHFPCI-[(D)Lys]-F-Lys[(PEG11-Palm)]-PRSK-[SAR]-CK-NH$_2$ | — | — | — |
| 42 | 42 | Isovaleric acid-DTHFPCI-[(D)Lys]-F-Lys[(PEG11-Palm)]-PRSK-[SAR]-C-[(D)Lys]-NH$_2$ | — | — | — |
| 43 | 43 | Isovaleric acid-DTHFPCI-[(D)Lys]-F-Lys[(PEG11-Palm)]-PRS-[(D)Lys]-[SAR]-CK-NH$_2$ | — | — | — |
| 44 | 44 | Isovaleric acid-DTHFPCI-[(D)Lys]-F-Lys[(PEG11-Palm)]-PR-[(D)Ser]-K-[SAR]-CK-NH$_2$ | — | — | — |
| 45 | 45 | Isovaleric acid-DTHFPCI-[(D)Lys]-F-Lys[(PEG11-Palm)]-P-[(D)Arg]-SK-[SAR]-CK-NH$_2$ | — | — | — |
| 46 | 46 | Isovaleric acid-DTHFPCI-[(D)Lys]-F-Lys[(PEG11-Palm)]-PRTK-[SAR]-C-[(D)Lys]-NH$_2$ | — | — | — |
| 47 | 47 | Isovaleric acid-DTHFPCI-[(D)Lys]-F-Lys[(PEG11-Palm)]-PKTR-[SAR]-C-[(D)Lys]-NH$_2$ | — | — | — |
| 48 | 48 | Isovaleric acid-DTHFPCI-[(D)Lys]-F-Lys[(PEG11-Palm)]-P-[N-MeArg]-TK-[SAR]-C-[(D)Lys]-NH$_2$ | — | — | — |
| 49 | 49 | Isovaleric acid-DTHFPCI-[(D)Lys]-F-Lys[(PEG11-Palm)]-P-[(D)Arg]-TK-[SAR]-C-[(D)Lys]-NH$_2$ | — | — | — |
| 50 | 50 | Isovaleric acid-DTHFPCI-[(D)Lys]-F-Lys[(PEG11-Palm)]-PDTH-[SAR]-C-[(D)Lys]-NH$_2$ | — | — | — |
| 51 | 51 | Isovaleric acid-DTHFPCI-[(D)Lys]-F-Lys[(PEG11-Palm)]-P-[(D)Arg]-T-[N-MeLys]-[SAR]-C-[(D)Lys]-NH$_2$ | — | — | — |
| 52 | 52 | Isovaleric acid-DTHFPCI-[(D)Lys]-F-Lys[(PEG11-Palm)]-[NPC]-[N-MeArg]-TH-[SAR]-C-[(D)Lys]-NH$_2$ | — | — | — |
| 53 | 53 | Isovaleric acid-DTHFPCIKF-Lys[PEG11-Palm]-PRSK-[SAR]-[Pen]-K-NH$_2$ | — | — | — |
| 54 | 54 | Isovaleric acid-DTHFPCI-[(D)Lys]-F-Lys[PEG11-Palm]-[Pen]-NH$_2$ | — | — | — |
| 55 | 55 | kc-{SAR}-ksrp-k [PEG11-Palm]-fkicpfhtdl-NH$_2$ (Retroinverso of 659 (D)Leu for IVA) | — | — | — |
| 56 | 56 | Isovaleric acid-DTHF-[NPC]-CI-[(D)Lys]-F-Lys[PEG11-Palm]-C-NH$_2$ | — | — | — |
| 57 | 57 | Isovaleric acid-DTHF-[(D)NPC]-CI-[(D)Lys]-F-Lys[PEG11-Palm]-C-NH$_2$ | — | — | — |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 58 | 58 | Isovaleric acid-DTHF-[(D)Pro]-CI-[(D)Lys]-F-Lys[PEG11-Palm]-C-NH$_2$ | — | — | — |
| 59 | 59 | Isovaleric acid-DTHF-[(D)bhPro]-CI-[(D)Lys]-F-Lys[PEG11-Palm]-C-NH$_2$ | — | — | — |
| 60 | 60 | Isovaleric acid-DTHF-[bhPro]-CI-[(D)Lys]-F-Lys[PEG11-Palm]-C-NH$_2$ | — | — | — |
| 62 | 62 | Isovaleric acid-DTH-[BIP]-PCI-[(D)Lys]-F-Lys[PEG11-Palm]-C-NH$_2$ | — | — | — |
| 63 | 63 | Isovaleric acid-DTH-[BIP]-[NPC]-CI-[(D)Lys]-F-Lys[PEG11-Palm]-C-NH$_2$ | — | — | — |
| 65 | 65 | Isovaleric acid-DTHFPCI-[(D)Lys]-F-C-Lys[PEG11-Palm]-NH$_2$ | — | — | — |
| 66 | 66 | Isovaleric acid-DTHF-[NPC]-CI-[(D)Lys]-F-Lys[PEG11-Palm]-C-NH$_2$ | — | — | — |
| 67 | 67 | Isovaleric acid-DTHFPC(SH)I-[Lys]-[Phe]-Lys[PEG11-Palm]-Pro-C(SH)-NH$_2$ | 13 | — | — |
| 68 | 68 | Isovaleric acid-DTHFPC(SH)I-[(D)Lys]-[Phe]-Lys[PEG11-Palm]-C(SH)-NH$_2$ | 12 | — | — |
| 69 | 69 | Isovaleric acid-DTHFPC(SH)I-[Lys]-[Phe]-Lys[PEG11-Palm]-C(SH)-NH$_2$ | 9 | — | — |
| 70 | 70 | Isovaleric acid-DTHFPCI-[(D)Lys]-[Phe]-Lys[PEG11-Palm]-PC-NH$_2$ | 5 | — | — |
| 71 | 71 | Isovaleric acid-DTHFPCI-[(D)Lys]-[Phe]-Lys[PEG11-Palm]-PRC-NH$_2$ | 8 | — | — |
| 72 | 72 | Isovaleric acid-DTHFPCI-[(D)Lys]-[Phe]-Lys[PEG11-Palm]-PRSC-NH$_2$ | 12 | — | — |
| 73 | 73 | Isovaleric acid-DTHFPCI-[(D)Lys]-[Phe]-Lys[PEG11-Palm]-PRSKC-NH$_2$ | 11 | — | — |
| 74 | 74 | Isovaleric acid-DTHFPCI-[(D)Lys]-[Phe]-Lys[PEG11-Palm]-PRSKSarC-NH$_2$ | 9 | — | — |
| 75 | 75 | Isovaleric acid-DTHFPCI-[(D)Lys]-[Phe]-Lys[PEG11-Palm]-PRSKCK-NH$_2$ | 14 | — | — |
| 76 | 76 | Isovaleric acid-DTHFPCI-[(D)Lys]-[Phe]-Lys[PEG11-Palm]-PPRSCK-NH$_2$ | 16 | — | — |
| 77 | 77 | Isovaleric acid-DTHFPCI-[(D)Lys]-[Phe]-Lys[PEG11-Palm]-PRCK-NH$_2$ | 15 | — | — |

TABLE 3A-continued

Illustrative Monomer Hepcidin Analoques

| Compd ID | SEQ ID No. | Peptide | FPN IC$_{50}$ (nM) | SIF Half life (min) | SGF Half life (min) |
|---|---|---|---|---|---|
| 78 | 78 | Isovaleric acid-DTHFPCI-[(D)Lys]-[Phe]-Lys[PEG11-Palm]-CK-NH$_2$ | 17 | — | — |
| 79 | 79 | Isovaleric acid-DTHFPCI-[(D)Lys]-[Phe]-Lys[PEG11-Palm]-RC-NH$_2$ | 22 | — | — |
| 80 | 80 | Isovaleric acid-DTHFPCI-[(D)Lys]-[Phe]-Lys[PEG11-Palm]-KC-NH$_2$ | 14 | <5 | 7 |
| 81 | 81 | Isovaleric acid-DTHFPCI-[(D)Lys]-[Phe]-Lys[PEG11-Palm]-[(D)Arg]-C-NH$_2$ | 9 | — | — |
| 82 | 82 | Isovaleric acid-DTHFPCI-[(D)Lys]-[Phe]-Lys[PEG11-Palm]-[(D)Lys]-C-NH$_2$ | 13 | 122 | 2 |
| 83 | 83 | Isovaleric acid-DTHFPCI-[(D)Lys]-[Phe]-Lys[PEG11-Palm]-Lys-C-[(D)Lys]-NH$_2$ | 40 | — | — |
| 84 | 84 | Isovaleric acid-DTHFPCI-[(D)Lys]-[Phe]-Lys[PEG11-Palm]-HC-[(D)His]-NH$_2$ | 16 | — | — |
| 85 | 85 | Isovaleric acid-DTHFPCI-[(D)Lys]-[Phe]-Lys[PEG11-Palm]-RC-[(D)Arg]-NH$_2$ | 27 | — | — |
| 86 | 86 | Isovaleric acid-DTHFPCI-[(D)Lys]-[Phe]-Lys-[Ahx-Palm]-KC-NH$_2$ | 9 | — | — |
| 87 | 87 | Isovaleric acid-DTHFPCI-[(D)Lys]-[Phe]-Lys[PEG2-Palm]-KC-NH$_2$ | 15 | — | — |
| 88 | 88 | Isovaleric acid-DTHFPCI-[(D)Lys]-[Phe]-Lys[PEG2-PEG2-Palm]-KC-NH$_2$ | 13 | — | — |
| 89 | 89 | Isovaleric acid-DTHFPCI-[(D)Lys]-[Phe]-Lys[PEG2-PEG2-C18 acid]-KC-NH$_2$ | 27 | — | — |
| 90 | 90 | Isovaleric acid-DTHFPCI-[(D)Lys]-[Phe]-Lys[PEG2-PEG2-Ahx-Palm]-KC-NH$_2$ | 11 | — | — |
| 91 | 91 | Isovaleric acid-DTHFPCI-[(D)Lys]-[Phe]-Lys[PEG4-Palm]-KC-NH$_2$ | 14 | — | — |
| 92 | 92 | Isovaleric acid-DTHFPCI-[(D)Lys]-[Phe]-Lys[PEG4-Ahx-Palm]-KC-NH$_2$ | 21 | — | — |
| 93 | 93 | Isovaleric acid-DTHFPCI-[(D)Lys]-[Phe]-Lys[PEG4-PEG4-Palm]-KC-NH$_2$ | 18 | — | — |
| 94 | 94 | Isovaleric acid-DTHFPCI-[(D)Lys]-[Phe]-Lys[PEG4-isoGlu-Palm]-KC-NH$_2$ | 9 | — | — |
| 95 | 95 | Isovaleric acid-DTHFPCI-[(D)Lys]-[Phe]-Lys[PEG8-Palm]-KC-NH$_2$ | 28 | — | — |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 96 | 96 | Isovaleric acid-DTHFPCI-[(D)Lys]-[Phe]-Lys-[Behenic acid]-KC-NH$_2$ | 30 | — | — |
| 97 | 97 | Isovaleric acid-DTHFPCI-[(D)Lys]-F-Lys[PEG11-Palm]-K-[(D)Cys]-NH$_2$ | 41 | <15 min (1%) | <15 min (11%) |
| 98 | 98 | Isovaleric acid-DTHFPCI-[(D)Lys]-F-Lys[PEG11-Palm]-K-[Pen]-NH$_2$ | 40 | <15 min (1%) | 30 |
| 99 | 99 | Isovaleric acid-DTHFPCI-[(D)Lys]-F-Lys[PEG11-Palm]-Dap-[Cys]-NH$_2$ | 21 | 68 | <15 min (2%) |
| 100 | 100 | Isovaleric acid-DTHFPCI-[(D)Lys]-[Dpa]-Lys[PEG11-Palm]-K-[Cys]-NH$_2$ | 16 | <5 | <5 |
| 101 | 101 | Isovaleric acid-DTHFPCI-[(D)Lys]-[b-homoPhe]-Lys[PEG11-Palm]-K-[Cys]-NH$_2$ | 24 | <5 | <15% (2%) |
| 102 | 102 | Isovaleric acid-DTHFPCI-[(D)Lys]-[Nal]-Lys[PEG11-Palm]-K-[Cys]-NH$_2$ | 17 | <5 | <15% (4%) |
| 103 | 103 | Isovaleric acid-DTHFPCI-[(D)Lys]-[bhomoPhe]-Lys[PEG11-Palm]-K-[Cys]-NH$_2$ | 20 | <5 | <15% (20%) |
| 104 | 104 | Isovaleric acid-D-T-H-[Dpa]-P-C-I-[(D)Lys]-F-Lys[PEG11-Palm]-K-[Cys]-NH$_2$ | 27 | <5 | 145 |
| 105 | 105 | Isovaleric acid-D-T-H-[Dpa]-P-C-I-[(D)Lys]-[b-homoPhe]-Lys[PEG11-Palm]-[(D)Lys]-[Cys]-NH$_2$ | 31 | 99 | 833 |
| 106 | 106 | Isovaleric acid-DTHFPCI-F-Lys[PEG11-Palm]-K-[Cys]-NH$_2$ | 40 | 319 | <5 |
| 107 | 107 | Isovaleric acid-DTHFPCI-[(D)Lys]-F-(D)Lys[PEG11-Palm]-[(D)Lys]-[Cys]-NH$_2$ | 60 | 73 | <5 |
| 109 | 109 | Isovaleric acid-DTH-[Dpa]-[Npc]-C-I-[(D)Lys]-F-[Lys(Peg11-Palm)]-K-C-NH$_2$ | 2 | <5 | 188 |
| 110 | 110 | Isovaleric acid-DTH-[Dpa]-[Npc]-C-I-[(D)Lys]-[Phe(4-tBu)]-[Lys(Peg11-Palm)]-K-C-NH$_2$ | 3 | <5 | 820 |
| 111 | 111 | Isovaleric acid-DTH-[Dpa]-[Npc]-C-I-[(D)Lys]-[Phe[4-(2-aminoethoxy)]-[Lys(Peg11-Palm)]-K-C-NH$_2$ | >3000 | <5 | 1111 |
| 112 | 112 | Isovaleric acid-DTH-[Dpa]-[Npc]-C-I-[(D)Lys]-[2-Nal]-[Lys(Peg11-Palm)]-K-C-NH$_2$ | 4 | <5 | 48 |
| 113 | 113 | Isovaleric acid-DTH-[Dpa]-[Npc]-C-I-[(D)Lys]-[Phe(4-COOH)]-[Lys(Peg11-Palm)]-K-C-NH$_2$ | — | <5 | 311 |
| 114 | 114 | Isovaleric acid-DTH-F-PCI-[(D)Lys]-F-[Lys(Peg11-Palm)]-K-[a-MeCys]-NH$_2$ | 3 | <5 | 2 |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 115 | 115 | Isovaleric acid-DTHFP-[a-MeCys]-I-[(D)Lys]-F-[Lys(Peg11-Palm)]-K-[a-MeCys]-NH$_2$ | 4 | <5 | 7 |
| 116 | 116 | Isovaleric acid-DTHFP-[a-MeCys]-I-[(D)Lys]-F-[Lys(Peg11-Palm)]-K-C-NH$_2$ | 11 | <5 | 11 |
| 117 | 117 | Isovaleric acid-DTH-[Dpa]-[Npc]-C-I-[(D)Lys]-F-[Lys(Peg11-Palm)]-[(D)Lys]-C-NH$_2$ | 2 | 52 | 1072 |
| 118 | 118 | Isovaleric acid-DTH-F-[Npc]-C-I-[(D)Lys]-F-[Lys(Peg11-Palm)]-[(D)Lys]-C-NH$_2$ | 6 | 63 | 1513 |
| 119 | 119 | Isovaleric acid-DTH-[Dpa]-[β-hPro]-C-I-[(D)Lys]-F-[Lys(Peg11-Palm)]-[(D)Lys]-C-NH$_2$ | — | 107 | 482 |
| 120 | 120 | Isovaleric acid-DTH-[Phe(4-COOH)-PCI-[(D)Lys]-F-[Lys(Peg11-Palm)]-[(D)Lys]-C-NH$_2$ | >1000 | 582 | 18 |
| 121 | 121 | Isovaleric acid-DTH-[b-hPhe]-PCI-[(D)Lys]-F-[Lys(Peg11-Palm)]-[(D)Lys]-C-NH$_2$ | 9 | 95 | >1440 (94%) |
| 122 | 122 | Isovaleric acid-DTH-[Dpa]-PCI-[(D)Lys]-[b-hPhe]-[Lys(Peg11-Palm)]-[(D)Lys]-C-NH$_2$ | 5 | 49 | 794 |
| 125 | 125 | Isovaleric acid-DTH-[Dpa]-[Npc]-C-I-[(D)Lys]-[a-MePhe]-[Lys(Peg11-Palm)]-K-C-NH$_2$ | — | 17 | 840 |
| 126 | 126 | Isovaleric acid-DTH-[Dpa]-[Npc]-C-I-[(D)Lys]-[Phe(4-CN)]-[Lys(Peg11-Palm)]-K-C-NH$_2$ | — | <5 | 128 |
| 127 | 127 | Isovaleric acid-DTH-[Dpa]-[Npc]-C-I-[(D)Lys]-[Phe(3,4-diF)-[Lys(Peg11-Palm)]-K-C-NH$_2$ | 3 | <5 | 26 |
| 128 | 128 | Isovaleric acid-DTH-[a-MePhe]-PCI-[(D)Lys]-F-[Lys(Peg11-Palm)]-[(D)Lys]-C-NH$_2$ | 204 | 583 | >1440 (62%) |
| 129 | 129 | Isovaleric acid-DTH-[Phe[4-(2-aminoethoxy)]-PCI-[(D)Lys]-F-[Lys(Peg11-Palm)]-[(D)Lys]-C-NH$_2$ | >3000 | Fluctuate | >1440 (81%) |
| 130 | 130 | Isovaleric acid-DIH-[Dpa]-PCI-[(D)Lys]-F-[Lys(Peg11-Palm)]-[(D)Lys]-C-NH$_2$ | 169 | 14 | 157 |
| 131 | 131 | Isovaleric acid-DTH-[Dpa]-PCI-[(D)Lys]-[Dpa]-[Lys(Peg11-Palm)]-[(D)Lys]-C-NH$_2$ | 14 | 14 | 614 |
| 132 | 132 | Isovaleric acid-DTH-[Dpa]-PCI-[(D)Lys]-F-[Lys(Peg11-Palm)]-[(D)Lys]-Pen-NH$_2$ | 4 | 97 | 934 |
| 133 | 133 | Isovaleric acid-DTH-[Dpa]-PCI-[(D)Lys]-F-[Lys(Peg11-Palm)]-K-[N-Me-Cys]-NH$_2$ | 13.5 | 47 | 543 |
| 134 | 134 | Isovaleric acid-DTH-[Dpa]-PCI-[(D)Lys]-F-[Lys(Peg11-Palm)]-[(D)Lys]-[N-Me-Cys]-NH$_2$ | 22.5 | 44 | 701 |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 135 | 135 | Isovaleric acid-DTH-[Dpa]-PCI-[(D)Lys]-F-[Lys(Peg11-Palm)]-C-NH$_2$ | 22 | 61 >1440 (78%) | 364 |
| 136 | 136 | Isovaleric acid-DTH-[Dpa]-PCI-[(D)Lys]-F-[Lys(Peg11-Palm)]-[Orn]-C-NH$_2$ | 27 | 53 | 330 |
| 137 | 137 | Isovaleric acid-DTH-[Dpa]-PCI-[(D)Lys]-F-[Lys(Peg11-Palm)]-[Dab]-C-NH$_2$ | 23 | 40 | 525 |
| 138 | 138 | Isovaleric acid-DTH-[Dpa]-PCI-[(D)Lys]-F-[Lys(Peg11-Palm)]-[b-hLys]-C-NH$_2$ | 20.5 | 51 | 569 |
| 139 | 139 | Isovaleric acid-DTH-[Dpa]-PCI-[(D)Lys]-F-[Lys(Peg11-Palm)]-[(D)Lys]-C-NH$_2$ | 19.5 | 67 | 707 |
| 140 | 140 | Isovaleric acid-DTH-[Dpa]-PCI-[(D)Lys]-F-[Lys(Peg11-Palm)]-[Dap]-[Pen]-NH$_2$ | 51 | | 364 |
| 141 | 141 | Isovaleric acid-DTH-[Dpa]-P-[Hcy]-I-[(D)Lys]-F-[Lys(Peg11-Palm)]-[Dap]-C-NH$_2$ | 26.5 | | 896 |
| 142 | 142 | Isovaleric acid-DTH-[Dpa]-P-[Hcy]-I-[(D)Lys]-F-[Lys(Peg11-Palm)]-[Dap]-[Hcy]-NH$_2$ | 12 | 69 | 395 |
| 143 | 143 | Isovaleric acid-DTH-[Dpa]-PCI-[(D)Lys]-F-[Lys(Peg11-Palm)]-[Dap]-[Hcy]-NH$_2$ | 18 | 46 | 377 |
| 144 | 144 | Isovaleric acid-DTHFPCI-[(D)Lys]-F-[Lys(Peg11-Palm)]-CK-NH$_2$ | 32 | | 13 |
| 145 | 145 | Isovaleric acid-DTH-[Dpa]-PCI-[bAla]-[b-hPhe]-[Lys(Peg11-Palm)]-[(D)Lys]-C-NH$_2$ | 18 | | >1440 (59%) |
| 146 | 146 | Isovaleric acid-DTH-[Dpa]-PCI-[(D)Ala]-[b-hPhe]-[Lys(Peg11-Palm)]-[(D)Lys]-C-NH$_2$ | 11 | 1391 | 726 |
| 147 | 147 | Isovaleric acid-DTH-[Dpa]-PCII-[b-hPhe]-[Lys(Peg11-Palm)]-[(D)Lys]-C-NH$_2$ | 24 | 505 | >1440 (49%) |
| 148 | 148 | Isovaleric acid-DTH-[Dpa]-PCI-[b-hPhe]-[Lys(Peg11-Palm)]-[(D)Lys]-C-NH$_2$ | 12 | 635 | 1097 |
| 149 | 149 | Isovaleric acid-DTH-[Dpa]-[Npc]-CI-[(D)Lys]-[Phe(4-tButyl)]-[Lys(Peg11-Palm)]-[(D)Lys]-C-NH$_2$ | 17 | >1440 (54%) | >1440 (77%) |
| 150 | 150 | Isovaleric acid-DTH-[Dpa]-[Npc]-CI-[(D)Lys]-[Phe(4-tButyl)]-[Lys(Peg11-Palm)]-C-[(D)Lys]-NH$_2$ | 22 | >1440 (68%) | >1440 (51%) |
| 151 | 151 | Isovaleric acid-DTH-[Dpa]-PCI-[(D)Lys]-[b-hPhe]-[Lys(Ahx-Palm)]-[Dap]-[N-Me-Cys]-NH$_2$ | 28.5 | fluctuate | 1343 |
| 152 | 152 | Isovaleric acid-DTH-[Dpa]-PCI-[(D)Lys]-[b-hPhe]-[Lys(Ac)]-[(D)Lys]-C-NH$_2$ | 146.5 | >1440 (97%) | >1440 (87%) |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 153 | 153 | Isovaleric acid-DTH-[Dpa]-PCI-[(D)Lys-Peg11*]-[b-hPhe]-[Lys(Peg11-Palm)]-[(D)Lys-Peg11*]-C-NH$_2$ | 19 | | >1440 (64%) |
| 154 | 154 | Isovaleric acid-DTH-[Dpa]-PCI-[(D)Lys]-[b-hPhe]-[Lys-Peg11]-[(D)Lys]-C-NH$_2$ | 404 | | >1440 (108%) |
| 155 | 155 | Isovaleric acid-DTH-[Dpa]-PCI-[(D)Lys]-[b-hPhe]-[Lys(Peg11-Octane)]-[(D)Lys]-C-NH$_2$ | 279 | >1440 | >1440 (102%) |
| 156 | 156 | Isovaleric acid-DTH-[Dpa]-PCI-[(D)Lys]-[b-hPhe]-[Lys(Peg11-Lauryl)]-[(D)Lys]-C-NH$_2$ | 125 | >1440 | >1440 (84%) |
| 157 | 157 | Isovaleric acid-DTH-[Dpa]-PCI-[(D)Lys]-[b-hPhe]-[Lys-Peg11*]-[(D)Lys]-C-NH$_2$ | 347 | >1440 | >1440 (99%) |
| 158 | 158 | Isovaleric acid-DTH-[Dpa]-PCI-[(D)Lys]-[b-hPhe]-[Lys(IsoGlu-Palm)]-[(D)Lys]-C-NH$_2$ | 6 | >1440 | 840 |
| 159 | 159 | Isovaleric acid-DTH-[Dpa]-PCI-[(D)Lys-Ac]-[b-hPhe]-[Lys(Peg11-Palm)]-[(D)Lys-Ac]-C-NH$_2$ | 4 | >1440 | 244 |
| 160 | 160 | Isovaleric acid-DTH-[Dpa]-PCI-[(D)Lys]-[b-hPhe]-[Lys(Dap-Palm)]-C-NH$_2$ | 4 | | 410 |
| 161 | 161 | Isovaleric acid-DTH-[Dpa]-PCI-[(D)Lys]-[b-hPhe]-[Lys(dDap-Palm)]-C-NH$_2$ | 10 | | 810 |
| 162 | 162 | Isovaleric acid-DTH-[Dpa]-PCI-[(D)Lys]-[b-hPhe]-[Dap(Dap-Palm)]-C-NH$_2$ | 8 | | 1153 |
| 163 | 163 | Isovaleric acid-DTH-[Dpa]-PCI-[(D)Lys]-[b-hPhe]-[Dap(dDap-Palm)]-C-NH$_2$ | 7 | | 642 |
| 164 | 164 | Isovaleric acid-DTH-[Dpa]-PCI-[(D)Lys]-[b-hPhe]-[Dap(dDap-Palm)]-C-NH$_2$ | 6 | | 798 |
| 165 | 165 | Isovaleric acid-DTH-[Dpa]-PCI-[(D)Lys]-[b-hPhe]-[Lys(Ahx-Palm)]-[(D)Lys]-C-NH$_2$ | 6 | >1440 | 822 |
| 166 | 166 | Isovaleric acid-DTH-[Dpa]-PCI-[(D)Lys-Peg11*]-[b-hPhe]-[Lys(Ahx-Palm)]-[(D)Lys-Peg11*]-C-NH$_2$ | 6 | >1440 | >1440 (92%) |
| 167 | 167 | Isovaleric Acid-D-T-H-[Dpa]-(D)Pro-C-I-(D)Lys-F-[Lys_Peg11_Palm]-(D)Lys-C-NH$_2$ | 81 | 936 | >1440 |
| 168 | 168 | Isovaleric_Acid-D-T-H-bhPhe-(D)Pro-C-I-(D)Lys-F-[Lys_Peg11_Palm]-(D)Lys-C-NH$_2$ | 54 | >1440 | >1440 |
| 169 | 169 | Isovaleric_Acid-dD-T-H-[Dpa]-P-C-I-(D)Lys-bhPhe-[Lys_Peg11_Palm]-(D)Lys-C-NH$_2$ | 12 | 1182 | >1440 |
| 170 | 170 | Isovaleric_Acid-D-T-H-[Dpa]-P-C-I-(D)Lys-bhPhe-[Lys_Peg11_Palm]-C-(D)Lys-NH$_2$ | 10 | >1440 | 335 |

TABLE 3A-continued

Illustrative Monomer Hepcidin Analogues

| Compd ID | SEQ ID No. | Peptide | FPN IC$_{50}$ (nM) | SIF Half life (min) | SGF Half life (min) |
|---|---|---|---|---|---|
| 171 | 171 | Isovaleric Acid-D-T-H-bhPhe-P-C-I-(D)Lys-F-[Lys_Peg11_Palm]-C-(D)Lys-NH$_2$ | 47 | >1440 | >1440 |
| 172 | 172 | Isovaleric_Acid-D-T-H-bhPhe-Npc-C-I-(D)Lys-F-[Lys_Peg11_Palm]-C-(D)Lys-NH$_2$ | 39 | >1440 | >1440 |
| 173 | 173 | Isovaleric_Acid-D-T-H-[Dpa]-Npc-C-I-(D)Lys-bhPhe-[Lys_Peg11_Palm]-C-(D)Lys-NH$_2$ | | >1440 | 1314 |
| 174 | 174 | Isovaleric_Acid-D-T-H-[Dpa]-P-C-I-(D)Gln-bhPhe-[Lys_Peg11_Palm]-(D)Lys-C-NH$_2$ | | >1440 | 511 |
| 175 | 175 | Isovaleric_Acid-D-T-H-[Dpa]-P-C-I-(D)Lys-bhPhe-[Lys_Peg11_Palm]-dLys_Ac-C-NH$_2$ | 5 | >1440 | 570 |
| 176 | 176 | Isovaleric_Acid-D-T-H-bhPhe-(D)Pro-C-I-(D)Lys-bhPhe-[Lys_Peg11_Palm]-C-(D)Lys-NH$_2$ | | | |
| 177 | 177 | Isovaleric_Acid-D-T-H--[Dpa]-P-C-I-(D)Lys-bhPhe-[Lys_Ahx_Palm]-R-C-NH$_2$ | | | |
| 178 | 178 | Isovaleric_Acid-D-T-H-[Dpa]-P-C-I-(D)Lys-[N-MePhe]-[Lys_Ahx_Palm]-(D)Lys-C-NH$_2$ | | | |
| 179 | 179 | Isovaleric_Acid-D-T-H-[Dpa]-P-[N-MeCys]-I-(D)Lys-bhPhe-[Lys_Ahx_Palm]-(D)Lys-C-NH$_2$ | | | |
| 180 | 180 | Isovaleric_Acid-D-T-H-[N-MePhe-P-C-I-(D)Lys-bhPhe-[Lys_Ahx_Palm]-(D)Lys-C-NH$_2$ | | | |
| 181 | 181 | Isovaleric_Acid-D-T-H--[Dpa]-P-C-I-(D)Lys-bhPhe-[Lys_Ahx_Palm]-(D)Lys-[N-MeCys]-NH$_2$ | | | |

*PEG11-OMe

TABLE 3B

Illustrative Monomer Hepcidin Analogues

| Compd ID | SEQ ID No. | Peptide | FPN IC50 (nM) | SIF Half life (min) | SGF Half life (min) |
|---|---|---|---|---|---|
| 201 | 201 | Isovaleric acid-DTHFPCI-Lys[isoGlu-Palm]-FEPRSKGC-NH$_2$ | 9 | 3 | <15 (4%) |
| 202 | 202 | Isovaleric acid-DTHFPCI-Lys[isoGlu-Palm]-FEPRSKC-NH$_2$ | 11 | 3 | <15 (6%) |
| 203 | 203 | Isovaleric acid-DTHFPCI-Lys[isoGlu-Palm]-FEPRSC-NH$_2$ | 15 | 6 | <15 (7%) |
| 204 | 204 | Isovaleric acid-DTHFPCI-Lys[isoGlu-Palm]-FEPRC-NH$_2$ | 14 | 7 | <15 (12%) |
| 205 | 205 | Isovaleric acid-DTHFPCI-Lys[isoGlu-Palm]-FEPC-NH$_2$ | 64 | 36 | 45 |
| 206 | 206 | Isovaleric acid-DTHFPCI-Lys[isoGlu-Palm]-FEC-NH$_2$ | 267 | 66 | 36 |

TABLE 3B-continued

Illustrative Monomer Hepcidin Analoques

| Compd ID | SEQ ID No. | Peptide | FPN IC50 (nM) | SIF Half life (min) | SGF Half life (min) |
|---|---|---|---|---|---|
| 207 | 207 | Isovaleric acid-DTHFPCI-Lys[isoGlu-Palm]-FC-NH$_2$ | 64 | >300 (86%) | 101 |
| 208 | 183 | Isovaleric acid-DTHFPCI-Lys[isoGlu-Palm]-FEPCK-NH$_2$ | 22 | 16 | 216 |
| 209 | 184 | Isovaleric acid-DTHFPCI-Lys[isoGlu-Palm]-FEPC-[(D)Lys]-NH$_2$ | 47 | 24 | 174 |
| 210 | 210 | Isovaleric acid-DTHFPCI-Lys[isoGlu-Palm]-FCK-NH$_2$ | 60 | 109 | |
| 211 | 211 | Isovaleric acid-DTHFPCI-Lys[isoGlu-Palm]-FRCK-NH$_2$ | 24 | <15 (1%) | |
| 212 | 212 | Isovaleric acid-DTHFPCI-[(D)Lys[isoGlu-Palm]]-[NMe-Phe]-GC-NH$_2$ | 403 | >180 (96%) | |
| 213 | 185 | Isovaleric acid-DTHFPCI-[(D)Lys[isoGlu-Palm]]-FC-NH$_2$ | 1751 | varible | |
| 214 | 214 | Isovaleric acid-DTHFPCI-Lys[isoGlu-Palm]-[β-homoPhe]-C-NH$_2$ | 36 | >180 (70%) | 110 |
| 215 | 215 | Isovaleric acid-DTHFPCI-Lys[isoGlu-Palm]-[α-MePhe]-C-NH$_2$ | 96 | >180 (85%) | <15 (5%) |
| 216 | 216 | Isovaleric acid-DTH-[DIP]-PCI-Lys[isoGlu-Palm]-[α-MePhe]-C-NH$_2$ | 16 | >180 (87%) | 208 |
| 217 | 217 | Isovaleric acid-DTH-[α-MePhe]-PCI-Lys[isoGlu-Palm]-[α-MePhe]-C-NH$_2$ | >3000 | >180 (81%) | 269 |
| 218 | 218 | Isovaleric acid-DTH-[N-MethylPhe]-PCI-Lys[isoGlu-Palm]-[α-MePhe]-C-NH$_2$ | >3000 | >180 (80%) | >300 (79%) |
| 219 | 219 | Isovaleric acid-DTH-[β-homoPhe]-PCI-Lys[isoGlu-Palm]-[α-MePhe]-C-NH$_2$ | 182 | >180 (86%) | >300 (126%) |
| 220 | 220 | Isovaleric acid-DTHWPCI-Lys[isoGlu-Palm]-[α-MePhe]-C-NH$_2$ | 871 | >180 (82%) | 187 |
| 221 | 221 | Isovaleric acid-DTHF-[NPC]-CI-Lys[isoGlu-Palm]-[α-MePhe]-C-NH$_2$ | 79 | >180 (66%) | 189 |
| 222 | 222 | Isovaleric acid-DTHFPCI-Lys[Peg11-Palm]-FC-NH$_2$ | 4 | <5 | <15 |
| 223 | 223 | Isovaleric acid-DTHFPCI-Lys[isoGlu-Palm]-FC-NH$_2$ | 47 | | |
| 224 | 224 | Isovaleric acid-DTHFPCI-(D)Lys[Peg11-Palm]-F-Lys-C-NH$_2$ | 33 | 7 | <15 |
| 225 | 225 | Isovaleric acid-DTHFPCI-(D)Lys[Peg11-Palm]-F-(D)Lys-C-NH$_2$ | 26 | 339 | <15 |
| 226 | 226 | Isovaleric acid-DTHFPCI-(D)Lys[Peg11-Palm]-F-(D)Arg-C-NH$_2$ | 23 | 15 | <15 |
| 227 | 227 | Isovaleric acid-DTHFPCI-Lys[isoGlu-Palm]-F-Lys-C-NH$_2$ | 114 | <5 | 8 |
| 228 | 228 | Isovaleric acid-DTH-Dpa-PCI-Lys[Peg11-Palm]-bhPhe-(D)Lys-C-NH$_2$ | | 462 | 1194 |
| 229 | 229 | Isovaleric acid-DTH-Dpa-PCI-Lys[Ahx-Palm]-bhPhe-C-NH$_2$ | | | |
| 230 | 230 | Isovaleric acid-DTH-Dpa-PCI-Lys[Ahx-Palm]-bhPhe-(D)Lys-C-NH$_2$ | 6 | | >1440 |

In certain embodiment, the present invention includes a hepcidin analogue having a structure or comprising an amino acid sequence set forth below:

Isovaleric acid-DTHFPCI-Lys[isoGlu-Palm]-FEPRSKGCK-NH₂; (SEQ ID NO: 186)

Isovaleric acid-DTHFPCI-Lys[isoGlu-Palm]-FEPRSKGC-NH₂; (SEQ ID NO: 201)

Isovaleric acid-DTHFPCI-Lys[isoGlu-Palm]-FEPRSKC-NH₂; (SEQ ID NO: 202)

Isovaleric acid-DTHFPCI-Lys[isoGlu-Palm]-FEPRSC-NH₂; (SEQ ID NO: 203)

Isovaleric acid-DTHFPCI-Lys[isoGlu-Palm]-FEPRC-NH₂; (SEQ ID NO: 204)

Isovaleric acid-DTHFPCI-Lys[isoGlu-Palm]-FEPC-NH₂; (SEQ ID NO: 205)

Isovaleric acid-DTHFPCI-Lys[isoGlu-Palm]-FEC-NH₂; (SEQ ID NO: 206)

Isovaleric acid-DTHFPCI-Lys[isoGlu-Palm]-FC-NH₂; (SEQ ID NO: 207)

Isovaleric acid-DTHFPCI-Lys[isoGlu-Palm]-FEPCK-NH₂; (SEQ ID NO: 208)

Isovaleric acid-DTHFPCI-Lys[isoGlu-Palm]-FEPC-[(D)Lys]-NH₂; (SEQ ID NO: 209)

Isovaleric acid-DTHFPCI-Lys[isoGlu-Palm]-FCK-NH₂; (SEQ ID NO: 210)

Isovaleric acid-DTHFPCI-Lys[isoGlu-Palm]-FRCK-NH₂; (SEQ ID NO: 211)

Isovaleric acid-DTHFPCI-[(D)Lys[isoGlu-Palm]]-[NMe-Phe]-GC-NH₂; (SEQ ID NO: 212)

Isovaleric acid-DTHFPCI-[(D)Lys[isoGlu-Palm]]-FC-NH₂; (SEQ ID NO: 213)

Isovaleric acid-DTHFPCI-Lys[isoGlu-Palm]-[b-homoPhe]-C-NH₂; (SEQ ID NO: 214)

Isovaleric acid-DTHFPCI-Lys[isoGlu-Palm]-[a-MePhe]-C-NH₂; (SEQ ID NO: 215)

Isovaleric acid-DTH-[Dpa]-PCI-Lys[isoGlu-Palm]-[a-MePhe]-C-NH₂; (SEQ ID NO: 216)

Isovaleric acid-DTH-[a-MePhe]-PCI-Lys[isoGlu-Palm]-[a-MePhe]-C-NH₂; (SEQ ID NO: 217)

Isovaleric acid-DTH-[N-MethylPhe]-PCI-Lys[isoGlu-Palm]-[a-MePhe]-C-NH₂; (SEQ ID NO: 218)

Isovaleric acid-DTH-[b-homoPhe]-PCI-Lys[isoGlu-Palm]-[a-MePhe]-C-NH₂; (SEQ ID NO: 219)

Isovaleric acid-DTHWPCI-Lys[isoGlu-Palm]-[a-MePhe]-C-NH₂; (SEQ ID NO: 220)

or

Isovaleric acid-DTHF-[NPC]-CI-Lys[isoGlu-Palm-[a-MePhe]-C-NH₂; (SEQ ID NO: 221)

and wherein the peptide is cyclized via a disulfide bond between two Cys.

In certain embodiment, the present invention includes a hepcidin analogue having a structure or comprising an amino acid sequence set forth below:

Isovaleric acid-DTHFPCI-Lys[Peg11-Palm]-FC-NH₂; (SEQ ID NO: 222)

Isovaleric acid-DTHFPCI-Lys[isoGlu-Palm1]-FC-NH₂; (SEQ ID NO: 223)

Isovaleric acid-DTHFPCI-(D)Lys[Peg11-Palm]-F-Lys-C-NH₂; (SEQ ID NO: 224)

Isovaleric acid-DTHFPCI-(D)Lys[Peg11-Palm]-F-(D)Lys-C-NH₂; (SEQ ID NO: 225)

Isovaleric acid-DTHFPCI-(D)Lys[Peg11-Palm]-F-(D)Arg-C-NH₂; (SEQ ID NO: 226)

Isovaleric acid-DTHFPCI-Lys[isoGlu-Palm]-F-Lys-C-NH₂; (SEQ ID NO: 227)

Isovaleric acid-DTH-Dpa-PCI-Lys[Peg11-Palm]-bhPhe-(D)Lys-C-NH₂; (SEQ ID NO: 228)

```
                                              (SEQ ID NO: 229)
Isovaleric acid-DTH-Dpa-PCI-Lys[Ahx-Palm]- bhPhe-C-NH₂;
or
                                              (SEQ ID NO: 230)
Isovaleric acid-DTH-Dpa-PCI-Lys[Ahx-Palm]- bhPhe-(D)Lys-C-NH₂;
``` and wherein the peptide is cyclized via a disulfide bond between two Cys.

In certain embodiment, the present invention provides a peptide or a peptide dimer thereof, wherein the peptide comprises or consists of any one of the peptides disclosed herein or listed in any of Tables 2A, 2B, 3A, 3B and 4. In one embodiment, the peptide comprises a disulfide bond between the two Cys, Cys and N-MeCys, or Cys and Pen residues; or wherein the compound ID is 3-107, 109-122, 125-181 or 201-230. In a particular embodiment, the peptide is any one of peptides wherein the FPN activity is <100 nM. In another particular embodiment, the peptide is any one of peptides wherein the FPN activity is <50 nM. In another particular embodiment, the peptide is any one of peptides wherein the FPN activity is <20 nM. In another particular embodiment, the peptide is any one of peptides wherein the FPN activity is <10 nM. In more particular embodiment, the peptide is any one of peptides wherein the FPN activity is <5 nM.

In certain embodiment, the peptide is selected from a group of peptides listed in Table 2A, 2B, 3A, 3B, and 4, and wherein the SIF half life is >24 h.

In certain embodiment, the peptide is

```
                                              (SEQ ID NO: 10)
Isovaleric acid-DTHFPCI-[(D)Lys]-[Phe]-

Lys[PEG11-Palm]C-NH₂;

(SEQ ID NO: 135)
Isovaleric acid-DTH[Dpa]-PCI-[(D)Lys]-

F-[Lys(Peg11-Palm)]-C-NH₂;

(SEQ ID NO: 149)
Isovaleric acid-DTH-[Dpa]-[Npc]-CI[(D)Lys]-

[Phe(4-tButyl)-[Lys(Peg11-Palm)]-[(D)Lys]-

C-NH₂;

(SEQ ID NO: 150)
Isovaleric acid-DTH-[Dpa]-[Npc]-CI-[(D)Lys]-

[Phe(4-tButyl)-[Lys(Peg11-Palm)]-C-

[(D)Lys]-NH₂;

(SEQ ID NO: 152)
Isovaleric acid-DTH-[Dpa]-PCI-[(D)Lys]-[b- hPhe]-[Lys(Ac)]-[(D)Lys]-C-NH₂;

(SEQ ID NO: 155)
Isovaleric acid-DTH-[Dpa]-PCI-[(D)Lys]-[b- hPhe]-[Lys(Peg11-Octane)]-[(D)Lys]-C-NH₂;

(SEQ ID NO: 156)
Isovaleric acid-DTH-[Dpa]-PCI-[(D)Lys]-[b- hPhe]-[Lys(Peg11-Lauryl)]-[(D)Lys]-C-NH₂;

(SEQ ID NO: 157)
Isovaleric acid-DTH-[Dpa]-PCI-[(D)Lys]-[b- hPhe]-[Lys-Peg11*]-[(D)Lys]-C-NH₂;

(SEQ ID NO: 158)
Isovaleric acid-DTH-[Dpa]-PCI-[(D)Lys]-[b- hPhe]-[Lys(IsoGlu-Palm)]-[(D)Lys]-C-NH₂;

(SEQ ID NO: 159)
Isovaleric acid-DTH-[Dpa]-PCI-[(D)Lys-Ac]-

[b-hPhe]-[Lys(Peg11-Palm)]-[(D)Lys-Ac]-C-NH₂;

(SEQ ID NO: 165)
Isovaleric acid-DTH-[Dpa]-PCI-[(D)Lys]-[b- hPhe]-Lys(Ahx-Palm)]-[(D)Lys]-C-NH₂;

(SEQ ID NO: 166)
Isovaleric acid-DTH-[Dpa]-PCI-[(D)Lys-

Peg11*]-[b-hPhe]-[Lys(Ahx-Palm)]-

[(D)Lys-Peg11*]-C-NH₂;

(SEQ ID NO: 168)
Isovaleric_Acid-D-T-H-bhPhe-(D)Pro-C-I-(D)Lys-

F-[Lys_Peg11_Palm]-(D)Lys-C-NH₂;

(SEQ ID NO: 170)
Isovaleric_Acid-D-T-H-[Dpa]-P-C-I-(D)LysbhPhe-[Lys_Peg11_Palm]-C-(D)Lys-NH₂;

(SEQ ID NO: 171)
Isovaleric_Acid-D-T-H-bhPhe-P-C-I-(D)Lys-F-

[Lys_Peg11_Palm]-C-(D)Lys-NH₂;

(SEQ ID NO: 172)
Isovaleric_Acid-D-T-H-bhPhe-Npc-C-I-(D)Lys-F-

[Lys_Peg11_Palm]-C-(D)Lys-NH₂;

(SEQ ID NO: 173)
Isovaleric_Acid-D-T-H-[Dpa]-Npc-C-I-(D)LysbhPhe-[Lys_Peg11_Palm]-C-(D)Lys-NH₂;

(SEQ ID NO: 174)
Isovaleric_Acid-D-T-H-[Dpa]-P-C-I-(D)GlnbhPhe-[Lys_Peg11_Palm]-(D)Lys-C-NH₂;
or
                                              (SEQ ID NO: 175)
Isovaleric_Acid-D-T-H-[Dpa]-P-C-I-(D)LysbhPhe-[Lys_Peg11_Palm]-dLys_Ac-C-NH₂;
``` and wherein the peptide is cyclized via a disulfide bond between two Cys.

In certain embodiment, the peptide is selected from a group of peptides listed in Table 3A and wherein the SGF half life is >24 h.

In certain embodiment, the peptide is:

```
                                              (SEQ ID NO: 121)
Isovaleric acid-DTHb-[B-hPhe]-PCI-(D)Lys-F-

Lys(Peg11-Palm)]-[(D)Lys]-C-NH₂;
```

(SEQ ID NO: 128)
Isovaleric acid-DTH-[a-MePhe]-PCI-[(D)Lys]-F-Lys(Peg11-Palm)]-[(D)Lys]-C-NH₂;

(SEQ ID NO: 129)
Isovaleric acid-DTH-[Phe[4-(2-aminoethoxy)]-PCI-[(D)Lys]-F-[Lys(Peg11-Palm)]-[(D)Lys]-C-NH₂;

(SEQ ID NO: 145)
Isovaleric acid-DTH-[Dpa]-PCI-[BALa]-[b-hPhe]-[Lys(Peg11-Palm)]-[(D)Lys]-C-NH₂;

(SEQ ID NO: 147)
Isovaleric acid-DTH-[Dpa]-PCII-[b-hPhe]-Lys(Peg11-Palm)]-[(D)Lys]-C-NH₂;

(SEQ ID NO: 149)
Isovaleric acid-DTH-[Dpa]-[Npc]-CI-[(D)Lys]-[Phe(4-tButyl)]-[Lys(Peg11-Palm)][(D)Lys]-C-NH₂;

(SEQ ID NO: 150)
Isovaleric acid-DTH-[Dpa]-[Npc]-CI-[(D)Lys1-[Phe(4-tButyl)]-[Lys(Peg11-Palm)]-C-[(D)Lys]-NH₂;

(SEQ ID NO: 152)
Isovaleric acid-DTH-[Dpa]-PCI-[(D)Lys-[b-hPhe]-Lys(Ac)]-[(D)Lys]-C-NH₂;

(SEQ ID NO: 153)
Isovaleric acid-DTH-[Dpa]-PCI-[(D)Lys-Peg11*]-[b-hPhe]-Lys(Peg11-Palm)]-[(D)Lys-Peg11*]C-NH₂;

(SEQ ID NO: 154)
Isovaleric acid-DTH-[Dpa]-PCI-[(D)Lys]-[b-hPhe]-[Lys-Peg11]-[(D)Lys]-C-NH₂;

(SEQ ID NO: 155)
Isovaleric acid-DTH-[Dpa]-PCI-[(D)Lys]-[b-hPhe-[Lys-(Peg11-Octane)]-[(D)Lys]-C-NH₂;

(SEQ ID NO: 156)
Isovaleric acid-DTH-[Dpa]-PCI-[(D)Lys]-[b-hPhe]-Lys(Peg11-Lauryl)]-[(D)Lys]-C-NH₂;

(SEQ ID NO: 157)
Isovaleric acid-DTH-[Dpa]-PCI-[(D)Lys]-[b-hPhe]-[Lys-Peg11*]-[(D)Lys]-C-NH₂;

(SEQ ID NO: 166)
Isovaleric acid-DTH-[Dpa]-PCI-[(D)Lys-Peg11*]-[b-hPhe]-[Lys(Ahx-Palm)]-[(D)Lys-Peg11*]-C-NH₂;

(SEQ ID NO: 167)
Isovaleric_Acid-D-T-H-[Dpa]-(D)Pro-C-I-(D)Lys-F-[Lys_Peg11_Palm]-(D)Lys-C-NH₂;

(SEQ ID NO:168)
Isovaleric_Acid-D-T-H-bhPhe-(D)Pro-C-I-(D)Lys-F-[Lys_Peg11_Palm]-(D)Lys-C-NH₂;

(SEQ ID NO: 169)
Isovaleric_Acid-D-T-H-[Dpa]-PCI-(D)Lys-bhPhe-[Lys_Peg11_Palm]-(D)Lys-C-NH₂;

(SEQ ID NO: 171)
Isovaleric_Acid-D-T-H-bhPhe-P-C-I-(D)Lys-F-[Lys_Peg11_Palm]-C-(D)Lys-NH₂;
or (SEQ ID NO: 172)
Isovaleric_Acid-D-T-H-bhPhe-Npc-C-I-(D)Lys-F-[Lys_Peg11_Palm]-C-(D)Lys-NH₂;

and wherein the peptide is cyclized via a disulfide bond between two Cys.

In certain embodiment, the peptide is selected from a group of peptides listed in Table 3A and wherein the SIF half life is >10 h.

In certain embodiment, the peptide is:

(SEQ ID NO: 16)
Isovaleric acid-DTHFPCIIF-Lys[PEG11-Palm]-C-NH₂;

(SEQ ID NO: 146)
Isovaleric acid-DTH-[Dpa]-PCI-[(D)Ala]-[b-hPhe]-[Lys(Peg11-Palm)]-[(D)Lys]-C-NH₂;

(SEQ ID NO: 148)
Isovaleric acid-DTH-[Dpa]-PCI-[b-hPhe]-[Lys(Peg11-Palm)]-[(D)Lys]-C-NH₂;

(SEQ ID NO: 167)
Isovaleric acid-D-T-H-[Dpa]-(D)Pro-C-I-(D)Lys-F-[Lys_Peg11_Palm]-(D)Lys-C-NH₂;
or (SEQ ID NO: 169)
Isovaleric acid-dD-T-H-[Dpa]-P-C-I-(D)Lys-bhPhe-[Lys_Peg11_Palm]-(D)Lys-C-NH₂;

and wherein the peptide is cyclized via a disulfide bond between two Cys.

In certain embodiment, the peptide is selected from a group of peptides listed in Table 3A and wherein the SGF half life is >10 h.

In certain embodiment, the peptide is:

(SEQ ID NO: 105)
Isovaleric acid-D-T-H-[Dpa]-P-C-I-[(D)Lys]-[b-homoPhe]-Lys[PEG11-Palm]-[(D)Lys]-[Cys]-NH₂;

(SEQ ID NO: 110)
Isovaleric acid-DTH-[Dpa]-[Npc]-C-I-[(D)Lys]-[Phe(4-tBu)]-[Lys(Peg11-Palm)]-K-C-NH₂;

(SEQ ID NO: 111)
Isovaleric acid-DTH-[Dpa]-[Npc]-C-I-[(D)Lys]-

(SEQ ID NO: 117)
[Phe[4-(2-aminoethoxy)]-[Lys(Peg11-Palm)]-K-C-NH$_2$;

(SEQ ID NO: 117)
Isovaleric acid-DTH-[Dpa]-[Npc]-C-I-[(D)Lys]-F-[Lys(Peg11-Palm)]-[(D)Lys]-C-NH$_2$;

(SEQ ID NO: 118)
Isovaleric acid-DTH-F-[Npc]-C-I-[(D)Lys]-F-[Lys(Peg11-Palm)]-[(D)Lys]-C-NH$_2$;

(SEQ ID NO: 122)
Isovaleric acid-DTH-[Dpa]-PCI-[(D)Lys]-[b-hPhe]-[Lys(Peg11-Palm)]-[(D)Lys]-C-NH$_2$;

(SEQ ID NO: 125)
Isovaleric acid-DTH-[Dpa]-[Npc]-C-I-[(D)Lys]-[a-MePhe]-[Lys(Peg11-Palm)]-K-C-NH$_2$;

(SEQ ID NO: 131)
Isovaleric acid-DTH-[Dpa]-PCI-[(D)Lys]-[Dpa]-[Lys(Peg11-Palm)]-[(D)Lys]-C-NH$_2$;

(SEQ ID NO: 132)
Isovaleric acid-DTH-[Dpa]-PCI-[(D)Lys]-F-[Lys(Peg11-Palm)]-[(D)Lys]-Pen-NH$_2$;

(SEQ ID NO: 134)
Isovaleric acid-DTH-[Dpa]-PCI-[(D)Lys]-F-[Lys(Peg11-Palm)]-[(D)Lys]-[N-Me-Cys]-NH$_2$;

(SEQ ID NO: 139)
Isovaleric acid-DTH-[Dpa]-PCI-[(D)Lys]-F-[Lys(Peg11-Palm)]-[(D)Lys]-C-NH$_2$;

(SEQ ID NO: 141)
Isovaleric acid-DTH-[Dpa]-P-[Hcy]-I-[(D)Lys]-F-[Lys(Peg11-Palm)]-|]Dap|-C-NH$_2$;

(SEQ ID NO: 146)
Isovaleric acid-DTH-[Dpa]-PCI-[(D)Ala]-[b-hPhe]-[Lys(Peg11-Palm)]-[(D)Lys]-C-NH$_2$;

(SEQ ID NO: 148)
Isovaleric acid-DTH-[Dpa]-PCI-[b-hPhe]-[Lys(Peg11-Palm)]-[(D)Lys]-C-NH$_2$;

(SEQ ID NO: 151)
Isovaleric acid-DTH-[Dpa]-PCI-[(D)Lys]-[b-hPhe]-[Lys(Ahx-Palm)]-[Dap]-[N-Me-Cys]-NH$_2$;

(SEQ ID NO: 158)
Isovaleric acid-DTH-[Dpa]-PCI-[(D)Lys]-[b-hPhe]-[Lys(IsoGlu-Palm)]-[(D)Lys]-C-NH$_2$;

(SEQ ID NO: 161)
Isovaleric acid-DTH-[Dpa]-PCI-[(D)Lys]-[b-hPhe]-[Lys(dDap-Palm)]-C-NH$_2$;

(SEQ ID NO: 162)
Isovaleric acid-DTH-[Dpa]-PCI-[(D)Lys]-[b-hPhe]-[Dap(Dap-Palm)]-C-NH$_2$;

(SEQ ID NO: 163)
Isovaleric acid-DTH-[Dpa]-PCI-[(D)Lys]-[b-hPhe]-[Dap(dDap-Palm)]-C-NH$_2$;

(SEQ ID NO: 164)
Isovaleric acid-DTH-[Dpa]-PCI-[(D)Lys]-[b-hPhe]-[Dap(dDap-Palm)]-C-NH$_2$;

(SEQ ID NO: 165)
Isovaleric acid-DTH-[Dpa]-PCI-[(D)Lys]-[b-hPhe]-[Lys(Ahx-Palm)]-[(D)Lys]-C-NH$_2$;
or (SEQ ID NO: 173)
lsovaleric_Acid-D-T-H-[Dpa]-Npc-C-I-(D)Lys-bhPhe-[Lys_Peg11_Palm|-C-(D)Lys-NH$_2$;

and wherein the peptide is cyclized via a disulfide bond between two Cys.

In certain embodiment, the peptide is selected from a group of peptides listed in Table 3A and wherein the SGF half life and SIF half life is >24 h.

In certain embodiment, the peptide is:

(SEQ ID NO: 149)
Isovaleric acid-DTH-[Dpa]-[Npc]-CI-[(D)Lys]-[Phe(4-tButyl)]-[Lys(Peg11-Palm)]-[(D)Lys]-C-NH$_2$;

(SEQ ID NO: 150)
Isovaleric acid-DTH-[Dpa]-[Npc]-CI-[(D)Lys]-[Phe(4-tButyl)]-[Lys(Peg11-Palm)]-C-[(D)Lys]-NH$_2$;

(SEQ ID NO: 152)
Isovaleric acid-DTH-[Dpa]-PCI-[(D)Lys]-[b-hPhe]-[Lys(Ac)]-[(D)Lys]-C-NH$_2$;

(SEQ ID NO: 155)
Isovaleric acid-DTH-[Dpa]-PCI-[(D)Lys]-[b-hPhe]-Lys(Peg11-Octane)]-[(D)Lys]-C-NH$_2$;

(SEQ ID NO: 156)
Isovaleric acid-DTH-[Dpa]-PCI-[(D)Lys]-[b-hPhe]-[Lys(Peg11-Lauryl)]-[(D)Lys]-C-NH$_2$;

(SEQ ID NO: 157)
Isovaleric acid-DTH-[Dpa]-PCI-[(D)Lys]-[b-hPhe]-[Lys-Peg11*]-[(D)Lys]-C-NH$_2$;

(SEQ ID NO: 166)
Isovaleric acid-DTH-[Dpa]-PCI-[(D)Lys-Peg11*]-[b-hPhe]-[Lys(Ahx-Palm)]-[(D)Lys-Peg11*]-C-NH$_2$;

(SEQ ID NO: 168)
Isovaleric_Acid-D-T-H-bhPhe-(D)Pro-C-I-(D)Lys-F-[Lys_Peg11_Palm]-(D)Lys-C-NH$_2$;

(SEQ ID NO: 171)
Isovaleric_Acid-D-T-H-bhPhe-P-C-I-(D)Lys-F-[Lys_Peg11_Palm]-C-(D)Lys-NH$_2$;

(SEQ ID NO: 172)
Isoyaleric_Acid-D-T-H-bhPhe-Npc-C-I-(D)Lys-F-[Lys_Peg11_Palm]-C-(D)Lys-NH$_2$;
or (SEQ ID NO: 173)
Isoyaleric_Acid-D-T-H-[Dpa]-Npc-C-I-(D)Lys-bhPhe-[Lys_Peg11_Palm]-C-(D)Lys-NH$_2$;

and wherein the peptide is cyclized via a disulfide bond between two Cys.

In certain embodiments, the peptide is:

(SEQ ID NO: 114)
Isovaleric acid-DTHFPCI-[(D)Lys]-[Phe]-Lys[PEG11-Palm]-K-[a-MeCys]-NH$_2$;

(SEQ ID NO: 187)
Isovaleric acid-DTHFPCI-[(D)Lys]-[Phe]-Lys[PEG11-Palm]-[Orn]-C-NH$_2$;

(SEQ ID NO: 188)
Isovaleric acid-DTHFPCI-[(D)Lys]-[Phe]-Lys[PEG11-Palm]-[Dab]-C-NH$_2$;

(SEQ ID NO: 189)
Isovaleric acid-DTHFPCI-[(D)Lys]-[Phe]-Lys[PEG11-Palm]-[homoLys]-C-NH$_2$;

(SEQ ID NO: 190)
Isovaleric acid-DTHFPCI-[(D)Lys]-[Dab]-Lys[PEG11-Palm]-KC-NH$_2$;

(SEQ ID NO: 191)
Isovaleric acid-DTH[Dpa]PCI-[(D)Lys]-[bhPhe]-Lys[PEG11-Palm]-KC-NH$_2$;

(SEQ ID NO: 192)
Isovaleric acid-DTHFPCI-[(D)Lys]-[Phe]-[(D)Lys]-[PEG11-Palm]-KC-NH$_2$;
or (SEQ ID NO: 107)
Isovaleric acid-DTHFPCI-[(D)Lys]-[Phe]-[(D)Lys]-[PEG11-Palm]-[(D)Lys]-C-NH$_2$;

and wherein the peptide is cyclized via a disulfide bond between two Cys.

In certain embodiments, the peptide is:

(SEQ ID NO: 167)
Isoyaleric_Acid-D-T-H[Dpa]-(D)Pro-C-I-(D)Lys-F-[Lys_Peg11_Palm]-(D)Lys-C-NH$_2$;

(SEQ ID NO: 168)
Isoyaleric_Acid-D-T-H-bhPhe-(D)Pro-C-I-(D)Lys-F-[Lys_Peg11_Palm]-(D)Lys-C-NH$_2$;

(SEQ ID NO: 169)
Isoyaleric_Acid-dD-T-H[Dpa]-P-C-I-(D)Lys-bhPhe-[Lys_Peg11_Palm]-(D)Lys-C-NH$_2$;

(SEQ ID NO: 170)
Isoyaleric_Acid-D-T-[Dpa]-P-C-I-(D)Lys-bhPhe-[Lys_Peg11_Palm]-C-(D)Lys-NH$_2$;

(SEQ ID NO: 171)
Isoyaleric_Acid-D-T-H-bhPhe-P-C-I-(D)Lys-F-[Lys_Peg11_Palm]-C-(D)Lys-NH$_2$;

SEQ ID NO: 172)
Isoyaleric_Acid-D-T-H-bhPhe-Npc-C-I-(D)Lys-F-[Lys_Peg11_Palm]-C-(D)Lys-NH$_2$;

(SEQ ID NO: 173)
Isoyaleric_Acid-D-T-H-[Dpa]-Npc-C-I-(D)Lys-bhPhe-[Lys_Peg11_Palm]-C-(D)Lys-NH$_2$;

(SEQ ID NO: 174)
Isoyaleric_Acid-D-T-H-[Dpa]-P-C-I-(D)Gln-bhPhe-[Lys_Peg11_Palm]-(D)Lys-C-NH$_2$;

(SEQ ID NO: 175)
Isoyaleric_Acid-D-T-H-[Dpa]-P-C-I-(D)Lys-bhPhe-[Lys_Peg11_Palm]-dLys_Ac-C-NH$_2$;
or (SEQ ID NO: 176)
Isoyaleric_Acid-D-T-H-bhPhe-(D)Pro-C-I-(D)Lys-bhPhe-[Lys_Peg11_Pal]-C-(D)Lys-NH$_2$;

and wherein the peptide is cyclized via a disulfide bond between two Cys.

In certain embodiment, the present invention includes a peptide having a structure or comprising an amino acid sequence set forth below:

(SEQ ID NO: 145)
Isovaleric acid-DTH-[Dpa]-PCI[b-Ala]-[b-hPhe]-[Lys(Peg11-Palm)]-[(D)Lys]-C-NH$_2$;

(SEQ ID NO: 150)
Isovaleric acid-DTH-[Dpa]-[Npc]-CI-[(D)Lys]-[Phe(4-tButyl)-[Lys(Peg11-Palm)]-C-[(D)Lys]-NH$_2$;

(SEQ ID NO: 160)
Isovaleric acid-DTH-[Dpa]-PCI-[(D)Lys]-[b-hPhe]-Lys(Dap-Palm)]-C-NH$_2$;

(SEQ ID NO: 161)
Isovaleric acid-DTH-[Dpa]-PCI-[(D)Lys]-[b-hPhe]-Lys(dDap-Palm)]-C-NH$_2$;

(SEQ ID NO: 162)
Isovaleric acid-DTH-[Dpa]-PCI-[(D)Lys]-[b-hPhe]-[Dap(Dap-Palm)]-C-NH$_2$;

(SEQ ID NO: 163)
Isovaleric acid-DTH-[Dpa]-PCI-[(D)Lys]-[b-hPhe]-[Dap(dDap-Palm)]-C-NH$_2$;

(SEQ ID NO: 164)
Isovaleric acid-DTH-[Dpa]-PCI-[(D)Lys]-[b-hPhe]-[Dap(dDap-Palm)]-C-NH$_2$;

-continued

```
                                              (SEQ ID NO: 165)
Isovaleric acid-DTH-[Dpa]-PCI-[(D)Lys]-b- hPhe]-Lys(Ahx-Palm)]-[(D)Lys]-C-NH2;
or (SEQ ID NO: 168)
Isovaleric_Acid-D-T-H-bhPhe-(D)Pro-C-I-

(D)Lys-F-[Lys_Peg11_Palm]-(D)Lys-C-NH2;
``` and wherein the peptide is cyclized via a disulfide bond between two Cys.

In certain embodiment, the present invention includes a peptide having a structure or comprising an amino acid sequence set forth below:

```
                                              (SEQ ID NO:169)
Isovaleric_Acid-dD-T-H-[Dpa]-P-C-I-(D)Lys-bhPhe-

[Lys_Peg11_Palm]-(D)Lys-C-NH2;

SEQ ID NO: 173)
Isovaleric_Acid-D-T-H-[Dpa]-Npc-C-I-(D)Lys-bhPhe-

[Lys_Peg11_Palm]-C-(D)Lys-NH2;
or (SEQ ID NO: 166)
Isovaleric acid-DTH-[Dpa]-PCI-[(D)Lys-Peg11*]-[b- hPhe]-[Lys(Ahx-Palm)]-[(D)Lys-Peg11*]-C-NH2;
``` and wherein the peptide is cyclized via a disulfide bond between two Cys.

In certain embodiment, the present invention includes a peptide having a structure or comprising an amino acid sequence set forth below:

```
                                              (SEQ ID NO: 25)
Isovaleric acid-DTHFPCI-[(D)Lys]-[Phe]-Lys[Ahx- Palm]-C-NH2;

(SEQ ID NO: 70)
Isovaleric acid-DTHFPCI-[(D)Lys]-[Phe]-Lys[PEG11-

Palm]-PC-NH2;

(SEQ ID NO: 71)
Isovaleric acid-DTHFPCI-[(D)Lys]-[Phe]-Lys[PEG11-

Palm]-PRC-NH2;

(SEQ ID NO: 72)
Isovaleric acid-DTHFPCI-[(D)Lys]-[Phe]-Lys[PEG11-

Palm]-PRSC-NH2;

(SEQ ID NO: 73)
Isovaleric acid-DTHFPCI-[(D)Lys]-[Phe]-Lys[PEG11-

Palm]-PRSKC-NH2;

(SEQ ID NO: 74)
Isovaleric acid-DTHFPCI-[(D)Lys]-[Phe]-Lys[PEG11-

Palm]-PRSKSarC-NH2;
or (SEQ ID NO: 75)
Isovaleric acid-DTHFPCI-[(D)Lys]-[Phe]-Lys[PEG11-

Palm]-PRSKCK-NH2;
``` and wherein the peptide is cyclized via a disulfide bond between two Cys.

In certain embodiment, the present invention includes a peptide having a structure or comprising an amino acid sequence set forth below:

```
                                              (SEQ ID NO: 80)
Isovaleric acid-DTHFPCI-[(D)Lys]-[Phe]-Lys[PEG11-

Palm]-KC-NH2;

(SEQ ID NO: 105)
Isovaleric acid-D-T-H-[Dpa]-P-C-I-[(D)Lys]-[b- homoPhe]-Lys[PEG11-Palm]-[(D)Lys]-[Cys]-NH2;

(SEQ ID NO: 145)
Isovaleric acid-DTH-[Dpa]-PCI-[bAla]-[b-hPhe]-[Lys (Peg11-Palm)]-[(D)Lys]-C-NH2;

(SEQ ID NO: 146)
Isovaleric acid-DTH-[Dpa]-PCI-[(D)Ala]-[b-hPhe]-

[Lys(Peg11-Palm)]-[(D)Lys]-C-NH2;

(SEQ ID NO: 147)
Isovaleric acid-DTH-[Dpa]-PCII-[b-hPhe]-[Lys(Peg11-

Palm)]-[(D)Lys]-C-NH2;

(SEQ ID NO: 148)
Isovaleric acid-DTH-[Dpa]-PCI-[b-hPhe]-[Lys(Peg11-

Palm)]-[(D)Lys]-C-NH2;

(SEQ ID NO: 149)
Isovaleric acid-DTH-[Dpa]-[Npc]-CI-[(D)Lys]-[Phe(4- tButyl)]-[Lys(Peg11-Palm)]-[(D)Lys]-C-NH2;

(SEQ ID NO: 150)
Isovaleric acid-DTH-[Dpa]-[Npc]-CI-[(D)Lys]-[Phe(4- tButyl)]-[Lys(Peg11-Palm)]-C-[(D)Lys]-NH2;

(SEQ ID NO: 162)
Isovaleric acid-DTH-[Dpa]-PCI-[(D)Lys]-[b-hPhe]-

[Dap(Dap-Palm)]-C-NH2;

(SEQ ID NO: 163)
Isovaleric acid-DTH-[Dpa]-PCI-[(D)Lys]-[b-hPhe]-

[Dap(dDap-Palm)]-C-NH2;

(SEQ ID NO: 164)
Isovaleric acid-DTH-[Dpa]-PCI-[(D)Lys]-[b-hPhe]-

[Dap(dDap-Palm)]-C-NH2;

(SEQ ID NO: 165)
Isovaleric acid-DTH-[Dpa]-PCI-[(D)Lys]-[b-hPhe]-

[Lys(Ahx-Palm)]-[(D)Lys]-C-NH2;

(SEQ ID NO: 166)
Isovaleric acid-DTH-[Dpa]-PCI-[(D)Lys-Peg11*]-[b- hPhe]-[Lys(Ahx-Palm)]-[(D)Lys-Peg11*]-C-NH2;

(SEQ ID NO: 167)
Isovaleric_Acid-D-T-H-[Dpa]-(D)Pro-C-I-(D)Lys-F-

[Lys_Peg11_Palm]-(D)Lys-C-NH2;

(SEQ ID NO: 168)
Isovaleric_Acid-D-T-H-bhPhe-(D)Pro-C-I-(D)Lys-F-

[Lys_Peg11_Palm]-(D)Lys-C-NH2;
```

-continued

```
                                              (SEQ ID NO: 169)
Isovaleric_Acid-dD-T-H-[Dpa]-P-C-I-(D)Lys-bhPhe-

[Lys_Peg11_Palm]-(D)Lys-C-NH2;

(SEQ ID NO: 170)
Isovaleric_Acid-D-T-H-[Dpa]-P-C-I-(D)Lys-bhPhe-

[Lys_Peg11_Palm]-C-(D)Lys-NH2;

(SEQ ID NO: 171)
Isovaleric_Acid-D-T-H-bhPhe-P-C-I-(D)Lys-F-[Lys_

Peg11_Palm]-C-(D)Lys-NH2;

(SEQ ID NO: 172)
Isovaleric_Acid-D-T-H-bhPhe-Npc-C-I-(D)Lys-F-[Lys_

Peg11_Palm]-C-(D)Lys-NH2;

(SEQ ID NO: 173)
Isovaleric_Acid-D-T-H-[Dpa]-Npc-C-I-(D)Lys-bhPhe-

[Lys_Peg11_Palm]-C-(D)Lys-NH2;

(SEQ ID NO: 174)
Isovaleric_Acid-D-T-H-[Dpa]-P-C-I-(D)Gln-bhPhe-

[Lys_Peg11_Palm]-(D)Lys-C-NH2;
or (SEQ ID NO: 175)
Isovaleric_Acid-D-T-H-[Dpa]-P-C-I-(D)Lys-bhPhe-

[Lys_Peg11_Palm]-dLys_Ac-C-NH2;
``` and wherein the peptide is cyclized via a disulfide bond between two Cys.

In certain embodiment, the present invention includes a peptide having a structure or comprising an amino acid sequence of

```
                                              (SEQ ID NO: 165)
Isovaleric acid-DTH-[Dpa]-PCI-[(D)Lys]-[b-hPhe]-

[Lys(Ahx-Palm)]-[(D)Lys]-C-NH2;
``` and wherein the peptide is cyclized via a disulfide bond between two Cys.

In certain embodiment, the present invention includes a peptide having a structure or comprising an amino acid sequence of

```
                                              (SEQ ID NO: 105)
Isovaleric acid-D-T-H-[Dpa]-P-C-I-[(D)Lys]-[b- homoPhe]-Lys[PEG11-Palm]-[(D)Lys]-[Cys]-NH2;
``` and wherein the peptide is cyclized via a disulfide bond between two Cys.

In certain embodiment, the present invention provides a cyclized form of any one of the hepcidin analogues listed in any of Tables 2A, 2B, 3A, 3B and 4, comprising a disulfide bond between the two Cys and/or Pen residues; and wherein the compound ID is 3-107, 109-122, 125-181 or 201-230. In a particular embodiment, the ID is 80, 105, 145, 146, 147, 148, 149, 150, 162, 163, 164, 165, 166, 167, 168, 169, 170, 171, 172, 173, 174, 175, 10, 71, 73, 75, 86, 118, 121, 122, 130, 131, 132, 136, 137, 138, 139, 144, 151, 154, 158, 159, 160, 161, or 176. In a more particular embodiment, the ID is 80, 105, 145, 146, 147, 148, 149, 150, 162, 163, 164, 165, 166, 167, 168, 169, 170, 171, 172, 173, 174, or 175. The conjugated half-life extension moiety and the amino acid residue to which it is conjugated are indicated by parentheses and brackets, respectively.

Peptide Dimer Hepcidin Analogues

In certain embodiments, the present invention includes dimer hepcidin analogues, which include dimers of any of the monomer hepcidin analogues described herein, including dimers comprising any of the monomer peptides sequences or structures set forth in the formulaes described herein, e.g., various embodiments of Formulas I, I', (A-I)-(A-XXIVb), and (B-I)-(B-XIVb), and certain dimers of sequences or structures set forth in Table 2A, Table 2B, Table 3A and Table 3B. These dimers fall within the scope of the general term "hepcidin analogues" as used herein. The term "dimers," as in peptide dimers, refers to compounds in which two peptide monomer subunits are linked. A peptide dimer of the present invention may comprise two identical monomer subunits, resulting in a homodimer, or two non-identical monomer subunits, resulting in a heterodimer. A cysteine dimer comprises two peptide monomer subunits linked through a disulfide bond between a cysteine residue in one monomer subunit and a cysteine residue in the other monomer subunit.

In certain embodiments, a dimer hepcidin analogue comprises two polypeptide sequences of Formula (I'):

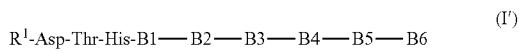

or a pharmaceutically acceptable salt or solvate thereof, wherein:
R¹, B1, B2, B3, B4, B5, and B6 are as described for Formula (A-I): the dimers are linked via a linker moiety and through a disulfide bond between two B3s; and wherein the dimer hepcidin analogue comprises a conjugated half-life extension moiety.

In one embodiment, the monomers are linked via B8B9 (L1Z)R2 and wherein each B8 and B9 is independently Lys, D-Lys, homoLys, or a-Me-Lys; L1, Z, and R2 are as described herein; and wherein one of the B6s is attached to N^ε of B8.

In one embodiment, the peptide dimer is according to formula A-II:

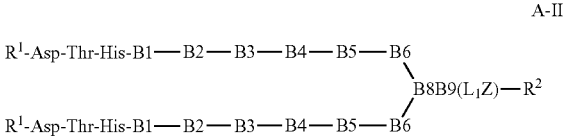

and wherein each B8 and B9 is independently Lys, D-Lys, homoLys, or a-Me-Lys; B1-B6, L1, Z, and R2 are as described for Formula (A-I); and wherein one of the B6s is attached to N^ε of B8.

In one embodiment, B9 is Lys. In another embodiment, B8 is Lys or D-Lys.

In certain embodiments, the hepcidin analogue comprises two polypeptide sequences of Formula (I"):

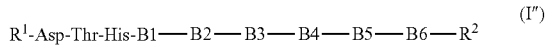

or a pharmaceutically acceptable salt or solvate thereof, wherein:

R¹, B1, B2, B3, B4, B5, and B6 are as described for Formula (A-I); the dimers are linked via a linker moiety and through a disulfide bond between two B3s; and wherein the dimer hepcidin analogue comprises a conjugated half-life extension moiety.

In one embodiment, the peptide dimer is according to formula A-III:

$$\begin{array}{c} R^1\text{-Asp-Thr-His-B1-B2-B3-B4-B5-B6-R}^2 \\ \diagdown \\ \text{IDA(B10Z)} \\ \diagup \\ R^1\text{-Asp-Thr-His-B1-B2-B3-B4-B5-B6-R}^2 \end{array} \quad \text{A-III}$$

R¹, B1, B2, B3, B4, B5, and B6 are as described for Formula (A-I); the dimers are linked via a linker moiety and through a disulfide bond between two B3s; B10 is a natural or unnatural amino acid; and Z is a half-life extending moiety.

In certain embodiments, the peptide dimer is according to Formula A-I or III, and B1 is Phe.

In certain embodiments, the peptide dimer is according to Formula A-I or III, and B2 is Pro.

In certain embodiments, the peptide dimer is according to Formula A-I or III, and B3 is Cys.

In certain embodiments, the peptide dimer is according to Formula A-I or III, and B4 is Ile.

In certain embodiments, the peptide dimer is according to Formula A-I or III, and B6 is Phe.

In one embodiment, the peptide dimer is according to Formula A-I, and each B8 and B9 is independently lower or higher homolog of Lys.

In one embodiment, the peptide dimer is according to Formula A-I, and one of the B6s is attached to Nᵋ of B8.

In one embodiment, the peptide dimer is according to Formula A-II, and B10 is b-Ala.

In one embodiment, the peptide dimer is according to Formula A-II, and B10 is b-Ala.

In one embodiment, the peptide dimer is according to Formula A-II, and one of the carboxy of IDA is attached to B5 of a first monomer; and the other carboxy of IDA is attached to B5 of a second monomer.

In particular embodiments, the linker moiety is bound to the C-terminus of each hepcidin analogue. In particular embodiments, the linker moiety is bound to the N-terminus of each hepcidin analogue. In particular embodiments, the linker moiety is bound to the N-terminus of one hepcidin analogue and the C-terminus of the other hepcidin analogue present in the dimer.

In certain embodiments, the half-life extension moiety is conjugated to the linker moiety.

In some embodiments, the hepcidin analogues of the present invention are active in a dimer conformation, in particular when free cysteine residues are present in the peptide. In certain embodiments, this occurs either as a synthesized dimer or, in particular, when a free cysteine monomer peptide is present and under oxidizing conditions, dimerizes. In some embodiments, the dimer is a homodimer. In other embodiments, the dimer is a heterodimer.

In certain embodiments, a hepcidin analogue dimer of the present invention is a peptide dimer comprising two hepcidin analogue peptide monomers of the invention.

In certain embodiment, the present invention includes a polypeptide comprising an amino acid sequence set forth in any of Tables 2A, 2B, 3A, 3B, or 4 (with or without the indicated linker moieties and half-life extension moieties), or having any amino acid sequence with at least 85%, at least 90%, at least 92%, at least 94%, or at least 95% identity to any of these amino acid sequences. In related embodiments, the present invention includes a dimer comprising two polypeptides, each comprising an amino acid sequence set forth in any of Tables 2A, 2B, 3A, or 3B (with or without the indicated linker moieties and half-life extension moieties), or having any amino acid sequence with at least 85%, at least 90%, at least 92%, at least 94%, or at least 95% identity to any of these amino acid sequences. In particular embodiments, a peptide dimer hepcidin analogue comprises one or more, e.g., two, peptide monomer subunits shown in any of Tables 2A, 2B, 3A or 3B. The conjugated half-life extension moiety and the amino acid residue to which it is conjugated may be indicated by parentheses and/or brackets. Table 4 shows dimer hepcidin analogues, each comprising a dimer of the sequences in parentheses followed by a subscript "2", which are linked by the indicated one or more linkers, e.g., Lys or IDA, and conjugated to the indicated half-life extension moiety, e.g., octanoic acid or Palm.

TABLE 4

Illustrative Dimer Hepcidin Analogues

| Compd ID | SEQ ID No. | Peptide | FPN IC50 | SIF Half life (min) | SGF Half life (min) |
|---|---|---|---|---|---|
| 501 | 231 | (Isovaleric acid-DTHFPCIKF)2K-Lys[isoGlu-Palm]-NH₂ | 28 nM | 50 | 49 |
| 502 | 232 | (Isovaleric acid-DTHFPCIKF)₂-[D-Lys]-Lys[isoGlu-Palm]-NH₂ | 33 nM | 43 | 173 |
| 503 | 233 | (Isovaleric acid-DTHFPCI-[D-Lys]-F)₂-Lys[isoGlu-Palm]-NH₂ | 21 nM | >1440 (65%) | 52 |
| 504 | 234 | (Isovaleric acid-DTHFPCIK-[Phe(4-OCH2CH2NH₂)])₂K-Lys[isoGlu-Palm]-NH₂ | 20 nM | 13 | 16 |
| 505 | 235 | (Isovaleric acid-DTHFPCIK-[a-MePhe])₂K-Lys[isoGlu-Palm]-NH₂ | 18 nM | 596 | 192 |

TABLE 4-continued

Illustrative Dimer Hepcidin Analogues

| Compd ID | SEQ ID No. | Peptide | FPN IC50 | SIF Half life (min) | SGF Half life (min) |
|---|---|---|---|---|---|
| 506 | 236 | (Isovaleric acid-DTHFPCI-[D-Lys]-F)$_2$-IDA-[(b-Ala)-Palm]-NH$_2$ | 4 nM | >1290 (100%) | >1290 (57%) |
| 507 | 237 | (Isovaleric acid-DTHFPCIK-[NMe-Phe])$_2$-IDA-[(b-Ala)-Palm]-NH$_2$ | 10 nM | >1290 (100%) | 26 |
| 508 | 238 | (Isovaleric acid-DTHFPCIK-[a-MePhe])$_2$-IDA-[(b-Ala)-Palm]-NH$_2$ | 9 nM | >1290 (80%) | 35 |
| 509 | 239 | (Isovaleric acid-DTHFPCIIF-[D-Lys])$_2$-IDA-[(b-Ala)-Palm]-NH$_2$ | 433 nM | >1290 (54%) | variable |
| 510 | 240 | (Isovaleric acid-DTHFPCI-[D-Lys]-[a-MePhe])$_2$-K-Lys[isoGlu-Palm]-NH$_2$ | 8 nM | 1441 | 187 |
| 511 | 241 | (Isovaleric acid-DTH-[BIP]-PCI-[D-Lys]-F)$_2$-K-Lys[isoGlu-Palm]-NH$_2$ | TBC | 449 | >1440 (89%) |
| 512 | 242 | (Isovaleric acid-DTHFPCIK-[b-homoPhe])$_2$K-Lys[isoGlu-Palm]-NH$_2$ | 5 nM | >1440 (93%) | 283 |
| 513 | 243 | (Isovaleric acid-DTHFPCIK-[b-homoPhe])$_2$K-Lys[isoGlu-Palm]-NH$_2$ | 5 nM | >1440 (71%) | 109 |
| 514 | 244 | (Isovaleric acid-DTHFPCI-[D-Lys]-[NMe-Phe])$_2$-IDA-[(b-Ala)-Palm]-NH$_2$ | 4 nM | >1440 (80%) | 117 |
| 515 | 245 | (Isovaleric acid-DTH-[BIP]-PCI-[D-Lys]-[NMe-Phe])$_2$-IDA-[(b-Ala)-Palm]-NH$_2$ | 26 nM | variable | 345 |
| 516 | 246 | (Isovaleric acid-DTHFPCIK-[b-homoPhe])$_2$-IDA-[(b-Ala)-Palm]-NH$_2$ | 6 nM | variable | 1249 |
| 517 | 247 | (Isovaleric acid-DTHFPCI-[D-Lys]-[b-homoPhe])$_2$-IDA-[(b-Ala)-Palm]-NH$_2$ | 5 nM | >240 (86%) | >1440 (51%) |
| 518 | 248 | (Isovaleric acid-DTHF-[Npc]-CI-[D-Lys]-[NMe-Phe])$_2$-IDA-[(b-Ala)-Palm]-NH$_2$ | 8 nM | variable | 1241 |

In particular embodiments, the monomer subunits may be dimerized by a disulfide bridge between two cysteine residues, one in each peptide monomer subunit, or they may be dimerized by another suitable linker moiety, including those described herein. Some of the monomer subunits are shown having C- and/or N-termini that both comprise free amine. Thus, to produce a peptide dimer inhibitor, the monomer subunit may be modified to eliminate either the C- or N-terminal free amine, thereby permitting dimerization at the remaining free amine. Further, in some instances, a terminal end of one or more monomer subunits is acylated with an acylating organic compound selected from the group consisting of 2-me-Trifluorobutyl, Trifluoropentyl, Acetyl, Octonyl, Butyl, Pentyl, Hexyl, Palmityl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, monomer subunits comprise both a free carboxy terminal and a free amino terminal, whereby a user may selectively modify the subunit to achieve dimerization at a desired terminus. One having skill in the art will, therefore, appreciate that the monomer subunits of the instant invention may be selectively modified to achieve a single, specific amine for a desired dimerization.

It is further understood that the C-terminal residues of the monomer subunits disclosed herein may be amides, unless otherwise indicated. Further, it is understood that, in certain embodiments, dimerization at the C-terminus is facilitated by using a suitable amino acid with a side chain having amine functionality, as is generally understood in the art. Regarding the N-terminal residues, it is generally understood that dimerization may be achieved through the free amine of the terminal residue, or may be achieved by using a suitable amino acid side chain having a free amine, as is generally understood in the art.

Moreover, it is understood that the side chains of one or more internal residue comprised in the hepcidin analogue peptide monomers of the present invention can be utilized for the purpose of dimerization. In such embodiments, the side chain is in some embodiments a suitable natural amino acid (e.g., Lys), or alternatively it is an unnatural amino acid comprising a side chain suitable for conjugation, e.g., to a suitable linker moiety, as defined herein.

The linker moieties connecting monomer subunits may include any structure, length, and/or size that is compatible with the teachings herein. In at least one embodiment, a linker moiety is selected from the non-limiting group consisting of: cysteine, lysine, DIG, PEG4, PEG4-biotin, PEG13, PEG25, PEG1K, PEG2K, PEG3.4K, PEG4K, PEG5K, IDA, IDA-Palm, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, suitable aliphatics, aromatics, heteroaromatics, and polyethylene glycol based linkers having a molecular weight from approximately 400 Da to approximately 40,000 Da. Non-limiting examples of suitable linker moieties are provided in Table 5. In particular embodiment, any of these linker moieties may alternatively link a half-life extension moiety to a hepcidin analogue.

TABLE 5

Illustrative Linker Moieties

| Abbreviation | Description | Structure |
|---|---|---|
| DIG | DIGlycolic acid | 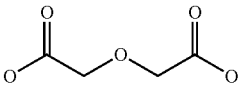 |
| PEG4 | Bifunctional PEG linker with 4 PolyEthylene Glycol units | 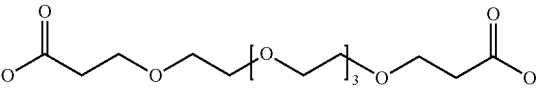 |
| PEG13 | Bifunctional PEG linker with 13 PolyEthylene Glycol units | 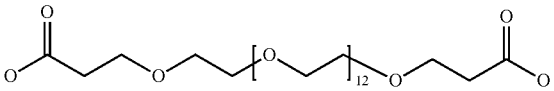 |
| PEG25 | Bifunctional PEG linker with 25 PolyEthylene Glycol units | 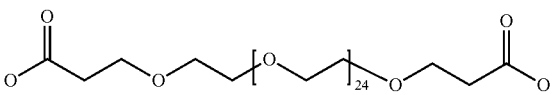 |
| PEG1K | Bifunctional PEG linker with PolyEthylene Glycol Mol wt of 1000 Da | |
| PEG2K | Bifunctional PEG linker with PolyEthylene Glycol Mol wt of 2000 Da | |
| PEG3.4K | Bifunctional PEG linker with PolyEthylene Glycol Mol wt of 3400 Da | |
| PEG5K | Bifunctional PEG linker with PolyEthylene Glycol Mol wt of 5000 Da | |
| DIG | Diglycolic acid | 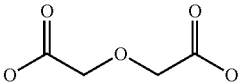 |
| β-Ala-IDA | β-Ala-Iminodiacetic acid | 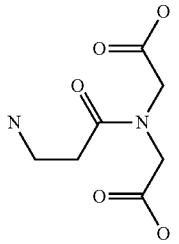 |

TABLE 5-continued

Illustrative Linker Moieties

| Abbreviation | Description | Structure |
|---|---|---|
| Boc-β-Ala-IDA | Boc-β-Ala-Iminodiacetic acid | 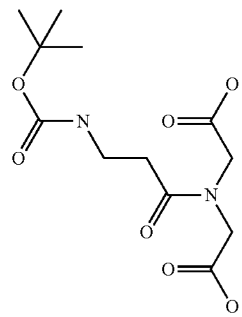 [SMILES: CC(C)(C)OC(=O)NCCC(=O)N(CC(=O)O)CC(=O)O] |
| Ac-β-Ala-IDA | Ac-β-Ala-Iminodiacetic acid | 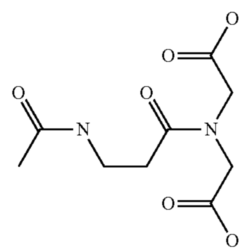 [SMILES: CC(=O)NCCC(=O)N(CC(=O)O)CC(=O)O] |
| Palm-β-Ala-IDA- | Palmityl-β-Ala-Iminodiacetic acid | 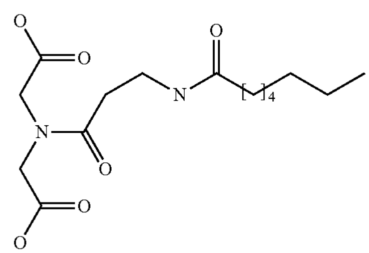 |
| GTA | Glutaric acid | 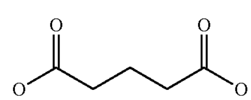 |
| PMA | Pemilic acid | 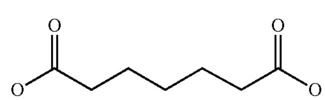 [SMILES: O=C(O)CCCCCC(=O)O] |
| AZA | Azelaic acid | 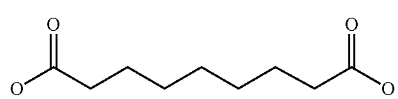 [SMILES: O=C(O)CCCCCCCC(=O)O] |
| DDA | Dodecanedioic acid | 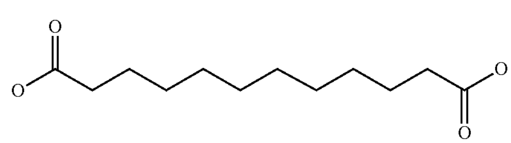 [SMILES: O=C(O)CCCCCCCCCCC(=O)O] |
| IPA | Isopthalic acid | 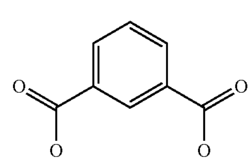 [SMILES: O=C(O)c1cccc(C(=O)O)c1] |

TABLE 5-continued
Illustrative Linker Moieties
| Abbreviation | Description | Structure |
|---|---|---|
| 1,3-PDA | 1,3-Phenylenediacetic acid | 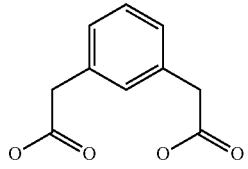 [SMILES: O=C(O)Cc1cccc(CC(=O)O)c1] |
| 1,4-PDA | 1,4-Phenylenediacetic acid | 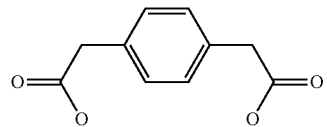 |
| 1,2-PDA | 1,2-Phenylenediacetic acid | 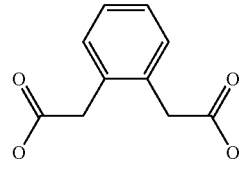 [SMILES: O=C(O)Cc1ccccc1CC(=O)O] |
| Triazine | Amino propyl Triazine di-acid | 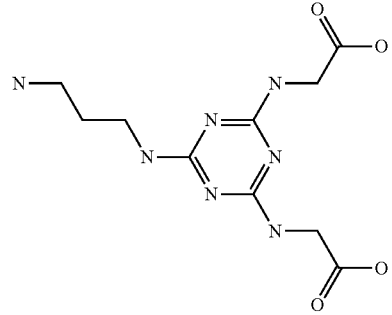 [SMILES: NCCCNc1nc(NCC(=O)O)nc(NCC(=O)O)n1] |
| Boc-Triazine | Boc-Triazine di-acid | 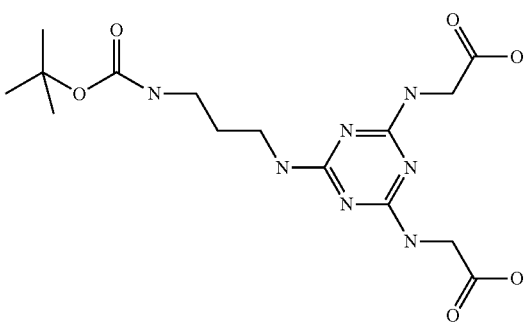 [SMILES: CC(C)(C)OC(=O)NCCCNc1nc(NCC(=O)O)nc(NCC(=O)O)n1] |
| IDA | Iminodiacetic acid | 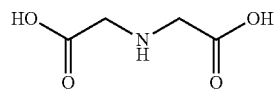 |
| AIDA | n-Acetyl imino acetic acid | 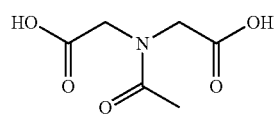 |

TABLE 5-continued

Illustrative Linker Moieties

| Abbreviation | Description | Structure |
|---|---|---|
| Biotin-β-ala-IDA- | N-Biotin-β-Ala-Iminodiacetic acid | 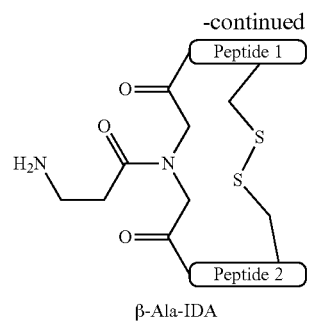 |
| Lys | Lysine | 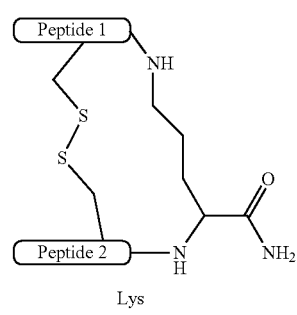 |

One having skill in the art will appreciate that the C- and N-terminal and internal linker moieties disclosed herein are non-limiting examples of suitable linker moieties, and that the present invention may include any suitable linker moiety.

In certain embodiments of any of the hepcidin analogue peptide dimers, the N-terminus of each peptide monomer subunit is connected by a linker moiety.

In certain embodiments of any of the hepcidin analogue peptide dimers, the C-terminus of each peptide monomer subunit is connected by a linker moiety.

In certain embodiments, the side chains of one or more internal amino acid residues (e.g., Lys residues) comprised in each peptide monomer subunit of a hepcidin analogue peptide dimer are connected by a linker moiety.

In certain embodiments of any of the hepcidin analogue peptide dimers, the C-terminus, the N terminus, or an internal amino acid (e.g., a lysine sidechain) of each peptide monomer subunit is connected by a linker moiety and at least two cysteine or Pen residues of the hepcidin analogue peptide dimers are linked by a disulfide bridge. In some embodiments, a peptide dimer has a general structure shown below. Non-limiting schematic examples of such hepcidin analogues are shown in the following illustration:

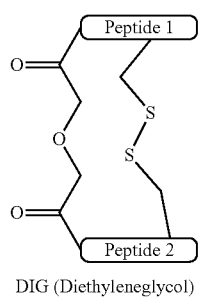

DIG (Diethyleneglycol)

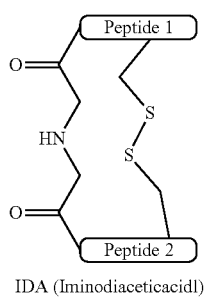

IDA (Iminodiaceticacidl)

β-Ala-IDA

Lys

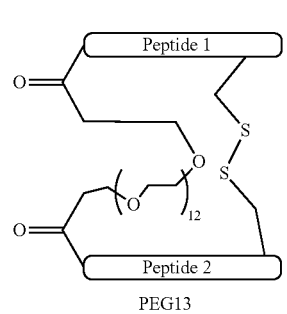

PEG13

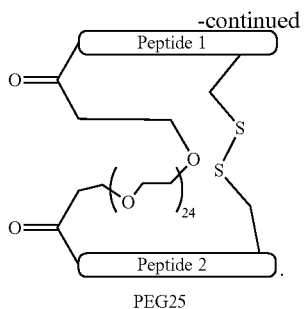

PEG25

Peptide Analogue Conjugates

In certain embodiments, hepcidin analogues of the present invention, including both monomers and dimers, comprise one or more conjugated chemical substituents, such as lipophilic substituents and polymeric moieties, collectively referred to herein as half-life extension moieties. Without wishing to be bound by any particular theory, it is believed that the lipophilic substituent binds to albumin in the bloodstream, thereby shielding the hepcidin analogue from enzymatic degradation, and thus enhancing its half-life. In addition, it is believed that polymeric moieties enhance half-life and reduce clearance in the bloodstream, and in some cases enhance permeability through the epithelium and retention in the lamina propria. Moreover, it is also surmised that these substituents in some cases may enhance permeability through the epithelium and retention in the lamina propria. The skilled person will be well aware of suitable techniques for preparing the compounds employed in the context of the invention. For examples of non-limiting suitable chemistry, see, e.g., WO98/08871, WO00/55184, WO00/55119, Madsen et al (J. Med. Chem. 2007, 50, 6126-32), and Knudsen et al. 2000 (J. Med Chem. 43, 1664-1669).

In one embodiment, the side chains of one or more amino acid residues (e.g., Lys residues) in a hepcidin analogue of the invention is further conjugated (e.g., covalently attached) to a lipophilic substituent or other half-life extension moiety. The lipophilic substituent may be covalently bonded to an atom in the amino acid side chain, or alternatively may be conjugated to the amino acid side chain via one or more spacers or linker moieties. The spacer or linker moiety, when present, may provide spacing between the hepcidin analogue and the lipophilic substituent. In particular embodiments, the half-life extension moiety is conjugated to the hepcidin analogue via a linker moiety, which in certain embodiments is a linker moiety shown in Table 5 or Table 7, or depicted in any of the illustrative compounds shown in Table 2A, 2B, 3A, 3B, and 4.

In certain embodiments, the lipophilic substituent or half-life extension moiety comprises a hydrocarbon chain having from 4 to 30 C atoms, for example at least 8 or 12 C atoms, and preferably 24 C atoms or fewer, or 20 C atoms or fewer. The hydrocarbon chain may be linear or branched and may be saturated or unsaturated. In certain embodiments, the hydrocarbon chain is substituted with a moiety which forms part of the attachment to the amino acid side chain or the spacer, for example an acyl group, a sulfonyl group, an N atom, an O atom or an S atom. In some embodiments, the hydrocarbon chain is substituted with an acyl group, and accordingly the hydrocarbon chain may form part of an alkanoyl group, for example palmitoyl, caproyl, lauroyl, myristoyl or stearoyl.

A lipophilic substituent may be conjugated to any amino acid side chain in a hepcidin analogue of the invention. In certain embodiment, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. In certain embodiments, the lipophilic substituent is conjugated to Lys. An amino acid shown as Lys in any of the formula provided herein may be replaced by, e.g., Dbu, Dpr or Orn where a lipophilic substituent is added.

In further embodiments of the present invention, alternatively or additionally, the side-chains of one or more amino acid residues in a hepcidin analogue of the invention may be conjugated to a polymeric moiety or other half-life extension moiety, for example, in order to increase solubility and/or half-life in vivo (e.g., in plasma) and/or bioavailability. Such modifications are also known to reduce clearance (e.g. renal clearance) of therapeutic proteins and peptides.

As used herein, "Polyethylene glycol" or "PEG" is a polyether compound of general formula H—(O—CH$_2$—CH$_2$)$_n$—OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g., viscosity) due to chain length effects, their chemical properties are nearly identical. The polymeric moiety is preferably water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Also encompassed are PEGs that are prepared for purpose of half-life extension, for example, mono-activated, alkoxy-terminated polyalkylene oxides (POA's) such as mono-methoxy-terminated polyethyeelene glycols (mPEG's); bis activated polyethylene oxides (glycols) or other PEG derivatives are also contemplated. Suitable polymers will vary substantially by weights ranging from about 200 to about 40,000 are usually selected for the purposes of the present invention. In certain embodiments, PEGs having molecular weights from 200 to 2,000 daltons or from 200 to 500 daltons are used. Different forms of PEG may also be used, depending on the initiator used for the polymerization process, e.g., a common initiator is a mono-functional methyl ether PEG, or methoxypoly(ethylene glycol), abbreviated mPEG. Other suitable initiators are known in the art and are suitable for use in the present invention.

Lower-molecular-weight PEGs are also available as pure oligomers, referred to as monodisperse, uniform, or discrete. These are used in certain embodiments of the present invention.

PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear. The numbers that are often included in the names of PEGs indicate their average molecular weights (e.g. a PEG with n=9 would have an average molecular weight of approximately 400 daltons, and would be labeled PEG 400.

As used herein, "PEGylation" is the act of coupling (e.g., covalently) a PEG structure to the hepcidin analogue of the invention, which is in certain embodiments referred to as a "PEGylated hepcidin analogue". In certain embodiments, the PEG of the PEGylated side chain is a PEG with a molecular weight from about 200 to about 40,000. In certain embodiments, the PEG portion of the conjugated half-life extension moiety is PEG3, PEG4, PEG5, PEG6, PEG7, PEG8, PEG9, PEG10, or PEG11. In particular embodiments, it is PEG11. In certain embodiments, the PEG of a PEGylated spacer is PEG3 or PEG8. In some embodiments, a spacer is PEGylated. In certain embodiments, the PEG of a PEGylated spacer is PEG3, PEG4, PEG5, PEG6, PEG7, PEG8, PEG9, PEG10, or PEG11. In certain embodiments, the PEG of a PEGylated spacer is PEG3 or PEG8.

In some embodiments, the present invention includes a hepcidin analogue peptide (or a dimer thereof) conjugated with a PEG that is attached covalently, e.g., through an amide, a thiol, via click chemistry, or via any other suitable means known in the art. In particular embodiments PEG is attached through an amide bond and, as such, certain PEG derivatives used will be appropriately functionalized. For example, in certain embodiments, PEG11, which is O-(2-aminoethyl)-O'-(2-carboxyethyl)-undecaethyleneglycol, has both an amine and carboxylic acid for attachment to a peptide of the present invention. In certain embodiments, PEG25 contains a diacid and 25 glycol moieties.

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57 and Tsukada, et al. (1984), J. Natl. Cancer Inst., vol. 73: 721-729. The polymeric moiety may be straight-chain or branched. In some embodiments, it has a molecular weight of 500-40,000 Da, for example 500-10,000 Da, 1000-5000 Da, 10,000-20,000 Da, or 20,000-40,000 Da.

In some embodiments, a hepcidin analogue of the invention may comprise two or more such polymeric moieties, in which case the total molecular weight of all such moieties will generally fall within the ranges provided above.

In some embodiments, the polymeric moiety may be coupled (by covalent linkage) to an amino, carboxyl or thiol group of an amino acid side chain. Certain examples are the thiol group of Cys residues and the epsilon amino group of Lys residues, and the carboxyl groups of Asp and Glu residues may also be involved.

The skilled worker will be well aware of suitable techniques which can be used to perform the coupling reaction. For example, a PEG moiety bearing a methoxy group can be coupled to a Cys thiol group by a maleimido linkage using reagents commercially available from Nektar Therapeutics AL. See also WO 2008/101017, and the references cited above, for details of suitable chemistry. A maleimide-functionalised PEG may also be conjugated to the side-chain sulfhydryl group of a Cys residue.

As used herein, disulfide bond oxidation can occur within a single step or is a two-step process. As used herein, for a single oxidation step, the trityl protecting group is often employed during assembly, allowing deprotection during cleavage, followed by solution oxidation. When a second disulfide bond is required, one has the option of native or selective oxidation. For selective oxidation requiring orthogonal protecting groups, Acm and Trityl is used as the protecting groups for cysteine. Cleavage results in the removal of one protecting pair of cysteine allowing oxidation of this pair. The second oxidative deprotection step of the cysteine protected Acm group is then performed. For native oxidation, the trityl protecting group is used for all cysteines, allowing for natural folding of the peptide.

A skilled worker will be well aware of suitable techniques which can be used to perform the oxidation step.

In particular embodiments, a hepcidin analogue of the present invention comprises a half-life extension moiety, which may be selected from but is not limited to the following: Ahx-Palm, PEG2-Palm, PEG11-Palm, isoGlu-Palm, dapa-Palm, isoGlu-Lauric acid, isoGlu-Mysteric acid, and isoGlu-Isovaleric acid.

In particular embodiments, a hepcidin analogue comprises a half-life extension moiety having the structure shown below, wherein n=0 to 24 or n=14 to 24:

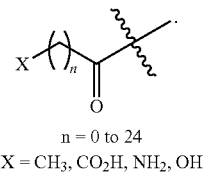

n = 0 to 24
X = CH$_3$, CO$_2$H, NH$_2$, OH

In certain embodiments, a hepcidin analogue of the present invention comprises a conjugated half-life extension moiety shown in Table 6.

TABLE 6

Illustrative Half-Life Extension Moieties

| # | Conjugates |
|---|---|
| C1 | C12 (Lauric acid) |

TABLE 6-continued
Illustrative Half-Life Extension Moieties
| # | Conjugates |
|---|---|
| C2 | 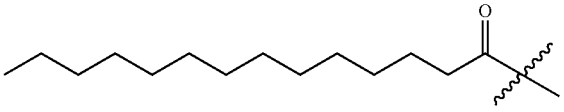<br>C14 (Mysteric acid) |
| C3 | 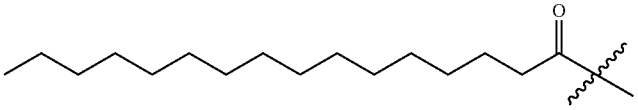<br>C16 (Palm or Palmitic acid) |
| C4 | 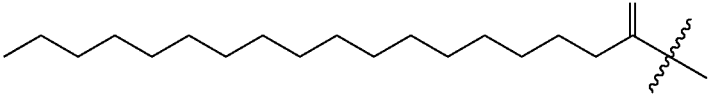<br>C18 (Stearic acid) |
| C5 | 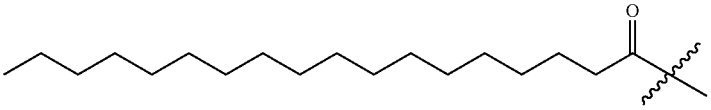<br>C20 |
| C6 | 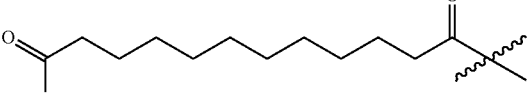<br>C12 diacid |
| C7 | 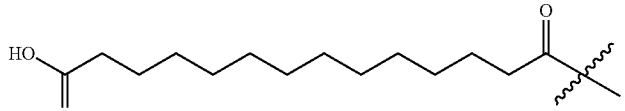<br>C14 diacid |
| C8 | 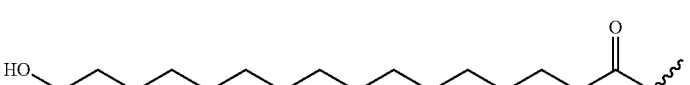<br>C16 diacid |
| C9 | 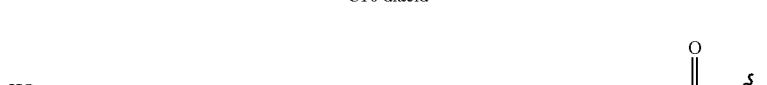<br>C18 diacid |
| C10 | 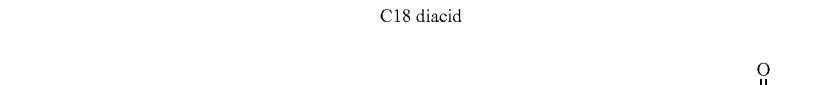<br>C20 diacid |

TABLE 6-continued

Illustrative Half-Life Extension Moieties

| # | Conjugates |
|---|---|
| C11 | 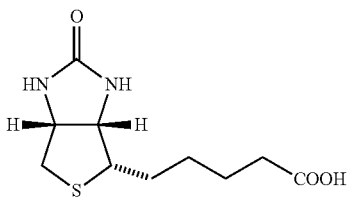<br>Biotin |
| C12 | 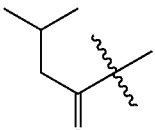<br>Isovaleric acid |

In certain embodiments, a half-life extension moiety is conjugated directly to a hepcidin analogue, while in other embodiments, a half-life extension moiety is conjugated to a hepcidin analogue peptide via a linker moiety, e.g., any of those depicted in Tables 5 or 7.

TABLE 7

Illustrative Linker Moieties

| # | Linker Moiety |
|---|---|
| L1 | 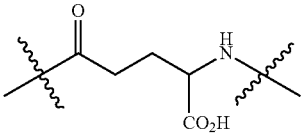<br>IsoGlu |
| L2 | 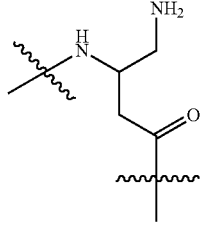<br>Dapa |
| L3 | 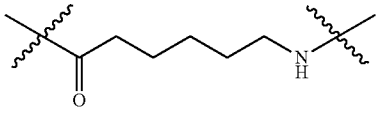<br>Ahx |
| L4 | Lipdic based linkers:<br>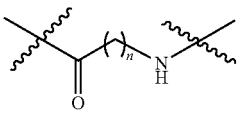<br>n = 1 to 24 |

TABLE 7-continued
Illustrative Linker Moieties
| # | Linker Moiety |
|---|---|
| L5 | 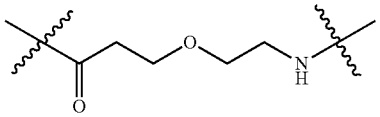<br>PEG1 |
| L6 | 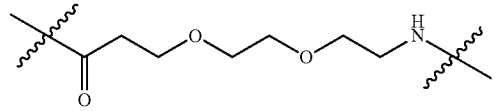<br>PEG2 |
| L7 | 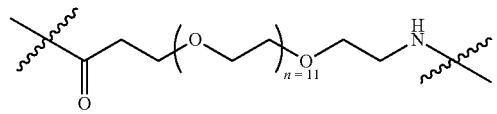<br>PEG11 (40 atoms) |
| L8 | 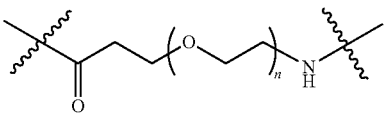<br>PEG based linkers<br>n = 1 to 25 |
| L9 | 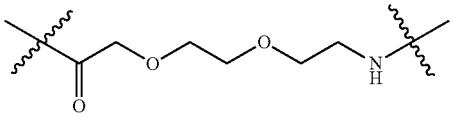<br>OEG |
| L10 | 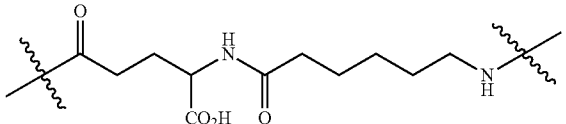<br>IsoGlu-Ahx |
| L11 | 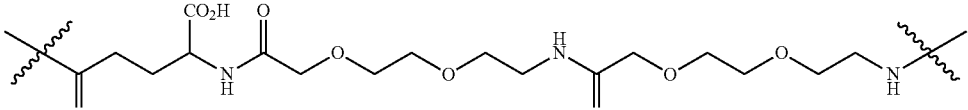<br>IsoGlu-OEG-OEG |
| L12 | 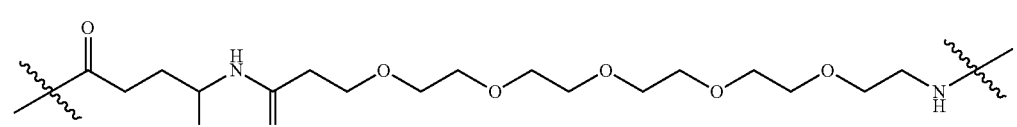<br>IsoGlu-PEG5 |
| L13 | 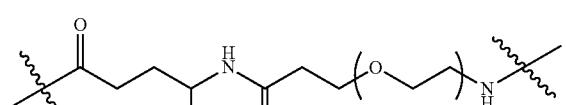<br>IsoGlu-PEGn |

TABLE 7-continued

Illustrative Linker Moieties

| # | Linker Moiety |
|---|---|
| L14 | βAla-PEG2 |
| L15 | βAla-PEG11 (40 atoms) |

With reference to linker structures shown in Table 7, reference to n=1 to 24 or n=1 to 25, or the like, (e.g., in L4, L8 or L13) indicates that n may be any integer within the recited range. For example, for L4 shown in Table 7, n could be 1, 2, 3, etc., wherein when n=5, L4 has the structure shown in L3 (Ahx).

In particular embodiments, a hepcidin analogue of the present invention comprises any of the linker moieties shown in Table 7 and any of the half-life extension moieties shown in Table 6, including any of the following combinations shown in Table 8.

TABLE 8

Illustrative Combinations of Linkers and Half-Life Extension Moieties in Hepcidin Analogues

| Linker | Half-Life Extension Moiety |
|---|---|
| L1 | C1 |
| L2 | C1 |
| L3 | C1 |
| L4 | C1 |
| L5 | C1 |
| L6 | C1 |
| L7 | C1 |
| L8 | C1 |
| L9 | C1 |
| L10 | C1 |
| L11 | C1 |
| L12 | C1 |
| L13 | C1 |
| L14 | C1 |
| L15 | C1 |
| L1 | C2 |
| L2 | C2 |
| L3 | C2 |
| L4 | C2 |
| L5 | C2 |
| L6 | C2 |
| L7 | C2 |
| L8 | C2 |
| L9 | C2 |
| L10 | C2 |
| L11 | C2 |
| L12 | C2 |
| L13 | C2 |
| L14 | C2 |
| L15 | C2 |
| L1 | C3 |
| L2 | C3 |
| L3 | C3 |
| L4 | C3 |
| L5 | C3 |
| L6 | C3 |
| L7 | C3 |
| L8 | C3 |
| L9 | C3 |
| L10 | C3 |
| L11 | C3 |
| L12 | C3 |
| L13 | C3 |
| L14 | C3 |
| L15 | C3 |
| L1 | C4 |
| L2 | C4 |
| L3 | C4 |
| L4 | C4 |
| L5 | C4 |
| L6 | C4 |
| L7 | C4 |
| L8 | C4 |
| L9 | C4 |
| L10 | C4 |
| L11 | C4 |
| L12 | C4 |
| L13 | C4 |
| L14 | C4 |
| L15 | C4 |
| L1 | C5 |
| L2 | C5 |
| L3 | C5 |
| L4 | C5 |
| L5 | C5 |
| L6 | C5 |
| L7 | C5 |
| L8 | C5 |
| L9 | C5 |
| L10 | C5 |
| L11 | C5 |
| L12 | C5 |
| L13 | C5 |
| L14 | C5 |
| L15 | C5 |
| L1 | C6 |
| L2 | C6 |
| L3 | C6 |
| L4 | C6 |
| L5 | C6 |

TABLE 8-continued

Illustrative Combinations of Linkers and Half-Life Extension Moieties in Hepcidin Analogues

| Linker | Half-Life Extension Moiety |
|---|---|
| L6 | C6 |
| L7 | C6 |
| L8 | C6 |
| L9 | C6 |
| L10 | C6 |
| L11 | C6 |
| L12 | C6 |
| L13 | C6 |
| L14 | C6 |
| L15 | C6 |
| L1 | C7 |
| L2 | C7 |
| L3 | C7 |
| L4 | C7 |
| L5 | C7 |
| L6 | C7 |
| L7 | C7 |
| L8 | C7 |
| L9 | C7 |
| L10 | C7 |
| L11 | C7 |
| L12 | C7 |
| L13 | C7 |
| L14 | C7 |
| L15 | C7 |
| L1 | C8 |
| L2 | C8 |
| L3 | C8 |
| L4 | C8 |
| L5 | C8 |
| L6 | C8 |
| L7 | C8 |
| L8 | C8 |
| L9 | C8 |
| L10 | C8 |
| L11 | C8 |
| L12 | C8 |
| L13 | C8 |
| L14 | C8 |
| L15 | C8 |
| L1 | C9 |
| L2 | C9 |
| L3 | C9 |
| L4 | C9 |
| L5 | C9 |
| L6 | C9 |
| L7 | C9 |
| L8 | C9 |
| L9 | C9 |
| L10 | C9 |
| L11 | C9 |
| L12 | C9 |
| L13 | C9 |
| L14 | C9 |
| L15 | C9 |
| L1 | C10 |
| L2 | C10 |
| L3 | C10 |
| L4 | C10 |
| L5 | C10 |
| L6 | C10 |
| L7 | C10 |
| L8 | C10 |
| L9 | C10 |
| L10 | C10 |
| L11 | C10 |
| L12 | C10 |
| L13 | C10 |
| L14 | C10 |
| L15 | C10 |
| L1 | C11 |
| L2 | C11 |
| L3 | C11 |
| L4 | C11 |
| L5 | C11 |
| L6 | C11 |
| L7 | C11 |
| L8 | C11 |
| L9 | C11 |
| L10 | C11 |
| L11 | C11 |
| L12 | C11 |
| L13 | C11 |
| L14 | C11 |
| L15 | C11 |
| L1 | C12 |
| L2 | C12 |
| L3 | C12 |
| L4 | C12 |
| L5 | C12 |
| L6 | C12 |
| L7 | C12 |
| L8 | C12 |
| L9 | C12 |
| L10 | C12 |
| L11 | C12 |
| L12 | C12 |
| L13 | C12 |
| L14 | C12 |
| L15 | C12 |

In certain embodiments, a hepcidin analogue comprises two or more linkers. In particular embodiments, the two or more linkers are concatamerized, i.e., bound to each other.

In related embodiments, the present invention includes polynucleotides that encode a polypeptide having a peptide sequence present in any of the hepcidin analogues described herein.

In addition, the present invention includes vectors, e.g., expression vectors, comprising a polynucleotide of the present invention.

Methods of Treatment

In some embodiments, the present invention provides methods for treating a subject afflicted with a disease or disorder associated with dysregulated hepcidin signaling, wherein the method comprises administering to the subject a hepcidin analogue of the present invention. In some embodiments, the hepcidin analogue that is administered to the subject is present in a composition (e.g., a pharmaceutical composition). In one embodiment, a method is provided for treating a subject afflicted with a disease or disorder characterized by increased activity or expression of ferroportin, wherein the method comprises administering to the individual a hepcidin analogue or composition of the present invention in an amount sufficient to (partially or fully) bind to and agonize ferroportin in the subject. In one embodiment, a method is provided for treating a subject afflicted with a disease or disorder characterized by dysregulated iron metabolism, wherein the method comprises administering to the subject a hepcidin analogue or composition of the present invention.

In some embodiments, methods of the present invention comprise providing a hepcidin analogue or a composition of the present invention to a subject in need thereof. In particular embodiments, the subject in need thereof has been diagnosed with or has been determined to be at risk of developing a disease or disorder characterized by dysregulated iron levels (e.g., diseases or disorders of iron metabolism; diseases or disorders related to iron overload; and diseases or disorders related to abnormal hepcidin activity or expression). In particular embodiments, the subject is a mammal (e.g., a human).

In certain embodiments, the disease or disorder is a disease of iron metabolism, such as, e.g., an iron overload disease, iron deficiency disorder, disorder of iron biodistribution, or another disorder of iron metabolism and other disorder potentially related to iron metabolism, etc. In particular embodiments, the disease of iron metabolism is hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia, beta thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, transfusion-dependent anemia, hemolytic anemia, erythropoietin resistance, iron deficiency of obesity, other anemias, benign or malignant tumors that overproduce hepcidin or induce its overproduction, conditions with hepcidin excess, Friedreich ataxia, gracile syndrome, Hallervorden-Spatz disease, Wilson's disease, pulmonary hemosiderosis, hepatocellular carcinoma, cancer (e.g., liver cancer), hepatitis, cirrhosis of liver, pica, chronic renal failure, insulin resistance, diabetes, atherosclerosis, neurodegenerative disorders, dementia, multiple sclerosis, Parkinson's disease, Huntington's disease, or Alzheimer's disease.

In certain embodiments, the disease or disorder is related to iron overload diseases such as iron hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia.

In certain embodiments, the disease or disorder is one that is not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, peptides of the invention may be used to treat these diseases and conditions. Those skilled in the art are readily able to determine whether a given disease can be treated with a peptide according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In certain embodiments, the disease or disorder is postmenopausal osteoporosis.

In certain embodiments of the present invention, the diseases of iron metabolism are iron overload diseases, which include hereditary hemochromatosis, iron-loading anemias, alcoholic liver diseases, heart disease and/or failure, cardiomyopathy, and chronic hepatitis C.

In particular embodiments, any of these diseases, disorders, or indications are caused by or associated with a deficiency of hepcidin or iron overload.

In some embodiments, methods of the present invention comprise providing a hepcidin analogue of the present invention (i.e., a first therapeutic agent) to a subject in need thereof in combination with a second therapeutic agent. In certain embodiments, the second therapeutic agent is provided to the subject before and/or simultaneously with and/or after the pharmaceutical composition is administered to the subject. In particular embodiments, the second therapeutic agent is iron chelator. In certain embodiments, the second therapeutic agent is selected from the iron chelators Deferoxamine and Deferasirox (Exjade™). In another embodiment, the method comprises administering to the subject a third therapeutic agent.

The present invention provides compositions (for example pharmaceutical compositions) comprising one or more hepcidin analogues of the present invention and a pharmaceutically acceptable carrier, excipient or diluent. A pharmaceutically acceptable carrier, diluent or excipient refers to a non-toxic solid, semi-solid or liquid filler, diluent, encapsulating material or formulation auxiliary of any type. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, PA, USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

In certain embodiments, the compositions comprise two or more hepcidin analogues disclosed herein. In certain embodiments, the combination is selected from one of the following: (i) any two or more of the hepcidin analogue peptide monomers shown therein; (ii) any two or more of the hepcidin analogue peptide dimers disclosed herein: (iii) any one or more of the hepcidin analogue peptide monomers disclosed herein, and any one or more of the hepcidin analogue peptide dimers disclosed herein.

It is to be understood that the inclusion of a hepcidin analogue of the invention (i.e., one or more hepcidin analogue peptide monomers of the invention or one or more hepcidin analogue peptide dimers of the present invention) in a pharmaceutical composition also encompasses inclusion of a pharmaceutically acceptable salt or solvate of a hepcidin analogue of the invention. In particular embodiments, the pharmaceutical compositions further comprise one or more pharmaceutically acceptable carrier, excipient, or vehicle.

In certain embodiments, the invention provides a pharmaceutical composition comprising a hepcidin analogue, or a pharmaceutically acceptable salt or solvate thereof, for treating a variety of conditions, diseases, or disorders as disclosed herein or elsewhere (see, e.g., Methods of Treatment, herein). In particular embodiments, the invention provides a pharmaceutical composition comprising a hepcidin analogue peptide monomer, or a pharmaceutically acceptable salt or solvate thereof, for treating a variety of conditions, diseases, or disorders as disclosed herein elsewhere (see, e.g., Methods of Treatment, herein). In particular embodiments, the invention provides a pharmaceutical composition comprising a hepcidin analogue peptide dimer, or a pharmaceutically acceptable salt or solvate thereof, for treating a variety of conditions, diseases, or disorders as disclosed herein.

The hepcidin analogues of the present invention may be formulated as pharmaceutical compositions which are suited for administration with or without storage, and which typically comprise a therapeutically effective amount of at least one hepcidin analogue of the invention, together with a pharmaceutically acceptable carrier, excipient or vehicle.

In some embodiments, the hepcidin analogue pharmaceutical compositions of the invention are in unit dosage form. In such forms, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration, e.g., any one of the routes and means of administration disclosed herein.

In particular embodiments, the hepcidin analogue, or the pharmaceutical composition comprising a hepcidin analogue, is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. One embodiment of a biodegradable matrix is a matrix of one of either polylactide, polyglycolide, or polylactide co-glycolide (co-polymers of lactic acid and glycolic acid).

In certain embodiments, the compositions are administered parenterally, subcutaneously or orally. In particular embodiments, the compositions are administered orally, intracisternally, intravaginally, intraperitoneally, intrarectally, topically (as by powders, ointments, drops, suppository, or transdermal patch, including delivery intravitreally, intranasally, and via inhalation) or buccally. The term "parenteral" as used herein refers to modes of administration which include intravenous, intramuscular, intraperitoneal, intrasternal, subcutaneous, intradermal and intra-articular injection and infusion. Accordingly, in certain embodiments, the compositions are formulated for delivery by any of these routes of administration.

In certain embodiments, pharmaceutical compositions for parenteral injection comprise pharmaceutically acceptable sterile aqueous or nonaqueous solutions, dispersions, suspensions or emulsions, or sterile powders, for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, beta-cyclodextrin, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants. These compositions may also contain adjuvants such as preservative, wetting agents, emulsifying agents, and dispersing agents. Prolonged absorption of an injectable pharmaceutical form may be brought about by the inclusion of agents which delay absorption, such as aluminum monostearate and gelatin.

Injectable depot forms include those made by forming microencapsule matrices of the hepcidin analogue in one or more biodegradable polymers such as polylactide-polyglycolide, poly(orthoesters), poly(anhydrides), and (poly)glycols, such as PEG. Depending upon the ratio of peptide to polymer and the nature of the particular polymer employed, the rate of release of the hepcidin analogue can be controlled. Depot injectable formulations are also prepared by entrapping the hepcidin analogue in liposomes or microemulsions compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Hepcidin analogues of the present invention may also be administered in liposomes or other lipid-based carriers. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a hepcidin analogue of the present invention, stabilizers, preservatives, excipients, and the like. In certain embodiments, the lipids comprise phospholipids, including the phosphatidyl cholines (lecithins) and serines, both natural and synthetic. Methods to form liposomes are known in the art.

Pharmaceutical compositions to be used in the invention suitable for parenteral administration may comprise sterile aqueous solutions and/or suspensions of the peptide inhibitors made isotonic with the blood of the recipient, generally using sodium chloride, glycerin, glucose, mannitol, sorbitol, and the like.

In some aspects, the invention provides a pharmaceutical composition for oral delivery. Compositions and hepcidin analogues of the instant invention may be prepared for oral administration according to any of the methods, techniques, and/or delivery vehicles described herein. Further, one having skill in the art will appreciate that the hepcidin analogues of the instant invention may be modified or integrated into a system or delivery vehicle that is not disclosed herein, yet is well known in the art and compatible for use in oral delivery of peptides.

In certain embodiments, formulations for oral administration may comprise adjuvants (e.g. resorcinols and/or nonionic surfactants such as polyoxyethylene oleyl ether and n-hexadecylpolyethylene ether) to artificially increase the permeability of the intestinal walls, and/or enzymatic inhibitors (e.g. pancreatic trypsin inhibitors, diisopropylfluorophosphate (DFF) or trasylol) to inhibit enzymatic degradation. In certain embodiments, the hepcidin analogue of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

In particular embodiments, oral dosage forms or unit doses compatible for use with the hepcidin analogues of the present invention may include a mixture of hepcidin analogue and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of hepcidin analogue, wherein the dosage form comprises at least one of a pill, a tablet, a capsule, a gel, a paste, a drink, a syrup, ointment, and suppository. In some instances, an oral dosage form is provided that is designed and configured to achieve delayed release of the hepcidin analogue in the subject's small intestine and/or colon.

In one embodiment, an oral pharmaceutical composition comprising a hepcidin analogue of the present invention comprises an enteric coating that is designed to delay release of the hepcidin analogue in the small intestine. In at least some embodiments, a pharmaceutical composition is provided which comprises a hepcidin analogue of the present invention and a protease inhibitor, such as aprotinin, in a delayed release pharmaceutical formulation. In some instances, pharmaceutical compositions of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In one embodiment, a pharmaceutical composition comprising a hepcidin analogue of the present invention is provided in an enteric coating, the enteric coating being designed to protect and release the pharmaceutical composition in a controlled manner within the subject's lower gastrointestinal system, and to avoid systemic side effects. In addition to enteric coatings, the hepcidin analogues of the instant invention may be encapsulated, coated, engaged or otherwise associated within any compatible oral drug delivery system or component. For example, in some embodiments a hepcidin analogue of the present invention is provided in a lipid carrier system comprising at least one of polymeric hydrogels, nanoparticles, microspheres, micelles, and other lipid systems.

To overcome peptide degradation in the small intestine, some embodiments of the present invention comprise a hydrogel polymer carrier system in which a hepcidin analogue of the present invention is contained, whereby the hydrogel polymer protects the hepcidin analogue from proteolysis in the small intestine and/or colon. The hepcidin analogues of the present invention may further be formulated for compatible use with a carrier system that is designed to increase the dissolution kinetics and enhance intestinal absorption of the peptide. These methods include the use of liposomes, micelles and nanoparticles to increase GI tract permeation of peptides.

Various bioresponsive systems may also be combined with one or more hepcidin analogue of the present invention to provide a pharmaceutical agent for oral delivery. In some embodiments, a hepcidin analogue of the instant invention is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for a hepcidin analogue disclosed herein, wherein the surface of the hepcidin analogue surface is modified to comprise mucoadhesive properties through hydrogen bonds, polymers with linked mucins or/and hydrophobic interactions. These modified peptide molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the hepcidin analogue.

Other embodiments comprise a method for oral delivery of a hepcidin analogue of the present invention, wherein the hepcidin analogue is provided to a subject in combination with permeation enhancers that promote the transport of the peptides across the intestinal mucosa by increasing paracellular or transcellular permeation. For example, in one embodiment, a permeation enhancer is combined with a hepcidin analogue, wherein the permeation enhancer comprises at least one of a long-chain fatty acid, a bile salt, an amphiphilic surfactant, and a chelating agent. In one embodiment, a permeation enhancer comprising sodium N-[hydroxy benzoyl)amino] caprylate is used to form a weak noncovalent association with the hepcidin analogue of the instant invention, wherein the permeation enhancer favors membrane transport and further dissociation once reaching the blood circulation. In another embodiment, a hepcidin analogue of the present invention is conjugated to oligoarginine, thereby increasing cellular penetration of the peptide into various cell types. Further, in at least one embodiment a noncovalent bond is provided between a peptide inhibitor of the present invention and a permeation enhancer selected from the group consisting of a cyclodextrin (CD) and a dendrimers, wherein the permeation enhancer reduces peptide aggregation and increasing stability and solubility for the hepcidin analogue molecule.

Other embodiments of the invention provide a method for treating a subject with a hepcidin analogue of the present invention having an increased half-life. In one aspect, the present invention provides a hepcidin analogue having a half-life of at least several hours to one day in vitro or in vivo (e.g., when administered to a human subject) sufficient for daily (q.d.) or twice daily (b.i.d.) dosing of a therapeutically effective amount. In another embodiment, the hepcidin analogue has a half-life of three days or longer sufficient for weekly (q.w.) dosing of a therapeutically effective amount. Further, in another embodiment, the hepcidin analogue has a half-life of eight days or longer sufficient for bi-weekly (b.i.w.) or monthly dosing of a therapeutically effective amount. In another embodiment, the hepcidin analogue is derivatized or modified such that is has a longer half-life as compared to the underivatized or unmodified hepcidin analogue. In another embodiment, the hepcidin analogue contains one or more chemical modifications to increase serum half-life.

When used in at least one of the treatments or delivery systems described herein, a hepcidin analogue of the present invention may be employed in pure form or, where such forms exist, in pharmaceutically acceptable salt form.

Dosages

The total daily usage of the hepcidin analogues and compositions of the present invention can be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, the age, body weight, general health, sex and diet of the patient; d) the time of administration, route of administration, and rate of excretion of the specific hepcidin analogue employed; e) the duration of the treatment; f) drugs used in combination or coincidental with the specific hepcidin analogue employed, and like factors well known in the medical arts.

In particular embodiments, the total daily dose of the hepcidin analogues of the invention to be administered to a human or other mammal host in single or divided doses may be in amounts, for example, from 0.0001 to 300 mg/kg body weight daily or 1 to 300 mg/kg body weight daily. In certain embodiments, a dosage of a hepcidin analogue of the present invention is in the range from about 0.0001 to about 100 mg/kg body weight per day, such as from about 0.0005 to about 50 mg/kg body weight per day, such as from about 0.001 to about 10 mg/kg body weight per day, e.g. from about 0.01 to about 1 mg/kg body weight per day, administered in one or more doses, such as from one to three doses. In particular embodiments, a total dosage is about 1 mg, about 2 mg, about 3 mg, about 4 mg, about 5 mg, about 6 mg, about 7 mg, about 8 mg, about 9 mg, or about 10 mg about once or twice weekly, e.g., for a human patient. In particular embodiments, the total dosage is in the range of about 1 mg to about 5 mg, or about 1 mg to about 3 mg, or about 2 mg to about 3 mg per human patient, e.g., about once weekly.

In various embodiments, a hepcidin analogue of the invention may be administered continuously (e.g. by intravenous administration or another continuous drug administration method), or may be administered to a subject at intervals, typically at regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like.

Such regular hepcidin analogue administration regimens of the invention may, in certain circumstances such as, e.g., during chronic long-term administration, be advantageously interrupted for a period of time so that the medicated subject reduces the level of or stops taking the medication, often referred to as taking a "drug holiday." Drug holidays are useful for, e.g., maintaining or regaining sensitivity to a drug especially during long-term chronic treatment, or to reduce unwanted side-effects of long-term chronic treatment of the subject with the drug. The timing of a drug holiday depends on the timing of the regular dosing regimen and the purpose for taking the drug holiday (e.g., to regain drug sensitivity and/or to reduce unwanted side effects of continuous, long-term administration). In some embodiments, the drug holiday may be a reduction in the dosage of the drug (e.g. to below the therapeutically effective amount for a certain interval of time). In other embodiments, administration of the drug is stopped for a certain interval of time before administration is started again using the same or a different dosing regimen (e.g. at a lower or higher dose and/or frequency of administration). A drug holiday of the invention may thus be selected from a wide range of time-periods and dosage regimens. An exemplary drug holiday is two or more days, one or more weeks, or one or more months, up to about 24 months of drug holiday. So, for example, a regular daily dosing regimen with a peptide, a peptide analogue, or a dimer of the invention may, for example, be interrupted by a drug holiday of a week, or two weeks, or four weeks, after which time the preceding, regular dosage regimen (e.g. a daily or a weekly dosing regimen) is resumed. A variety of other drug holiday regimens are envisioned to be useful for administering the hepcidin analogues of the invention.

Thus, the hepcidin analogues may be delivered via an administration regime which comprises two or more administration phases separated by respective drug holiday phases.

During each administration phase, the hepcidin analogue is administered to the recipient subject in a therapeutically effective amount according to a pre-determined administration pattern. The administration pattern may comprise continuous administration of the drug to the recipient subject over the duration of the administration phase. Alternatively, the administration pattern may comprise administration of a plurality of doses of the hepcidin analogue to the recipient subject, wherein said doses are spaced by dosing intervals.

A dosing pattern may comprise at least two doses per administration phase, at least five doses per administration phase, at least 10 doses per administration phase, at least 20 doses per administration phase, at least 30 doses per administration phase, or more.

Said dosing intervals may be regular dosing intervals, which may be as set out above, including once daily, twice daily, once every two, three, four, five or six days, once or twice weekly, once or twice monthly, or a regular and even less frequent dosing interval, depending on the particular dosage formulation, bioavailability, and pharmacokinetic profile of the hepcidin analogue of the present invention.

An administration phase may have a duration of at least two days, at least a week, at least 2 weeks, at least 4 weeks, at least a month, at least 2 months, at least 3 months, at least 6 months, or more.

Where an administration pattern comprises a plurality of doses, the duration of the following drug holiday phase is longer than the dosing interval used in that administration pattern. Where the dosing interval is irregular, the duration of the drug holiday phase may be greater than the mean interval between doses over the course of the administration phase. Alternatively the duration of the drug holiday may be longer than the longest interval between consecutive doses during the administration phase.

The duration of the drug holiday phase may be at least twice that of the relevant dosing interval (or mean thereof), at least 3 times, at least 4 times, at least 5 times, at least 10 times, or at least 20 times that of the relevant dosing interval or mean thereof.

Within these constraints, a drug holiday phase may have a duration of at least two days, at least a week, at least 2 weeks, at least 4 weeks, at least a month, at least 2 months, at least 3 months, at least 6 months, or more, depending on the administration pattern during the previous administration phase.

An administration regime comprises at least 2 administration phases. Consecutive administration phases are separated by respective drug holiday phases. Thus the administration regime may comprise at least 3, at least 4, at least 5, at least 10, at least 15, at least 20, at least 25, or at least 30 administration phases, or more, each separated by respective drug holiday phases.

Consecutive administration phases may utilise the same administration pattern, although this may not always be desirable or necessary. However, if other drugs or active agents are administered in combination with a hepcidin analogue of the invention, then typically the same combination of drugs or active agents is given in consecutive administration phases. In certain embodiments, the recipient subject is human.

In some embodiments, the present invention provides compositions and medicaments comprising at least one hepcidin analogue as disclosed herein. In some embodiments, the present invention provides a method of manufacturing medicaments comprising at least one hepcidin analogue as disclosed herein for the treatment of diseases of iron metabolism, such as iron overload diseases. In some embodiments, the present invention provides a method of manufacturing medicaments comprising at least one hepcidin analogue as disclosed herein for the treatment of diabetes (Type I or Type II), insulin resistance, or glucose intolerance. Also provided are methods of treating a disease of iron metabolism in a subject, such as a mammalian subject, and preferably a human subject, comprising administering at least one hepcidin analogue, or composition as disclosed herein to the subject. In some embodiments, the hepcidin analogue or the composition is administered in a therapeutically effective amount. Also provided are methods of treating diabetes (Type I or Type II), insulin resistance, or glucose intolerance in a subject, such as a mammalian subject, and preferably a human subject, comprising administering at least one hepcidin analogue or composition as disclosed herein to the subject. In some embodiments, the hepcidin analogue or composition is administered in a therapeutically effective amount.

In some embodiments, the invention provides a process for manufacturing a hepcidin analogue or a hepcidin analogue composition (e.g., a pharmaceutical composition), as disclosed herein.

In some embodiments, the invention provides a device comprising at least one hepcidin analogue of the present invention, or pharmaceutically acceptable salt or solvate thereof for delivery of the hepcidin analogue to a subject.

In some embodiments, the present invention provides methods of binding a ferroportin or inducing ferroportin internalization and degradation which comprises contacting the ferroportin with at least one hepcidin analogue, or hepcidin analogue composition as disclosed herein.

In some embodiments, the present invention provides kits comprising at least one hepcidin analogue, or hepcidin analogue composition (e.g., pharmaceutical composition) as disclosed herein packaged together with a reagent, a device, instructional material, or a combination thereof.

In some embodiments, the present invention provides a method of administering a hepcidin analogue or hepcidin analogue composition (e.g., pharmaceutical composition) of the present invention to a subject via implant or osmotic pump, by cartridge or micro pump, or by other means appreciated by the skilled artisan, as well-known in the art. In some embodiments, the present invention provides complexes which comprise at least one hepcidin analogue as disclosed herein bound to a ferroportin, preferably a human ferroportin, or an antibody, such as an antibody which specifically binds a hepcidin analogue as disclosed herein, Hep25, or a combination thereof.

In some embodiments, the hepcidin analogue of the present invention has a measurement (e.g., an EC50) of less than 500 nM within the FPN internalization assay. As a skilled person will realize, the function of the hepcidin analogue is dependent on the tertiary structure of the hepcidin analogue and the binding surface presented. It is therefore possible to make minor changes to the sequence encoding the hepcidin analogue that do not affect the fold or are not on the binding surface and maintain function. In other embodiments, the present invention provides a hepcidin analogue having 85% or higher (e.g., 85%, 90%, 91%, 92%, 93%, 94%, 95%, 96%, 97%, 98%, 99%, or 99.5%) identity or homology to an amino acid sequence of any hepcidin analogue described herein that exhibits an activity (e.g., hepcidin activity), or lessens a symptom of a disease or indication for which hepcidin is involved.

In other embodiments, the present invention provides a hepcidin analogue having 85% or higher (e.g., 85%, 90%, 91%, 92%, 93%, 94%, 95%, 96%, 97%, 98%, 99%, or 99.5%) identity or homology to an amino acid sequence of any hepcidin analogue presented herein, or a peptide according to any one of the formulae or hepcidin analogues described herein.

In some embodiments, a hepcidin analogue of the present invention may comprise functional fragments or variants thereof that have at most 10, 9, 8, 7, 6, 5, 4, 3, 2, or 1 amino acid substitutions compared to one or more of the specific peptide analogue sequences recited herein.

In addition to the methods described in the Examples herein, the hepcidin analogues of the present invention may be produced using methods known in the art including chemical synthesis, biosynthesis or in vitro synthesis using recombinant DNA methods, and solid phase synthesis. See e.g. Kelly & Winkler (1990) Genetic Engineering Principles and Methods, vol. 12, J. K. Setlow ed., Plenum Press, NY, pp. 1-19: Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, IL, which are herein incorporated by reference. The hepcidin analogues of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and Scopes (1982) Protein Purification, Springer-Verlag, NY, which are herein incorporated by reference. Alternatively, the hepcidin analogues of the present invention may be made by recombinant DNA techniques known in the art. Thus, polynucleotides that encode the polypeptides of the present invention are contemplated herein. In certain preferred embodiments, the polynucleotides are isolated. As used herein "isolated polynucleotides" refers to polynucleotides that are in an environment different from that in which the polynucleotide naturally occurs.

EXAMPLES

The following examples demonstrate certain specific embodiments of the present invention. The following examples were carried out using standard techniques that are well known and routine to those of skill in the art, except where otherwise described in detail. It is to be understood that these examples are for illustrative purposes only and do not purport to be wholly definitive as to conditions or scope of the invention. As such, they should not be construed in any way as limiting the scope of the present invention.

Abbreviations

DCM: dichloromethane
DMF: N,N-dimethylformamide
NMP: N-methylpyrolidone
HBTU: O-(Benzotriazol-1-yl)-N,N,N',N'-tetramethyluronium hexafluorophosphate
HATU: 2-(7-aza-1H-benzotriazole-1-yl)-1,1,3,3-tetramethyluronium hexafluorophosphate
DCC: Dicyclohexylcarbodiimide
NHS: N-hydoxysuccinimide
DIPEA: diisopropylethylamine
EtOH: ethanol
Et2O: diethyl ether
Hy: hydrogen
TFA: trifluoroacetic acid
TIS: triisopropylsilane
ACN: acetonitrile
HPLC: high performance liquid chromatography
ESI-MS: electron spray ionization mass spectrometry
PBS: phosphate-buffered saline
Boc: t-butoxy carbonyl
Fmoc: Fluorenylmethyloxycarbonyl
Acm: acetamidomethyl
IVA: Isovaleric acid (or Isovaleryl)
K( ): In the peptide sequences provided herein, wherein a compound or chemical group is presented in parentheses directly after a Lysine residue, it is to be understood that the compound or chemical group in the parentheses is a side chain conjugated to the Lysine residue. So, e.g., but not to be limited in any way, K-[(PEG8)]- indicates that a PEG8 moiety is conjugated to a side chain of this Lysine.
Palm: Indicates conjugation of a palmitic acid (palmitoyl).
As used herein "C( )" refers to a cysteine residue involved in a particular disulfide bridge. For example, in Hepcidin, there are four disulfide bridges: the first between the two C(1) residues: the second between the two C(2) residues; the third between the two C(3) residues; and the fourth between the two C(4) residues. Accordingly, in some embodiments, the sequence for Hepcidin is written as follows:

(SEQ ID NO: 156)
Hy-DTHFPIC(1)IFC(2)C(3)GC(2)C(4)HRSKC(3)GMC(4)C(1)
KT-OH;

and the sequence for other peptides may also optionally be written in the same manner.

Example 1

Synthesis of Peptide Analogues

Unless otherwise specified, reagents and solvents employed in the following were available commercially in standard laboratory reagent or analytical grade, and were used without further purification.

Procedure for Solid-Phase Synthesis of Peptides
Method A

Peptide analogues of the invention were chemically synthesized using optimized 9-fluorenylmethoxy carbonyl (Fmoc) solid phase peptide synthesis protocols. For C-terminal amides, rink-amide resin was used, although wang and trityl resins were also used to produce C-terminal acids. The side chain protecting groups were as follows: Glu, Thr and Tyr: O-tButyl: Trp and Lys: t-Boc (t-butyloxycarbonyl): Arg: N-gamma-2,2,4,6,7-pentamethyldihydrobenzofuran-5-sulfonyl: His, Gln, Asn, Cys: Trityl. For selective disulfide bridge formation, Acm (acetamidomethyl) was also used as a Cys protecting group. For coupling, a four to ten-fold excess of a solution containing Fmoc amino acid, HBTU and DpaEA (1:1:1.1) in DMF was added to swelled resin [HBTU: O-(Benzotriazol-1-yl)-N,N,N',N'-tetramethyluronium hexafluorophosphate: DpaEA: diisopropylethylamine; DMF: dimethylformamide]. HATU (O-(7-azabenzotriazol-1-yl)-1,1,3,3,-tetramethyluronium hexafluorophosphate) was used instead of HBTU to improve coupling efficiency in difficult regions. Fmoc protecting group removal was achieved by treatment with a DMF, piperidine (2:1) solution.
Method B Alternatively, peptides were synthesized utilizing the CEM liberty Blue Microwave assisted peptide synthesizer. Using the Liberty Blue, FMOC deprotection was carried out by addition of 20% 4-methylpiperdine in DMF with 0.1M Oxyma in DMF and then heating to 90° C. using microwave irradiation for 4 min. After DMF washes the FMOC-amino acids were coupled by addition of 0.2M amino acid (4-6 eq), 0.5M DIC (4-6 eq) and 1M Oxyma (with 0.1M DIEA) 4-6 eq (all in DMF). The coupling solution is heated using microwave radiation to 90° C. for 4 min. A second coupling is employed when coupling Arg or other sterically hindered amino acids. When coupling with histidine, the reaction is heated to 50° C. for 10 min. The cycles are repeated until the full length peptide is obtained.

Procedure for Cleavage of Peptides Off Resin

Side chain deprotection and cleavage of the peptide analogues of the invention (e.g., Compound No. 2) was achieved by stirring dry resin in a solution containing trifluoroacetic acid, water, ethanedithiol and tri-isopropylsilane (90:5:2.5:2.5) for 2 to 4 hours. Following TFA removal, peptide was precipitated using ice-cold diethyl ether. The solution was centrifuged and the ether was decanted, followed by a second diethyl ether wash. The peptide was dissolved in an acetonitrile, water solution (1:1) containing 0.1% TFA (trifluoroacetic acid) and the resulting solution was filtered. The linear peptide quality was assessed using electrospray ionization mass spectrometry (ESI-MS).

Procedure for Purification of Peptides

Purification of the peptides of the invention (e.g., Compound No. 2) was achieved using reverse-phase high performance liquid chromatography (RP-HPLC). Analysis was performed using a C18 column (3 µm, 50×2 mm) with a flow rate of 1 mL/min. Purification of the linear peptides was achieved using preparative RP-HPLC with a C18 column (5 µm, 250×21.2 mm) with a flow rate of 20 mL/min. Separation was achieved using linear gradients of buffer B in A (Buffer A: Aqueous 0.05% TFA; Buffer B: 0.043% TFA, 90% acetonitrile in water).

Procedure for Oxidation of Peptides

Method A (Single disulfide oxidation). Oxidation of the unprotected peptides of the invention was achieved by adding drop-wise iodine in MeOH (1 mg per 1 mL) to the peptide in a solution (ACN: $H_2O$, 7: 3, 0.5% TFA). After stirring for 2 min, ascorbic acid portion wise was added until the solution was clear and the sample was immediately loaded onto the HPLC for purification.

Method B (Selective oxidation of two disulfides). When more than one disulfide was present, selective oxidation was often performed. Oxidation of the free cysteines was achieved at pH 7.6 $NH_4CO_3$ solution at 1 mg/10 mL of peptide. After 24 h stirring and prior to purification the solution was acidified to pH 3 with TFA followed by lyophilization. The resulting single oxidized peptides (with ACM protected cysteines) were then oxidized/selective deprotection using iodine solution. The peptide (1 mg per 2 mL) was dissolved in $MeOH/H_2O$, 80:20 iodine dissolved in the reaction solvent was added to the reaction (final concentration: 5 mg/mL) at room temperature. The solution was stirred for 7 minutes before ascorbic acid was added portion wise until the solution is clear. The solution was then loaded directly onto the HPLC.

Method C (Native oxidation). When more than one disulfide was present and when not performing selective oxidations, native oxidation was performed. Native oxidation was achieved with 100 mM NH4CO3 (pH7.4) solution in the presence of oxidized and reduced glutathione (peptide/GSH/GSSG. 1:100:10 molar ratio) of (peptide: GSSG: GSH. 1:10, 100). After 24 h stirring and prior to RP-HPLC purification the solution was acidified to pH 3 with TFA followed by lyophilization.

Procedure of Cysteine Oxidation to Produce Dimers.

Oxidation of the unprotected peptides of the invention was achieved by adding drop-wise iodine in MeOH (1 mg per 1 mL) to the peptide in a solution (ACN: H2O, 7: 3, 0.5% TFA). After stirring for 2 min, ascorbic acid portion wise was added until the solution was clear and the sample was immediately loaded onto the HPLC for purification.

Procedure for Dimerization.

Glyoxylic acid (DIG), IDA, or Fmoc-β-Ala-IDA was pre-activated as the N-hydoxysuccinimide ester by treating 1 equivalent (abbreviated "eq") of the acid with 2.2 eq of both N-hydroxysuccinimide (NHS) and dicyclohexyl carbodiimide (DCC) in NMP (N-methyl pyrolidone) at a 0.1 M final concentration. For the PEG13 and PEG25 linkers, these chemical entities were purchased pre-formed as the activated succinimide ester. The activated ester ~0.4 eq was added slowly to the peptide in NMP (1 mg/mL) portionwise. The solution was left stirring for 10 min before 2-3 additional aliquots of the linker ~0.05 eq were slowly added. The solution was left stirring for a further 3 h before the solvent was removed under vaccuo and the residue was purified by reverse phase HPLC. An additional step of stirring the peptide in 20% piperidine in DMF (2×10 min) before an additional reverse phase HPLC purification was performed.

One of skill in the art will appreciate that standard methods of peptide synthesis may be used to generate the compounds of the invention.

Linker Activation and Dimerization

Peptide monomer subunits were linked to form hepcidin analogue peptide dimers as described below.

Small Scale DIG Linker Activation Procedure: 5 mL of NMP was added to a glass vial containing IDA diacid (304.2 mg, 1 mmol), N-hydroxysuccinimide (NHS, 253.2 mg, 2.2 eq. 2.2 mmol) and a stirring bar. The mixture was stirred at room temperature to completely dissolve the solid starting materials. N, N'-Dicyclohexylcarbodiimide (DCC, 453.9 mg, 2.2 eq., 2.2 mmol) was then added to the mixture. Precipitation appeared within 10 min and the reaction mixture was further stirred at room temperature overnight. The reaction mixture was then filtered to remove the precipitated dicyclohexylurea (DCU). The activated linker was kept in a closed vial prior to use for dimerization. The nominal concentration of the activated linker was approximately 0.20 M.

For dimerization using PEG linkers, there was no pre-activation step involved. Commercially available pre-activated bi-functional PEG linkers were used.

Dimerization Procedure: 2 mL of anhydrous DMF was added to a vial containing peptide monomer (0.1 mmol). The pH of the peptide was the adjusted to 8~9 with DIEA. Activated linker (IDA or PEG13, PEG 25) (0.48 eq relative to monomer, 0.048 mmol) was then added to the monomer solution. The reaction mixture was stirred at room temperature for one hour. Completion of the dimerization reaction was monitored using analytical HPLC. The time for completion of dimerization reaction varied depending upon the linker. After completion of reaction, the peptide was precipitated in cold ether and centrifuged. The supernatant ether layer was discarded. The precipitation step was repeated twice. The crude dimer was then purified using reverse phase HPLC (Luna C18 support, 10u, 100A, Mobile phase A: water containing 0.1% TFA, mobile phase B: Acetonitrile (ACN) containing 0.1% TFA, gradient of 15% B and change to 45% B over 60 min, flow rate 15 ml/min). Fractions containing pure product were then freeze-dried on a lyophilizer.

Conjugation of Half-Life Extension Moieties

Conjugation of peptides were performed on resin. Lys (ivDde) was used as the key amino acid. After assembly of the peptide on resin, selective deprotection of the ivDde group occurred using 3×5 min 2% hydrazine in DMF for 5 min. Activation and acylation of the linker using HBTU, DIEA 1-2 equivalents for 3 h, and Fmoc removal followed by a second acylation with the lipidic acid gave the conjugated peptide.

Example 2

Activity of Peptide Analogues

Peptide analogues were tested in vitro for induction of internalization of the human ferroportin protein. Following internalization, the ferroporin protein is degraded. The assay used (FPN activity assay) measures a decrease in fluorescence of the receptor.

The cDNA encoding the human ferroportin (SLC40A1) was cloned from a cDNA clone from Origene (NM_014585). The DNA encoding the ferroportin was amplified by PCR using primers also encoding terminal restriction sites for subcloning, but without the termination codon. The ferroportin receptor was subcloned into a mammalian GFP expression vector containing a neomycin (G418) resistance marker in such that the reading frame of the ferroportin was fused in frame with the GFP protein. The fidelity of the DNA encoding the protein was confirmed by DNA sequencing. HEK293 cells were used for transfection of the ferroportin-GFP receptor expression plasmid. The cells were grown according to standard protocol in growth medium and transfected with the plasmids using Lipofectamine (manufacturer's protocol, Invitrogen). The cells stably expressing ferroportin-GFP were selected using G418 in the growth medium (in that only cells that have taken up and incorporated the cDNA expression plasmid survive) and sorted several times on a Cytomation MoFlo™ cell sorter to obtain the GFP-positive cells (488 nm/530 nm). The cells were propagated and frozen in aliquots.

To determine activity of the hepcidin analogues (compounds) on the human ferroportin, the cells were incubated in 96 well plates in standard media, without phenol red.

Compound was added to desired final concentration for at least 18 hours in the incubator. Following incubation, the remaining GFP-fluorescence was determined either by whole cell GFP fluorescence (Envision plate reader, 485/535 filter pair), or by Beckman Coulter Quanta™ flow cytometer (express as Geometric mean of fluorescence intensity at 485 nm/525 nm). Compound was added to desired final concentration for at least 18 hours but no more than 24 hours in the incubator.

In certain experiments, reference compounds included native Hepcidin, Mini-Hepcidin, and R1-Mini-Hepcidin, which is an analog of mini-hepcidin. The "RI" in RI-Mini-Hepcidin refers to Retro Inverse. A retro inverse peptide is a peptide with a reversed sequence in all D amino acids. An example is that Hy-Glu-Thr-His-$NH_2$ becomes Hy-DHis-DThr-DGlu-$NH_2$. The $EC_{50}$ of these reference compounds for ferroportin internalization/degradation was determined according to the FPN activity assay described above. These peptides served as control standards.

analog at 30 h and 36 h post-administration. Iron content in plasma/serum was measured using a colorimetric assay on the Cobas c 111 according to instructions from the manufacturer of the assay (assay: IRON2: ACN 661).

These studies demonstrate that hepcidin analogues of the present invention reduce serum iron levels for at least 30 hours, thus demonstrating their increased serum stability.

Example 4

In Vitro Validation of Peptide Analogues

Based in part on the structure activity relationships (SAR) determined from the results of the experiments described herein, a variety of Hepcidin-like peptides of the present invention were synthesized using the method described in Example 1, and in vitro activity was tested as described in Example 2. Reference compounds included native Hepcidin, Mini-Hepcidin, RI-Mini-Hepcidin, Reference Compound 1

TABLE 9

Reference compounds

| Name | Sequence | Potency $EC_{50}$ (nM) |
|---|---|---|
| Hepcidin | Hy-DTHFPIC(1)IFC(2)C(3)GC(2)C(4)HRSKC(3)GMC(4)C(1)KT-OH (SEQ ID NO: 256) | 34 |
| Mini-Hepcidin 1-9 | Hy-DTHFPICIF-$NH_2$ (SEQ ID NO: 257) | 712 |
| RI-Mini Hepcidin | Hy-DPhe-DIle-DCys-DIle-DPro-DPhe-DHis-DThr-DAsp-$NH_2$ (SEQ ID NO: 258) | >10 µM |
| Ref. Compd 1 | Isovaleric acid-DTHFPCIKF-Lys[PEG11-Palm]-PRSKGCK-$NH_2$ (SEQ ID NO: 1) | 30 |
| Ref. Compd. 2 | Isovaleric acid-DTHFPCIKF-Lys[PEG11-Palm]-PRSK-[SAR]-CK-$NH_2$ (SEQ ID NO: 2) | 13 |

The potency $EC_{50}$ values (nM) determined for various peptide analogues of the present invention are provided in Tables 3A, 3B, and 4. These values were determined as described herein.

Example 3

In Vivo Validation of Peptide Analogues

Hepcidin analogues of the present invention were tested for in vivo activity, to determine their ability to decrease free Fe2+ in serum.

A hepcidin analogue or vehicle control were administered to mice (n=3/group) at 1000 nmol/kg either intravenously or subcutaneously. Serum samples were taken from groups of mice administered with the hepcidin analog at 30 min, 1 h, 2 h, 4 h, 10 h, 24 h, 30 h, 36 h, and 48 h post-administration. Iron content in plasma/serum was measured using a colorimetric assay on the Cobas c 111 according to instructions from the manufacturer of the assay (assay: IRON2: ACN 661).

In another experiment, various hepcidin analogues or vehicle control were administered to mice (n=3/group) at 1000 nmol/kg subcutaneously. Serum samples were taken from groups of mice administered with vehicle or hepcidin and Reference Compound 2. $EC_{50}$ values of the peptides are shown in summary Table 3A and Table 3B.

Example 5

Plasma Stability

Plasma stability experiments were undertaken to complement the in vivo results and assist in the design of potent, stable Ferroportin agonists. In order to predict the stability in rat and mouse plasma, ex vivo stability studies were initially performed in these matrices.

Peptides of interest (20 µM) were incubated with pre-warmed plasma (BioreclamationIVT) at 37° C. Aliquots were taken at various time points up to 24 hours (e.g. 0, 0.25, 1, 3, 6 and 24 hr), and immediately quenched with 4 volumes of organic solvent (acetonitrile/methanol (1:1) and 0.1% formic acid, containing 1 µM internal standard). Quenched samples were stored at 4° C. until the end of the experiment and centrifuged at 17,000 g for 15 minutes. The supernatant were diluted 1:1 with deionized water and analyzed using LC-MS. Percentage remaining at each time point was calculated based on the peak area ratio (analyte over internal standard) relative to the initial level at time zero. Half-lives were calculated by fitting to a first-order exponential decay equation using GraphPad. Table 9 shows the results of this study.

TABLE 9

Plasma Stability of Representative Compounds

| Compound ID# | Stability in Mouse Plasma (hr) | Stability in Rat Plasma (hr) |
|---|---|---|
| 10 | | 3.83 |
| 27 | | 24 |
| 80 | 11 | 3.5 |
| 86 | 15.8 | |
| 105 | 17.3 | 4.34 |
| 117 | | 3.7 |
| 118 | | 3.05 |
| 121 | | 3.3 |
| 122 | | 3.63 |
| 131 | | 3 |
| 132 | | 3.9 |
| 152 | | 24 |
| 154 | | 24 |
| 155 | | 1 |
| 156 | | 4.23 |
| 157 | | 24 |
| 158 | | 24 |
| 165 | | 14.8 |

Example 6

Reduction of Serum Iron in Mice

Figure 1B:
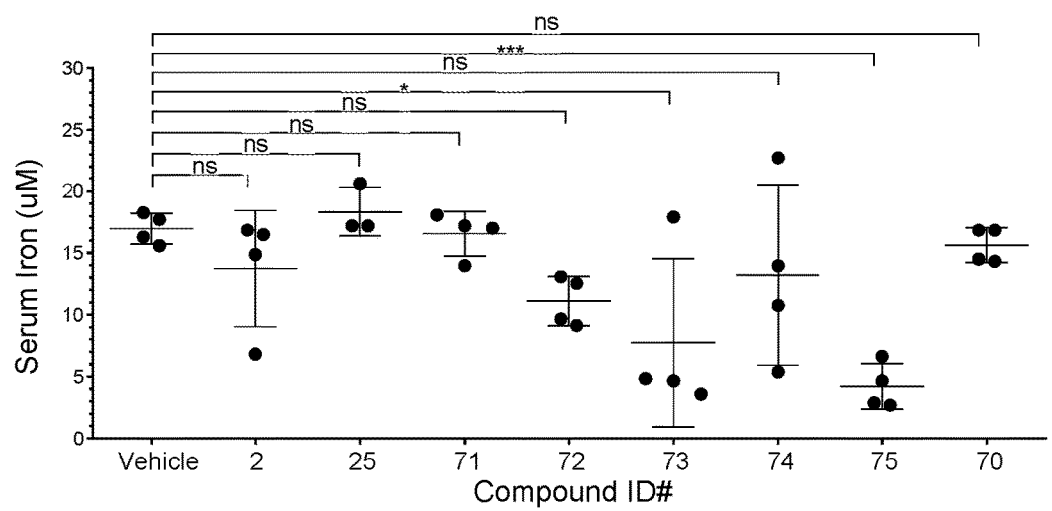

Hepcidin mimetic compounds, designed for oral stability, were tested for systemic absorption by PO dosing in a wild type mouse model C57BL/6. The animals were acclimatized in normal rodent diet for 4-5 days prior to study start and fasted overnight prior to study start. Groups of 4 animals each received either Vehicle or the Compounds as shown in FIGS. 1A & 1B. The compounds were formulated in Saline at a concentration of 5 mg/mL. The mice received dosing solution via oral gavage at volume of 200 µl per animal of body weight 20 g. Each group received 1 dose of compounds at 50 mg/kg/dose. The group marked for vehicle received only the formulation. Blood was drawn at 4 hours post-dose and serum was prepared for PK and PD measurements. The compound concentration was measured by mass spectrometry method and iron concentration in the samples was measured using the colorimetric method on Roche cobas c system.

In this triage experiment, multiple compounds were tested (Compound ID #2, 25, 71, 72, 73, 74, 75, 70) for systemic serum iron reduction with oral dosing of the compounds. The compound ID #73 and 75 showed significant reduction in serum iron, FIG. 1B, and also greater than 100 ng/mL serum concentration (except for one animal dosed with Cmpd #73) as shown in FIG. 1A. There was a good correlation between the observed serum concentration of compounds #73 & #75 and the serum iron reduction in the animals.

Example 7

Reduction of Serum Iron in Mice

In another experiment, a new set of compounds were tested for systemic absorption by PO dosing in a wild type mouse model C57BL/6. The animals were acclimatized in normal rodent diet for 4-5 days prior to study start. Over the night prior to the first dose, the mice were switched to a low iron diet (with 2 ppm iron) and this diet was maintained during the rest of the study. Groups of 5 animals each received either Vehicle or the Compounds as shown in FIG. 1. The concentration of compounds was at 30 mg/mL, formulated in 0.7% NaCl+10 mM NaAcetate buffer. Food was withdrawn around 2 hours prior to each dose to ensure that the stomach was clear of any food particles prior to PO dosing. The mice received dosing solution via oral gavage at volume of 200 µl per animal of body weight 20 g. Each group received 2 doses of compound at 300 mg/kg/dose, on successive days. The group marked for vehicle received only the formulation. Blood was drawn at 4.5 hours post-last-dose and serum was prepared for PD measurements. Serum iron concentration was measured using the colorimetric method on Roche cobas c system.

Figure 2:
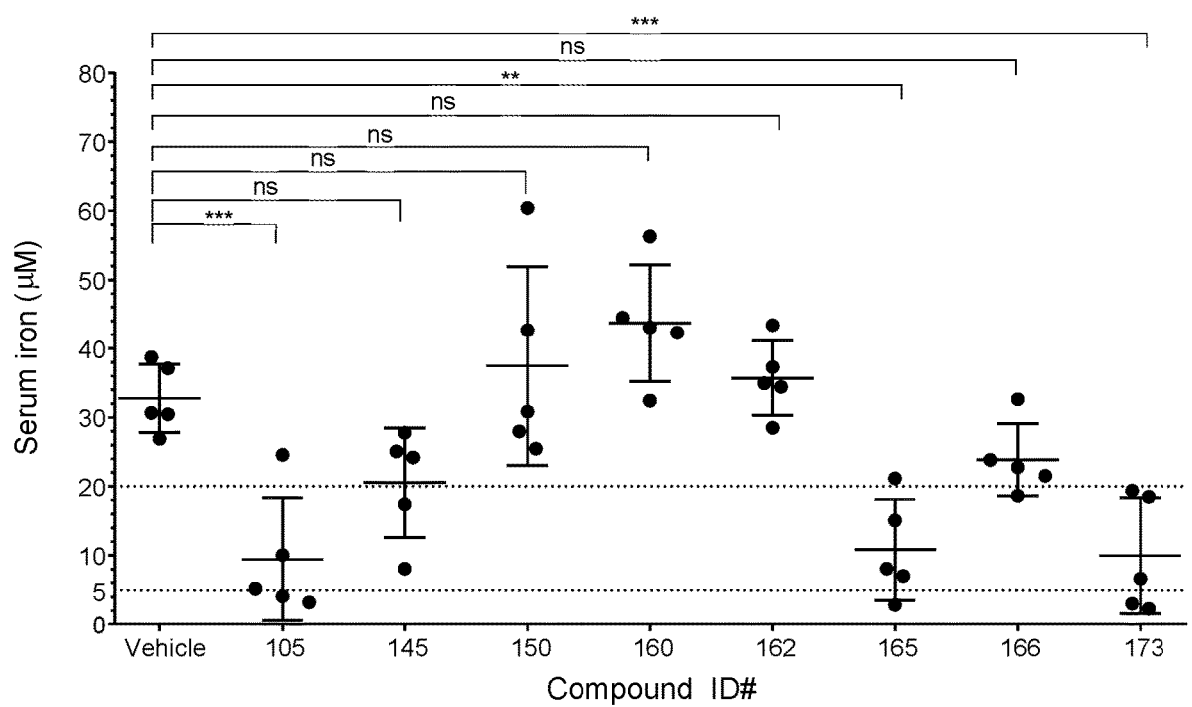
FIG. 2 shows the reduction of serum iron concentration after dosing of compounds ID 105, 145, 150, 160, 162, 165, 166, and 173 in mice.

In this triage experiment, multiple compounds were tested (Compound ID #105, 145, 150, 160, 162, 165, 166, 173) for systemic serum iron reduction with oral dosing of the compounds. The compound ID #105, 165 and 173 showed significant reduction in serum iron, FIG. 2.

Example 8

Figure 3:
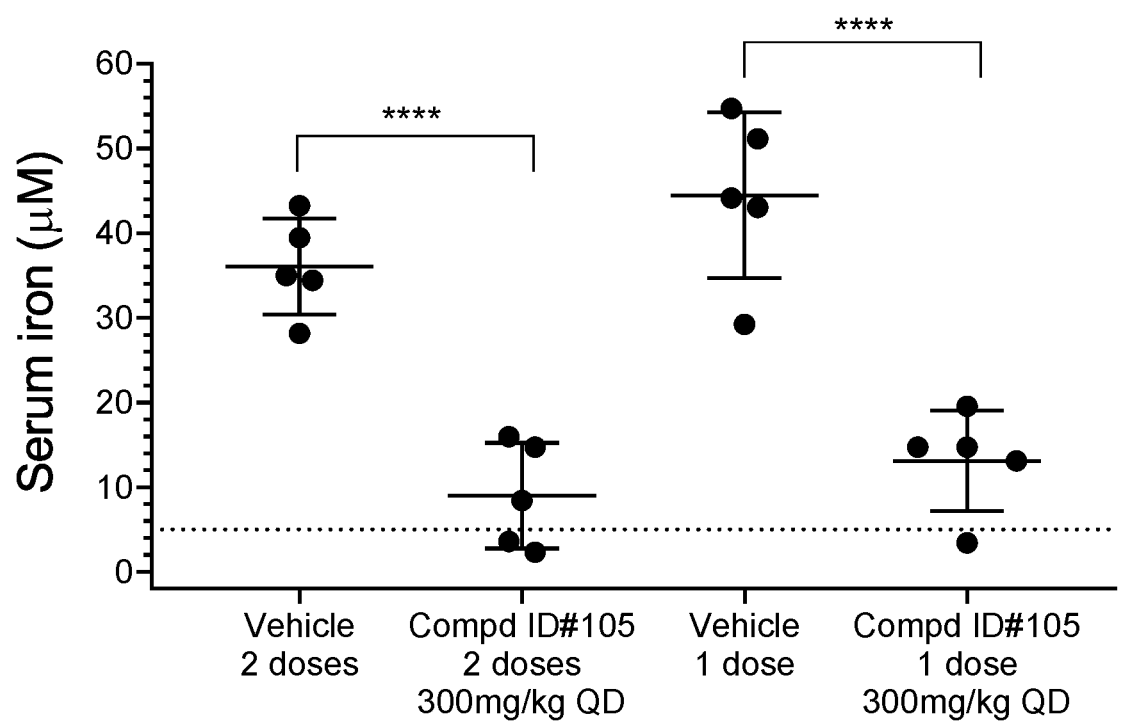
FIG. 3 shows PD effects for in vivo serum iron reducing abilities of Compound ID 105 in mice.

Pharmacodynamic Effects for the Serum Iron Reducing Abilities of Compound #105 in Mice In a second in vivo study, the Compound ID #105 was tested for pharmacodynamic effect with a single dose of 300 mg/kg/dose vs. 2 doses of 300 mg/kg over two days QD (once per day). C57BL/6 mice were acclimatized in normal rodent diet for 4-5 days prior to study start. Over the night prior to the first dose, the mice were switched to a low iron diet (with 2 ppm iron) and this diet was maintained during the rest of the study. Groups of 5 animals each received either Vehicle or the Compounds as shown in FIG. 3. The compound was formulated in 0.7% NaCl+10 mM NaAcetate buffer at 30 mg/mL concentration. Food was withdrawn around 2 hours prior to each dose to ensure that the stomach was clear of any food particles prior to PO dosing. The mice received dosing solution via oral gavage at volume of 200 µl per animal of body weight 20 g. As shown in the FIG. 3, both groups that were treated with Compound ID #105 showed significant reductions in serum iron concentration as compared to their respective vehicle groups.

Example 9

Pk/Pd Effects of Oral Dosing of Compound #105 in Mice

In another in vivo study with healthy Wild Type mouse model C57/BL6, Compound ID #105 was tested for PK and PD effect with multiple dosing over three days. The mice were maintained under normal rodent feed during the acclimatization and switched to iron-deficient diet (with ~2 ppm iron) one night prior to the first dose. Groups of 5 mice each received a total of 6 doses of either vehicle or CompoundID #105 at different dose strengths, in a BID format over three days. Mice were dosed via. oral gavage with Compound ID #105 formulated in 0.7% saline and 10 mM Sodium Acetate. The different groups received either vehicle, 150 mg/kg/dose BID, 75 mg/kg/dose BID, 37.5 mg/kg/dose BID, or 18.75 mg/kg/dose BID. An additional group received 100 mg/kg/dose BID in addition to a total of 100 mg/kg/day of compound in drinking water (DW), thereby receiving a total dose of 300 g/kg/day. At 3 hours post-last-dose the vehicle group marked for iron-challenge and all the CmpdID #105 dosed groups received iron solution via. oral gavage at 4 mg/kg iron per animal. Blood was collected at 90 min post-iron-challenge to prepare serum for PK and PD measurements. The compound concentration was measured by mass spectrometry method and iron concentration in the samples was measured using the colorimetric method on Roche cobas c system.

Figure 4A:
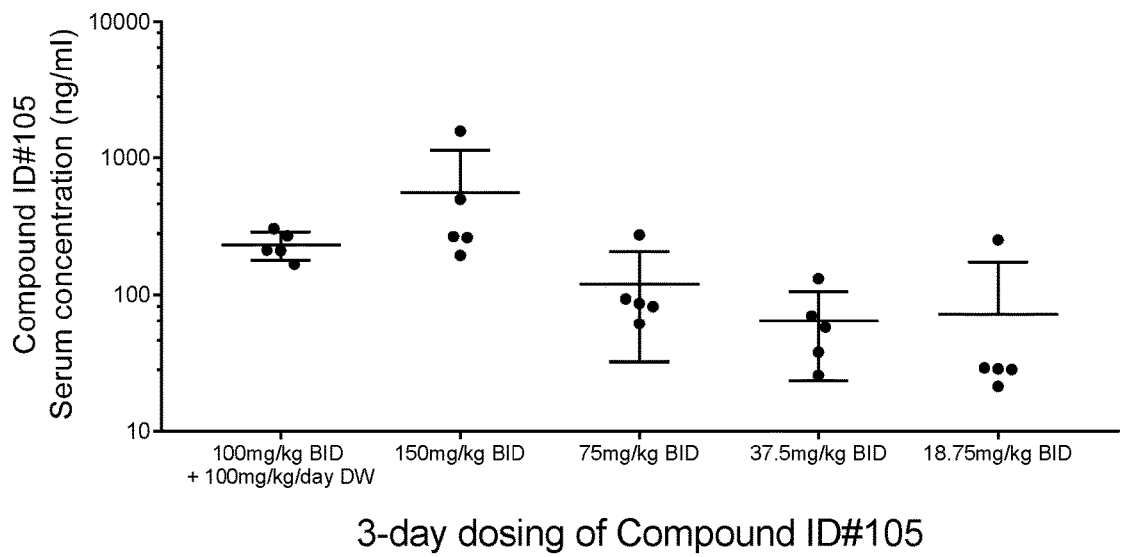
FIGS. 4A and 4B show PK and PD effect of serum iron reduction of Compound ID 105 in wild type mice.
Figure 4B:
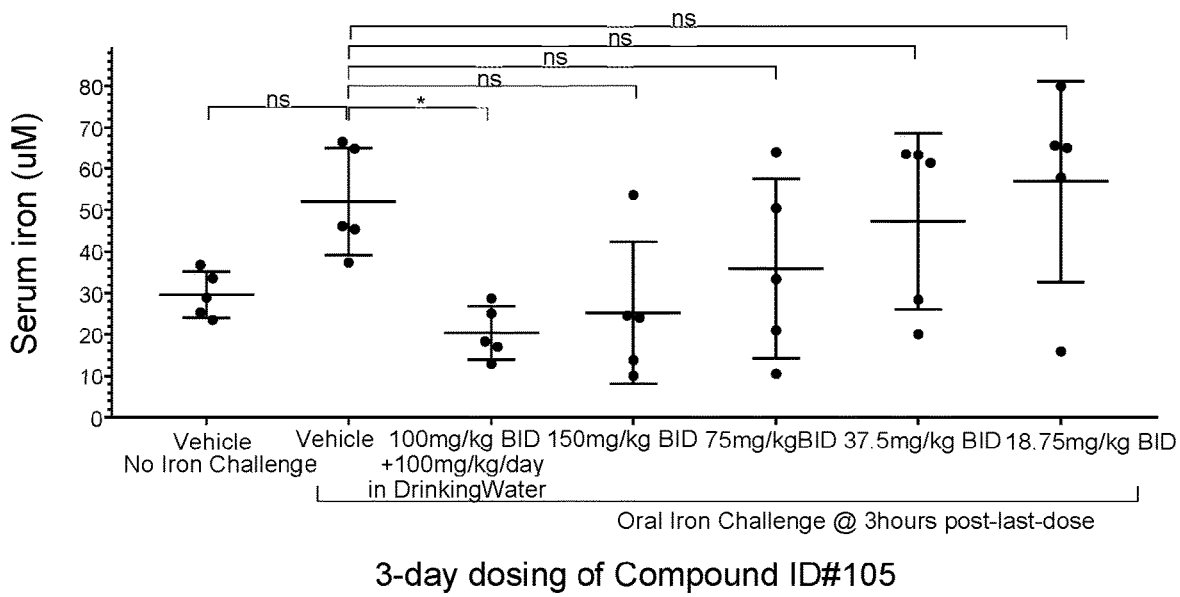

As shown in FIG. 4A, there was an increased absorption of the orally dosed Cmpd #105, when the dose was higher at 300 mg/kg/day (in groups receiving 150 mg/kg BID or 100 mg/kg BID+compound in drinking water). Also, there was a dose dependent decrease in this absorption, at 75 mg/kg BID and lower doses. In correlation, the PD effect of reduced absorption of orally provided iron solution was maximum in groups that received 300 mg/kg/day; i.e. groups dosed either 150 mg/kg BID or 100 mg/kg BID+100 mg/kg in DW, FIG. 4B. At lower doses, the PD effect was lower, in correlation with the observed serum iron concentration.

Example 10

Reduction of Serum Iron in Mice

In a separate triage, a new set of compounds were tested for their pharmacodynamic effect when dosed orally in the wild type mouse model C57BL/6. The animals were acclimatized in normal rodent diet for 4-5 days prior to study start. The group of 5 animals designated to receive two doses of Compound ID #105 received an iron-deficient diet (with 2-ppm iron) on the night prior to the first dose and all the other groups designated for single dose of different compounds were treated with iron-deficient diet for two nights prior to the compound dosing. The concentration of compounds in the dosing solution was at 30 mg/mL, formulated in 0.7% NaCl+10 mM NaAcetate buffer. Food was withdrawn around 2 hours prior to any dosing to ensure that the stomach was clear of any food particles prior to PO dosing. The mice received dosing solution via oral gavage at volume of 200 µl per animal of body weight 20 g. The group marked for vehicle received only the formulation. Blood was drawn at 4.5 hours post-last-dose and serum was prepared for PD measurements. Serum iron concentration was measured using the colorimetric method on Roche cobas c system.

Figure 5:
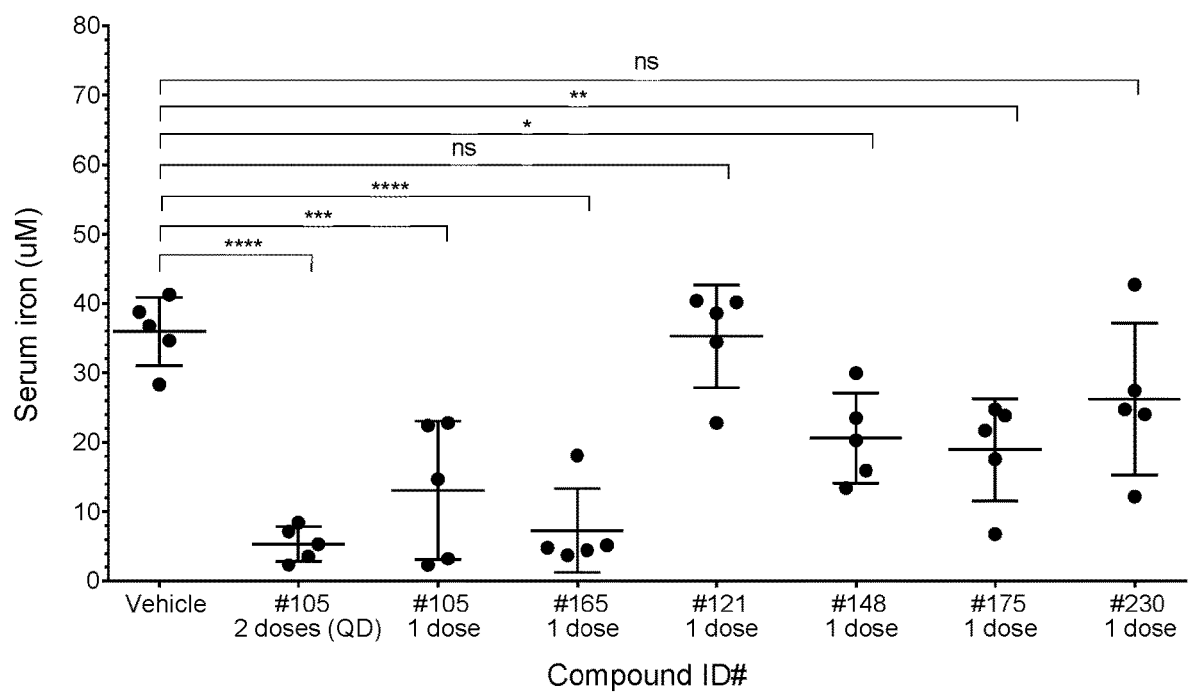
FIG. 5 shows the reduction of serum iron concentration with oral dosing of compounds ID 105, 165, 148, and 175 in mice.

In this triage experiment, multiple compounds were tested (Compound ID #105, 165, 121, 148, 175 and 230) for systemic serum iron reduction with oral dosing of the compounds. The compounds ID #105 (both single dose and 2-doses), 165, 148 and 175 showed significant reduction in serum iron, as shown in FIG. 5.

Example 11

Stability in Simulated Gastric Fluid

Blank SGF was prepared by adding 2 g sodium chloride, 7 mL hydrochloric acid (37%) in a final volume of 1 L water, and adjusted pH to 1.2.

SGF was prepared by dissolving 320 mg Pepsin (Sigma®, P6887, from Porcine Stomach Mucosa) in 100 mL Blank SGF and stirred at room temperature for 30 minutes. The solution was filtered through 0.45 µm membrane and aliquot and stored at −20° C.

Experimental compounds of interest (at a concentration of 20 µM) were incubated with pre-warmed SGF at 37° C. Aliquots were taken at various time points up to 24 hours (e.g., 0, 0.25, 1, 3, 6 and 24 hr), and immediately quenched with 4 volumes of organic solvent (acetonitrile/methanol (1:1) and 0.1% formic acid, containing 1 µM internal standard). Quenched samples were stored at 4° C. until the end of the experiment and centrifuged at 4,000 rpm for 10 minutes. The supernatant were diluted 1:1 with deionized water and analyzed using LC-MS. Percentage remaining at each time point was calculated based on the peak area ratio (analyte over internal standard) relative to the initial level at time zero. Half-lives were calculated by fitting to a first-order exponential decay equation using GraphPad.

Example 12

Stability in Simulated Intestinal Fluids

Blank FaSSIF was prepared by dissolving 0.348 g NaOH, 3.954 g sodium phosphate monobasic monohydrate and 6.186 g NaCl in a final volume of 1 liter water (pH adjusted to 6.5).

FaSSIF was prepared by dissolving 1.2 g porcine pancreatin (Chem-supply, PL378) in 100 mL Blank FaSSIF and stirred at room temperature for 30 minutes. The solution was filtered through 0.45 µm membrane and aliquot and stored at −20° C.

Experimental compounds of interest (20 M) were incubated with pre-warmed FaSSIF (1% pancreatin in final incubation mixture) at 37° C. Aliquots were taken at various time points up to 24 hours (e.g. 0, 0.25, 1, 3, 6 and 24 hr), and immediately quenched with 4 volumes of organic solvent (acetonitrile/methanol (1:1) and 0.1% formic acid, containing 1 µM internal standard). Quenched samples were stored at 4° C. until the end of the experiment and centrifuged at 4,000 rpm for 10 minutes. The supernatant were diluted 1:1 with deionized water and analyzed using LC-MS. Percentage remaining at each time point was calculated based on the peak area ratio (analyte over internal standard) relative to the initial level at time zero. Half-lives were calculated by fitting to a first-order exponential decay equation using GraphPad. Results are shown in Tables 3A, 3B, and 4.

Example 13

Modified Experimental for Peptides Prone to "Non-Specific Binding"

Compounds of interest (at concentration of 20 µM) were mixed with pre-warmed FaSSIF (1% pancreatin in final working solution). The solution mixture was aliquoted and incubated at 37° C. The number of aliquots required was equivalent to the number of time points (e.g. 0, 0.25, 1, 3, 6 and 24 hr). At each time point, one aliquot was taken and immediately quenched with 4 volumes of organic solvent (acetonitrile/methanol (1:1) and 0.1% formic acid, containing 1 µM internal standard). The remaining steps were the same as the generic experimental.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

SEQUENCE LISTING

```
Sequence total quantity: 258
SEQ ID NO: 1              moltype = AA  length = 17
FEATURE                   Location/Qualifiers
REGION                    1..17
                          note = hepcidin analogue
SITE                      10
                          note = PEG11-Palm conjugated half-life extension moiety
source                    1..17
                          mol_type = protein
                          organism = synthetic construct
SEQUENCE: 1
DTHFPCIKFK PRSKGCK                                                          17

SEQ ID NO: 2              moltype = AA  length = 17
FEATURE                   Location/Qualifiers
REGION                    1..17
                          note = hepcidin analogue
SITE                      10
                          note = PEG11-Palm conjugated half-life extension moiety
MOD_RES                   15
                          note = MeGly
source                    1..17
                          mol_type = protein
                          organism = synthetic construct
SEQUENCE: 2
DTHFPCIKFK PRSKXCK                                                          17

SEQ ID NO: 3              moltype = AA  length = 16
FEATURE                   Location/Qualifiers
REGION                    1..16
                          note = hepcidin analogue
SITE                      10
                          note = PEG11-Palm conjugated half-life extension moiety
source                    1..16
                          mol_type = protein
                          organism = synthetic construct
SEQUENCE: 3
DTHFPCIKFK PRSKGC                                                           16

SEQ ID NO: 4              moltype = AA  length = 15
FEATURE                   Location/Qualifiers
REGION                    1..15
                          note = hepcidin analogue
SITE                      10
                          note = PEG11-Palm conjugated half-life extension moiety
source                    1..15
                          mol_type = protein
                          organism = synthetic construct
SEQUENCE: 4
DTHFPCIKFK PRSKC                                                            15

SEQ ID NO: 5              moltype = AA  length = 14
FEATURE                   Location/Qualifiers
REGION                    1..14
                          note = hepcidin analogue
SITE                      10
                          note = PEG11-Palm conjugated half-life extension moiety
source                    1..14
                          mol_type = protein
                          organism = synthetic construct
SEQUENCE: 5
DTHFPCIKFK PRSC                                                             14

SEQ ID NO: 6              moltype = AA  length = 13
FEATURE                   Location/Qualifiers
REGION                    1..13
                          note = hepcidin analogue
SITE                      10
                          note = PEG11-Palm conjugated half-life extension moiety
source                    1..13
                          mol_type = protein
                          organism = synthetic construct
SEQUENCE: 6
DTHFPCIKFK PRC                                                              13

SEQ ID NO: 7              moltype = AA  length = 12
FEATURE                   Location/Qualifiers
REGION                    1..12
```

```
                    note = hepcidin analogue
SITE                10
                    note = PEG11-Palm conjugated half-life extension moiety
source              1..12
                    mol_type = protein
                    organism = synthetic construct
SEQUENCE: 7
DTHFPCIKFK PC                                                              12

SEQ ID NO: 8        moltype = AA   length = 11
FEATURE             Location/Qualifiers
REGION              1..11
                    note = hepcidin analogue
SITE                10
                    note = PEG11-Palm conjugated half-life extension moiety
source              1..11
                    mol_type = protein
                    organism = synthetic construct
SEQUENCE: 8
DTHFPCIKFK C                                                               11

SEQ ID NO: 9        moltype = AA   length = 13
FEATURE             Location/Qualifiers
REGION              1..13
                    note = hepcidin analogue
SITE                10
                    note = PEG11-Palm conjugated half-life extension moiety
source              1..13
                    mol_type = protein
                    organism = synthetic construct
SEQUENCE: 9
DTHFPCIKFK PCK                                                             13

SEQ ID NO: 10       moltype = AA   length = 11
FEATURE             Location/Qualifiers
REGION              1..11
                    note = hepcidin analogue
SITE                8
                    note = D-Lysine
SITE                10
                    note = PEG11-Palm conjugated half-life extension moiety
source              1..11
                    mol_type = protein
                    organism = synthetic construct
SEQUENCE: 10
DTHFPCIKFK C                                                               11

SEQ ID NO: 11       moltype = AA   length = 11
FEATURE             Location/Qualifiers
REGION              1..11
                    note = hepcidin analogue
MOD_RES             8
                    note = Orn
SITE                10
                    note = PEG11-Palm conjugated half-life extension moiety
source              1..11
                    mol_type = protein
                    organism = synthetic construct
SEQUENCE: 11
DTHFPCIXFK C                                                               11

SEQ ID NO: 12       moltype = AA   length = 11
FEATURE             Location/Qualifiers
REGION              1..11
                    note = hepcidin analogue
MOD_RES             8
                    note = Homoserine
SITE                10
                    note = Site - PEG11-Palm conjugated half-life extension
                     moiety
source              1..11
                    mol_type = protein
                    organism = synthetic construct
SEQUENCE: 12
DTHFPCIXFK C                                                               11

SEQ ID NO: 13       moltype = AA   length = 11
FEATURE             Location/Qualifiers
REGION              1..11
```

```
                            note = hepcidin analogue
SITE                        10
                            note = PEG11-Palm conjugated half-life extension moiety
source                      1..11
                            mol_type = protein
                            organism = synthetic construct
SEQUENCE: 13
DTHFPCIQFK C                                                                    11

SEQ ID NO: 14               moltype = AA  length = 11
FEATURE                     Location/Qualifiers
REGION                      1..11
                            note = hepcidin analogue
SITE                        8
                            note = ACETYLATION
SITE                        10
                            note = PEG11-Palm conjugated half-life extension moiety
source                      1..11
                            mol_type = protein
                            organism = synthetic construct
SEQUENCE: 14
DTHFPCIKFK C                                                                    11

SEQ ID NO: 15               moltype = AA  length = 11
FEATURE                     Location/Qualifiers
REGION                      1..11
                            note = hepcidin analogue
MOD_RES                     8
                            note = Nle
SITE                        10
                            note = PEG11-Palm conjugated half-life extension moiety
source                      1..11
                            mol_type = protein
                            organism = synthetic construct
SEQUENCE: 15
DTHFPCIXFK C                                                                    11

SEQ ID NO: 16               moltype = AA  length = 11
FEATURE                     Location/Qualifiers
REGION                      1..11
                            note = hepcidin analogue
SITE                        10
                            note = PEG11-Palm conjugated half-life extension moiety
source                      1..11
                            mol_type = protein
                            organism = synthetic construct
SEQUENCE: 16
DTHFPCIIFK C                                                                    11

SEQ ID NO: 17               moltype = AA  length = 11
FEATURE                     Location/Qualifiers
REGION                      1..11
                            note = hepcidin analogue
MOD_RES                     9
                            note = N-Methyl-Phenylalanine
SITE                        10
                            note = PEG11-Palm conjugated half-life extension moiety
source                      1..11
                            mol_type = protein
                            organism = synthetic construct
SEQUENCE: 17
DTHFPCIKXK C                                                                    11

SEQ ID NO: 18               moltype = AA  length = 11
FEATURE                     Location/Qualifiers
REGION                      1..11
                            note = hepcidin analogue
MOD_RES                     9
                            note = Alpha-Methyl-Phenylalanine
SITE                        10
                            note = PEG11-Palm conjugated half-life extension moiety
source                      1..11
                            mol_type = protein
                            organism = synthetic construct
SEQUENCE: 18
DTHFPCIKFK C                                                                    11

SEQ ID NO: 19               moltype = AA  length = 11
FEATURE                     Location/Qualifiers
```

```
REGION                  1..11
                        note = hepcidin analogue
MOD_RES                 9
                        note = Beta homophenylalanine
SITE                    10
                        note = PEG11-Palm conjugated half-life extension moiety
source                  1..11
                        mol_type = protein
                        organism = synthetic construct
SEQUENCE: 19
DTHFPCIKXK C                                                                    11

SEQ ID NO: 20           moltype = AA  length = 11
FEATURE                 Location/Qualifiers
REGION                  1..11
                        note = hepcidin analogue
SITE                    10
                        note = PEG11-Palm conjugated half-life extension moiety
source                  1..11
                        mol_type = protein
                        organism = synthetic construct
SEQUENCE: 20
DTHFPCIKWK C                                                                    11

SEQ ID NO: 21           moltype = AA  length = 11
FEATURE                 Location/Qualifiers
REGION                  1..11
                        note = hepcidin analogue
SITE                    8
                        note = D-Lysine
SITE                    10
                        note = PEG8-Palm conjugated half-life extension moiety
source                  1..11
                        mol_type = protein
                        organism = synthetic construct
SEQUENCE: 21
DTHFPCIKFK C                                                                    11

SEQ ID NO: 22           moltype = AA  length = 11
FEATURE                 Location/Qualifiers
REGION                  1..11
                        note = hepcidin analogue
SITE                    8
                        note = D-Lysine
SITE                    10
                        note = PEG4-Palm conjugated half-life extension moiety
source                  1..11
                        mol_type = protein
                        organism = synthetic construct
SEQUENCE: 22
DTHFPCIKFK C                                                                    11

SEQ ID NO: 23           moltype = AA  length = 11
FEATURE                 Location/Qualifiers
REGION                  1..11
                        note = hepcidin analogue
SITE                    8
                        note = D-Lysine
SITE                    10
                        note = PEG2-Palm conjugated half-life extension moiety
source                  1..11
                        mol_type = protein
                        organism = synthetic construct
SEQUENCE: 23
DTHFPCIKFK C                                                                    11

SEQ ID NO: 24           moltype = AA  length = 11
FEATURE                 Location/Qualifiers
REGION                  1..11
                        note = hepcidin analogue
SITE                    8
                        note = D-Lysine
SITE                    10
                        note = PEG1-Palm conjugated half-life extension moiety
source                  1..11
                        mol_type = protein
                        organism = synthetic construct
SEQUENCE: 24
DTHFPCIKFK C                                                                    11
```

| | | |
|---|---|---|
| SEQ ID NO: 25 | moltype = AA   length = 11 | |
| FEATURE | Location/Qualifiers | |
| REGION | 1..11 | |
| | note = hepcidin analogue | |
| SITE | 8 | |
| | note = D-Lysine | |
| SITE | 10 | |
| | note = Aminohexanoic acid-palmityl conjugated half-life extension moiety | |
| source | 1..11 | |
| | mol_type = protein | |
| | organism = synthetic construct | |
| SEQUENCE: 25 | | |
| DTHFPCIKFK C | | 11 |
| | | |
| SEQ ID NO: 26 | moltype = AA   length = 11 | |
| FEATURE | Location/Qualifiers | |
| REGION | 1..11 | |
| | note = hepcidin analogue | |
| SITE | 8 | |
| | note = D-Lysine | |
| SITE | 10 | |
| | note = PEG2-hexadecanoyl-gamma-Glu conjugated half-life extension moiety | |
| source | 1..11 | |
| | mol_type = protein | |
| | organism = synthetic construct | |
| SEQUENCE: 26 | | |
| DTHFPCIKFK C | | 11 |
| | | |
| SEQ ID NO: 27 | moltype = AA   length = 11 | |
| FEATURE | Location/Qualifiers | |
| REGION | 1..11 | |
| | note = hepcidin analogue | |
| SITE | 8 | |
| | note = D-Lysine | |
| SITE | 10 | |
| | note = Hexadecanoyl-gamma-Glu conjugated half-life extension moiety | |
| source | 1..11 | |
| | mol_type = protein | |
| | organism = synthetic construct | |
| SEQUENCE: 27 | | |
| DTHFPCIKFK C | | 11 |
| | | |
| SEQ ID NO: 28 | moltype = AA   length = 11 | |
| FEATURE | Location/Qualifiers | |
| REGION | 1..11 | |
| | note = hepcidin analogue | |
| SITE | 8 | |
| | note = D-Lysine | |
| SITE | 10 | |
| | note = IsoGlu-PEG2-Palm conjugated half-life extension moiety | |
| source | 1..11 | |
| | mol_type = protein | |
| | organism = synthetic construct | |
| SEQUENCE: 28 | | |
| DTHFPCIKFK C | | 11 |
| | | |
| SEQ ID NO: 29 | moltype = AA   length = 11 | |
| FEATURE | Location/Qualifiers | |
| REGION | 1..11 | |
| | note = hepcidin analogue | |
| SITE | 8 | |
| | note = D-Lysine | |
| SITE | 10 | |
| | note = PEG2-Ahx-Palm conjugated half-life extension moiety | |
| source | 1..11 | |
| | mol_type = protein | |
| | organism = synthetic construct | |
| SEQUENCE: 29 | | |
| DTHFPCIKFK C | | 11 |
| | | |
| SEQ ID NO: 30 | moltype = AA   length = 11 | |
| FEATURE | Location/Qualifiers | |
| REGION | 1..11 | |
| | note = hepcidin analogue | |

```
SITE                      8
                          note = D-Lysine
SITE                      10
                          note = Palm conjugated half-life extension moiety
source                    1..11
                          mol_type = protein
                          organism = synthetic construct
SEQUENCE: 30
DTHFPCIKFK C                                                                    11

SEQ ID NO: 31             moltype = AA   length = 17
FEATURE                   Location/Qualifiers
REGION                    1..17
                          note = hepcidin analogue
SITE                      10
                          note = MISC_FEATURE - PEG11-Palm conjugated half-life
                           extension moiety
MOD_RES                   15
                          note = MeGly
MOD_RES                   16
                          note = Penicillamine
source                    1..17
                          mol_type = protein
                          organism = synthetic construct
SEQUENCE: 31
DTHFPCIKFK PRSKXXK                                                              17

SEQ ID NO: 32             moltype = AA   length = 11
FEATURE                   Location/Qualifiers
REGION                    1..11
                          note = hepcidin analogue
SITE                      8
                          note = D-Lysine
SITE                      10
                          note = PEG11-Palm conjugated half-life extension moiety
MOD_RES                   11
                          note = Penicillamine
source                    1..11
                          mol_type = protein
                          organism = synthetic construct
SEQUENCE: 32
DTHFPCIKFK X                                                                    11

SEQ ID NO: 33             moltype = AA   length = 11
FEATURE                   Location/Qualifiers
REGION                    1..11
                          note = hepcidin analogue
MOD_RES                   5
                          note = Nipecotic acid
SITE                      8
                          note = D-Lysine
SITE                      10
                          note = PEG11-Palm conjugated half-life extension moiety
source                    1..11
                          mol_type = protein
                          organism = synthetic construct
SEQUENCE: 33
DTHFXCIKFK C                                                                    11

SEQ ID NO: 34             moltype = AA   length = 11
FEATURE                   Location/Qualifiers
REGION                    1..11
                          note = hepcidin analogue
MOD_RES                   5
                          note = D-Nipecotic acid
SITE                      8
                          note = D-Lysine
SITE                      10
                          note = PEG11-Palm conjugated half-life extension moiety
source                    1..11
                          mol_type = protein
                          organism = synthetic construct
SEQUENCE: 34
DTHFXCIKFK C                                                                    11

SEQ ID NO: 35             moltype = AA   length = 11
FEATURE                   Location/Qualifiers
REGION                    1..11
                          note = hepcidin analogue
```

```
SITE                    5
                        note = D-proline
SITE                    8
                        note = D-Lysine
SITE                    10
                        note = PEG11-Palm conjugated half-life extension moiety
source                  1..11
                        mol_type = protein
                        organism = synthetic construct
SEQUENCE: 35
DTHFPCIKFK C                                                              11

SEQ ID NO: 36           moltype = AA  length = 11
FEATURE                 Location/Qualifiers
REGION                  1..11
                        note = hepcidin analogue
MOD_RES                 5
                        note = D-beta homoproline
SITE                    8
                        note = D-Lysine
SITE                    10
                        note = PEG11-Palm conjugated half-life extension moiety
source                  1..11
                        mol_type = protein
                        organism = synthetic construct
SEQUENCE: 36
DTHFXCIKFK C                                                              11

SEQ ID NO: 37           moltype = AA  length = 11
FEATURE                 Location/Qualifiers
REGION                  1..11
                        note = hepcidin analogue
MOD_RES                 5
                        note = beta homoproline
SITE                    8
                        note = D-Lysine
SITE                    10
                        note = PEG11-Palm conjugated half-life extension moiety
source                  1..11
                        mol_type = protein
                        organism = synthetic construct
SEQUENCE: 37
DTHFXCIKFK C                                                              11

SEQ ID NO: 38           moltype = AA  length = 11
FEATURE                 Location/Qualifiers
REGION                  1..11
                        note = hepcidin analogue
MOD_RES                 4
                        note = biphenylalanine
SITE                    8
                        note = D-Lysine
SITE                    10
                        note = PEG11-Palm conjugated half-life extension moiety
source                  1..11
                        mol_type = protein
                        organism = synthetic construct
SEQUENCE: 38
DTHXPCIKFK C                                                              11

SEQ ID NO: 39           moltype = AA  length = 11
FEATURE                 Location/Qualifiers
REGION                  1..11
                        note = hepcidin analogue
MOD_RES                 4
                        note = biphenylalanine
MOD_RES                 5
                        note = Nipecotic acid
SITE                    8
                        note = D-Lysine
SITE                    10
                        note = PEG11-Palm conjugated half-life extension moiety
source                  1..11
                        mol_type = protein
                        organism = synthetic construct
SEQUENCE: 39
DTHXXCIKFK C                                                              11

SEQ ID NO: 40           moltype = AA  length = 11
```

```
FEATURE              Location/Qualifiers
REGION               1..11
                     note = hepcidin analogue
MOD_RES              5
                     note = Nipecotic acid
SITE                 8
                     note = D-Lysine
SITE                 10
                     note = PEG11-Palm conjugated half-life extension moiety
source               1..11
                     mol_type = protein
                     organism = synthetic construct
SEQUENCE: 40
DTHFXCIKFK C                                                              11

SEQ ID NO: 41        moltype = AA  length = 17
FEATURE              Location/Qualifiers
REGION               1..17
                     note = hepcidin analogue
SITE                 8
                     note = D-lysine
SITE                 10
                     note = PEG11-Palm conjugated half-life extension moiety
MOD_RES              15
                     note = MeGly
source               1..17
                     mol_type = protein
                     organism = synthetic construct
SEQUENCE: 41
DTHFPCIKFK PRSKXCK                                                        17

SEQ ID NO: 42        moltype = AA  length = 17
FEATURE              Location/Qualifiers
REGION               1..17
                     note = hepcidin analogue
SITE                 8
                     note = D-lysine
SITE                 10
                     note = PEG11-Palm conjugated half-life extension moiety
MOD_RES              15
                     note = MeGly
SITE                 17
                     note = D-lysine
source               1..17
                     mol_type = protein
                     organism = synthetic construct
SEQUENCE: 42
DTHFPCIKFK PRSKXCK                                                        17

SEQ ID NO: 43        moltype = AA  length = 17
FEATURE              Location/Qualifiers
REGION               1..17
                     note = hepcidin analogue
SITE                 8
                     note = D-lysine
SITE                 10
                     note = PEG11-Palm conjugated half-life extension moiety
SITE                 14
                     note = D-Lysine
MOD_RES              15
                     note = MeGly
source               1..17
                     mol_type = protein
                     organism = synthetic construct
SEQUENCE: 43
DTHFPCIKFK PRSKXCK                                                        17

SEQ ID NO: 44        moltype = AA  length = 17
FEATURE              Location/Qualifiers
REGION               1..17
                     note = hepcidin analogue
SITE                 8
                     note = D-lysine
SITE                 10
                     note = PEG11-Palm conjugated half-life extension moiety
SITE                 13
                     note = D-serine
MOD_RES              15
                     note = MeGly
```

```
source                    1..17
                          mol_type = protein
                          organism = synthetic construct
SEQUENCE: 44
DTHFPCIKFK PRSKXCK                                                              17

SEQ ID NO: 45             moltype = AA  length = 17
FEATURE                   Location/Qualifiers
REGION                    1..17
                          note = hepcidin analogue
SITE                      8
                          note = D-lysine
SITE                      10
                          note = PEG11-Palm conjugated half-life extension moiety
SITE                      12
                          note = D-arginine
MOD_RES                   15
                          note = MeGly
source                    1..17
                          mol_type = protein
                          organism = synthetic construct
SEQUENCE: 45
DTHFPCIKFK PRSKXCK                                                              17

SEQ ID NO: 46             moltype = AA  length = 17
FEATURE                   Location/Qualifiers
REGION                    1..17
                          note = hepcidin analogue
SITE                      8
                          note = D-Lysine
SITE                      10
                          note = PEG11-Palm conjugated half-life extension moiety
MOD_RES                   15
                          note = MeGly
SITE                      17
                          note = D-lysine
source                    1..17
                          mol_type = protein
                          organism = synthetic construct
SEQUENCE: 46
DTHFPCIKFK PRTKXCK                                                              17

SEQ ID NO: 47             moltype = AA  length = 17
FEATURE                   Location/Qualifiers
REGION                    1..17
                          note = hepcidin analogue
SITE                      8
                          note = D-lysine
SITE                      10
                          note = PEG11-Palm conjugated half-life extension moiety
MOD_RES                   15
                          note = MeGly
SITE                      17
                          note = D-lysine
source                    1..17
                          mol_type = protein
                          organism = synthetic construct
SEQUENCE: 47
DTHFPCIKFK PRTRXCK                                                              17

SEQ ID NO: 48             moltype = AA  length = 17
FEATURE                   Location/Qualifiers
REGION                    1..17
                          note = hepcidin analogue
SITE                      8
                          note = D-lysine
SITE                      10
                          note = PEG11-Palm conjugated half-life extension moiety
MOD_RES                   12
                          note = N-methylarginine
MOD_RES                   15
                          note = MeGly
SITE                      17
                          note = D-lysine
source                    1..17
                          mol_type = protein
                          organism = synthetic construct
SEQUENCE: 48
DTHFPCIKFK PXTKXCK                                                              17
```

```
SEQ ID NO: 49              moltype = AA   length = 17
FEATURE                    Location/Qualifiers
REGION                     1..17
                           note = hepcidin analogue
SITE                       8
                           note = D-lysine
SITE                       10
                           note = PEG11-Palm conjugated half-life extension moiety
SITE                       12
                           note = D-arginine
MOD_RES                    15
                           note = MeGly
SITE                       17
                           note = D-Lysine
source                     1..17
                           mol_type = protein
                           organism = synthetic construct
SEQUENCE: 49
DTHFPCIKFK PRTKXCK                                                          17

SEQ ID NO: 50              moltype = AA   length = 17
FEATURE                    Location/Qualifiers
REGION                     1..17
                           note = hepcidin analogue
SITE                       8
                           note = D-lysine
SITE                       10
                           note = PEG11-Palm conjugated half-life extension moiety
MOD_RES                    15
                           note = MeGly
SITE                       17
                           note = D-lysine
source                     1..17
                           mol_type = protein
                           organism = synthetic construct
SEQUENCE: 50
DTHFPCIKFK PDTHXCK                                                          17

SEQ ID NO: 51              moltype = AA   length = 17
FEATURE                    Location/Qualifiers
REGION                     1..17
                           note = hepcidin analogue
SITE                       8
                           note = D-lysine
SITE                       10
                           note = PEG11-Palm conjugated half-life extension moiety
SITE                       12
                           note = D-arginine
MOD_RES                    14
                           note = MeLys
MOD_RES                    15
                           note = MeGly
SITE                       17
                           note = D-lysine
source                     1..17
                           mol_type = protein
                           organism = synthetic construct
SEQUENCE: 51
DTHFPCIKFK PRTXXCK                                                          17

SEQ ID NO: 52              moltype = AA   length = 17
FEATURE                    Location/Qualifiers
REGION                     1..17
                           note = hepcidin analogue
SITE                       8
                           note = D-lysine
SITE                       10
                           note = PEG11-Palm conjugated half-life extension moiety
MOD_RES                    11
                           note = nipecotic acid
MOD_RES                    12
                           note = N-methylarginine
MOD_RES                    15
                           note = MeGly
SITE                       17
                           note = D-lysine
source                     1..17
                           mol_type = protein
```

```
                            organism = synthetic construct
SEQUENCE: 52
DTHFPCIKFK XXTHXCK                                                    17

SEQ ID NO: 53               moltype = AA   length = 17
FEATURE                     Location/Qualifiers
REGION                      1..17
                            note = hepcidin analogue
SITE                        10
                            note = PEG11-Palm conjugated half-life extension moiety
VARIANT                     15
                            note = Xaa can be any naturally occurring amino acid
MOD_RES                     16
                            note = Penicillamine
source                      1..17
                            mol_type = protein
                            organism = synthetic construct
SEQUENCE: 53
DTHFPCIKFK PRSKXXK                                                    17

SEQ ID NO: 54               moltype = AA   length = 11
FEATURE                     Location/Qualifiers
REGION                      1..11
                            note = hepcidin analogue
SITE                        8
                            note = D-lysine
SITE                        10
                            note = PEG11-Palm conjugated half-life extension moiety
MOD_RES                     11
                            note = Penicillamine
source                      1..11
                            mol_type = protein
                            organism = synthetic construct
SEQUENCE: 54
DTHFPCIKFK X                                                          11

SEQ ID NO: 55               moltype = AA   length = 18
FEATURE                     Location/Qualifiers
REGION                      1..18
                            note = hepcidin analogue
SITE                        1
                            note = D-lysine
SITE                        2
                            note = D-cysteine
MOD_RES                     3
                            note = MeGly
SITE                        4
                            note = D-lysine
SITE                        5
                            note = D-serine
SITE                        6
                            note = D-arginine
SITE                        7
                            note = D-proline
SITE                        8
                            note = D-lysine
SITE                        8
                            note = PEG11-Palm conjugated half-life extension moiety
SITE                        9
                            note = D-phenylalanine
SITE                        10
                            note = D-lysine
SITE                        11
                            note = D-isoleucine
SITE                        12
                            note = D-cysteine
SITE                        13
                            note = D-proline
SITE                        14
                            note = D-phenylalanine
SITE                        15
                            note = D-histidine
SITE                        16
                            note = D-threonine
SITE                        17
                            note = D-aspartic acid
SITE                        18
                            note = D-leucine
source                      1..18
```

```
                              -continued
                     mol_type = protein
                     organism = synthetic construct
SEQUENCE: 55
KCXKSRPKFK ICPFHTDL                                                    18

SEQ ID NO: 56        moltype = AA  length = 11
FEATURE              Location/Qualifiers
REGION               1..11
                     note = hepcidin analogue
MOD_RES              5
                     note = Nipecotic acid
SITE                 8
                     note = D-lysine
SITE                 10
                     note = PEG11-Palm conjugated half-life extension moiety
source               1..11
                     mol_type = protein
                     organism = synthetic construct
SEQUENCE: 56
DTHFXCIKFK C                                                           11

SEQ ID NO: 57        moltype = AA  length = 11
FEATURE              Location/Qualifiers
REGION               1..11
                     note = hepcidin analogue
MOD_RES              5
                     note = isoipecotic acid
SITE                 8
                     note = D-lysine
SITE                 10
                     note = PEG11-Palm conjugated half-life extension moiety
source               1..11
                     mol_type = protein
                     organism = synthetic construct
SEQUENCE: 57
DTHFXCIKFK C                                                           11

SEQ ID NO: 58        moltype = AA  length = 11
FEATURE              Location/Qualifiers
REGION               1..11
                     note = hepcidin analogue
SITE                 5
                     note = D-proline
SITE                 8
                     note = D-lysine
SITE                 10
                     note = PEG11-Palm conjugated half-life extension moiety
source               1..11
                     mol_type = protein
                     organism = synthetic construct
SEQUENCE: 58
DTHFPCIKFK C                                                           11

SEQ ID NO: 59        moltype = AA  length = 11
FEATURE              Location/Qualifiers
REGION               1..11
                     note = hepcidin analogue
MOD_RES              5
                     note = D-beta homoproline
SITE                 8
                     note = D-lysine
SITE                 10
                     note = PEG11-Palm conjugated half-life extension moiety
source               1..11
                     mol_type = protein
                     organism = synthetic construct
SEQUENCE: 59
DTHFXCIKFK C                                                           11

SEQ ID NO: 60        moltype = AA  length = 11
FEATURE              Location/Qualifiers
REGION               1..11
                     note = hepcidin analogue
MOD_RES              5
                     note = Beta homoproline
SITE                 8
                     note = D-lysine
SITE                 10
                     note = PEG11-Palm conjugated half-life extension moiety
```

```
source              1..11
                    mol_type = protein
                    organism = synthetic construct
SEQUENCE: 60
DTHFXCIKFK C                                                              11

SEQ ID NO: 61       moltype =   length =
SEQUENCE: 61
000

SEQ ID NO: 62       moltype = AA  length = 11
FEATURE             Location/Qualifiers
REGION              1..11
                    note = hepcidin analogue
MOD_RES             4
                    note = Biphenylalanine
SITE                8
                    note = D-lysine
SITE                10
                    note = PEG11-Palm conjugated half-life extension moiety
source              1..11
                    mol_type = protein
                    organism = synthetic construct
SEQUENCE: 62
DTHXPCIKFK C                                                              11

SEQ ID NO: 63       moltype = AA  length = 11
FEATURE             Location/Qualifiers
REGION              1..11
                    note = hepcidin analogue
MOD_RES             4
                    note = Biphenylalanine
MOD_RES             5
                    note = Nipecotic acid
SITE                8
                    note = D-lysine
SITE                10
                    note = PEG11-Palm conjugated half-life extension moiety
source              1..11
                    mol_type = protein
                    organism = synthetic construct
SEQUENCE: 63
DTHXXCIKFK C                                                              11

SEQ ID NO: 64       moltype =   length =
SEQUENCE: 64
000

SEQ ID NO: 65       moltype = AA  length = 11
FEATURE             Location/Qualifiers
REGION              1..11
                    note = hepcidin analogue
SITE                8
                    note = D-lysine
SITE                11
                    note = PEG11-Palm conjugated half-life extension moiety
source              1..11
                    mol_type = protein
                    organism = synthetic construct
SEQUENCE: 65
DTHFPCIKFC K                                                              11

SEQ ID NO: 66       moltype = AA  length = 11
FEATURE             Location/Qualifiers
REGION              1..11
                    note = hepcidin analogue
MOD_RES             5
                    note = Nipecotic acid
SITE                8
                    note = D-lysine
SITE                10
                    note = PEG11-Palm conjugated half-life extension moiety
source              1..11
                    mol_type = protein
                    organism = synthetic construct
SEQUENCE: 66
DTHFXCIKFK C                                                              11

SEQ ID NO: 67       moltype = AA  length = 12
```

```
FEATURE                   Location/Qualifiers
REGION                    1..12
                          note = hepcidin analogue
SITE                      6
                          note = Sulfhydryl (-SH) modification
SITE                      10
                          note = PEG11-Palm conjugated half-life extension moiety
SITE                      12
                          note = Sulfhydryl (-SH) modification
source                    1..12
                          mol_type = protein
                          organism = synthetic construct
SEQUENCE: 67
DTHFPCIKFK PC                                                                    12

SEQ ID NO: 68             moltype = AA  length = 11
FEATURE                   Location/Qualifiers
REGION                    1..11
                          note = hepcidin analogue
SITE                      6
                          note = Sulfhydryl (-SH) modification
SITE                      8
                          note = D-lysine
SITE                      10
                          note = PEG11-Palm conjugated half-life extension moiety
SITE                      11
                          note = Sulfhydryl (-SH) modification
source                    1..11
                          mol_type = protein
                          organism = synthetic construct
SEQUENCE: 68
DTHFPCIKFK C                                                                     11

SEQ ID NO: 69             moltype = AA  length = 11
FEATURE                   Location/Qualifiers
REGION                    1..11
                          note = hepcidin analogue
SITE                      6
                          note = Sulfhydryl (-SH) modification
SITE                      10
                          note = PEG11-Palm conjugated half-life extension moiety
SITE                      11
                          note = Sulfhydryl (-SH) modification
source                    1..11
                          mol_type = protein
                          organism = synthetic construct
SEQUENCE: 69
DTHFPCIKFK C                                                                     11

SEQ ID NO: 70             moltype = AA  length = 12
FEATURE                   Location/Qualifiers
REGION                    1..12
                          note = hepcidin analogue
SITE                      8
                          note = D-lysine
SITE                      10
                          note = PEG11-Palm conjugated half-life extension moiety
source                    1..12
                          mol_type = protein
                          organism = synthetic construct
SEQUENCE: 70
DTHFPCIKFK PC                                                                    12

SEQ ID NO: 71             moltype = AA  length = 13
FEATURE                   Location/Qualifiers
REGION                    1..13
                          note = hepcidin analogue
SITE                      8
                          note = D-lysine
SITE                      10
                          note = PEG11-Palm conjugated half-life extension moiety
source                    1..13
                          mol_type = protein
                          organism = synthetic construct
SEQUENCE: 71
DTHFPCIKFK PRC                                                                   13

SEQ ID NO: 72             moltype = AA  length = 14
FEATURE                   Location/Qualifiers
```

```
REGION                  1..14
                        note = hepcidin analogue
SITE                    8
                        note = D-lysine
SITE                    10
                        note = PEG11-Palm conjugated half-life extension moiety
source                  1..14
                        mol_type = protein
                        organism = synthetic construct
SEQUENCE: 72
DTHFPCIKFK PRSC                                                                 14

SEQ ID NO: 73           moltype = AA  length = 15
FEATURE                 Location/Qualifiers
REGION                  1..15
                        note = hepcidin analogue
SITE                    8
                        note = D-lysine
SITE                    10
                        note = PEG11-Palm conjugated half-life extension moiety
source                  1..15
                        mol_type = protein
                        organism = synthetic construct
SEQUENCE: 73
DTHFPCIKFK PRSKC                                                                15

SEQ ID NO: 74           moltype = AA  length = 16
FEATURE                 Location/Qualifiers
REGION                  1..16
                        note = hepcidin analogue
SITE                    8
                        note = D-lysine
SITE                    10
                        note = PEG11-Palm conjugated half-life extension moiety
MOD_RES                 15
                        note = MeGly
source                  1..16
                        mol_type = protein
                        organism = synthetic construct
SEQUENCE: 74
DTHFPCIKFK PRSKXC                                                               16

SEQ ID NO: 75           moltype = AA  length = 16
FEATURE                 Location/Qualifiers
REGION                  1..16
                        note = hepcidin analogue
SITE                    8
                        note = D-lysine
SITE                    10
                        note = PEG11-Palm conjugated half-life extension moiety
source                  1..16
                        mol_type = protein
                        organism = synthetic construct
SEQUENCE: 75
DTHFPCIKFK PRSCK                                                                16

SEQ ID NO: 76           moltype = AA  length = 16
FEATURE                 Location/Qualifiers
REGION                  1..16
                        note = hepcidin analogue
SITE                    8
                        note = D-lysine
SITE                    10
                        note = PEG11-Palm conjugated half-life extension moiety
source                  1..16
                        mol_type = protein
                        organism = synthetic construct
SEQUENCE: 76
DTHFPCIKFK PPRSCK                                                               16

SEQ ID NO: 77           moltype = AA  length = 14
FEATURE                 Location/Qualifiers
REGION                  1..14
                        note = hepcidin analogue
SITE                    8
                        note = D-lysine
SITE                    10
                        note = PEG11-Palm conjugated half-life extension moiety
source                  1..14
```

```
                         mol_type = protein
                         organism = synthetic construct
SEQUENCE: 77
DTHFPCIKFK PRCK                                                         14

SEQ ID NO: 78            moltype = AA   length = 12
FEATURE                  Location/Qualifiers
REGION                   1..12
                         note = hepcidin analogue
SITE                     8
                         note = D-lysine
SITE                     10
                         note = PEG11-Palm conjugated half-life extension moiety
source                   1..12
                         mol_type = protein
                         organism = synthetic construct
SEQUENCE: 78
DTHFPCIKFK CK                                                           12

SEQ ID NO: 79            moltype = AA   length = 12
FEATURE                  Location/Qualifiers
REGION                   1..12
                         note = hepcidin analogue
SITE                     8
                         note = D-lysine
SITE                     10
                         note = PEG11-Palm conjugated half-life extension moiety
source                   1..12
                         mol_type = protein
                         organism = synthetic construct
SEQUENCE: 79
DTHFPCIKFK RC                                                           12

SEQ ID NO: 80            moltype = AA   length = 12
FEATURE                  Location/Qualifiers
REGION                   1..12
                         note = hepcidin analogue
SITE                     8
                         note = D-lysine
SITE                     10
                         note = PEG11-Palm conjugated half-life extension moiety
source                   1..12
                         mol_type = protein
                         organism = synthetic construct
SEQUENCE: 80
DTHFPCIKFK KC                                                           12

SEQ ID NO: 81            moltype = AA   length = 12
FEATURE                  Location/Qualifiers
REGION                   1..12
                         note = hepcidin analogue
SITE                     8
                         note = D-lysine
SITE                     10
                         note = PEG11-Palm conjugated half-life extension moiety
SITE                     11
                         note = D-arginine
source                   1..12
                         mol_type = protein
                         organism = synthetic construct
SEQUENCE: 81
DTHFPCIKFK RC                                                           12

SEQ ID NO: 82            moltype = AA   length = 12
FEATURE                  Location/Qualifiers
REGION                   1..12
                         note = hepcidin analogue
SITE                     8
                         note = D-lysine
SITE                     10
                         note = PEG11-Palm conjugated half-life extension moiety
SITE                     11
                         note = D-lysine
source                   1..12
                         mol_type = protein
                         organism = synthetic construct
SEQUENCE: 82
DTHFPCIKFK KC                                                           12
```

| | | |
|---|---|---|
| SEQ ID NO: 83 | moltype = AA length = 13 | |
| FEATURE | Location/Qualifiers | |
| REGION | 1..13 | |
| | note = hepcidin analogue | |
| SITE | 8 | |
| | note = D-lysine | |
| SITE | 10 | |
| | note = PEG11-Palm conjugated half-life extension moiety | |
| SITE | 13 | |
| | note = D-lysine | |
| source | 1..13 | |
| | mol_type = protein | |
| | organism = synthetic construct | |
| SEQUENCE: 83 | | |
| DTHFPCIKFK KCK | | 13 |
| | | |
| SEQ ID NO: 84 | moltype = AA length = 13 | |
| FEATURE | Location/Qualifiers | |
| REGION | 1..13 | |
| | note = hepcidin analogue | |
| SITE | 8 | |
| | note = D-lysine | |
| SITE | 10 | |
| | note = PEG11-Palm conjugated half-life extension moiety | |
| SITE | 13 | |
| | note = D-histidine | |
| source | 1..13 | |
| | mol_type = protein | |
| | organism = synthetic construct | |
| SEQUENCE: 84 | | |
| DTHFPCIKFK HCH | | 13 |
| | | |
| SEQ ID NO: 85 | moltype = AA length = 13 | |
| FEATURE | Location/Qualifiers | |
| REGION | 1..13 | |
| | note = hepcidin analogue | |
| SITE | 8 | |
| | note = D-lysine | |
| SITE | 10 | |
| | note = PEG11-Palm conjugated half-life extension moiety | |
| SITE | 13 | |
| | note = D-arginine | |
| source | 1..13 | |
| | mol_type = protein | |
| | organism = synthetic construct | |
| SEQUENCE: 85 | | |
| DTHFPCIKFK RCR | | 13 |
| | | |
| SEQ ID NO: 86 | moltype = AA length = 12 | |
| FEATURE | Location/Qualifiers | |
| REGION | 1..12 | |
| | note = hepcidin analogue | |
| SITE | 8 | |
| | note = D-lysine | |
| SITE | 10 | |
| | note = Ahx-Palm conjugated half-life extension moiety | |
| source | 1..12 | |
| | mol_type = protein | |
| | organism = synthetic construct | |
| SEQUENCE: 86 | | |
| DTHFPCIKFK KC | | 12 |
| | | |
| SEQ ID NO: 87 | moltype = AA length = 12 | |
| FEATURE | Location/Qualifiers | |
| REGION | 1..12 | |
| | note = hepcidin analogue | |
| SITE | 8 | |
| | note = D-lysine | |
| SITE | 10 | |
| | note = PEG2-Palm conjugated half-life extension moiety | |
| source | 1..12 | |
| | mol_type = protein | |
| | organism = synthetic construct | |
| SEQUENCE: 87 | | |
| DTHFPCIKFK KC | | 12 |
| | | |
| SEQ ID NO: 88 | moltype = AA length = 12 | |
| FEATURE | Location/Qualifiers | |
| REGION | 1..12 | |

```
                         note = hepcidin analogue
SITE                     8
                         note = D-lysine
SITE                     10
                         note = PEG2-PEG2-Palm conjugated half-life extension moiety
source                   1..12
                         mol_type = protein
                         organism = synthetic construct
SEQUENCE: 88
DTHFPCIKFK KC                                                                      12

SEQ ID NO: 89            moltype = AA  length = 12
FEATURE                  Location/Qualifiers
REGION                   1..12
                         note = hepcidin analogue
SITE                     8
                         note = D-lysine
SITE                     10
                         note = PEG2-PEG2-C18 acid conjugated half-life extension
                          moiety
source                   1..12
                         mol_type = protein
                         organism = synthetic construct
SEQUENCE: 89
DTHFPCIKFK KC                                                                      12

SEQ ID NO: 90            moltype = AA  length = 12
FEATURE                  Location/Qualifiers
REGION                   1..12
                         note = hepcidin analogue
SITE                     8
                         note = D-lysine
SITE                     10
                         note = PEG2-PEG2-Ahx-Palm conjugated half-life extension
                          moiety
source                   1..12
                         mol_type = protein
                         organism = synthetic construct
SEQUENCE: 90
DTHFPCIKFK KC                                                                      12

SEQ ID NO: 91            moltype = AA  length = 12
FEATURE                  Location/Qualifiers
REGION                   1..12
                         note = hepcidin analogue
SITE                     8
                         note = D-lysine
SITE                     10
                         note = PEG4-Palm acid conjugated half-life extension moiety
source                   1..12
                         mol_type = protein
                         organism = synthetic construct
SEQUENCE: 91
DTHFPCIKFK KC                                                                      12

SEQ ID NO: 92            moltype = AA  length = 12
FEATURE                  Location/Qualifiers
REGION                   1..12
                         note = hepcidin analogue
SITE                     8
                         note = D-lysine
SITE                     10
                         note = PEG4-Ahx-Palm conjugated half-life extension moiety
source                   1..12
                         mol_type = protein
                         organism = synthetic construct
SEQUENCE: 92
DTHFPCIKFK KC                                                                      12

SEQ ID NO: 93            moltype = AA  length = 12
FEATURE                  Location/Qualifiers
REGION                   1..12
                         note = hepcidin analogue
SITE                     8
                         note = D-lysine
SITE                     10
                         note = PEG4-PEG4-Palm conjugated half-life extension moiety
source                   1..12
                         mol_type = protein
```

```
                        organism = synthetic construct
SEQUENCE: 93
DTHFPCIKFK KC                                                                   12

SEQ ID NO: 94           moltype = AA   length = 12
FEATURE                 Location/Qualifiers
REGION                  1..12
                        note = hepcidin analogue
SITE                    8
                        note = D-lysine
SITE                    10
                        note = PEG4-isoGlu-Palm conjugated half-life extension
                         moiety
source                  1..12
                        mol_type = protein
                        organism = synthetic construct
SEQUENCE: 94
DTHFPCIKFK KC                                                                   12

SEQ ID NO: 95           moltype = AA   length = 12
FEATURE                 Location/Qualifiers
REGION                  1..12
                        note = hepcidin analogue
SITE                    8
                        note = D-lysine
SITE                    10
                        note = PEG8-Palm conjugated half-life extension moiety
source                  1..12
                        mol_type = protein
                        organism = synthetic construct
SEQUENCE: 95
DTHFPCIKFK KC                                                                   12

SEQ ID NO: 96           moltype = AA   length = 12
FEATURE                 Location/Qualifiers
REGION                  1..12
                        note = hepcidin analogue
SITE                    8
                        note = D-lysine
SITE                    10
                        note = Behenic acid conjugated half-life extension moiety
source                  1..12
                        mol_type = protein
                        organism = synthetic construct
SEQUENCE: 96
DTHFPCIKFK KC                                                                   12

SEQ ID NO: 97           moltype = AA   length = 12
FEATURE                 Location/Qualifiers
REGION                  1..12
                        note = hepcidin analogue
SITE                    8
                        note = D-lysine
SITE                    10
                        note = PEG11-Palm conjugated half-life extension moiety
SITE                    12
                        note = D-cysteine
source                  1..12
                        mol_type = protein
                        organism = synthetic construct
SEQUENCE: 97
DTHFPCIKFK KC                                                                   12

SEQ ID NO: 98           moltype = AA   length = 12
FEATURE                 Location/Qualifiers
REGION                  1..12
                        note = hepcidin analogue
SITE                    8
                        note = D-lysine
SITE                    10
                        note = PEG11-Palm conjugated half-life extension moiety
MOD_RES                 12
                        note = Penicillamine
source                  1..12
                        mol_type = protein
                        organism = synthetic construct
SEQUENCE: 98
DTHFPCIKFK KC                                                                   12
```

```
SEQ ID NO: 99           moltype = AA   length = 12
FEATURE                 Location/Qualifiers
REGION                  1..12
                        note = hepcidin analogue
SITE                    8
                        note = D-lysine
SITE                    10
                        note = PEG11-Palm conjugated half-life extension moiety
MOD_RES                 11
                        note = Diaminopropionic acid
source                  1..12
                        mol_type = protein
                        organism = synthetic construct
SEQUENCE: 99
DTHFPCIKFK XC                                                              12

SEQ ID NO: 100          moltype = AA   length = 12
FEATURE                 Location/Qualifiers
REGION                  1..12
                        note = hepcidin analogue
SITE                    8
                        note = D-lysine
MOD_RES                 9
                        note = beta,beta-diphenylalanine
SITE                    10
                        note = PEG11-Palm conjugated half-life extension moiety
source                  1..12
                        mol_type = protein
                        organism = synthetic construct
SEQUENCE: 100
DTHFPCIKXK KC                                                              12

SEQ ID NO: 101          moltype = AA   length = 12
FEATURE                 Location/Qualifiers
REGION                  1..12
                        note = hepcidin analogue
SITE                    8
                        note = D-lysine
MOD_RES                 9
                        note = Beta homophenylalanine
SITE                    10
                        note = PEG11-Palm conjugated half-life extension moiety
source                  1..12
                        mol_type = protein
                        organism = synthetic construct
SEQUENCE: 101
DTHFPCIKXK KC                                                              12

SEQ ID NO: 102          moltype = AA   length = 12
FEATURE                 Location/Qualifiers
REGION                  1..12
                        note = hepcidin analogue
SITE                    8
                        note = D-lysine
MOD_RES                 9
                        note = Napthylalanine
SITE                    10
                        note = PEG11-Palm conjugated half-life extension moiety
source                  1..12
                        mol_type = protein
                        organism = synthetic construct
SEQUENCE: 102
DTHFPCIKXK KC                                                              12

SEQ ID NO: 103          moltype = AA   length = 12
FEATURE                 Location/Qualifiers
REGION                  1..12
                        note = hepcidin analogue
SITE                    8
                        note = D-lysine
MOD_RES                 9
                        note = Beta homophenylalanine
SITE                    10
                        note = PEG11-Palm conjugated half-life extension moiety
source                  1..12
                        mol_type = protein
                        organism = synthetic construct
SEQUENCE: 103
DTHFPCIKXK KC                                                              12
```

```
SEQ ID NO: 104          moltype = AA   length = 12
FEATURE                 Location/Qualifiers
REGION                  1..12
                        note = hepcidin analogue
MOD_RES                 4
                        note = beta,beta-diphenylalanine
SITE                    8
                        note = D-lysine
SITE                    10
                        note = PEG11-Palm conjugated half-life extension moiety
source                  1..12
                        mol_type = protein
                        organism = synthetic construct
SEQUENCE: 104
DTHXPCIKFK KC                                                            12

SEQ ID NO: 105          moltype = AA   length = 12
FEATURE                 Location/Qualifiers
REGION                  1..12
                        note = hepcidin analogue
MOD_RES                 4
                        note = beta,beta-diphenylalanine
SITE                    8
                        note = D-lysine
MOD_RES                 9
                        note = Beta homophenylalanine
SITE                    10
                        note = PEG11-Palm conjugated half-life extension moiety
SITE                    11
                        note = D-lysine
source                  1..12
                        mol_type = protein
                        organism = synthetic construct
SEQUENCE: 105
DTHXPCIKXK KC                                                            12

SEQ ID NO: 106          moltype = AA   length = 11
FEATURE                 Location/Qualifiers
REGION                  1..11
                        note = hepcidin analogue
SITE                    9
                        note = PEG11-Palm conjugated half-life extension moiety
source                  1..11
                        mol_type = protein
                        organism = synthetic construct
SEQUENCE: 106
DTHFPCIFKK C                                                             11

SEQ ID NO: 107          moltype = AA   length = 12
FEATURE                 Location/Qualifiers
REGION                  1..12
                        note = hepcidin analogue
SITE                    8
                        note = D-lysine
SITE                    10
                        note = D-lysine
SITE                    10
                        note = PEG11-Palm conjugated half-life extension moiety
SITE                    11
                        note = D-lysine
source                  1..12
                        mol_type = protein
                        organism = synthetic construct
SEQUENCE: 107
DTHFPCIKFK KC                                                            12

SEQ ID NO: 108          moltype =      length =
SEQUENCE: 108
000

SEQ ID NO: 109          moltype = AA   length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
```

```
SITE                    8
                        note = D-lysine
SITE                    10
                        note = PEG11-Palm conjugated half-life extension moiety
source                  1..12
                        mol_type = protein
                        organism = synthetic construct
SEQUENCE: 109
DTHXXCIKFK KC                                                                       12

SEQ ID NO: 110          moltype = AA  length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
MOD_RES                 9
                        note = Phenylalanine (4-tBu)
SITE                    10
                        note = PEG11-Palm conjugated half-life extension moiety
source                  1..12
                        mol_type = protein
                        organism = synthetic construct
SEQUENCE: 110
DTHXXCIKXK KC                                                                       12

SEQ ID NO: 111          moltype = AA  length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
SITE                    9
                        note = Phenylalanine (4-(2-aminoethoxy))
SITE                    10
                        note = PEG11-Palm conjugated half-life extension moiety
source                  1..12
                        mol_type = protein
                        organism = synthetic construct
SEQUENCE: 111
DTHXXCIKXK KC                                                                       12

SEQ ID NO: 112          moltype = AA  length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
MOD_RES                 9
                        note = 2-Napthylalanine
SITE                    10
                        note = PEG11-Palm conjugated half-life extension moiety
source                  1..12
                        mol_type = protein
                        organism = synthetic construct
SEQUENCE: 112
DTHXXCIKXK KC                                                                       12

SEQ ID NO: 113          moltype = AA  length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
```

```
                              note = D-lysine
MOD_RES                       9
                              note = Phenylalanine (4-COOOH)
SITE                          10
                              note = PEG11-Palm conjugated half-life extension moiety
source                        1..12
                              mol_type = protein
                              organism = synthetic construct
SEQUENCE: 113
DTHXXCIKXK KC                                                                       12

SEQ ID NO: 114                moltype = AA  length = 12
FEATURE                       Location/Qualifiers
REGION                        1..12
                              note = hepcidin analogue
SITE                          8
                              note = D-lysine
SITE                          10
                              note = PEG11-Palm conjugated half-life extension moiety
MOD_RES                       12
                              note = Alpha-methylcysteine
source                        1..12
                              mol_type = protein
                              organism = synthetic construct
SEQUENCE: 114
DTHFPCIKFK KX                                                                       12

SEQ ID NO: 115                moltype = AA  length = 12
FEATURE                       Location/Qualifiers
REGION                        1..12
                              note = hepcidin analogue
MOD_RES                       6
                              note = Alpha-methylcysteine
SITE                          8
                              note = D-lysine
SITE                          10
                              note = PEG11-Palm conjugated half-life extension moiety
MOD_RES                       12
                              note = Alpha-methylcysteine
source                        1..12
                              mol_type = protein
                              organism = synthetic construct
SEQUENCE: 115
DTHFPXIKFK KX                                                                       12

SEQ ID NO: 116                moltype = AA  length = 12
FEATURE                       Location/Qualifiers
REGION                        1..12
                              note = hepcidin analogue
MOD_RES                       6
                              note = Alpha-methylcysteine
SITE                          8
                              note = D-lysine
SITE                          10
                              note = PEG11-Palm conjugated half-life extension moiety
source                        1..12
                              mol_type = protein
                              organism = synthetic construct
SEQUENCE: 116
DTHFPXIKFK KC                                                                       12

SEQ ID NO: 117                moltype = AA  length = 12
FEATURE                       Location/Qualifiers
REGION                        1..12
                              note = hepcidin analogue
MOD_RES                       4
                              note = beta,beta-diphenylalanine
MOD_RES                       5
                              note = Nipecotic acid
SITE                          8
                              note = D-lysine
SITE                          10
                              note = PEG11-Palm conjugated half-life extension moiety
SITE                          11
                              note = D-lysine
source                        1..12
                              mol_type = protein
                              organism = synthetic construct
SEQUENCE: 117
```

```
DTHXXCIKFK KC                                                                                 12

SEQ ID NO: 118         moltype = AA  length = 12
FEATURE                Location/Qualifiers
REGION                 1..12
                       note = hepcidin analogue
MOD_RES                5
                       note = Nipecotic acid
SITE                   8
                       note = D-lysine
SITE                   10
                       note = PEG11-Palm conjugated half-life extension moiety
SITE                   11
                       note = D-lysine
source                 1..12
                       mol_type = protein
                       organism = synthetic construct
SEQUENCE: 118
DTHFXCIKFK KC                                                                                 12

SEQ ID NO: 119         moltype = AA  length = 12
FEATURE                Location/Qualifiers
REGION                 1..12
                       note = hepcidin analogue
MOD_RES                4
                       note = beta,beta-diphenylalanine
MOD_RES                5
                       note = Beta-homoproline
SITE                   8
                       note = D-lysine
SITE                   10
                       note = PEG11-Palm conjugated half-life extension moiety
SITE                   11
                       note = D-lysine
source                 1..12
                       mol_type = protein
                       organism = synthetic construct
SEQUENCE: 119
DTHXXCIKFK KC                                                                                 12

SEQ ID NO: 120         moltype = AA  length = 12
FEATURE                Location/Qualifiers
REGION                 1..12
                       note = hepcidin analogue
MOD_RES                4
                       note = Phenylalanine (4-COOH)
SITE                   8
                       note = D-lysine
SITE                   10
                       note = PEG11-Palm conjugated half-life extension moiety
SITE                   11
                       note = D-lysine
source                 1..12
                       mol_type = protein
                       organism = synthetic construct
SEQUENCE: 120
DTHXPCIKFK KC                                                                                 12

SEQ ID NO: 121         moltype = AA  length = 12
FEATURE                Location/Qualifiers
REGION                 1..12
                       note = hepcidin analogue
MOD_RES                4
                       note = Beta-homophenylalanine
SITE                   8
                       note = D-lysine
SITE                   10
                       note = PEG11-Palm conjugated half-life extension moiety
SITE                   11
                       note = D-lysine
source                 1..12
                       mol_type = protein
                       organism = synthetic construct
SEQUENCE: 121
DTHXPCIKFK KC                                                                                 12

SEQ ID NO: 122         moltype = AA  length = 12
FEATURE                Location/Qualifiers
REGION                 1..12
```

```
                        note = hepcidin analogue
MOD_RES                 4
                        note = beta,beta-diphenylalanine
SITE                    8
                        note = D-lysine
MOD_RES                 9
                        note = Beta-homophenylalanine
SITE                    10
                        note = PEG11-Palm conjugated half-life extension moiety
SITE                    11
                        note = D-lysine
source                  1..12
                        mol_type = protein
                        organism = synthetic construct
SEQUENCE: 122
DTHXPCIKXK KC                                                                    12

SEQ ID NO: 123          moltype =   length =
SEQUENCE: 123
000

SEQ ID NO: 124          moltype =   length =
SEQUENCE: 124
000

SEQ ID NO: 125          moltype = AA   length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
MOD_RES                 9
                        note = Alpha-methylphenylalanine
SITE                    10
                        note = PEG11-Palm conjugated half-life extension moiety
source                  1..12
                        mol_type = protein
                        organism = synthetic construct
SEQUENCE: 125
DTHXXCIKXK KC                                                                    12

SEQ ID NO: 126          moltype = AA   length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
MOD_RES                 9
                        note = Phenylalanine (4-CN)
SITE                    10
                        note = PEG11-Palm conjugated half-life extension moiety
source                  1..12
                        mol_type = protein
                        organism = synthetic construct
SEQUENCE: 126
DTHXXCIKXK KC                                                                    12

SEQ ID NO: 127          moltype = AA   length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
MOD_RES                 9
                        note = Phenylalanine (3,4-diF)
SITE                    10
                        note = PEG11-Palm conjugated half-life extension moiety
```

```
source                      1..12
                            mol_type = protein
                            organism = synthetic construct
SEQUENCE: 127
DTHXXCIKXK KC                                                                              12

SEQ ID NO: 128              moltype = AA  length = 12
FEATURE                     Location/Qualifiers
REGION                      1..12
                            note = hepcidin analogue
MOD_RES                     4
                            note = Alpha-methylphenylalanine
SITE                        8
                            note = D-lysine
SITE                        10
                            note = PEG11-Palm conjugated half-life extension moiety
SITE                        11
                            note = D-lysine
source                      1..12
                            mol_type = protein
                            organism = synthetic construct
SEQUENCE: 128
DTHXPCIKFK KC                                                                              12

SEQ ID NO: 129              moltype = AA  length = 12
FEATURE                     Location/Qualifiers
REGION                      1..12
                            note = hepcidin analogue
MOD_RES                     4
                            note = Phenylalanine (4-(2-aminoethoxy))
SITE                        8
                            note = D-lysine
SITE                        10
                            note = PEG11-Palm conjugated half-life extension moiety
SITE                        11
                            note = D-lysine
source                      1..12
                            mol_type = protein
                            organism = synthetic construct
SEQUENCE: 129
DTHXPCIKFK KC                                                                              12

SEQ ID NO: 130              moltype = AA  length = 12
FEATURE                     Location/Qualifiers
REGION                      1..12
                            note = hepcidin analogue
MOD_RES                     4
                            note = beta,beta-diphenylalanine
SITE                        8
                            note = D-lysine
SITE                        10
                            note = PEG11-Palm conjugated half-life extension moiety
SITE                        11
                            note = D-lysine
source                      1..12
                            mol_type = protein
                            organism = synthetic construct
SEQUENCE: 130
DIHXPCIKFK KC                                                                              12

SEQ ID NO: 131              moltype = AA  length = 12
FEATURE                     Location/Qualifiers
REGION                      1..12
                            note = hepcidin analogue
MOD_RES                     4
                            note = beta,beta-diphenylalanine
SITE                        8
                            note = D-lysine
MOD_RES                     9
                            note = beta,beta-diphenylalanine
SITE                        10
                            note = PEG11-Palm conjugated half-life extension moiety
SITE                        11
                            note = D-lysine
source                      1..12
                            mol_type = protein
                            organism = synthetic construct
SEQUENCE: 131
DTHXPCIKXK KC                                                                              12
```

```
SEQ ID NO: 132          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
SITE                    10
                        note = PEG11-Palm conjugated half-life extension moiety
SITE                    11
                        note = D-lysine
MOD_RES                 12
                        note = Penicillamine
source                  1..12
                        mol_type = protein
                        organism = synthetic construct
SEQUENCE: 132
DTHXPCIKFK KX                                                               12

SEQ ID NO: 133          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
SITE                    10
                        note = PEG11-Palm conjugated half-life extension moiety
MOD_RES                 12
                        note = N-methyl-cysteine
source                  1..12
                        mol_type = protein
                        organism = synthetic construct
SEQUENCE: 133
DTHXPCIKFK KX                                                               12

SEQ ID NO: 134          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
SITE                    10
                        note = PEG11-Palm conjugated half-life extension moiety
SITE                    11
                        note = D-lysine
MOD_RES                 12
                        note = N-methyl-cysteine
source                  1..12
                        mol_type = protein
                        organism = synthetic construct
SEQUENCE: 134
DTHXPCIKFK KX                                                               12

SEQ ID NO: 135          moltype = AA  length = 11
FEATURE                 Location/Qualifiers
REGION                  1..11
                        note = hepcidin analogue
MOD_RES                 4
                        note = beta,beta-diphenylalanine
SITE                    8
                        note = D-lysine
SITE                    10
                        note = PEG11-Palm conjugated half-life extension moiety
source                  1..11
                        mol_type = protein
                        organism = synthetic construct
SEQUENCE: 135
DTHXPCIKFK C                                                                11

SEQ ID NO: 136          moltype = AA  length = 12
FEATURE                 Location/Qualifiers
REGION                  1..12
                        note = hepcidin analogue
```

```
MOD_RES         4
                note = beta,beta-diphenylalanine
SITE            8
                note = D-lysine
SITE            10
                note = PEG11-Palm conjugated half-life extension moiety
MOD_RES         11
                note = Orn
source          1..12
                mol_type = protein
                organism = synthetic construct
SEQUENCE: 136
DTHXPCIKFK XC                                                                 12

SEQ ID NO: 137         moltype = AA  length = 12
FEATURE                Location/Qualifiers
REGION                 1..12
                       note = hepcidin analogue
MOD_RES                4
                       note = beta,beta-diphenylalanine
SITE                   8
                       note = D-lysine
SITE                   10
                       note = PEG11-Palm conjugated half-life extension moiety
MOD_RES                11
                       note = Diaminobutyric acid
source                 1..12
                       mol_type = protein
                       organism = synthetic construct
SEQUENCE: 137
DTHXPCIKFK XC                                                                 12

SEQ ID NO: 138         moltype = AA  length = 12
FEATURE                Location/Qualifiers
REGION                 1..12
                       note = hepcidin analogue
MOD_RES                4
                       note = beta,beta-diphenylalanine
SITE                   8
                       note = D-lysine
SITE                   10
                       note = PEG11-Palm conjugated half-life extension moiety
MOD_RES                11
                       note = Beta-homolysine
source                 1..12
                       mol_type = protein
                       organism = synthetic construct
SEQUENCE: 138
DTHXPCIKFK XC                                                                 12

SEQ ID NO: 139         moltype = AA  length = 12
FEATURE                Location/Qualifiers
REGION                 1..12
                       note = hepcidin analogue
MOD_RES                4
                       note = beta,beta-diphenylalanine
SITE                   8
                       note = D-lysine
SITE                   10
                       note = PEG11-Palm conjugated half-life extension moiety
SITE                   11
                       note = D-lysine
source                 1..12
                       mol_type = protein
                       organism = synthetic construct
SEQUENCE: 139
DTHXPCIKFK KC                                                                 12

SEQ ID NO: 140         moltype = AA  length = 12
FEATURE                Location/Qualifiers
REGION                 1..12
                       note = hepcidin analogue
MOD_RES                4
                       note = beta,beta-diphenylalanine
SITE                   8
                       note = D-lysine
SITE                   10
                       note = PEG11-Palm conjugated half-life extension moiety
MOD_RES                11
```

```
                        note = Diaminopropionic acid
MOD_RES                 12
                        note = Penicillamine
source                  1..12
                        mol_type = protein
                        organism = synthetic construct
SEQUENCE: 140
DTHXPCIKFK XX                                                              12

SEQ ID NO: 141          moltype = AA  length = 12
FEATURE                 Location/Qualifiers
REGION                  1..12
                        note = hepcidin analogue
MOD_RES                 4
                        note = beta,beta-diphenylalanine
MOD_RES                 6
                        note = Homocysteine
SITE                    8
                        note = D-lysine
SITE                    10
                        note = PEG11-Palm conjugated half-life extension moiety
MOD_RES                 11
                        note = Diaminopropionic acid
source                  1..12
                        mol_type = protein
                        organism = synthetic construct
SEQUENCE: 141
DTHXPXIKFK XC                                                              12

SEQ ID NO: 142          moltype = AA  length = 12
FEATURE                 Location/Qualifiers
REGION                  1..12
                        note = hepcidin analogue
MOD_RES                 4
                        note = beta,beta-diphenylalanine
MOD_RES                 6
                        note = Homocysteine
SITE                    8
                        note = D-lysine
SITE                    10
                        note = PEG11-Palm conjugated half-life extension moiety
MOD_RES                 11
                        note = Diaminopropionic acid
MOD_RES                 12
                        note = Homocysteine
source                  1..12
                        mol_type = protein
                        organism = synthetic construct
SEQUENCE: 142
DTHXPXIKFK XX                                                              12

SEQ ID NO: 143          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
SITE                    10
                        note = PEG11-Palm conjugated half-life extension moiety
MOD_RES                 11
                        note = Diaminopropionic acid
MOD_RES                 12
                        note = Homocysteine
source                  1..12
                        mol_type = protein
                        organism = synthetic construct
SEQUENCE: 143
DTHXPCIKFK XX                                                              12

SEQ ID NO: 144          moltype = AA  length = 12
FEATURE                 Location/Qualifiers
REGION                  1..12
                        note = hepcidin analogue
SITE                    8
                        note = D-lysine
SITE                    10
                        note = PEG11-Palm conjugated half-life extension moiety
```

| | | |
|---|---|---|
| source | 1..12<br>mol_type = protein<br>organism = synthetic construct | |
| SEQUENCE: 144<br>DTHFPCIKFK CK | | 12 |
| SEQ ID NO: 145<br>FEATURE<br>REGION | moltype = AA  length = 12<br>Location/Qualifiers<br>1..12<br>note = hepcidin analogue | |
| MOD_RES | 4<br>note = beta,beta-diphenylalanine | |
| MOD_RES | 8<br>note = Beta-alanine | |
| MOD_RES | 9<br>note = Beta-homophenylalanine | |
| SITE | 10<br>note = PEG11-Palm conjugated half-life extension moiety | |
| SITE | 11<br>note = D-lysine | |
| source | 1..12<br>mol_type = protein<br>organism = synthetic construct | |
| SEQUENCE: 145<br>DTHXPCIXXK KC | | 12 |
| SEQ ID NO: 146<br>FEATURE<br>REGION | moltype = AA  length = 12<br>Location/Qualifiers<br>1..12<br>note = hepcidin analogue | |
| MOD_RES | 4<br>note = beta,beta-diphenylalanine | |
| SITE | 8<br>note = D-alanine | |
| MOD_RES | 9<br>note = Beta-homophenylalanine | |
| SITE | 10<br>note = PEG11-Palm conjugated half-life extension moiety | |
| SITE | 11<br>note = D-lysine | |
| source | 1..12<br>mol_type = protein<br>organism = synthetic construct | |
| SEQUENCE: 146<br>DTHXPCIAXK KC | | 12 |
| SEQ ID NO: 147<br>FEATURE<br>REGION | moltype = AA  length = 12<br>Location/Qualifiers<br>1..12<br>note = hepcidin analogue | |
| MOD_RES | 4<br>note = beta,beta-diphenylalanine | |
| MOD_RES | 9<br>note = Beta-homophenylalanine | |
| SITE | 10<br>note = PEG11-Palm conjugated half-life extension moiety | |
| SITE | 11<br>note = D-lysine | |
| source | 1..12<br>mol_type = protein<br>organism = synthetic construct | |
| SEQUENCE: 147<br>DTHXPCIIXK KC | | 12 |
| SEQ ID NO: 148<br>FEATURE<br>REGION | moltype = AA  length = 11<br>Location/Qualifiers<br>1..11<br>note = hepcidin analogue | |
| MOD_RES | 4<br>note = beta,beta-diphenylalanine | |
| MOD_RES | 8<br>note = Beta-homophenylalanine | |
| SITE | 9<br>note = PEG11-Palm conjugated half-life extension moiety | |
| SITE | 10<br>note = D-lysine | |
| source | 1..11<br>mol_type = protein<br>organism = synthetic construct | |

```
SEQUENCE: 148
DTHXPCIXKK C                                                          11

SEQ ID NO: 149          moltype = AA  length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
MOD_RES                 9
                        note = Phenylalanine (4-tButyl)
SITE                    10
                        note = PEG11-Palm conjugated half-life extension moiety
SITE                    11
                        note = D-lysine
source                  1..12
                        mol_type = protein
                        organism = synthetic construct
SEQUENCE: 149
DTHXXCIKXK KC                                                         12

SEQ ID NO: 150          moltype = AA  length = 12
FEATURE                 Location/Qualifiers
REGION                  1..12
                        note = hepcidin analogue
MOD_RES                 4
                        note = beta,beta-diphenylalanine
MOD_RES                 5
                        note = Nipecotic acid
SITE                    8
                        note = D-lysine
MOD_RES                 9
                        note = Phenylalanine (4-tButyl)
SITE                    10
                        note = PEG11-Palm conjugated half-life extension moiety
SITE                    12
                        note = D-lysine
source                  1..12
                        mol_type = protein
                        organism = synthetic construct
SEQUENCE: 150
DTHXXCIKXK CK                                                         12

SEQ ID NO: 151          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
MOD_RES                 9
                        note = Beta-homophenylalanine
SITE                    10
                        note = Ahx-Palm conjugated half-life extension moiety
MOD_RES                 11
                        note = Diaminopropionic acid
MOD_RES                 12
                        note = N-methyl-cysteine
source                  1..12
                        mol_type = protein
                        organism = synthetic construct
SEQUENCE: 151
DTHXPCIKXK XX                                                         12

SEQ ID NO: 152          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
MOD_RES                 9
                        note = Beta-homophenylalanine
```

```
SITE                    10
                        note = ACETYLATION
SITE                    11
                        note = D-lysine
source                  1..12
                        mol_type = protein
                        organism = synthetic construct
SEQUENCE: 152
DTHXPCIKXK KC                                                                    12

SEQ ID NO: 153          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
SITE                    8
                        note = PEG11-OMe conjugated half-life extension moiety
MOD_RES                 9
                        note = Beta-homophenylalanine
SITE                    10
                        note = PEG11-Palm conjugated half-life extension moiety
SITE                    11
                        note = D-lysine
SITE                    11
                        note = PEG11-OMe conjugated half-life extension moiety
source                  1..12
                        mol_type = protein
                        organism = synthetic construct
SEQUENCE: 153
DTHXPCIKXK KC                                                                    12

SEQ ID NO: 154          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
MOD_RES                 9
                        note = Beta-homophenylalanine
SITE                    10
                        note = PEG11 conjugated half-life extension moiety
SITE                    11
                        note = D-lysine
source                  1..12
                        mol_type = protein
                        organism = synthetic construct
SEQUENCE: 154
DTHXPCIKXK KC                                                                    12

SEQ ID NO: 155          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
MOD_RES                 9
                        note = Beta-homophenylalanine
SITE                    10
                        note = PEG11-octane conjugated half-life extension moiety
SITE                    11
                        note = D-lysine
source                  1..12
                        mol_type = protein
                        organism = synthetic construct
SEQUENCE: 155
DTHXPCIKXK KC                                                                    12

SEQ ID NO: 156          moltype = AA  length = 12
FEATURE                 Location/Qualifiers
REGION                  1..12
                        note = hepcidin analogue
MOD_RES                 4
```

```
                          note = beta,beta-diphenylalanine
SITE                      8
                          note = D-lysine
MOD_RES                   9
                          note = Beta-homophenylalanine
SITE                      10
                          note = PEG11-Lauryl conjugated half-life extension moiety
SITE                      11
                          note = D-lysine
source                    1..12
                          mol_type = protein
                          organism = synthetic construct
SEQUENCE: 156
DTHXPCIKXK KC                                                                          12

SEQ ID NO: 157            moltype = AA  length = 12
FEATURE                   Location/Qualifiers
REGION                    1..12
                          note = hepcidin analogue
MOD_RES                   4
                          note = beta,beta-diphenylalanine
SITE                      8
                          note = D-lysine
MOD_RES                   9
                          note = Beta-homophenylalanine
SITE                      10
                          note = PEG11-OMe conjugated half-life extension moiety
SITE                      11
                          note = D-lysine
source                    1..12
                          mol_type = protein
                          organism = synthetic construct
SEQUENCE: 157
DTHXPCIKXK KC                                                                          12

SEQ ID NO: 158            moltype = AA  length = 12
FEATURE                   Location/Qualifiers
REGION                    1..12
                          note = hepcidin analogue
MOD_RES                   4
                          note = beta,beta-diphenylalanine
SITE                      8
                          note = D-lysine
MOD_RES                   9
                          note = Beta-homophenylalanine
SITE                      10
                          note = IsoGlu-Palm conjugated half-life extension moiety
SITE                      11
                          note = D-lysine
source                    1..12
                          mol_type = protein
                          organism = synthetic construct
SEQUENCE: 158
DTHXPCIKXK KC                                                                          12

SEQ ID NO: 159            moltype = AA  length = 12
FEATURE                   Location/Qualifiers
REGION                    1..12
                          note = hepcidin analogue
MOD_RES                   4
                          note = beta,beta-diphenylalanine
SITE                      8
                          note = D-lysine
SITE                      8
                          note = ACETYLATION
MOD_RES                   9
                          note = Beta-homophenylalanine
SITE                      10
                          note = PEG11-Palm conjugated half-life extension moiety
SITE                      11
                          note = D-lysine
source                    1..12
                          mol_type = protein
                          organism = synthetic construct
SEQUENCE: 159
DTHXPCIKXK KC                                                                          12

SEQ ID NO: 160            moltype = AA  length = 11
FEATURE                   Location/Qualifiers
```

```
REGION                  1..11
                        note = hepcidin analogue
MOD_RES                 4
                        note = beta,beta-diphenylalanine
SITE                    8
                        note = D-lysine
MOD_RES                 9
                        note = Beta-homophenylalanine
SITE                    10
                        note = Dap-Palm conjugated half-life extension moiety
source                  1..11
                        mol_type = protein
                        organism = synthetic construct
SEQUENCE: 160
DTHXPCIKXK C                                                                    11

SEQ ID NO: 161          moltype = AA   length = 11
FEATURE                 Location/Qualifiers
REGION                  1..11
                        note = hepcidin analogue
MOD_RES                 4
                        note = beta,beta-diphenylalanine
SITE                    8
                        note = D-lysine
MOD_RES                 9
                        note = Beta-homophenylalanine
SITE                    10
                        note = D-Dap-Palm conjugated half-life extension moiety
source                  1..11
                        mol_type = protein
                        organism = synthetic construct
SEQUENCE: 161
DTHXPCIKXK C                                                                    11

SEQ ID NO: 162          moltype = AA   length = 11
FEATURE                 Location/Qualifiers
REGION                  1..11
                        note = hepcidin analogue
MOD_RES                 4
                        note = beta,beta-diphenylalanine
SITE                    8
                        note = D-lysine
MOD_RES                 9
                        note = Beta-homophenylalanine
MOD_RES                 10
                        note = Diaminopropionic acid
SITE                    10
                        note = Dap-Palm conjugated half-life extension moiety
source                  1..11
                        mol_type = protein
                        organism = synthetic construct
SEQUENCE: 162
DTHXPCIKXX C                                                                    11

SEQ ID NO: 163          moltype = AA   length = 11
FEATURE                 Location/Qualifiers
REGION                  1..11
                        note = hepcidin analogue
MOD_RES                 4
                        note = beta,beta-diphenylalanine
SITE                    8
                        note = D-lysine
MOD_RES                 9
                        note = Beta-homophenylalanine
MOD_RES                 10
                        note = Diaminopropionic acid
SITE                    10
                        note = D-Dap-Palm conjugated half-life extension moiety
source                  1..11
                        mol_type = protein
                        organism = synthetic construct
SEQUENCE: 163
DTHXPCIKXX C                                                                    11

SEQ ID NO: 164          moltype = AA   length = 11
FEATURE                 Location/Qualifiers
REGION                  1..11
                        note = hepcidin analogue
MOD_RES                 4
```

```
                        note = beta,beta-diphenylalanine
SITE                    8
                        note = D-lysine
MOD_RES                 9
                        note = Beta-homophenylalanine
MOD_RES                 10
                        note = Diaminopropionic acid
SITE                    10
                        note = D-Dap-Palm conjugated half-life extension moiety
source                  1..11
                        mol_type = protein
                        organism = synthetic construct
SEQUENCE: 164
DTHXPCIKXX C                                                                    11

SEQ ID NO: 165          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
MOD_RES                 9
                        note = Beta-homophenylalanine
SITE                    10
                        note = Ahx-Palm conjugated half-life extension moiety
SITE                    11
                        note = D-lysine
source                  1..12
                        mol_type = protein
                        organism = synthetic construct
SEQUENCE: 165
DTHXPCIKXK KC                                                                   12

SEQ ID NO: 166          moltype = AA  length = 12
FEATURE                 Location/Qualifiers
REGION                  1..12
                        note = hepcidin analogue
MOD_RES                 4
                        note = beta,beta-diphenylalanine
SITE                    8
                        note = D-lysine
SITE                    8
                        note = PEG11-OMe conjugated half-life extension moiety
MOD_RES                 9
                        note = Beta-homophenylalanine
SITE                    10
                        note = Ahx-Palm conjugated half-life extension moiety
SITE                    11
                        note = D-lysine
SITE                    11
                        note = PEG11-OMe conjugated half-life extension moiety
source                  1..12
                        mol_type = protein
                        organism = synthetic construct
SEQUENCE: 166
DTHXPCIKXK KC                                                                   12

SEQ ID NO: 167          moltype = AA  length = 12
FEATURE                 Location/Qualifiers
REGION                  1..12
                        note = hepcidin analogue
MOD_RES                 4
                        note = beta,beta-diphenylalanine
SITE                    5
                        note = D-proline
SITE                    8
                        note = D-lysine
SITE                    10
                        note = PEG11-Palm conjugated half-life extension moiety
SITE                    11
                        note = D-lysine
source                  1..12
                        mol_type = protein
                        organism = synthetic construct
SEQUENCE: 167
DTHXPCIKFK KC                                                                   12
```

-continued

| | | |
|---|---|---|
| SEQ ID NO: 168 | moltype = AA length = 12 | |
| FEATURE | Location/Qualifiers | |
| REGION | 1..12 | |
| | note = hepcidin analogue | |
| MOD_RES | 4 | |
| | note = Beta-homophenylalanine | |
| SITE | 5 | |
| | note = D-proline | |
| SITE | 8 | |
| | note = D-lysine | |
| SITE | 10 | |
| | note = PEG11-Palm conjugated half-life extension moiety | |
| SITE | 11 | |
| | note = D-lysine | |
| source | 1..12 | |
| | mol_type = protein | |
| | organism = synthetic construct | |
| SEQUENCE: 168 | | |
| DTHXPCIKFK KC | | 12 |
| | | |
| SEQ ID NO: 169 | moltype = AA length = 12 | |
| FEATURE | Location/Qualifiers | |
| REGION | 1..12 | |
| | note = hepcidin analogue | |
| SITE | 1 | |
| | note = D-aspartic acid | |
| MOD_RES | 4 | |
| | note = beta,beta-diphenylalanine | |
| SITE | 8 | |
| | note = D-lysine | |
| MOD_RES | 9 | |
| | note = Beta-homophenylalanine | |
| SITE | 10 | |
| | note = PEG11-Palm conjugated half-life extension moiety | |
| SITE | 11 | |
| | note = D-lysine | |
| source | 1..12 | |
| | mol_type = protein | |
| | organism = synthetic construct | |
| SEQUENCE: 169 | | |
| DTHXPCIKXK KC | | 12 |
| | | |
| SEQ ID NO: 170 | moltype = AA length = 12 | |
| FEATURE | Location/Qualifiers | |
| REGION | 1..12 | |
| | note = hepcidin analogue | |
| MOD_RES | 4 | |
| | note = beta,beta-diphenylalanine | |
| SITE | 8 | |
| | note = D-lysine | |
| MOD_RES | 9 | |
| | note = Beta-homophenylalanine | |
| SITE | 10 | |
| | note = PEG11-Palm conjugated half-life extension moiety | |
| SITE | 12 | |
| | note = D-lysine | |
| source | 1..12 | |
| | mol_type = protein | |
| | organism = synthetic construct | |
| SEQUENCE: 170 | | |
| DTHXPCIKXK CK | | 12 |
| | | |
| SEQ ID NO: 171 | moltype = AA length = 12 | |
| FEATURE | Location/Qualifiers | |
| REGION | 1..12 | |
| | note = hepcidin analogue | |
| MOD_RES | 4 | |
| | note = Beta-homophenylalanine | |
| SITE | 8 | |
| | note = D-lysine | |
| SITE | 10 | |
| | note = PEG11-Palm conjugated half-life extension moiety | |
| SITE | 12 | |
| | note = D-lysine | |
| source | 1..12 | |
| | mol_type = protein | |
| | organism = synthetic construct | |
| SEQUENCE: 171 | | |
| DTHXPCIKFK CK | | 12 |

```
SEQ ID NO: 172            moltype = AA  length = 12
FEATURE                   Location/Qualifiers
REGION                    1..12
                          note = hepcidin analogue
MOD_RES                   4
                          note = Beta-homophenylalanine
MOD_RES                   5
                          note = Nipecotic acid
SITE                      8
                          note = D-lysine
SITE                      10
                          note = PEG11-Palm conjugated half-life extension moiety
SITE                      12
                          note = D-lysine
source                    1..12
                          mol_type = protein
                          organism = synthetic construct
SEQUENCE: 172
DTHXXCIKFK CK                                                                    12

SEQ ID NO: 173            moltype = AA  length = 12
FEATURE                   Location/Qualifiers
REGION                    1..12
                          note = hepcidin analogue
MOD_RES                   4
                          note = beta,beta-diphenylalanine
MOD_RES                   5
                          note = Nipecotic acid
SITE                      8
                          note = D-lysine
MOD_RES                   9
                          note = Beta-homophenylalanine
SITE                      10
                          note = PEG11-Palm conjugated half-life extension moiety
SITE                      12
                          note = D-lysine
source                    1..12
                          mol_type = protein
                          organism = synthetic construct
SEQUENCE: 173
DTHXXCIKXK CK                                                                    12

SEQ ID NO: 174            moltype = AA  length = 12
FEATURE                   Location/Qualifiers
REGION                    1..12
                          note = hepcidin analogue
MOD_RES                   4
                          note = beta,beta-diphenylalanine
SITE                      8
                          note = D-glutamine
MOD_RES                   9
                          note = Beta-homophenylalanine
SITE                      10
                          note = PEG11-Palm conjugated half-life extension moiety
SITE                      11
                          note = D-lysine
source                    1..12
                          mol_type = protein
                          organism = synthetic construct
SEQUENCE: 174
DTHXPCIQXK KC                                                                    12

SEQ ID NO: 175            moltype = AA  length = 12
FEATURE                   Location/Qualifiers
REGION                    1..12
                          note = hepcidin analogue
MOD_RES                   4
                          note = beta,beta-diphenylalanine
SITE                      8
                          note = D-lysine
MOD_RES                   9
                          note = Beta-homophenylalanine
SITE                      10
                          note = PEG11-Palm conjugated half-life extension moiety
SITE                      11
                          note = D-lysine
SITE                      11
                          note = ACETYLATION
```

```
source                    1..12
                          mol_type = protein
                          organism = synthetic construct
SEQUENCE: 175
DTHXPCIKXK KC                                                              12

SEQ ID NO: 176            moltype = AA  length = 12
FEATURE                   Location/Qualifiers
REGION                    1..12
                          note = hepcidin analogue
MOD_RES                   4
                          note = Beta-homophenylalanine
SITE                      5
                          note = D-proline
SITE                      8
                          note = D-lysine
MOD_RES                   9
                          note = Beta-homophenylalanine
SITE                      10
                          note = PEG11-Palm conjugated half-life extension moiety
SITE                      12
                          note = D-lysine
source                    1..12
                          mol_type = protein
                          organism = synthetic construct
SEQUENCE: 176
DTHXPCIKXK CK                                                              12

SEQ ID NO: 177            moltype = AA  length = 12
FEATURE                   Location/Qualifiers
REGION                    1..12
                          note = hepcidin analogue
MOD_RES                   4
                          note = beta,beta-diphenylalanine
SITE                      8
                          note = D-lysine
MOD_RES                   9
                          note = Beta-homophenylalanine
SITE                      10
                          note = Ahx-Palm conjugated half-life extension moiety
source                    1..12
                          mol_type = protein
                          organism = synthetic construct
SEQUENCE: 177
DTHXPCIKXK RC                                                              12

SEQ ID NO: 178            moltype = AA  length = 12
FEATURE                   Location/Qualifiers
REGION                    1..12
                          note = hepcidin analogue
MOD_RES                   4
                          note = beta,beta-diphenylalanine
SITE                      8
                          note = D-lysine
MOD_RES                   9
                          note = N-Methylphenylalanine
SITE                      10
                          note = Ahx-Palm conjugated half-life extension moiety
SITE                      11
                          note = D-lysine
source                    1..12
                          mol_type = protein
                          organism = synthetic construct
SEQUENCE: 178
DTHXPCIKXK KC                                                              12

SEQ ID NO: 179            moltype = AA  length = 12
FEATURE                   Location/Qualifiers
REGION                    1..12
                          note = hepcidin analogue
MOD_RES                   4
                          note = beta,beta-diphenylalanine
SITE                      6
                          note = N-Methycysteine
SITE                      8
                          note = D-lysine
MOD_RES                   9
                          note = Beta-Homophenylalanine
SITE                      10
```

```
                          note = Ahx-Palm conjugated half-life extension moiety
SITE                      11
                          note = D-lysine
source                    1..12
                          mol_type = protein
                          organism = synthetic construct
SEQUENCE: 179
DTHXPXIKXK KC                                                                    12

SEQ ID NO: 180            moltype = AA   length = 12
FEATURE                   Location/Qualifiers
REGION                    1..12
                          note = hepcidin analogue
MOD_RES                   4
                          note = N-Methylphenylalanine
SITE                      8
                          note = D-lysine
MOD_RES                   9
                          note = Beta-homophenylalanine
SITE                      10
                          note = Ahx-Palm conjugated half-life extension moiety
SITE                      11
                          note = D-lysine
source                    1..12
                          mol_type = protein
                          organism = synthetic construct
SEQUENCE: 180
DTHXPCIKXK KC                                                                    12

SEQ ID NO: 181            moltype = AA   length = 12
FEATURE                   Location/Qualifiers
REGION                    1..12
                          note = hepcidin analogue
MOD_RES                   4
                          note = beta,beta-diphenylalanine
SITE                      8
                          note = D-lysine
MOD_RES                   9
                          note = Beta-homophenylalanine
SITE                      10
                          note = Ahx-Palm conjugated half-life extension moiety
SITE                      11
                          note = D-lysine
MOD_RES                   12
                          note = N-Methylcysteine
source                    1..12
                          mol_type = protein
                          organism = synthetic construct
SEQUENCE: 181
DTHXPCIKXK KX                                                                    12

SEQ ID NO: 182            moltype = AA   length = 12
FEATURE                   Location/Qualifiers
REGION                    1..12
                          note = hepcidin analogue
MOD_RES                   4
                          note = beta,beta-diphenylalanine
MOD_RES                   5
                          note = Nipecotic aCID
SITE                      8
                          note = D-lysine
MOD_RES                   9
                          note = Phenylalanine (4-tBu)
SITE                      10
                          note = D-lysine
SITE                      12
                          note = PEG11-Palm conjugated half-life extension moiety
source                    1..12
                          mol_type = protein
                          organism = synthetic construct
SEQUENCE: 182
DTHXXCIKXK CK                                                                    12

SEQ ID NO: 183            moltype = AA   length = 13
FEATURE                   Location/Qualifiers
REGION                    1..13
                          note = hepcidin analogue
SITE                      8
                          note = isoGlu-Palm conjugated half-life extension moiety
```

| | | |
|---|---|---|
| source | 1..13<br>mol_type = protein<br>organism = synthetic construct | |
| SEQUENCE: 183<br>DTHFPCIKFE PKC | | 13 |
| SEQ ID NO: 184<br>FEATURE<br>REGION | moltype = AA   length = 12<br>Location/Qualifiers<br>1..12<br>note = hepcidin analogue | |
| SITE | 8<br>note = isoGlu-Palm conjugated half-life extension moiety | |
| SITE | 11<br>note = D-lysine | |
| source | 1..12<br>mol_type = protein<br>organism = synthetic construct | |
| SEQUENCE: 184<br>DTHFPCIKFE KC | | 12 |
| SEQ ID NO: 185<br>FEATURE<br>REGION | moltype = AA   length = 11<br>Location/Qualifiers<br>1..11<br>note = hepcidin analogue | |
| SITE | 8<br>note = D-lysine | |
| SITE | 8<br>note = isoGlu-Palm conjugated half-life extension moiety | |
| source | 1..11<br>mol_type = protein<br>organism = synthetic construct | |
| SEQUENCE: 185<br>DTHFPCIKFG C | | 11 |
| SEQ ID NO: 186<br>FEATURE<br>REGION | moltype = AA   length = 17<br>Location/Qualifiers<br>1..17<br>note = hepcidin analogue | |
| SITE | 8<br>note = isoGlu-Palm conjugated half-life extension moiety | |
| source | 1..17<br>mol_type = protein<br>organism = synthetic construct | |
| SEQUENCE: 186<br>DTHFPCIKFE PRSKGCK | | 17 |
| SEQ ID NO: 187<br>FEATURE<br>REGION | moltype = AA   length = 12<br>Location/Qualifiers<br>1..12<br>note = hepcidin analogue | |
| SITE | 8<br>note = D-lysine | |
| SITE | 10<br>note = PEG11-Palm conjugated half-life extension moiety | |
| MOD_RES | 11<br>note = Ornithine | |
| source | 1..12<br>mol_type = protein<br>organism = synthetic construct | |
| SEQUENCE: 187<br>DTHFPCIKFK XC | | 12 |
| SEQ ID NO: 188<br>FEATURE<br>REGION | moltype = AA   length = 12<br>Location/Qualifiers<br>1..12<br>note = hepcidin analogue | |
| SITE | 8<br>note = D-lysine | |
| SITE | 10<br>note = PEG11-Palm conjugated half-life extension moiety | |
| MOD_RES | 11<br>note = diaminobutyric acid | |
| source | 1..12<br>mol_type = protein<br>organism = synthetic construct | |
| SEQUENCE: 188<br>DTHFPCIKFK XC | | 12 |
| SEQ ID NO: 189 | moltype = AA   length = 12 | |

```
FEATURE              Location/Qualifiers
REGION               1..12
                     note = hepcidin analogue
SITE                 8
                     note = D-lysine
SITE                 10
                     note = PEG11-Palm conjugated half-life extension moiety
MOD_RES              11
                     note = homolysine
source               1..12
                     mol_type = protein
                     organism = synthetic construct
SEQUENCE: 189
DTHFPCIKFK XC                                                                12

SEQ ID NO: 190       moltype =    length =
SEQUENCE: 190
000

SEQ ID NO: 191       moltype = AA  length = 12
FEATURE              Location/Qualifiers
REGION               1..12
                     note = hepcidin analogue
MOD_RES              4
                     note = beta,beta-diphenylalanine
SITE                 8
                     note = D-lysine
MOD_RES              9
                     note = Beta-homophenylalanine
SITE                 10
                     note = PEG11-Palm conjugated half-life extension moiety
source               1..12
                     mol_type = protein
                     organism = synthetic construct
SEQUENCE: 191
DTHXPCIKXK KC                                                                12

SEQ ID NO: 192       moltype = AA  length = 12
FEATURE              Location/Qualifiers
REGION               1..12
                     note = hepcidin analogue
SITE                 8
                     note = D-lysine
SITE                 10
                     note = D-lysine
SITE                 10
                     note = PEG11-Palm conjugated half-life extension moiety
source               1..12
                     mol_type = protein
                     organism = synthetic construct
SEQUENCE: 192
DTHFPCIKFK KC                                                                12

SEQ ID NO: 193       moltype =    length =
SEQUENCE: 193
000

SEQ ID NO: 194       moltype =    length =
SEQUENCE: 194
000

SEQ ID NO: 195       moltype =    length =
SEQUENCE: 195
000

SEQ ID NO: 196       moltype =    length =
SEQUENCE: 196
000

SEQ ID NO: 197       moltype =    length =
SEQUENCE: 197
000

SEQ ID NO: 198       moltype =    length =
SEQUENCE: 198
000

SEQ ID NO: 199       moltype =    length =
SEQUENCE: 199
```

```
000

SEQ ID NO: 200          moltype =    length =
SEQUENCE: 200
000

SEQ ID NO: 201          moltype = AA   length = 16
FEATURE                 Location/Qualifiers
REGION                  1..16
                        note = hepcidin analogue
SITE                    8
                        note = IsoGlu-Palm conjugated half-life extension moiety
source                  1..16
                        mol_type = protein
                        organism = synthetic construct
SEQUENCE: 201
DTHFPCIKFE PRSKGC                                                             16

SEQ ID NO: 202          moltype = AA   length = 15
FEATURE                 Location/Qualifiers
REGION                  1..15
                        note = hepcidin analogue
SITE                    8
                        note = IsoGlu-Palm conjugated half-life extension moiety
source                  1..15
                        mol_type = protein
                        organism = synthetic construct
SEQUENCE: 202
DTHFPCIKFE PRSKC                                                              15

SEQ ID NO: 203          moltype = AA   length = 14
FEATURE                 Location/Qualifiers
REGION                  1..14
                        note = hepcidin analogue
SITE                    8
                        note = IsoGlu-Palm conjugated half-life extension moiety
source                  1..14
                        mol_type = protein
                        organism = synthetic construct
SEQUENCE: 203
DTHFPCIKFE PRSC                                                               14

SEQ ID NO: 204          moltype = AA   length = 13
FEATURE                 Location/Qualifiers
REGION                  1..13
                        note = hepcidin analogue
SITE                    8
                        note = IsoGlu-Palm conjugated half-life extension moiety
source                  1..13
                        mol_type = protein
                        organism = synthetic construct
SEQUENCE: 204
DTHFPCIKFE PRC                                                                13

SEQ ID NO: 205          moltype = AA   length = 12
FEATURE                 Location/Qualifiers
REGION                  1..12
                        note = hepcidin analogue
SITE                    8
                        note = IsoGlu-Palm conjugated half-life extension moiety
source                  1..12
                        mol_type = protein
                        organism = synthetic construct
SEQUENCE: 205
DTHFPCIKFE PC                                                                 12

SEQ ID NO: 206          moltype = AA   length = 11
FEATURE                 Location/Qualifiers
REGION                  1..11
                        note = hepcidin analogue
SITE                    8
                        note = IsoGlu-Palm conjugated half-life extension moiety
source                  1..11
                        mol_type = protein
                        organism = synthetic construct
SEQUENCE: 206
DTHFPCIKFE C                                                                  11

SEQ ID NO: 207          moltype = AA   length = 10
```

```
FEATURE              Location/Qualifiers
REGION               1..10
                     note = hepcidin analogue
SITE                 8
                     note = IsoGlu-Palm conjugated half-life extension moiety
source               1..10
                     mol_type = protein
                     organism = synthetic construct
SEQUENCE: 207
DTHFPCIKFC                                                                    10

SEQ ID NO: 208       moltype = AA  length = 13
FEATURE              Location/Qualifiers
REGION               1..13
                     note = hepcidin analogue
SITE                 8
                     note = IsoGlu-Palm conjugated half-life extension moiety
source               1..13
                     mol_type = protein
                     organism = synthetic construct
SEQUENCE: 208
DTHFPCIKFE PCK                                                                13

SEQ ID NO: 209       moltype = AA  length = 13
FEATURE              Location/Qualifiers
REGION               1..13
                     note = hepcidin analogue
SITE                 8
                     note = IsoGlu-Palm conjugated half-life extension moiety
SITE                 13
                     note = D-lysine
source               1..13
                     mol_type = protein
                     organism = synthetic construct
SEQUENCE: 209
DTHFPCIKFE PCK                                                                13

SEQ ID NO: 210       moltype = AA  length = 11
FEATURE              Location/Qualifiers
REGION               1..11
                     note = hepcidin analogue
SITE                 8
                     note = IsoGlu-Palm conjugated half-life extension moiety
source               1..11
                     mol_type = protein
                     organism = synthetic construct
SEQUENCE: 210
DTHFPCIKFC K                                                                  11

SEQ ID NO: 211       moltype = AA  length = 12
FEATURE              Location/Qualifiers
REGION               1..12
                     note = hepcidin analogue
SITE                 8
                     note = IsoGlu-Palm conjugated half-life extension moiety
source               1..12
                     mol_type = protein
                     organism = synthetic construct
SEQUENCE: 211
DTHFPCIKFC RK                                                                 12

SEQ ID NO: 212       moltype = AA  length = 11
FEATURE              Location/Qualifiers
REGION               1..11
                     note = hepcidin analogue
SITE                 8
                     note = D-lysine
SITE                 8
                     note = IsoGlu-Palm conjugated half-life extension moiety
MOD_RES              9
                     note = N-Methyl-Phenylalanine
source               1..11
                     mol_type = protein
                     organism = synthetic construct
SEQUENCE: 212
DTHFPCIKXG C                                                                  11

SEQ ID NO: 213       moltype = AA  length = 10
FEATURE              Location/Qualifiers
```

```
REGION                    1..10
                          note = hepcidin analogue
SITE                      8
                          note = D-lysine
SITE                      8
                          note = IsoGlu-Palm conjugated half-life extension moiety
source                    1..10
                          mol_type = protein
                          organism = synthetic construct
SEQUENCE: 213
DTHFPCIKFC                                                              10

SEQ ID NO: 214            moltype = AA  length = 10
FEATURE                   Location/Qualifiers
REGION                    1..10
                          note = hepcidin analogue
SITE                      8
                          note = IsoGlu-Palm conjugated half-life extension moiety
MOD_RES                   9
                          note = Beta-homophenylalanine
source                    1..10
                          mol_type = protein
                          organism = synthetic construct
SEQUENCE: 214
DTHFPCIKXC                                                              10

SEQ ID NO: 215            moltype = AA  length = 10
FEATURE                   Location/Qualifiers
REGION                    1..10
                          note = hepcidin analogue
SITE                      8
                          note = IsoGlu-Palm conjugated half-life extension moiety
MOD_RES                   9
                          note = Alpha- Methylphenylalanine
source                    1..10
                          mol_type = protein
                          organism = synthetic construct
SEQUENCE: 215
DTHFPCIKXC                                                              10

SEQ ID NO: 216            moltype = AA  length = 10
FEATURE                   Location/Qualifiers
REGION                    1..10
                          note = hepcidin analogue
MOD_RES                   4
                          note = Beta,Beta-diphenylalanine
SITE                      8
                          note = IsoGlu-Palm conjugated half-life extension moiety
MOD_RES                   9
                          note = Alpha- Methylphenylalanine
source                    1..10
                          mol_type = protein
                          organism = synthetic construct
SEQUENCE: 216
DTHXPCIKXC                                                              10

SEQ ID NO: 217            moltype = AA  length = 10
FEATURE                   Location/Qualifiers
REGION                    1..10
                          note = hepcidin analogue
MOD_RES                   4
                          note = Alpha-Methyl Phenylalanine
SITE                      8
                          note = IsoGlu-Palm conjugated half-life extension moiety
MOD_RES                   9
                          note = Alpha- Methylphenylalanine
source                    1..10
                          mol_type = protein
                          organism = synthetic construct
SEQUENCE: 217
DTHXPCIKXC                                                              10

SEQ ID NO: 218            moltype = AA  length = 10
FEATURE                   Location/Qualifiers
REGION                    1..10
                          note = hepcidin analogue
MOD_RES                   4
                          note = N-Methyl Phenylalanine
SITE                      8
```

```
                        note = IsoGlu-Palm conjugated half-life extension moiety
MOD_RES                 9
                        note = Alpha- Methylphenylalanine
source                  1..10
                        mol_type = protein
                        organism = synthetic construct
SEQUENCE: 218
DTHXPCIKXC                                                                      10

SEQ ID NO: 219          moltype = AA   length = 10
FEATURE                 Location/Qualifiers
REGION                  1..10
                        note = hepcidin analogue
MOD_RES                 4
                        note = Beta-homophenylalanine
SITE                    8
                        note = IsoGlu-Palm conjugated half-life extension moiety
MOD_RES                 9
                        note = Alpha- Methylphenylalanine
source                  1..10
                        mol_type = protein
                        organism = synthetic construct
SEQUENCE: 219
DTHXPCIKXC                                                                      10

SEQ ID NO: 220          moltype = AA   length = 10
FEATURE                 Location/Qualifiers
REGION                  1..10
                        note = hepcidin analogue
SITE                    8
                        note = IsoGlu-Palm conjugated half-life extension moiety
MOD_RES                 9
                        note = Alpha- Methylphenylalanine
source                  1..10
                        mol_type = protein
                        organism = synthetic construct
SEQUENCE: 220
DTHWPCIKXC                                                                      10

SEQ ID NO: 221          moltype = AA   length = 10
FEATURE                 Location/Qualifiers
REGION                  1..10
                        note = hepcidin analogue
MOD_RES                 5
                        note = Nipecotic acid
SITE                    8
                        note = IsoGlu-Palm conjugated half-life extension moiety
MOD_RES                 9
                        note = Alpha- Methylphenylalanine
source                  1..10
                        mol_type = protein
                        organism = synthetic construct
SEQUENCE: 221
DTHFXCIKXC                                                                      10

SEQ ID NO: 222          moltype = AA   length = 10
FEATURE                 Location/Qualifiers
REGION                  1..10
                        note = hepcidin analogue
SITE                    8
                        note = PEG11-Palm conjugated half-life extension moiety
source                  1..10
                        mol_type = protein
                        organism = synthetic construct
SEQUENCE: 222
DTHFPCIKFC                                                                      10

SEQ ID NO: 223          moltype = AA   length = 10
FEATURE                 Location/Qualifiers
REGION                  1..10
                        note = hepcidin analogue
SITE                    8
                        note = isoGlu-Palm conjugated half-life extension moiety
source                  1..10
                        mol_type = protein
                        organism = synthetic construct
SEQUENCE: 223
DTHFPCIKFC                                                                      10
```

| | | |
|---|---|---|
| SEQ ID NO: 224 | moltype = AA   length = 11 | |
| FEATURE | Location/Qualifiers | |
| REGION | 1..11 | |
| | note = hepcidin analogue | |
| SITE | 8 | |
| | note = D-lysine | |
| SITE | 8 | |
| | note = PEG11-Palm conjugated half-life extension moiety | |
| source | 1..11 | |
| | mol_type = protein | |
| | organism = synthetic construct | |
| SEQUENCE: 224 | | |
| DTHFPCIKFK C | | 11 |
| | | |
| SEQ ID NO: 225 | moltype = AA   length = 11 | |
| FEATURE | Location/Qualifiers | |
| REGION | 1..11 | |
| | note = hepcidin analogue | |
| SITE | 8 | |
| | note = D-lysine | |
| SITE | 8 | |
| | note = PEG11-Palm conjugated half-life extension moiety | |
| SITE | 10 | |
| | note = D-lysine | |
| source | 1..11 | |
| | mol_type = protein | |
| | organism = synthetic construct | |
| SEQUENCE: 225 | | |
| DTHFPCIKFK C | | 11 |
| | | |
| SEQ ID NO: 226 | moltype = AA   length = 11 | |
| FEATURE | Location/Qualifiers | |
| REGION | 1..11 | |
| | note = hepcidin analogue | |
| SITE | 8 | |
| | note = D-lysine | |
| SITE | 8 | |
| | note = PEG11-Palm conjugated half-life extension moiety | |
| SITE | 10 | |
| | note = D-arginine | |
| source | 1..11 | |
| | mol_type = protein | |
| | organism = synthetic construct | |
| SEQUENCE: 226 | | |
| DTHFPCIKFR C | | 11 |
| | | |
| SEQ ID NO: 227 | moltype = AA   length = 11 | |
| FEATURE | Location/Qualifiers | |
| REGION | 1..11 | |
| | note = hepcidin analogue | |
| SITE | 8 | |
| | note = isoGlu-Palm conjugated half-life extension moiety | |
| source | 1..11 | |
| | mol_type = protein | |
| | organism = synthetic construct | |
| SEQUENCE: 227 | | |
| DTHFPCIKFK C | | 11 |
| | | |
| SEQ ID NO: 228 | moltype = AA   length = 11 | |
| FEATURE | Location/Qualifiers | |
| REGION | 1..11 | |
| | note = hepcidin analogue | |
| MOD_RES | 4 | |
| | note = Beta,Beta-diphenylalanine | |
| SITE | 8 | |
| | note = PEG11-Palm conjugated half-life extension moiety | |
| MOD_RES | 9 | |
| | note = Beta-homophenylalanine | |
| SITE | 10 | |
| | note = D-lysine | |
| source | 1..11 | |
| | mol_type = protein | |
| | organism = synthetic construct | |
| SEQUENCE: 228 | | |
| DTHXPCIKXK C | | 11 |
| | | |
| SEQ ID NO: 229 | moltype = AA   length = 10 | |
| FEATURE | Location/Qualifiers | |
| REGION | 1..10 | |

```
                        note = hepcidin analogue
MOD_RES                 4
                        note = Beta,Beta-diphenylalanine
SITE                    8
                        note = Ahx-Palm conjugated half-life extension moiety
MOD_RES                 9
                        note = Beta-homophenylalanine
source                  1..10
                        mol_type = protein
                        organism = synthetic construct
SEQUENCE: 229
DTHXPCIKXC                                                                    10

SEQ ID NO: 230          moltype = AA  length = 11
FEATURE                 Location/Qualifiers
REGION                  1..11
                        note = hepcidin analogue
MOD_RES                 4
                        note = Beta,Beta-diphenylalanine
SITE                    8
                        note = Ahx-Palm conjugated half-life extension moiety
MOD_RES                 9
                        note = Beta-homophenylalanine
SITE                    11
                        note = D-lysine
source                  1..11
                        mol_type = protein
                        organism = synthetic construct
SEQUENCE: 230
DTHXPCIKXC K                                                                  11

SEQ ID NO: 231          moltype = AA  length = 9
FEATURE                 Location/Qualifiers
REGION                  1..9
                        note = Dimer linked by K-K-isoGlu-Palm conjugated half-life
                         meoiety
source                  1..9
                        mol_type = protein
                        organism = synthetic construct
SEQUENCE: 231
DTHFPCIKF                                                                     9

SEQ ID NO: 232          moltype = AA  length = 9
FEATURE                 Location/Qualifiers
REGION                  1..9
                        note = Dimer linked by dK-K-isoGlu-Palm conjugated
                         half-life meoiety
source                  1..9
                        mol_type = protein
                        organism = synthetic construct
SEQUENCE: 232
DTHFPCIKF                                                                     9

SEQ ID NO: 233          moltype = AA  length = 9
FEATURE                 Location/Qualifiers
REGION                  1..9
                        note = Dimer linked by K-isoGlu-Palm conjugated half-life
                         meoiety
SITE                    8
                        note = D-lysine
source                  1..9
                        mol_type = protein
                        organism = synthetic construct
SEQUENCE: 233
DTHFPCIKF                                                                     9

SEQ ID NO: 234          moltype = AA  length = 9
FEATURE                 Location/Qualifiers
REGION                  1..9
                        note = Dimer linked by K-K-isoGlu-Palm conjugated half-life
                         moiety
MOD_RES                 9
                        note = Phe (4-OCH2CH2NH2)
source                  1..9
                        mol_type = protein
                        organism = synthetic construct
SEQUENCE: 234
DTHFPCIKX                                                                     9
```

```
SEQ ID NO: 235             moltype = AA   length = 9
FEATURE                    Location/Qualifiers
REGION                     1..9
                           note = Dimer linked by K-K-isoGlu-Palm conjugated half-life
                            meoiety
MOD_RES                    9
                           note = Alpha-Methylphenylalanine
source                     1..9
                           mol_type = protein
                           organism = synthetic construct
SEQUENCE: 235
DTHFPCIKX                                                                   9

SEQ ID NO: 236             moltype = AA   length = 9
FEATURE                    Location/Qualifiers
REGION                     1..9
                           note = Dimer linked by IDA [(beta-alanine)-Palm] conjugated
                            half-life meoiety
SITE                       8
                           note = D-lysine
source                     1..9
                           mol_type = protein
                           organism = synthetic construct
SEQUENCE: 236
DTHFPCIKF                                                                   9

SEQ ID NO: 237             moltype = AA   length = 9
FEATURE                    Location/Qualifiers
REGION                     1..9
                           note = Dimer linked by IDA [(beta-alanine)-Palm] conjugated
                            half-life meoiety
MOD_RES                    9
                           note = N-Methylphenylalanine
source                     1..9
                           mol_type = protein
                           organism = synthetic construct
SEQUENCE: 237
DTHFPCIKX                                                                   9

SEQ ID NO: 238             moltype = AA   length = 9
FEATURE                    Location/Qualifiers
REGION                     1..9
                           note = Dimer linked by IDA [(beta-alanine)-Palm] conjugated
                            half-life meoiety
MOD_RES                    9
                           note = Alpha-Methylphenylalanine
source                     1..9
                           mol_type = protein
                           organism = synthetic construct
SEQUENCE: 238
DTHFPCIKX                                                                   9

SEQ ID NO: 239             moltype = AA   length = 10
FEATURE                    Location/Qualifiers
REGION                     1..10
                           note = Dimer linked by IDA [(beta-alanine)-Palm] conjugated
                            half-life meoiety
SITE                       10
                           note = D-lysine
source                     1..10
                           mol_type = protein
                           organism = synthetic construct
SEQUENCE: 239
DTHFPCIIFK                                                                  10

SEQ ID NO: 240             moltype = AA   length = 9
FEATURE                    Location/Qualifiers
REGION                     1..9
                           note = Dimer linked by K-K-isoGlu-Palm conjugated half-life
                            moiety
SITE                       8
                           note = D-lysine
MOD_RES                    9
                           note = Alpha-Methylphenylalanine
source                     1..9
                           mol_type = protein
                           organism = synthetic construct
SEQUENCE: 240
DTHFPCIKX                                                                   9
```

```
SEQ ID NO: 241          moltype = AA  length = 9
FEATURE                 Location/Qualifiers
REGION                  1..9
                        note = Dimer linked by K-K-isoGlu-Palm conjugated half-life
                         moiety
MOD_RES                 4
                        note = Biphenylalanine
SITE                    8
                        note = D-lysine
source                  1..9
                        mol_type = protein
                        organism = synthetic construct
SEQUENCE: 241
DTHXPCIKF                                                                   9

SEQ ID NO: 242          moltype = AA  length = 9
FEATURE                 Location/Qualifiers
REGION                  1..9
                        note = Dimer linked by K-K-isoGlu-Palm conjugated half-life
                         moiety
MOD_RES                 9
                        note = Beta-homophenylalanine
source                  1..9
                        mol_type = protein
                        organism = synthetic construct
SEQUENCE: 242
DTHFPCIKX                                                                   9

SEQ ID NO: 243          moltype = AA  length = 9
FEATURE                 Location/Qualifiers
REGION                  1..9
                        note = Dimer linked by K-K-isoGlu-Palm conjugated half-life
                         moiety
MOD_RES                 9
                        note = Beta-homophenylalanine
source                  1..9
                        mol_type = protein
                        organism = synthetic construct
SEQUENCE: 243
DTHFPCIKX                                                                   9

SEQ ID NO: 244          moltype = AA  length = 9
FEATURE                 Location/Qualifiers
REGION                  1..9
                        note = Dimer linked by IDA [(beta-alanine)-Palm] conjugated
                         half-life meoiety
SITE                    8
                        note = D-lysine
MOD_RES                 9
                        note = N-Methylphenylalanine
source                  1..9
                        mol_type = protein
                        organism = synthetic construct
SEQUENCE: 244
DTHFPCIKX                                                                   9

SEQ ID NO: 245          moltype = AA  length = 9
FEATURE                 Location/Qualifiers
REGION                  1..9
                        note = Dimer linked by IDA [(beta-alanine)-Palm] conjugated
                         half-life meoiety
MOD_RES                 4
                        note = Biphenylalanine
SITE                    8
                        note = D-lysine
MOD_RES                 9
                        note = N-Methylphenylalanine
source                  1..9
                        mol_type = protein
                        organism = synthetic construct
SEQUENCE: 245
DTHXPCIKX                                                                   9

SEQ ID NO: 246          moltype = AA  length = 9
FEATURE                 Location/Qualifiers
REGION                  1..9
                        note = Dimer linked by IDA [(beta-alanine)-Palm] conjugated
                         half-life meoiety
```

```
MOD_RES              9
                     note = Beta-homophenylalanine
source               1..9
                     mol_type = protein
                     organism = synthetic construct
SEQUENCE: 246
DTHFPCIKX                                                                      9

SEQ ID NO: 247       moltype = AA   length = 9
FEATURE              Location/Qualifiers
REGION               1..9
                     note = Dimer linked by IDA [(beta-alanine)-Palm] conjugated
                      half-life meoiety
SITE                 8
                     note = D-lysine
MOD_RES              9
                     note = Beta-homophenylalanine
source               1..9
                     mol_type = protein
                     organism = synthetic construct
SEQUENCE: 247
DTHFPCIKX                                                                      9

SEQ ID NO: 248       moltype = AA   length = 9
FEATURE              Location/Qualifiers
REGION               1..9
                     note = Dimer linked by IDA [(beta-alanine)-Palm] conjugated
                      half-life meoiety
MOD_RES              5
                     note = Nipecotic acid
SITE                 8
                     note = D-lysine
MOD_RES              9
                     note = N-Methylphenylalanine
source               1..9
                     mol_type = protein
                     organism = synthetic construct
SEQUENCE: 248
DTHFXCIKX                                                                      9

SEQ ID NO: 249       moltype = AA   length = 4
FEATURE              Location/Qualifiers
REGION               1..4
                     note = peptide insert
source               1..4
                     mol_type = protein
                     organism = synthetic construct
SEQUENCE: 249
PRSK                                                                           4

SEQ ID NO: 250       moltype = AA   length = 5
FEATURE              Location/Qualifiers
REGION               1..5
                     note = peptide insert
MOD_RES              5
                     note = MeGly
source               1..5
                     mol_type = protein
                     organism = synthetic construct
SEQUENCE: 250
PRSKX                                                                          5

SEQ ID NO: 251       moltype = AA   length = 5
FEATURE              Location/Qualifiers
REGION               1..5
                     note = peptide insert
source               1..5
                     mol_type = protein
                     organism = synthetic construct
SEQUENCE: 251
PRSKG                                                                          5

SEQ ID NO: 252       moltype = AA   length = 17
FEATURE              Location/Qualifiers
REGION               1..17
                     note = hepcidin analogue
source               1..17
                     mol_type = protein
                     organism = synthetic construct
```

```
SEQUENCE: 252
DTHFPCIKFE PRSKGCK                                                                17

SEQ ID NO: 253          moltype = AA  length = 4
FEATURE                 Location/Qualifiers
REGION                  1..4
                        note = peptide insert
source                  1..4
                        mol_type = protein
                        organism = synthetic construct
SEQUENCE: 253
PRSC                                                                              4

SEQ ID NO: 254          moltype = AA  length = 5
FEATURE                 Location/Qualifiers
REGION                  1..5
                        note = peptide insert
source                  1..5
                        mol_type = protein
                        organism = synthetic construct
SEQUENCE: 254
PRSKC                                                                             5

SEQ ID NO: 255          moltype = AA  length = 6
FEATURE                 Location/Qualifiers
REGION                  1..6
                        note = peptide insert
source                  1..6
                        mol_type = protein
                        organism = synthetic construct
SEQUENCE: 255
PRSKCK                                                                            6

SEQ ID NO: 256          moltype = AA  length = 25
FEATURE                 Location/Qualifiers
source                  1..25
                        mol_type = protein
                        organism = Homo sapiens
SEQUENCE: 256
DTHFPICIFC CGCCHRSKCG MCCKT                                                       25

SEQ ID NO: 257          moltype = AA  length = 9
FEATURE                 Location/Qualifiers
source                  1..9
                        mol_type = protein
                        organism = Homo sapiens
SEQUENCE: 257
DTHFPICIF                                                                         9

SEQ ID NO: 258          moltype = AA  length = 9
FEATURE                 Location/Qualifiers
REGION                  1..9
                        note = hepcidin analogue
SITE                    1
                        note = D-phenylalanine
SITE                    2
                        note = D-isoleucine
SITE                    3
                        note = D-cysteine
SITE                    4
                        note = D-isoleucine
SITE                    5
                        note = D-proline
SITE                    6
                        note = D-phenylalanine
SITE                    7
                        note = D-histidine
SITE                    8
                        note = D-threonine
SITE                    9
                        note = D-aspartic acid
source                  1..9
                        mol_type = protein
                        organism = synthetic construct
SEQUENCE: 258
FICIPFHTD                                                                         9
```

What is claimed is:

1. A peptide or a peptide dimer thereof, wherein the peptide comprises or consists of:

(SEQ ID NO: 158)
Isovaleric acid-DTH-[Dpa]-PCI-[(D)Lys]-[b-hPhe]-
[Lys(IsoGlu-Palm)]-[(D)Lys]-C-NH₂;

(SEQ ID NO: 159)
Isovaleric acid-DTH-[Dpa]-PCI-[(D)Lys-Ac]-
[b-hPhe]-[Lys(Peg11-Palm)]-[(D)Lys-Ac1-C-NH₂;

(SEQ ID NO: 165)
Isovaleric acid-DTH-[Dpa]-PCI-[(D)Lys]-[b-hPhe]-
[Lys(Ahx-Palm)]-[(D)Lys]-C-NH₂;

(SEQ ID NO: 166)
Isovaleric acid-DTH-[Dpa]-PCI-[(D)Lys-(Peg11-
OMe)]-[b-hPhe]-[Lys(Ahx-Palm)]-[(D)Lys-
(Peg11-OMe)]-C-NH₂; or (SEQ ID NO: 175)
Isovaleric_Acid-D-T-H-[Dpa]-P-C-I-(D)Lys-bhPhe-
[Lys_Peg11_Palm]-dLys_Ac-C-NH₂, wherein the peptide is cyclized via a disulfide bond between two cysteines.

2. The peptide or peptide dimer thereof of claim 1, wherein the peptide comprises or consists of:
Isovaleric acid-DTH-[Dpa]-PCI-[(D)Lys]-[b-hPhe]-[Lys(IsoGlu-Palm)]-[(D)Lys]-C-NH₂ (SEQ ID NO: 158), wherein the peptide is cyclized via a disulfide bond between two cysteines.

3. The peptide or peptide dimer thereof of claim 1, wherein the peptide comprises or consists of:
Isovaleric acid-DTH-[Dpa]-PCI-[(D)Lys-Ac]-[b-hPhe]-[Lys(Peg11-Palm)]-[(D)Lys-Ac]-C-NH₂ (SEQ ID NO: 159), wherein the peptide is cyclized via a disulfide bond between two cysteines.

4. The peptide or peptide dimer thereof of claim 1, wherein the peptide comprises or consists of:
Isovaleric acid-DTH-[Dpa]-PCI-[(D)Lys]-[b-hPhe]-[Lys(Ahx-Palm)]-[(D)Lys]-C-NH₂ (SEQ ID NO: 165), wherein the peptide is cyclized via a disulfide bond between two Cys.

5. The peptide or peptide dimer thereof of claim 1, wherein the peptide comprises or consists of:
Isovaleric acid-DTH-[Dpa]-PCI-[(D)Lys-(Peg11-OMe)]-[b-hPhe]-[Lys(Ahx-Palm)]-[(D)Lys-(Peg11-OMe)]-C-NH₂ (SEQ ID NO: 166), wherein the peptide is cyclized via a disulfide bond between two cysteines.

6. The peptide or peptide dimer thereof of claim 1, wherein the peptide comprises or consists of:
Isovaleric_Acid-D-T-H-[Dpa]-P-C-I-(D)Lys-bhPhe-[Lys_Peg11_Palm]-dLys_Ac-C-NH₂ (SEQ ID NO: 175), wherein the peptide is cyclized via a disulfide bond between two cysteines.

7. The peptide of claim 1, consisting of a monomer of a peptide comprising:

(SEQ ID NO: 158)
Isovaleric acid-DTH-[Dpa]-PCI-[(D)Lys]-[b-hPhe]-
[Lys(IsoGlu-Palm)]-[(D)Lys]-C-NH₂;

(SEQ ID NO: 159)
Isovaleric acid-DTH-[Dpa]-PCI-[(D)Lys-Ac]-
[b-hPhe]-[Lys(Peg11-Palm)]-[(D)Lys-Ac1-C-NH₂;

(SEQ ID NO: 165)
Isovaleric acid-DTH-[Dpa]-PCI-[(D)Lys]-[b-hPhe]-
[Lys(Ahx-Palm)]-[(D)Lys]-C-NH₂;

(SEQ ID NO: 166)
Isovaleric acid-DTH-[Dpa]-PCI-[(D)Lys-(Peg11-
OMe)]-[b-hPhe]-[Lys(Ahx-Palm)]-[(D)Lys-
(Peg11-OMe)]-C-NH₂; or (SEQ ID NO: 175)
Isovaleric_Acid-D-T-H-[Dpa]-P-C-I-(D)Lys-bhPhe-
[Lys_Peg11_Palm]-dLys_Ac-C-NH₂, wherein the peptide is cyclized via a disulfide bond between two cysteines.

8. The peptide dimer of claim 1, consisting of a dimer of a peptide comprising:

(SEQ ID NO: 158)
Isovaleric acid-DTH-[Dpa]-PCI-[(D)Lys]-[b-hPhe]-
[Lys(IsoGlu-Palm)]-[(D)Lys]-C-NH₂;

(SEQ ID NO: 159)
Isovaleric acid-DTH-[Dpa]-PCI-[(D)Lys-Ac]-
[b-hPhe]-[Lys(Peg11-Palm)]-[(D)Lys-Ac1-C-NH₂;

(SEQ ID NO: 165)
Isovaleric acid-DTH-[Dpa]-PCI-[(D)Lys]-[b-hPhe]-
[Lys(Ahx-Palm)]-[(D)Lys]-C-NH₂;

(SEQ ID NO: 166)
Isovaleric acid-DTH-[Dpa]-PCI-[(D)Lys-(Peg11-
OMe)]-[b-hPhe]-[Lys(Ahx-Palm)]-[(D)Lys-
(Peg11-OMe)]-C-NH₂; or (SEQ ID NO: 175)
Isovaleric_Acid-D-T-H-[Dpa]-P-C-I-(D)Lys-bhPhe-
[Lys_Peg11_Palm]-dLys_Ac-C-NH₂, wherein the peptide is cyclized via a disulfide bond between two cysteines.

9. The peptide of claim 1, consisting of a monomer of:

(SEQ ID NO: 158)
Isovaleric acid-DTH-[Dpa]-PCI-[(D)Lys]-[b-hPhe]-
[Lys(IsoGlu-Palm)]-[(D)Lys]-C-NH₂;

(SEQ ID NO: 159)
Isovaleric acid-DTH-[Dpa]-PCI-[(D)Lys-Ac]-
[b-hPhe]-[Lys(Peg11-Palm)]-[(D)Lys-Ac1-C-NH₂;

(SEQ ID NO: 165)
Isovaleric acid-DTH-[Dpa]-PCI-[(D)Lys]-[b-hPhe]-
[Lys(Ahx-Palm)]-[(D)Lys]-C-NH₂;

(SEQ ID NO: 166)
Isovaleric acid-DTH-[Dpa]-PCI-[(D)Lys-(Peg11-
OMe)]-[b-hPhe]-[Lys(Ahx-Palm)]-[(D)Lys-
(Peg11-OMe)]-C-NH₂; or (SEQ ID NO: 175)
Isovaleric_Acid-D-T-H-[Dpa]-P-C-I-(D)Lys-bhPhe-
[Lys_Peg11_Palm]-dLys_Ac-C-NH₂, wherein the peptide is cyclized via a disulfide bond between two cysteines.

10. The peptide dimer of claim 1, consisting of a dimer of:

(SEQ ID NO: 158)
Isovaleric acid-DTH-[Dpa]-PCI-[(D)Lys]-[b-hPhe]-
[Lys(IsoGlu-Palm)]-[(D)Lys]-C-NH₂;

-continued

Isovaleric acid-DTH-[Dpa]-PCI-[(D)Lys-Ac]-[b-hPhe]-[Lys(Peg11-Palm)]-[(D)Lys-Ac1-C-NH$_2$; (SEQ ID NO: 159)

Isovaleric acid-DTH-[Dpa]-PCI-[(D)Lys]-[b-hPhe]-[Lys(Ahx-Palm)]-[(D)Lys]-C-NH$_2$; (SEQ ID NO: 165)

Isovaleric acid-DTH-[Dpa]-PCI-[(D)Lys-(Peg11-OMe)]-[b-hPhe]-[Lys(Ahx-Palm)]-[(D)Lys-(Peg11-OMe)]-C-NH$_2$; or (SEQ ID NO: 166)

Isovaleric_Acid-D-T-H-[Dpa]-P-C-I-(D)Lys-bhPhe-[Lys_Peg11_Palm]-dLys_Ac-C-NH$_2$, (SEQ ID NO: 175)

wherein the peptide is cyclized via a disulfide bond between two cysteines.

11. A pharmaceutical composition comprising the peptide or peptide dimer thereof of claim 1, and a pharmaceutically acceptable carrier, excipient or vehicle.

12. A method of binding a ferroportin or inducing ferroportin internalization and degradation, comprising contacting the ferroportin with at least one of the pharmaceutical composition(s) of claim 11.

13. A method for treating a disease of iron metabolism in a subject in need thereof comprising providing to the subject an effective amount of the pharmaceutical composition of claim 11.

14. The method of claim 13, wherein the pharmaceutical composition is provided to the subject by an oral route of administration.

15. The method of claim 13, wherein the disease of iron metabolism is an iron overload disease.

16. The method of claim 13, wherein the pharmaceutical composition is provided to the subject at most twice daily, at most once daily, at most once every two days, at most once a week, or at most once a month.

17. The method of claim 13, wherein the peptide or peptide dimer thereof is provided to the subject at a dosage of about 1 mg to about 100 mg.

18. A device comprising the pharmaceutical composition of claim 11, for delivery of the peptide or peptide dimer thereof to a subject, optionally orally.

* * * * *

UNITED STATES PATENT AND TRADEMARK OFFICE
CERTIFICATE OF CORRECTION

| | | |
|---|---|---|
| PATENT NO. | : 12,234,300 B2 | Page 1 of 1 |
| APPLICATION NO. | : 18/366558 | |
| DATED | : February 25, 2025 | |
| INVENTOR(S) | : Gregory Thomas Bourne et al. | |

It is certified that error appears in the above-identified patent and that said Letters Patent is hereby corrected as shown below:

In the Claims

At Column 237, Claim number 1, Line number 11, please replace "Acl-C-NH$_2$" with --Ac]-C-NH$_2$--;

At Column 237, Claim number 4, Line number 43, please replace "Cys" with --cysteines--;

At Column 237, Claim number 7, Line number 66, please replace "Acl-C-NH$_2$" with --Ac]-C-NH$_2$--;

At Column 238, Claim number 8, Line number 24, please replace "Acl-C-NH$_2$" with --Ac]-C-NH$_2$--;

At Column 238, Claim number 9, Line number 47, please replace "Acl-C-NH$_2$" with --Ac]-C-NH$_2$--;

At Column 239, Claim number 10, Line number 5, please replace "Acl-C-NH$_2$" with --Ac]-C-NH$_2$--.

Signed and Sealed this
Twenty-seventh Day of May, 2025

Coke Morgan Stewart
*Acting Director of the United States Patent and Trademark Office*